(12) United States Patent
Li et al.

(10) Patent No.: US 11,708,356 B2
(45) Date of Patent: Jul. 25, 2023

(54) ORGANIC ELECTROLUMINESCENT MATERIALS AND DEVICES

(71) Applicant: BEIJING SUMMER SPROUT TECHNOLOGY CO., LTD., Beijing (CN)

(72) Inventors: Feng Li, Beijing (CN); Le Wang, Beijing (CN); Changqing Li, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 403 days.

(21) Appl. No.: 16/803,280

(22) Filed: Feb. 27, 2020

(65) Prior Publication Data
US 2020/0277283 A1   Sep. 3, 2020

(30) Foreign Application Priority Data

Feb. 28, 2019   (CN) .......................... 201910149767.3

(51) Int. Cl.
| | |
|---|---|
| *C07D 405/14* | (2006.01) |
| *C07D 405/04* | (2006.01) |
| *C07D 403/04* | (2006.01) |
| *H01L 51/00* | (2006.01) |
| *H01L 51/42* | (2006.01) |

(Continued)

(52) U.S. Cl.
CPC ......... *C07D 405/14* (2013.01); *C07D 403/04* (2013.01); *C07D 405/04* (2013.01); *H10K 30/353* (2023.02); *H10K 85/622* (2023.02); *H10K 85/654* (2023.02); *H10K 85/6572* (2023.02); *H10K 85/6574* (2023.02)

(58) Field of Classification Search
None
See application file for complete search history.

(56) References Cited

U.S. PATENT DOCUMENTS

| | | |
|---|---|---|
| 5,703,436 A | 12/1997 | Forrest et al. |
| 5,707,745 A | 1/1998 | Forrest et al. |

(Continued)

FOREIGN PATENT DOCUMENTS

| | | |
|---|---|---|
| CN | 107188886 A | 9/2017 |
| CN | 108727358 A | 11/2018 |

(Continued)

OTHER PUBLICATIONS

Machine English translation of Pan et al. (WO 2018/103745 A1). Apr. 25, 2022.*

(Continued)

*Primary Examiner* — Jay Yang
(74) *Attorney, Agent, or Firm* — Barnes & Thornburg LLP; Jeffrey R. Stone

(57) ABSTRACT

An organic electroluminescent material and a device thereof are disclosed. The organic electroluminescent material uses a compound having a novel carbazole structure, and can be used as hole blocking material, host material in an electroluminescent device. These novel compounds can provide better device performance, such as obtaining device performance of very low driving-voltage, high efficiency, and long lifetime.

14 Claims, 2 Drawing Sheets

(51) Int. Cl.
  *H10K 30/30* (2023.01)
  *H10K 85/60* (2023.01)

(56) References Cited

U.S. PATENT DOCUMENTS

| | | | |
|---|---|---|---|
| 5,844,363 | A | 12/1998 | Gu et al. |
| 6,097,147 | A | 8/2000 | Baldo et al. |
| 6,303,238 | B1 | 10/2001 | Thompson et al. |
| 7,279,704 | B2 | 10/2007 | Walters et al. |
| 7,968,146 | B2 | 6/2011 | Wagner et al. |
| 2003/0230980 | A1 | 12/2003 | Forrest et al. |
| 2004/0067387 | A1* | 4/2004 | Kim et al. ............... 428/690 |
| 2004/0174116 | A1 | 9/2004 | Lu et al. |
| 2012/0223276 | A1 | 9/2012 | Parham et al. |
| 2014/0131665 | A1 | 5/2014 | Xia et al. |
| 2014/0158992 | A1 | 6/2014 | Xia et al. |
| 2015/0001471 | A1 | 1/2015 | Boudreault et al. |
| 2015/0053939 | A1 | 2/2015 | Adamovich et al. |
| 2015/0228908 | A1 | 8/2015 | Lee et al. |
| 2015/0243903 | A1 | 8/2015 | Zeng et al. |
| 2015/0349273 | A1 | 12/2015 | Hung et al. |
| 2016/0028021 | A1 | 1/2016 | Zeng et al. |
| 2016/0093808 | A1 | 3/2016 | Adamovich et al. |
| 2016/0359122 | A1 | 12/2016 | Boudreault et al. |
| 2017/0025618 | A1 | 1/2017 | Zheng et al. |
| 2017/0054087 | A1 | 2/2017 | Zeng |
| 2018/0166634 | A1 | 6/2018 | Numata et al. |
| 2018/0301639 | A1 | 10/2018 | Zeng et al. |
| 2019/0237674 | A1* | 8/2019 | Cha ....................... C07D 403/10 |

FOREIGN PATENT DOCUMENTS

| | | |
|---|---|---|
| EP | 2991128 A1 | 3/2016 |
| KR | 20180060474 A | 6/2018 |
| WO | 2013/100538 A1 | 7/2013 |
| WO | WO-2018/021854 A1 * | 2/2018 |
| WO | WO-2018/103745 A1 * | 6/2018 |
| WO | WO-2019/190230 A1 * | 10/2019 |

OTHER PUBLICATIONS

Machine English translation of Jang et al. (WO 2019/190230 A1). Apr. 25, 2022.*

Joyama et al., "Highly efficient organic light-emitting diodes from delayed fluorescence", Nature; vol. 492, pp. 234-238 (2012).

Tang et al., "Organic electroluminescent diodes", Applied Physics Letters, 51(12): 913-915 (1987).

Chinese First Office Action, for Chinese Application No. 201910149767.3 and its English translation, dated April 20, 2022.

* cited by examiner

ORGANIC ELECTROLUMINESCENT MATERIALS AND DEVICES

This application claims the benefit of Chinese Application No. 201910149767.3 filed on Feb. 28, 2019 to the China National Intellectual Property Administration, the entire content of which is incorporated herein by reference.

TECHNICAL FIELD

The present disclosure relates to compounds for organic electronic device, such as organic electroluminescent device. More specifically, it relates to novel carbazole compounds, and organic electroluminescent devices and a compound formulation comprising the same.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices. Among them, OLEDs are becoming more and more popular for their unique superior properties, such as having a wide color gamut, almost infinitely high contrast, extremely high response speed, flexibility, energy saving and etc.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

The carbazole-based organic semiconductor materials have a wide range of application in optoelectronic devices due to their superior optoelectronic properties, redox properties, stability and etc.

WO2013100538A1 disclosed carbazole compounds of the following structure

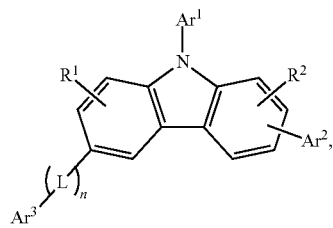

especially

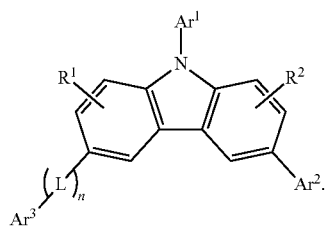

The inventor of this application noticed various advantages of the compound obtained by combining carbazole with an aza six-membered aromatic ring such as pyridine, pyrimidine, and triazine, but it did not explicitly recognize the unique advantages of the triazine structure. In addition, in the choice of the position where the triazine is connected to the carbazole ring, it is not aware of the advantages of substitution positions on the carbazole ring other than the 3-position explicitly disclosed in this invention, especially the 2-position substitution.

KR1020180060474A, EP2991128A1 and US20150228908A1 all have disclosed compounds in which the aza-ring structure such as triazine is connected to the 4-position of the carbazole ring through a single bond or a (hetero) arylene-based linking group. However, KR1020180060474A requires that a carbazole group further be connected to the carbazole unit, which may lead to unfavorable results of excessively enhanced hole transporting capabilities. EP2991128A1 mainly focuses on the combination use of a compound having a triazine substitution at the 4-position of carbazole and a specific second host compound having a bicarbazole and a benzothienopyrimidine or benzofuropyrimidine structure. US20150228908A1 also noticed the advantage of introducing an aza-aromatic ring at the 4-position of carbazole. It uses a series of aza-aromatic ring structures such as triazine, pyrimidine, quinoxaline, pyrimidopyrimidine, and pyrazinoimidazole. It is also unconscious about the advantages of substitution to other positions on the carbazole ring, especially the 2-position.

US20120223276A1 disclosed the following structure:

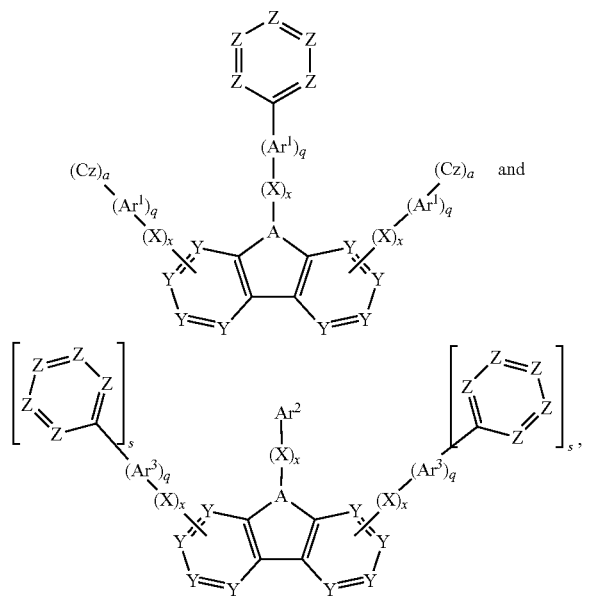

those two compounds containing carbazole or phosphofluorene structural units. In this application, the advantages of introducing an aza-aromatic ring structure on the carbazole ring are noted, but the position of introducing an aza-aromatic ring is variable, involving the 2-, 3- and 9-positions (on the nitrogen atom of carbazole) substituted compounds, and it does not realize the special advantage of fixing the triazine group at a specific position of the carbazole ring for substitution.

However, carbazole-based organic semiconductor materials reported currently have certain limitations in optoelectronic devices such as carrier transporting capabilities, efficiency, and lifetime. Therefore, the application potential of such materials deserves further research and development. The present invention discloses a new carbazole compound, which can improve the lifetime of a device and provide better device performance.

SUMMARY

The present disclosure aims to provide a series of compounds with novel carbazole structure to solve at least part of the above problems. The compound can be used as host material, hole blocking material in an organic electroluminescent device. These new compounds can provide better device performance, such as device performance of very low driving voltage, high efficiency, and long lifetime.

According to an embodiment of the present disclosure, a compound having the structure of Formula 1 is disclosed:

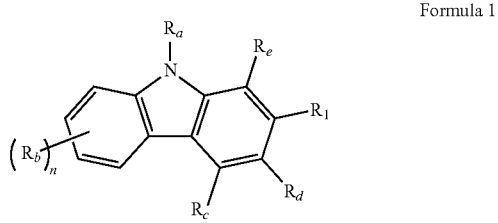

Formula 1 wherein
$R_a$ is selected from biphenyl, terphenyl, naphthyl, phenanthryl, triphenylene, fluorenyl, dibenzofuranyl;

n is the number of $R_b$, n is selected from 1, 2, 3 or 4; when n≥2, the $R_b$ is selected from the same or different structures, each of $R_b$ is independently selected from the group consisting of: hydrogen, deuterium, phenyl, biphenyl and terphenyl;

$R_c$, $R_d$ and $R_e$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

and, wherein $R_1$ has the structure of Formula 2:

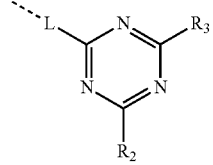

Formula 2

L is a single bond, or a substituted or unsubstituted arylene having 6 to 60 carbon atoms;

$R_2$ and $R_3$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 carbon atoms, a substituted or unsubstituted alkylsilyl group having 3 to 20 carbon atoms, a substituted or unsubstituted arylsilyl group having 6 to 20 carbon atoms, and combinations thereof;

when $R_2$ and $R_3$ are selected from a substituted group in the group, the substitution in the substituted group is selected from deuterium, halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted arylalkyl group having 7 to 30 carbon atoms, an unsubstituted alkoxy group having 1 to 20 carbon atoms, an unsubstituted aryl group having 6 to 30 carbon atoms, and combinations thereof.

According to another embodiment of the present disclosure, an electroluminescent device is also disclosed, which comprises an anode, a cathode, and an organic layer disposed between the anode and the cathode, wherein the organic layer comprising the compound having the structure of Formula 1 described above.

According to another embodiment of the present disclosure, a compound formulation comprising the compound having the structure of Formula 1 described above is also disclosed.

The compound having a novel carbazole structure disclosed in the present disclosure can be used as host material, hole blocking material in an organic electroluminescent device. Compared with existing compounds, these new compounds can provide better device performance, such as very low drive voltage, high efficiency, and long lifetime.

DETAILED DESCRIPTION

Figure 1:
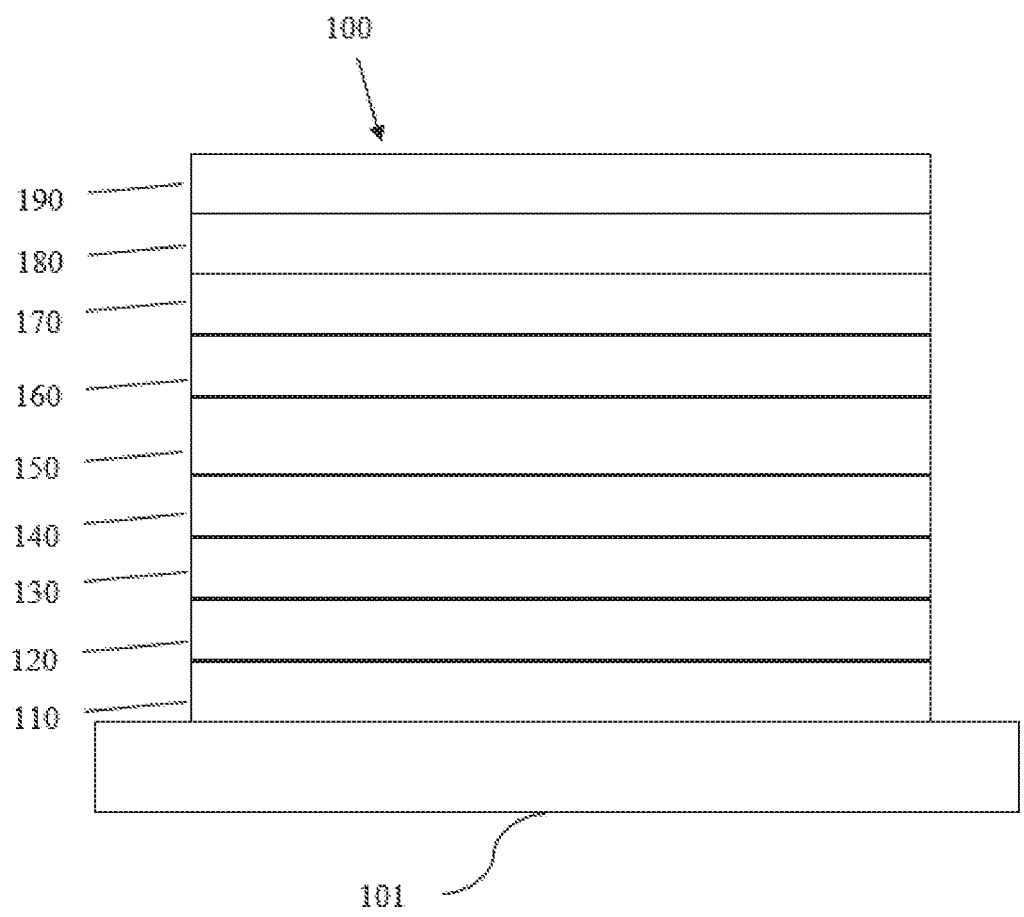
FIG. 1 schematically shows an organic light emitting device that can incorporate the compound and compound formulation disclosed herein.

OLEDs may be fabricated on various types of substrates such as glass, plastic, and metal foil. FIG. 1 schematically shows the organic light emitting device 100 without limitation. The figures are not necessarily drawn to scale. Some of the layers in the figures may also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting example. Functional OLEDs may be achieved by combining the various layers described in different ways, or layers may be omitted entirely. It may also include other layers not specifically described. Within each layer, a single material or a mixture of multiple materials may be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
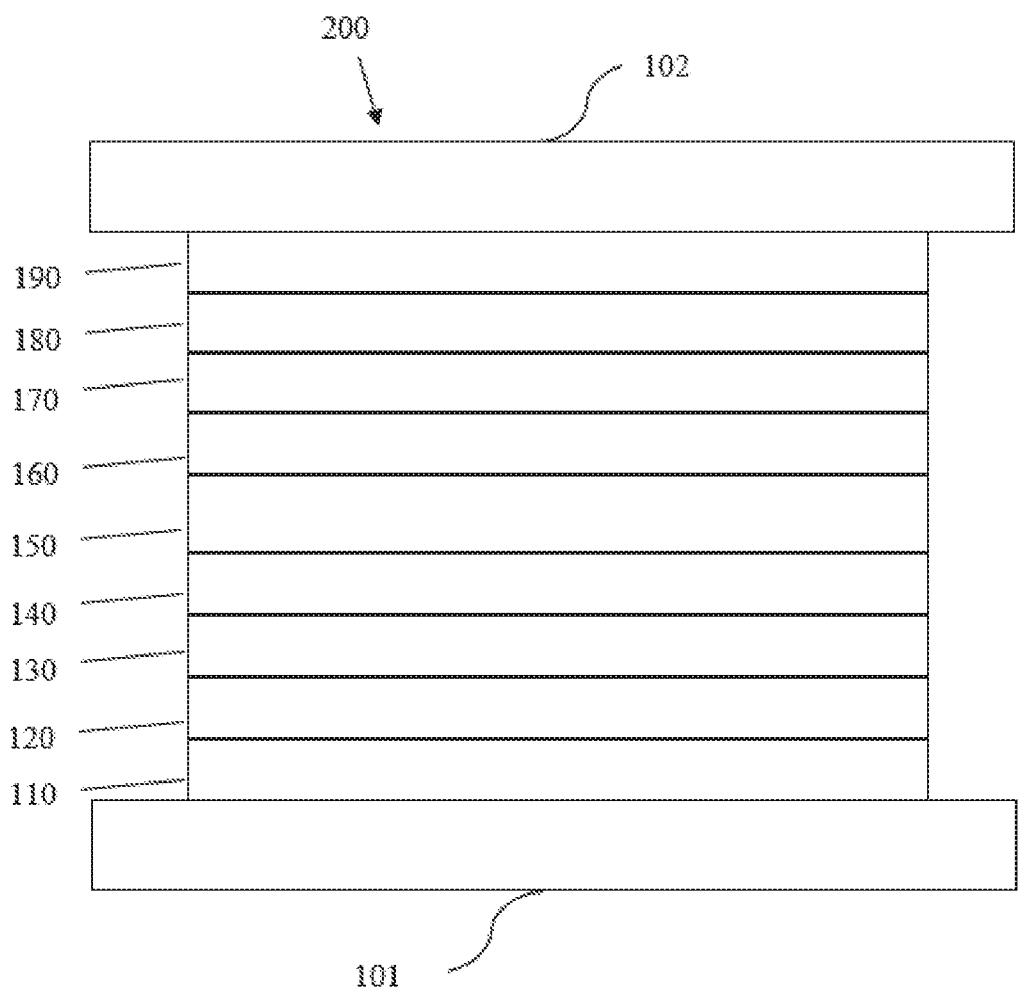
FIG. 2 schematically shows another organic light emitting device that can incorporate the compound and compound formulation disclosed herein.
Figure 3:
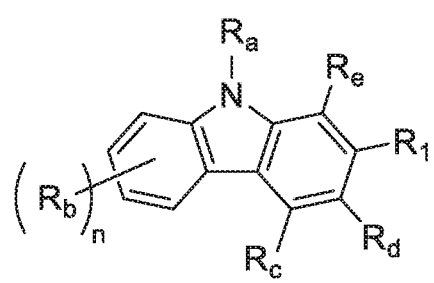
FIG. 3 shows the Structural Formula 1 of the compound disclosed herein.

An OLED may be encapsulated by a barrier layer. FIG. 2 schematically shows the organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that may provide the barrier function may be used as the barrier layer such as glass and organic-inorganic hybrid layers. The barrier layer should be placed directly or indirectly outside of the OLED device. Multilayer thin film encapsulation was described in U.S. Pat. No. 7,968,146, which is herein incorporated by reference in its entirety.

Devices fabricated in accordance with embodiments of the present disclosure may be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs may exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy may activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states may potentially reach 75%. The total singlet fraction may be 100%, far exceeding 25% of the spin statistics limit for electrically generated excitons.

E-type delayed fluorescence characteristics may be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, and 3-methylpentyl group. Additionally, the alkyl group may be optionally substituted. The carbons in the alkyl chain may be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing 2 to 15 carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl 1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing 2 to 15 carbon atoms. Additionally, the alkynyl group may be optionally substituted.

Aryl or aromatic group—as used herein includes noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein includes aromatic and non-aromatic cyclic groups. Heteroaromatic also means heteroaryl. Preferred non-aromatic heterocyclic groups are those containing 3 to 7 ring atoms which include at least one hetero atom such as nitrogen, oxygen, and sulfur. The heterocyclic group may also be an aromatic heterocyclic group having at least one heteroatom selected from nitrogen atom, oxygen atom, sulfur atom, and selenium atom.

Heteroaryl—as used herein includes noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha-naphthylmethyl group, 1-alpha-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art may readily envision other nitrogen analogs of the aza-derivatives described above, and all such analogs are intended to be encompassed by the terms as set forth herein.

In this disclosure, unless defined otherwise, when using any one of the terms of the group consisting of substituted alkyl, substituted cycloalkyl, substituted heteroalkyl, substituted aralkyl, substituted alkoxy, substituted aryloxy, substituted alkenyl, substituted aryl, substituted heteroaryl, substituted alkylsilyl, substituted arylsilyl, substituted amine, substituted acyl, substituted carbonyl, substituted carboxylic acid, substituted ester, substituted nitrile, substituted isonitrile, substituted thioalkyl, substituted sulfinyl, substituted sulfonyl, substituted phosphino refers to any one of alkyl, cycloalkyl, heteroalkyl, aralkyl, alkoxy, aryloxy, alkenyl, aromatic group, heteroaryl, alkylsilyl, arylsilyl, amine, acyl, carbonyl, carboxylic acid, ester, nitrile, isonitrile, thioalkyl, sulfinyl, sulfonyl, and phosphino may be substituted with one or more substituents selected from the group consisting of deuterium, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted arylalkyl group having 7 to 30 carbon atoms, an unsubstituted alkoxy group having 1 to 20 carbon atoms, an unsubstituted aryloxy group having 6 to 30 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, an unsubstituted alkylsilyl group having 3 to 20 carbon atoms, an unsubstituted arylsilyl group having 6 to 20 carbon atoms, an unsubstituted amino group having 0 to 20 carbon atoms, an acyl group, a carbonyl group, a carboxylic acid group, an ester group, a nitrile group, an isonitrile group, a thioalkyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms may be partially or fully replaced by deuterium. Other atoms such as carbon and nitrogen, may also be replaced by their other stable isotopes. The replacement by other stable isotopes in the compounds may be preferred due to its enhancements of device efficiency and stability.

In the compounds mentioned in this disclosure, multiple substitutions refer to a range that includes a double substitution, up to the maximum available substitutions. When a substituent in a compound mentioned in this disclosure represents a multi-substitution (including di-, tri-, tetra-, etc.), it means that the substituent may exist at multiple available substitution positions on its linking structure, the substituents present at multiple available substitution positions may be the same or different structures.

According to an embodiment of the present disclosure, a compound having the structure of Formula 1 is disclosed:

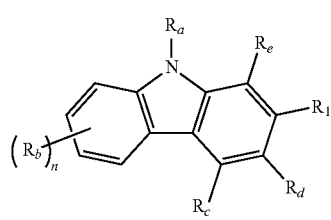

Formula 1 wherein $R_a$ is selected from biphenyl, terphenyl, naphthyl, phenanthryl, triphenylene, fluorenyl, dibenzofuranyl;

n is the number of $R_b$, n is selected from 1, 2, 3 or 4; when n≥2, the $R_b$ is selected from the same or different structures;

each of $R_b$ is independently selected from the group consisting of: hydrogen, deuterium, phenyl, biphenyl and terphenyl;

$R_c$, $R_d$ and $R_e$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

and $R_1$ has the structure of Formula 2:

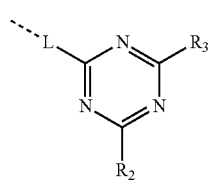

Formula 2

L is a single bond, or a substituted or unsubstituted arylene having 6 to 60 carbon atoms;

$R_2$ and $R_3$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 carbon atoms, a substituted or unsubstituted alkylsilyl group having 3 to 20 carbon atoms, a substituted or unsubstituted arylsilyl group having 6 to 20 carbon atoms, and combinations thereof;

when $R_2$ and $R_3$ are selected from a substituted group in the group, the substitution in the substituted group is selected from deuterium, halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted arylalkyl group having 7 to 30 carbon atoms, an unsubstituted alkoxy group having 1 to 20 carbon atoms, an unsubstituted aryl group having 6 to 30 carbon atoms, and combinations thereof.

According to an embodiment of the present disclosure, wherein $R_2$ and $R_3$ are unsubstituted aryl groups having 6 to 30 carbon atoms.

According to a preferred embodiment of the present disclosure, wherein $R_2$ and $R_3$ are each independently selected from phenyl, biphenyl or terphenyl.

According to another preferred embodiment of the present disclosure, wherein at least one of $R_2$ and $R_3$ is biphenyl or terphenyl.

According to an embodiment of the present disclosure, wherein L is selected from a substituted or unsubstituted arylene having 6 to 30 carbon atoms; further, L is selected from a substituted or unsubstituted arylene having 6 to 20 carbon atoms.

According to an embodiment of the present disclosure, wherein L is a single bond.

According to an embodiment of the present disclosure, wherein $R_b$ is hydrogen.

According to an embodiment of the present disclosure, wherein $R_c$, $R_d$ and $R_e$ is hydrogen.

According to an embodiment of the present disclosure, wherein the compound is selected from the group consisting of:

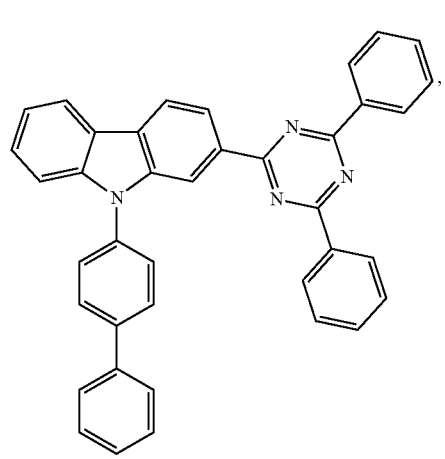

Compound 1

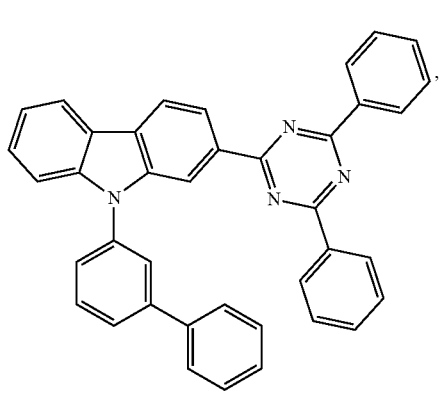

Compound 2

-continued
Compound 3
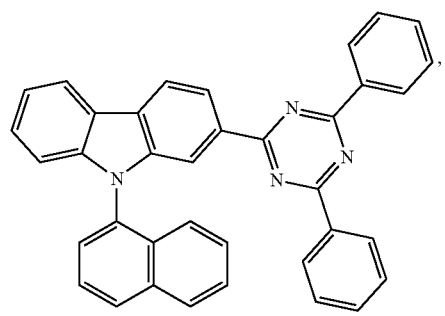
Compound 4
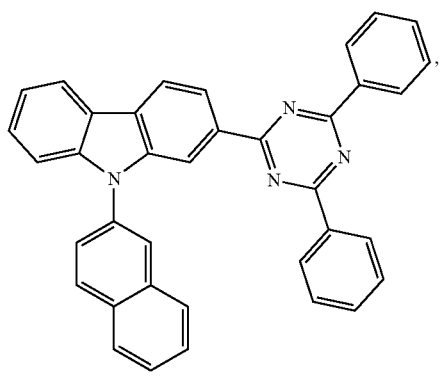
Compound 5
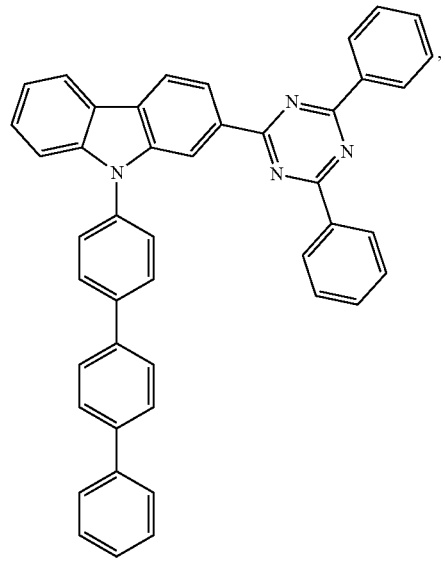
Compound 6
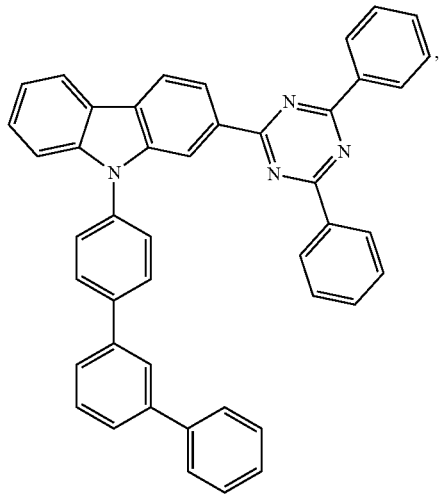
Compound 7
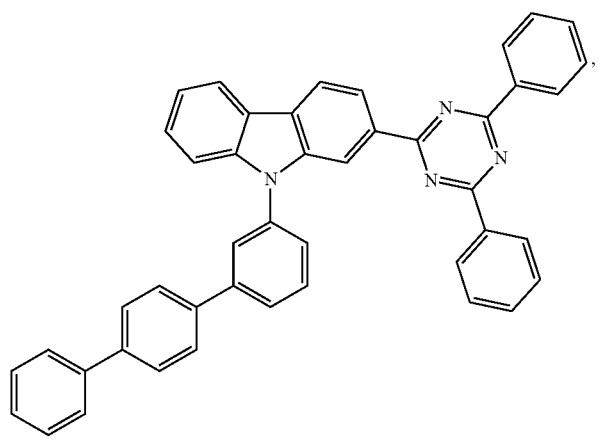
Compound 8
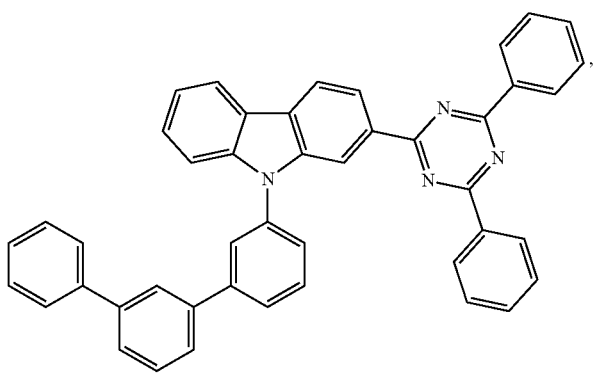

-continued
Compound 9
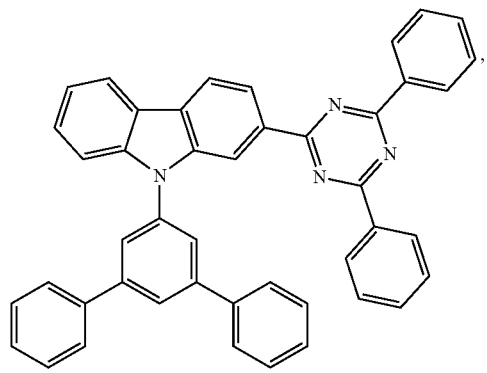
Compound 10
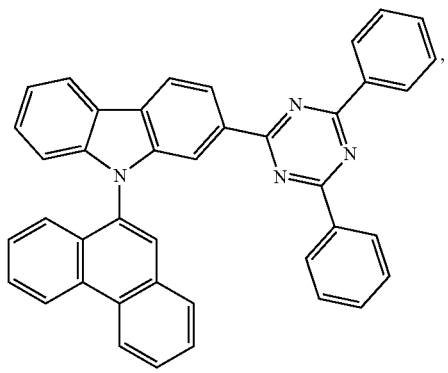
Compound 11
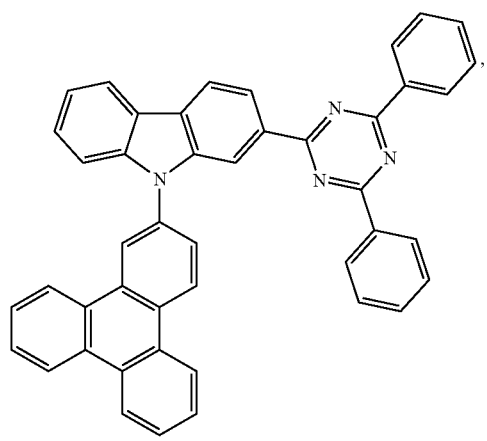
Compound 12
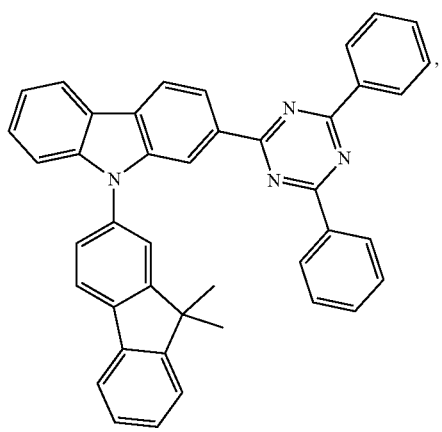
Compound 13
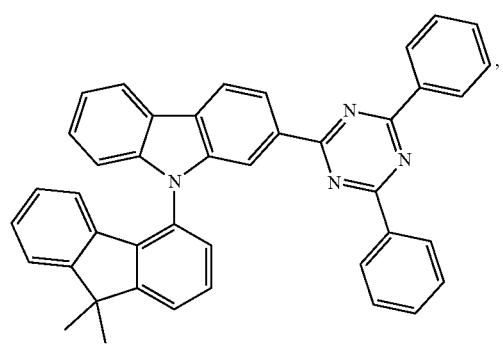
Compound 14
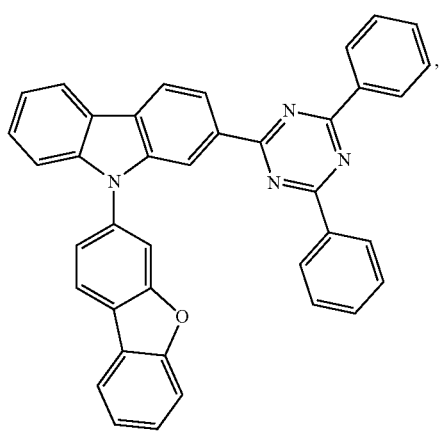

-continued
Compound 15
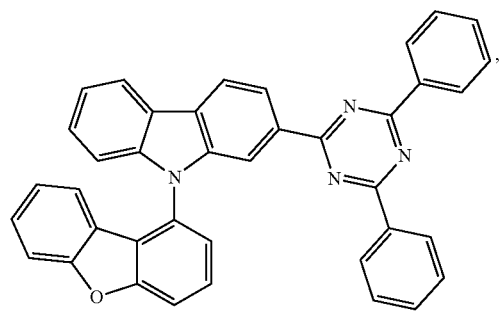
Compound 16
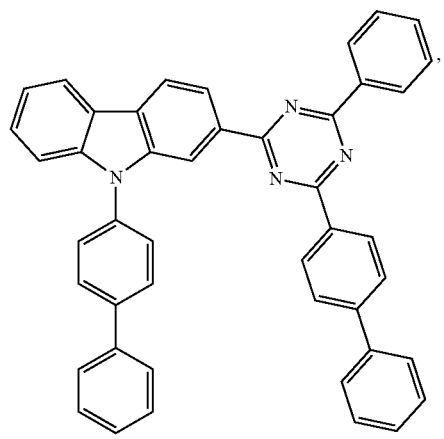
Compound 17
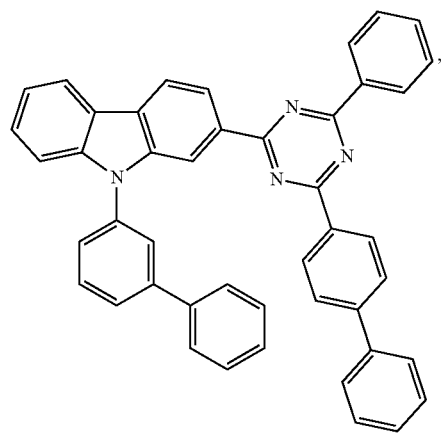
Compound 18
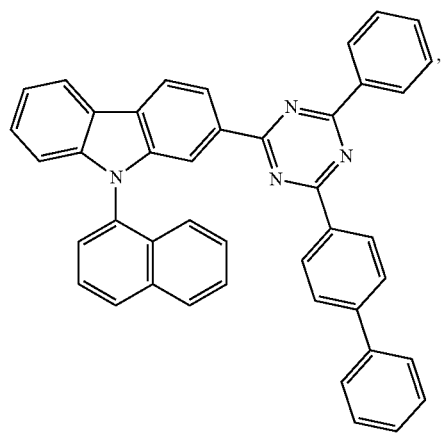
Compound 19
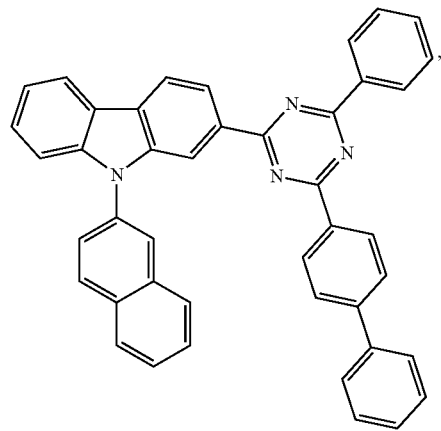
Compound 20
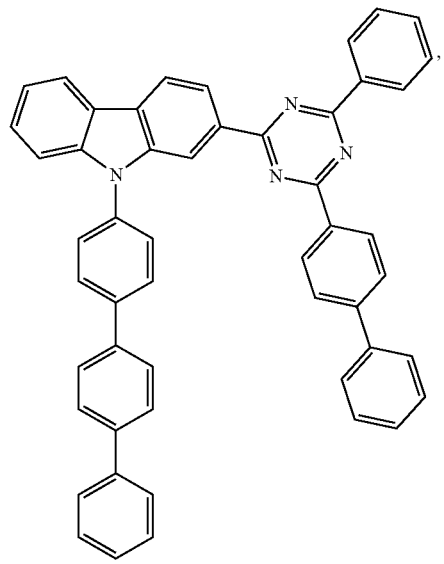

-continued
Compound 21
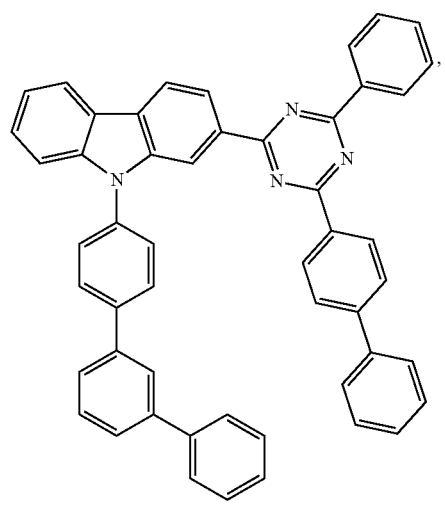
Compound 22
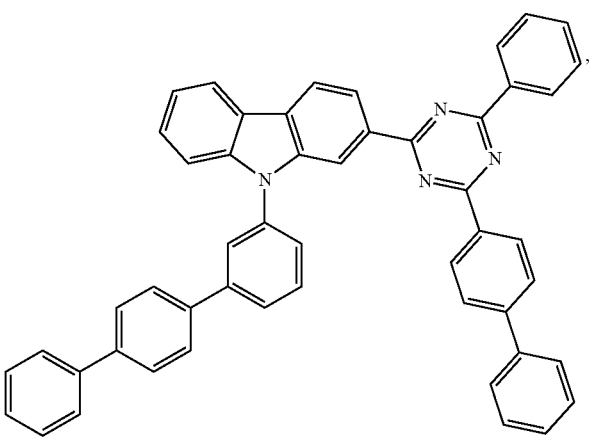
Compound 23
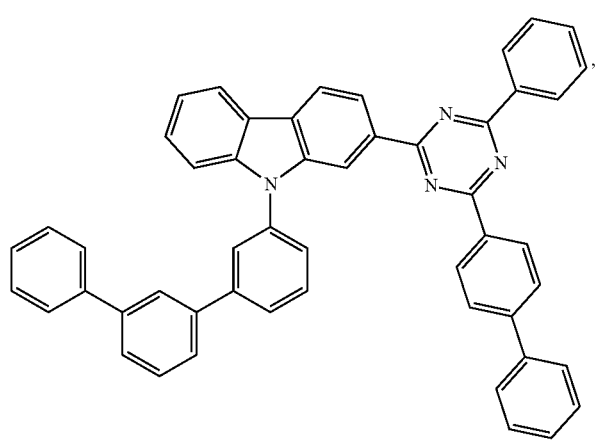
Compound 24
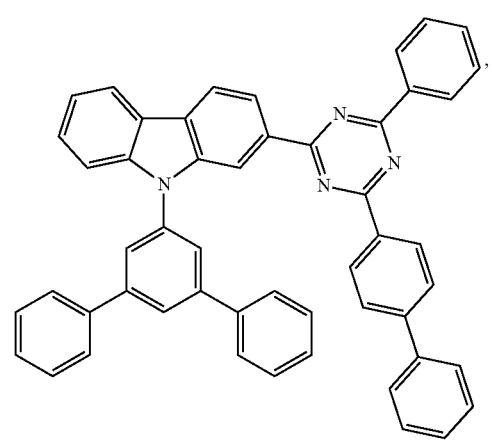
Compound 25
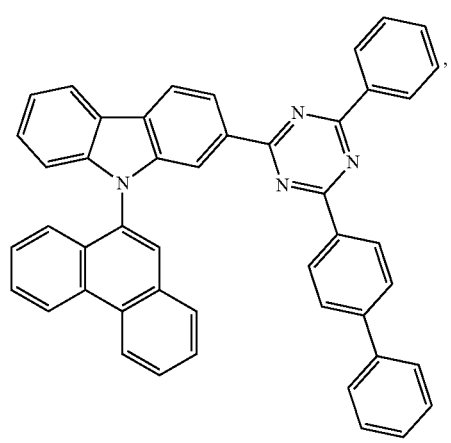
Compound 26
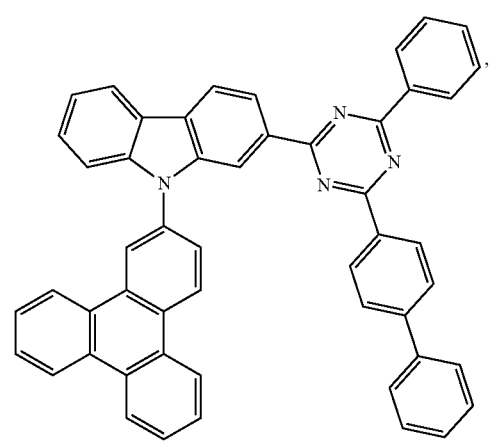

-continued
Compound 27
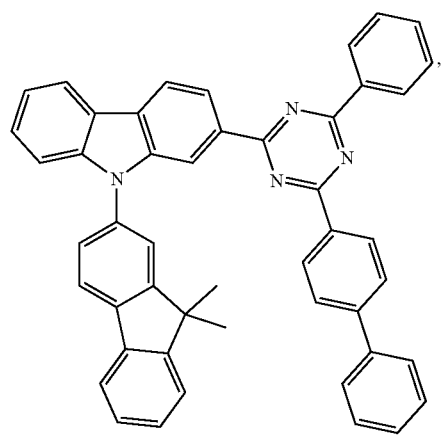
Compound 28
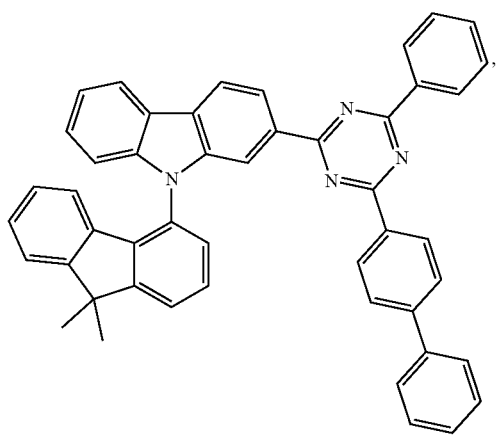
Compound 29
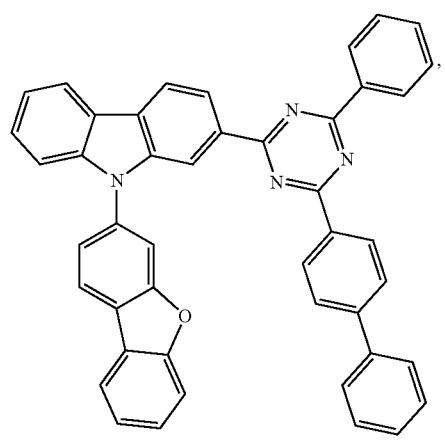
Compound 30
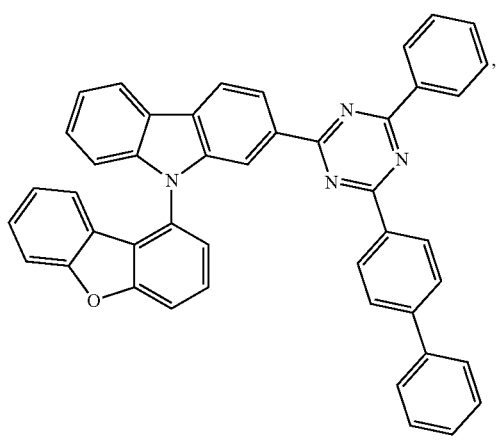
Compound 31
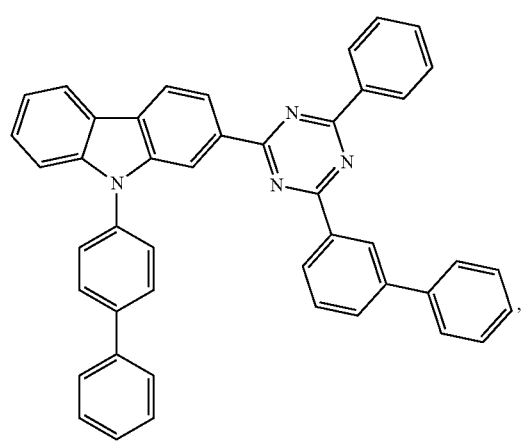
Compound 32
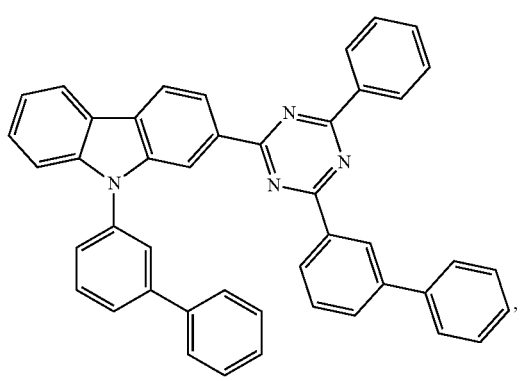

Compound 33
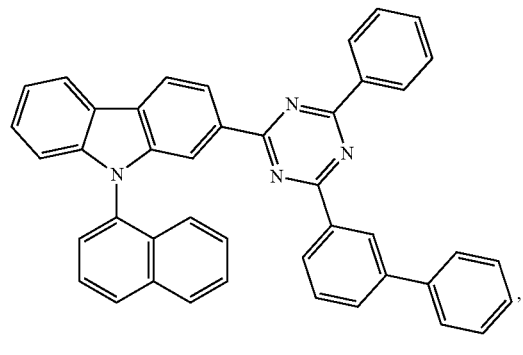
Compound 34
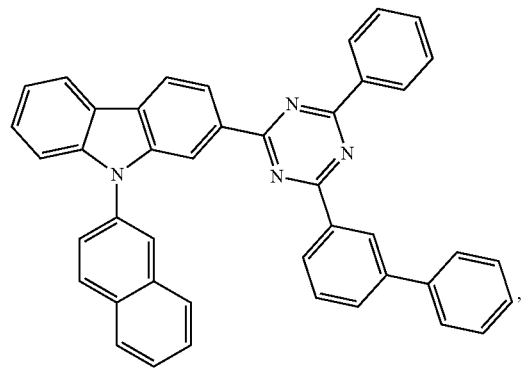
Compound 35
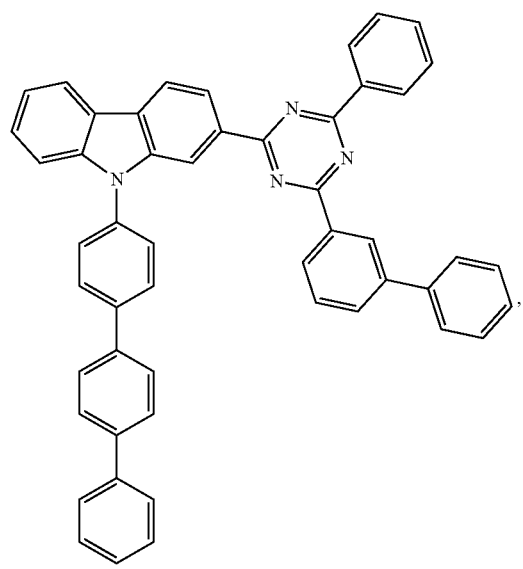
Compound 36
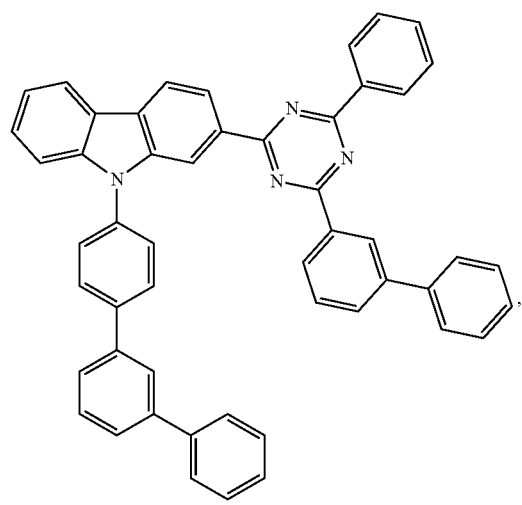
Compound 37
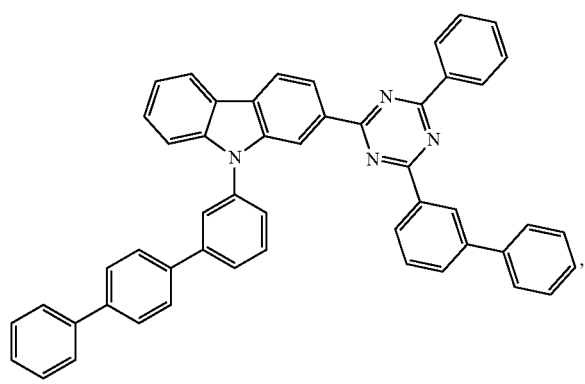
Compound 38
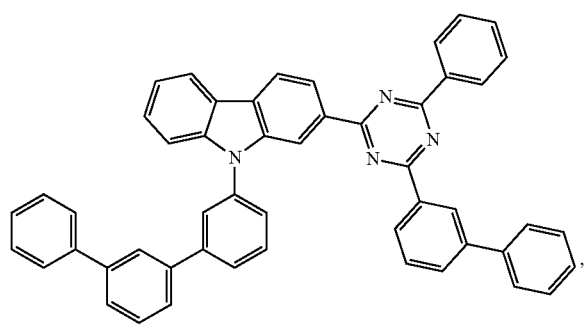

Compound 39
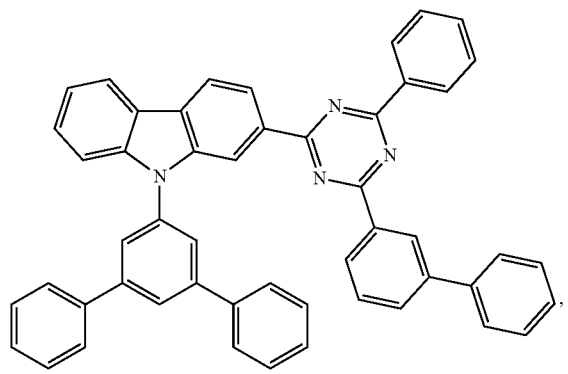
Compound 40
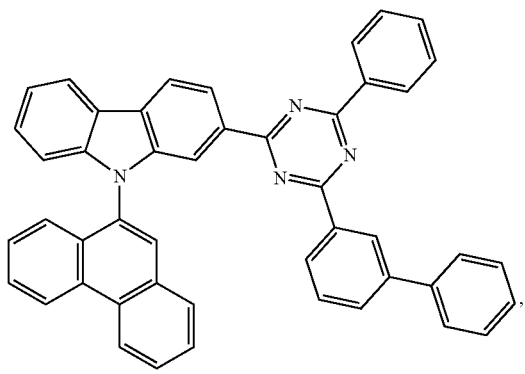
Compound 41
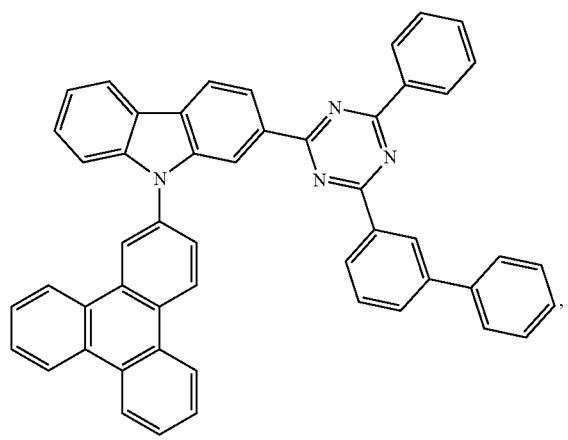
Compound 42
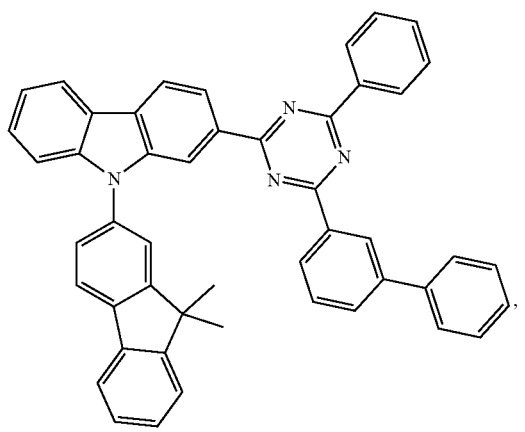
Compound 43
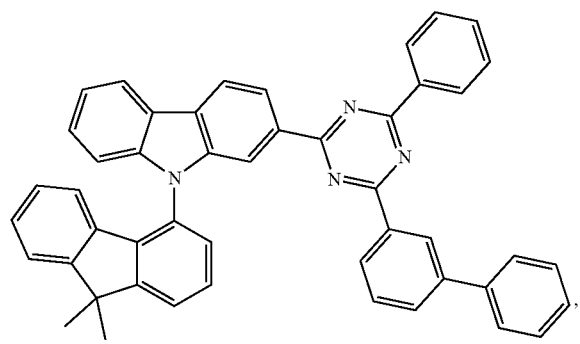
Compound 44
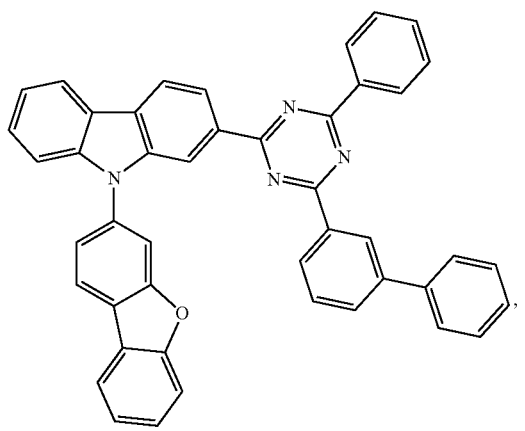

Compound 45
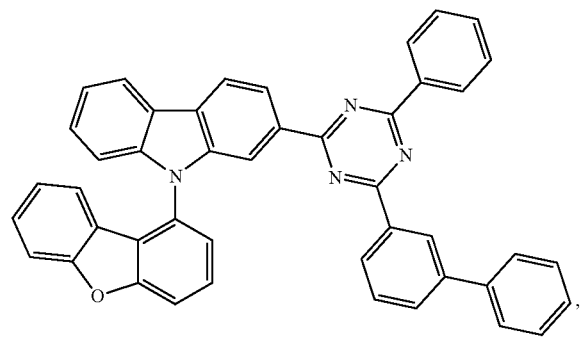
Compound 46
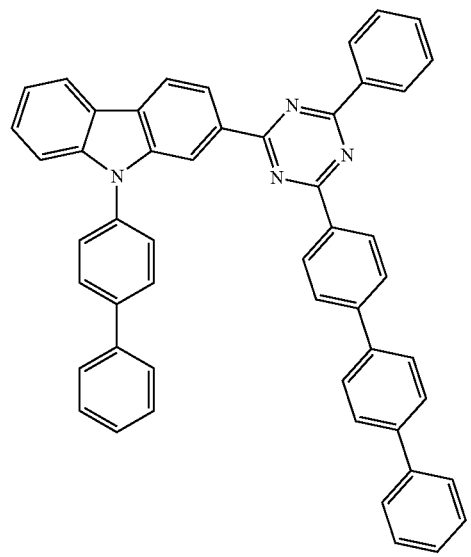
Compound 47
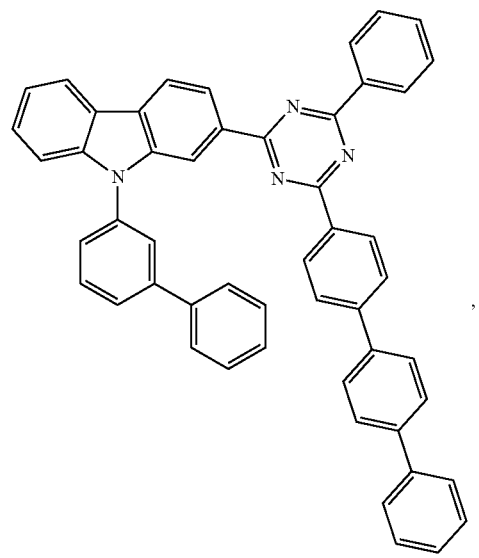
Compound 48
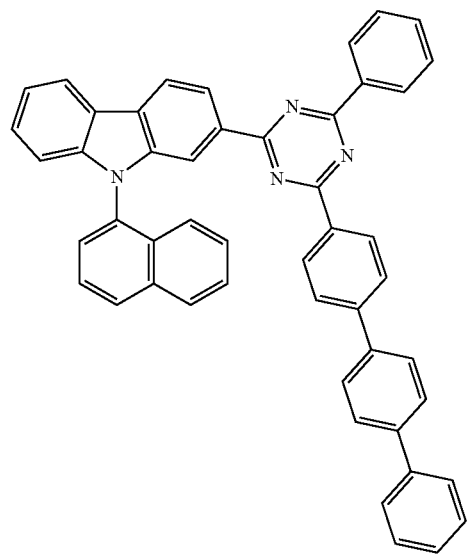

Compound 49
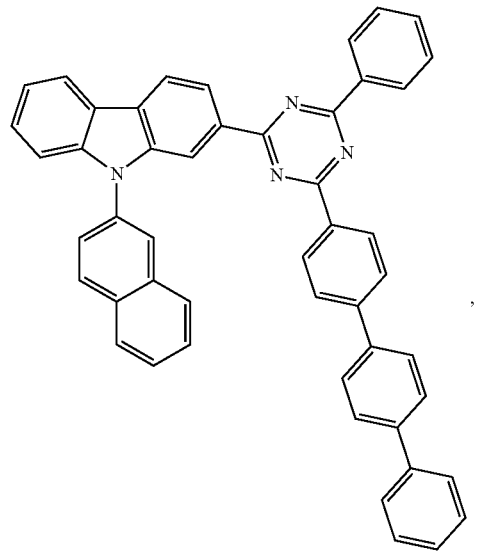
Compound 50
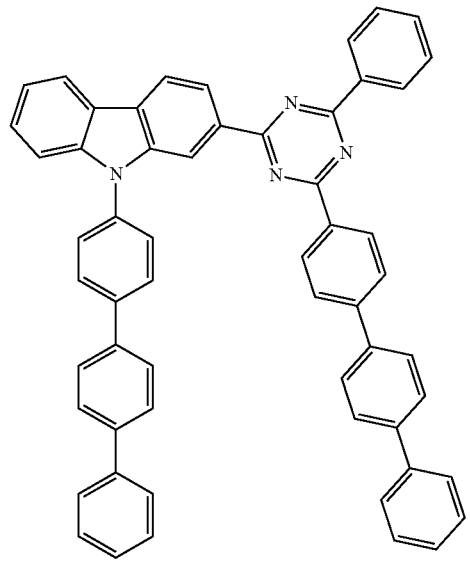
Compound 51
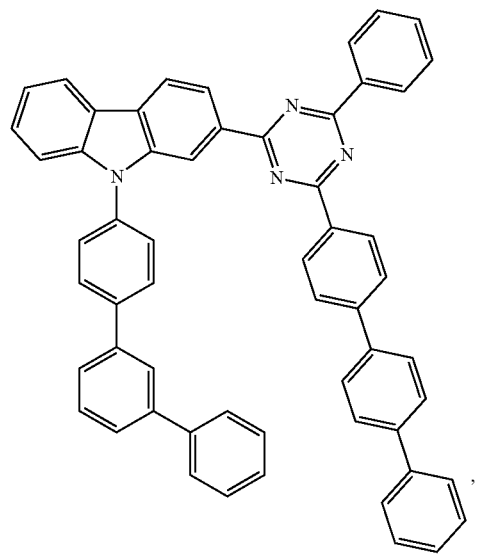
Compuond 52
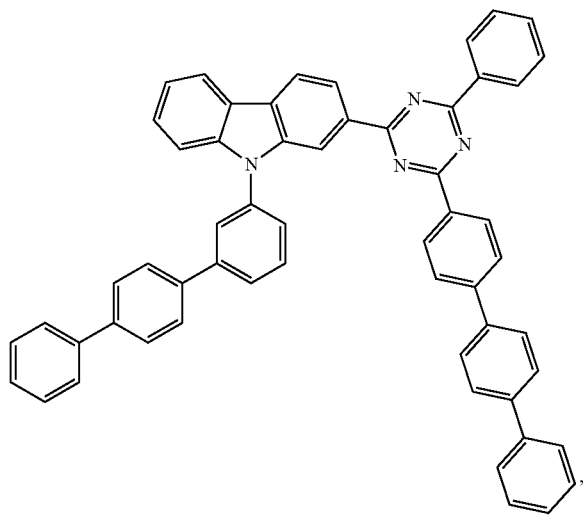

Compound 53
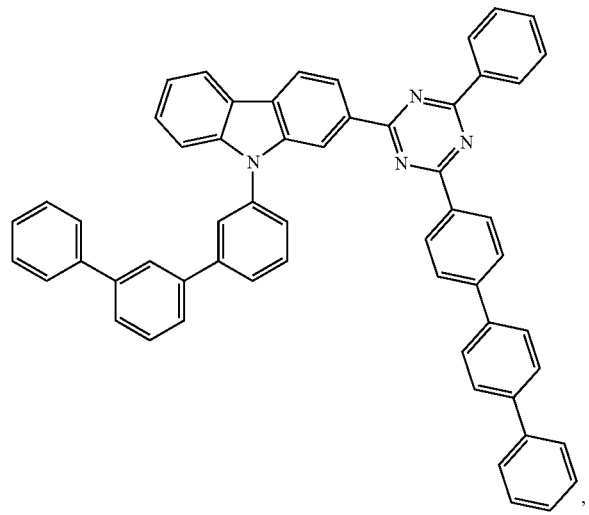
Compound 54
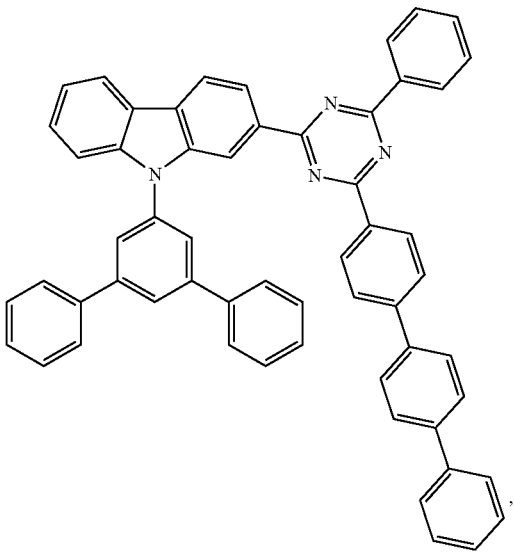
Compound 55
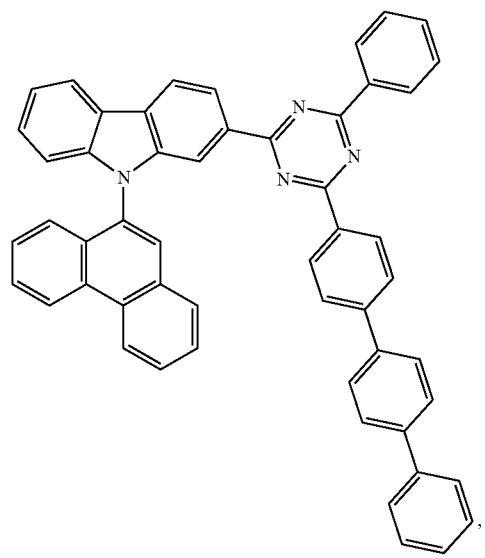
Compound 56
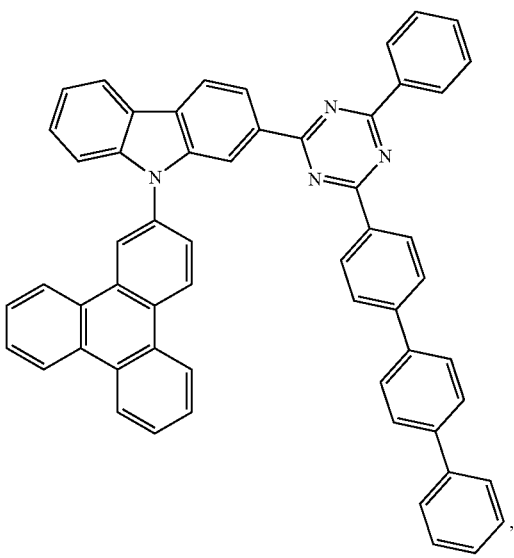

-continued
Compound 57
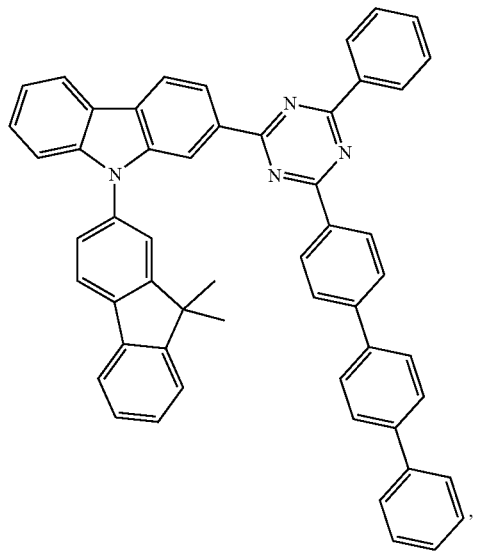
Compound 58
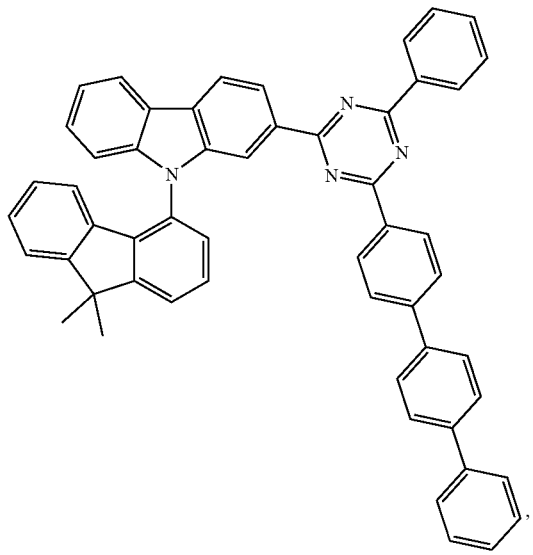
Compound 59
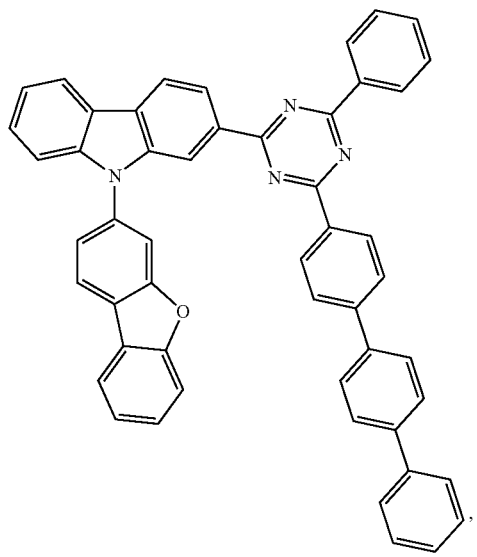
Compound 60
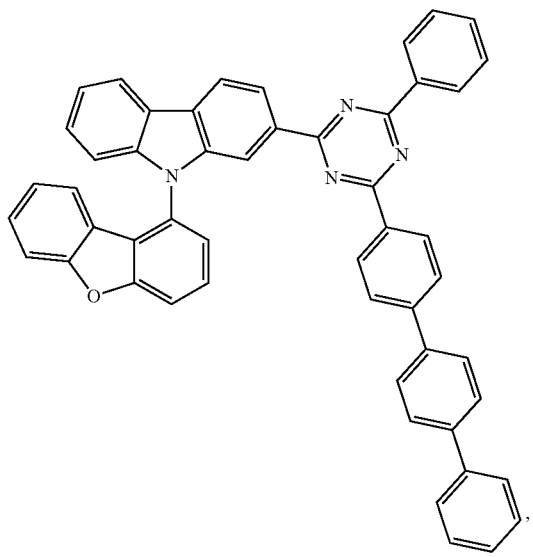
Compound 61
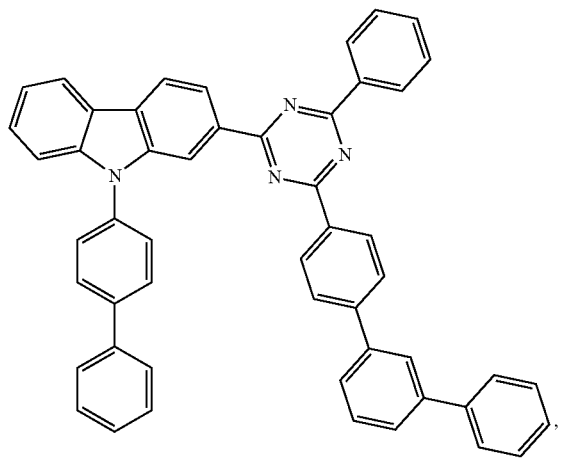
Compound 62
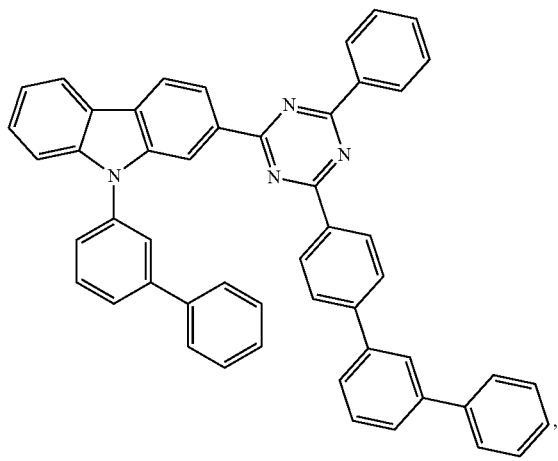

-continued
Compound 63
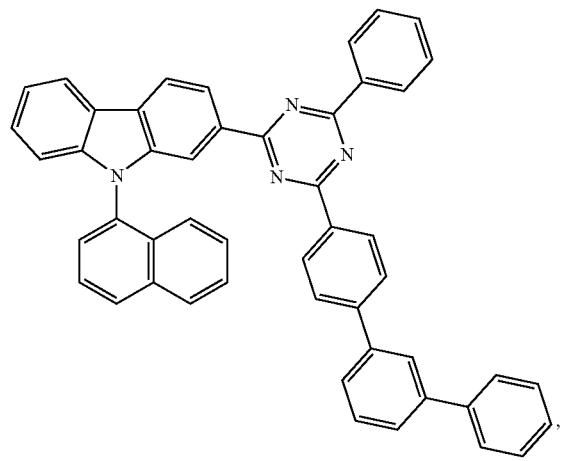
Compound 64
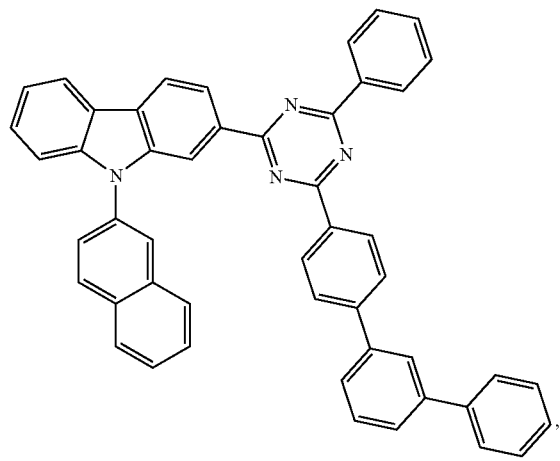
Compound 65
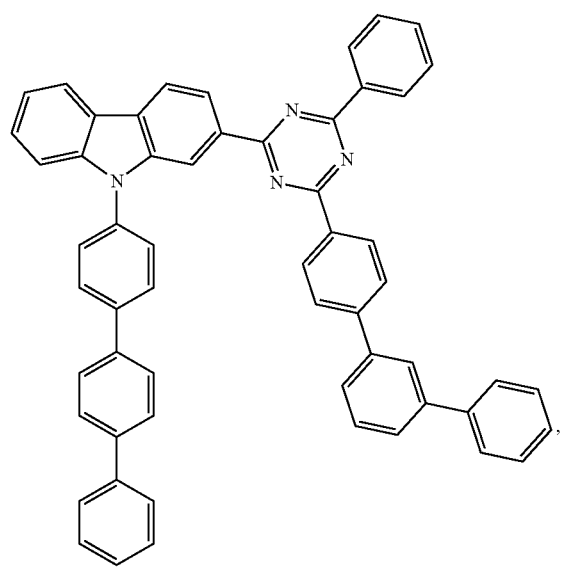
Compound 66
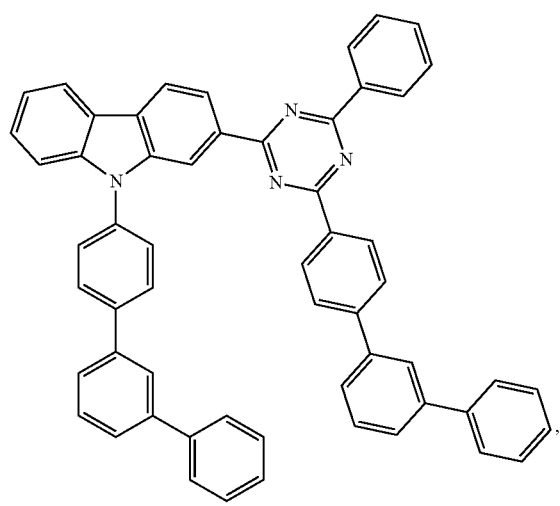
Compound 67
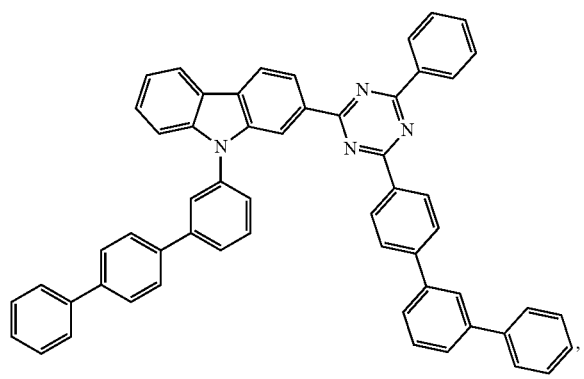
Compound 68
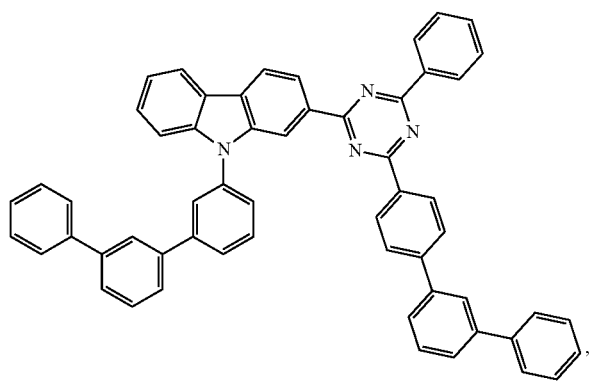

-continued
Compound 69
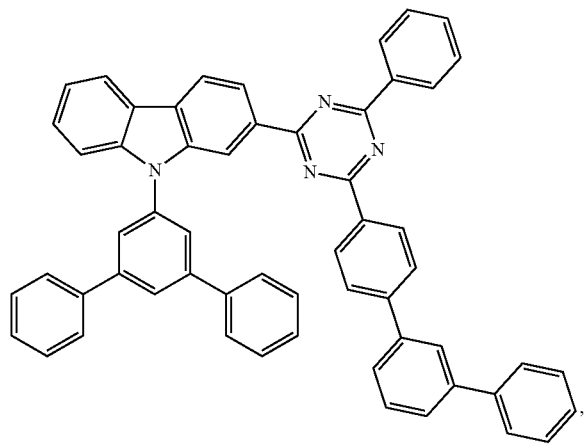
Compound 70
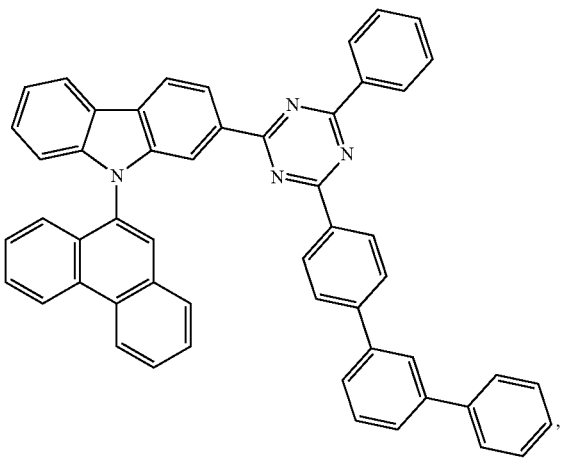
Compound 71
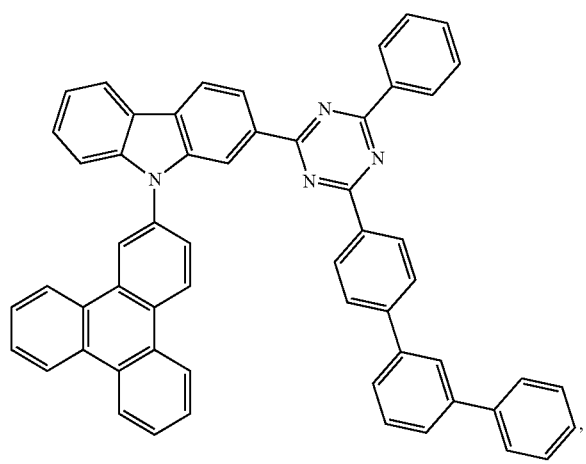
Compound 72
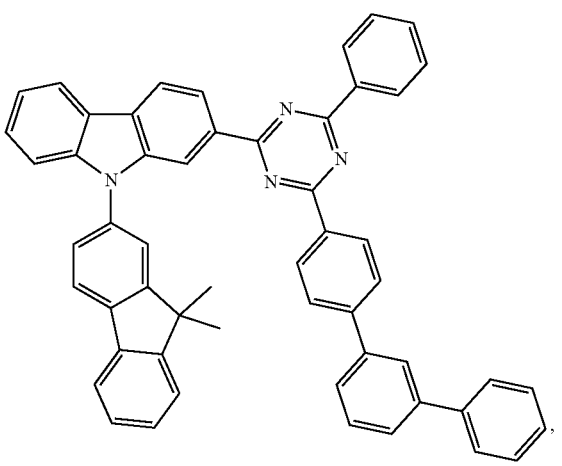
Compound 73
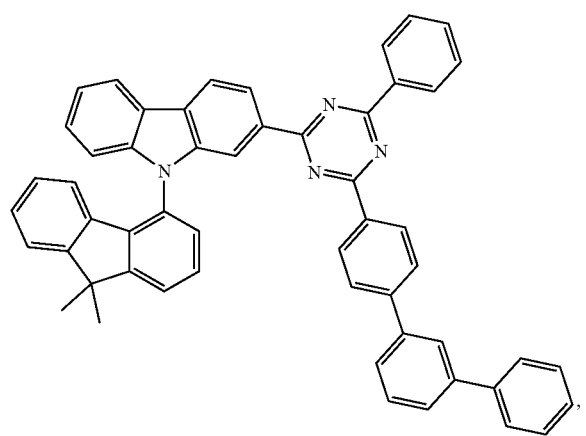
Compound 74
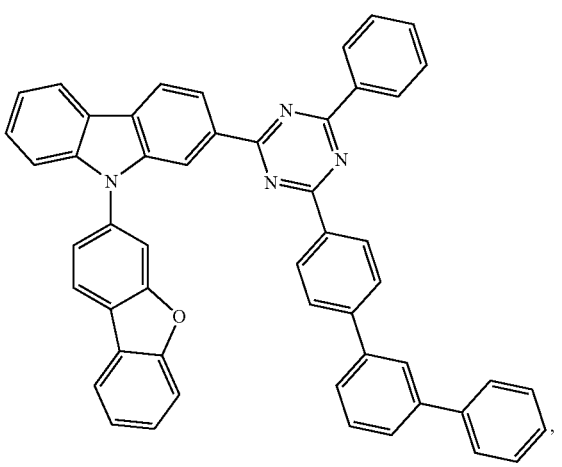

Compound 75
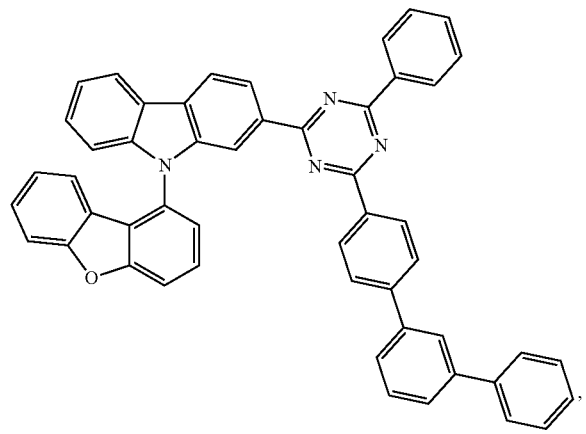
Compound 76
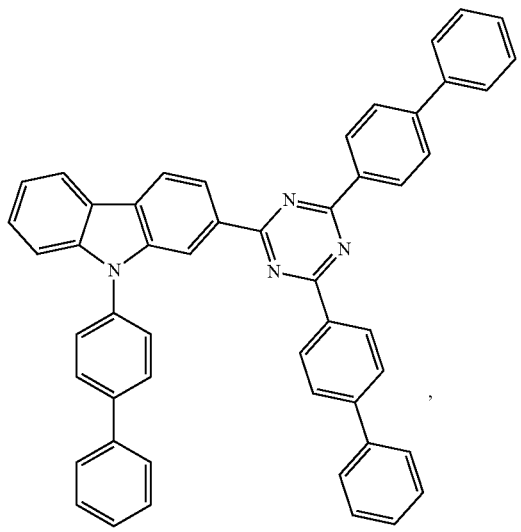
Compound 77
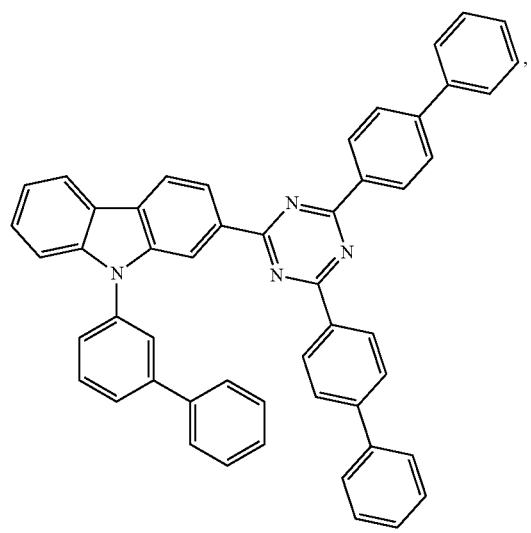
Compound 78
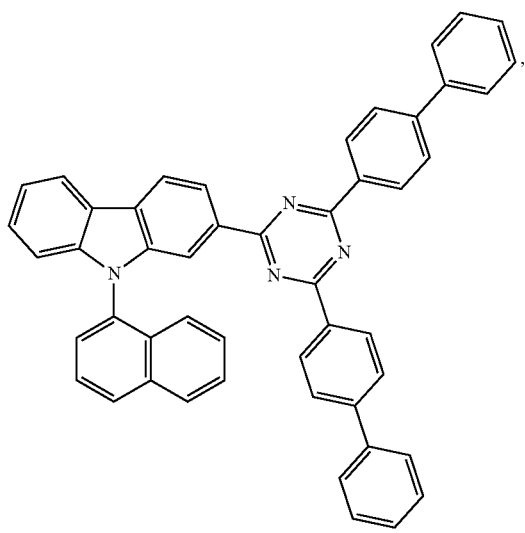

-continued
Compound 79
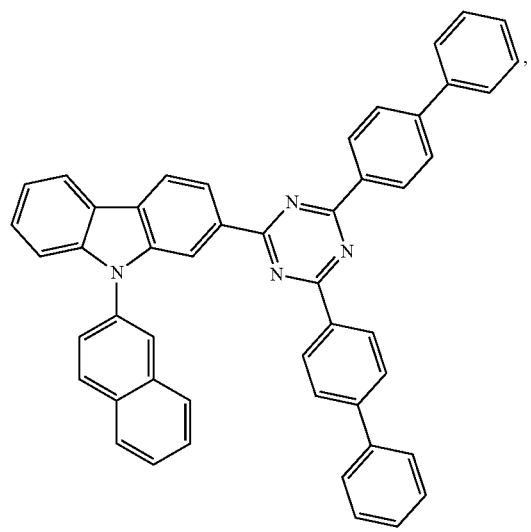
Compound 80
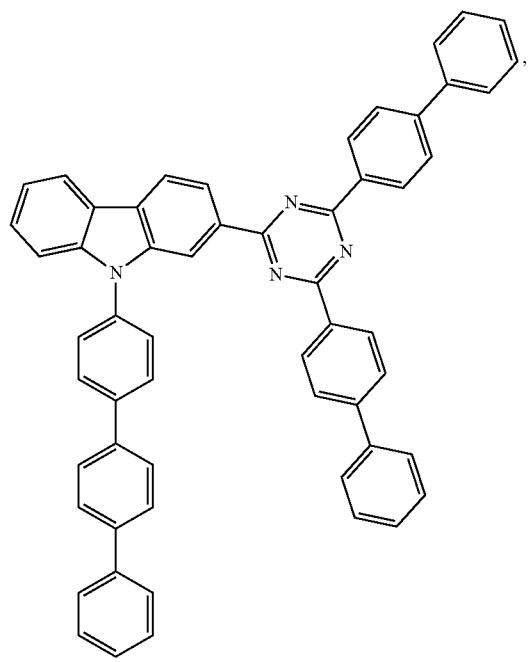
Compound 81
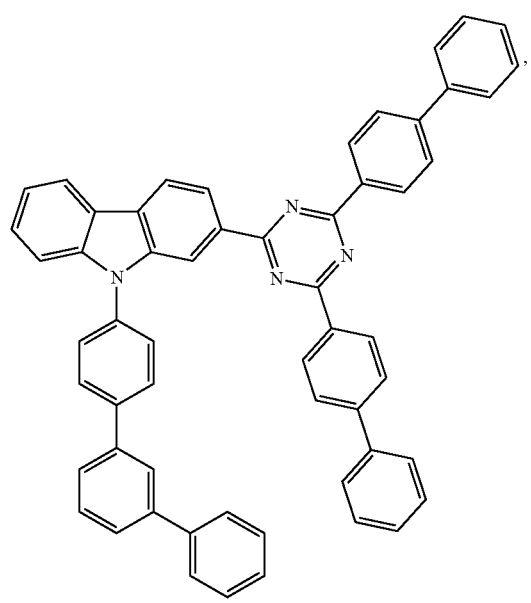
Compound 82
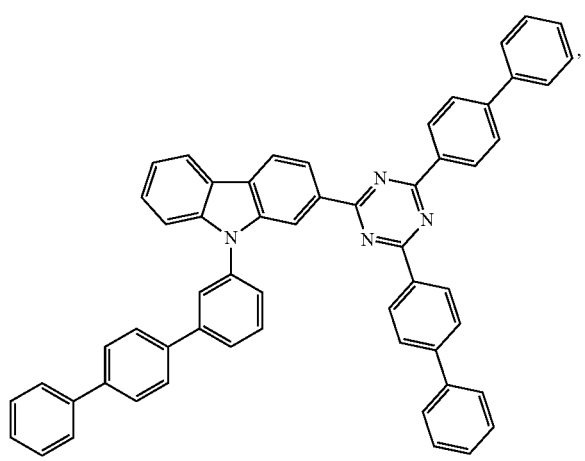

-continued
Compound 83
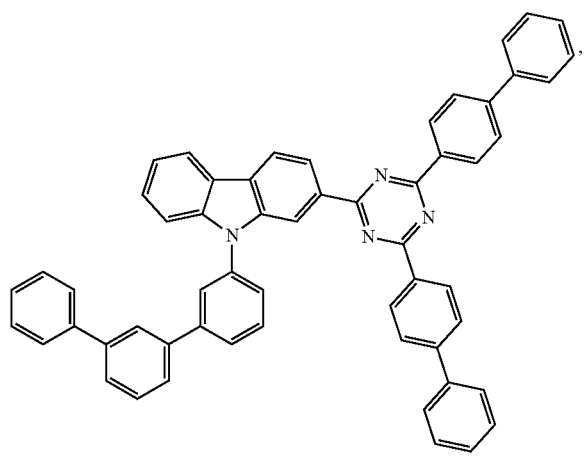
Compound 84
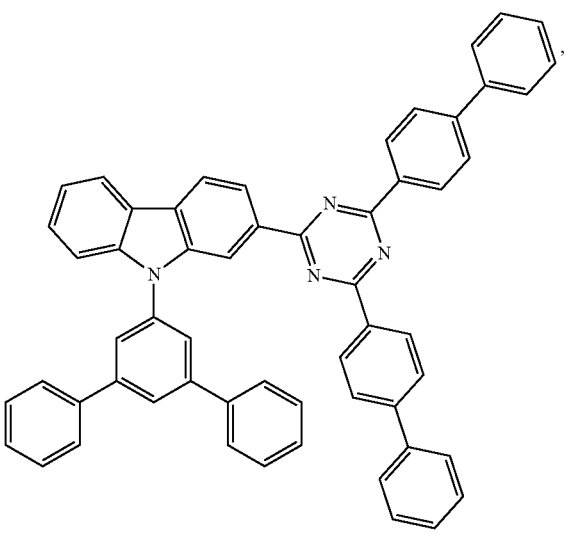
Compound 85
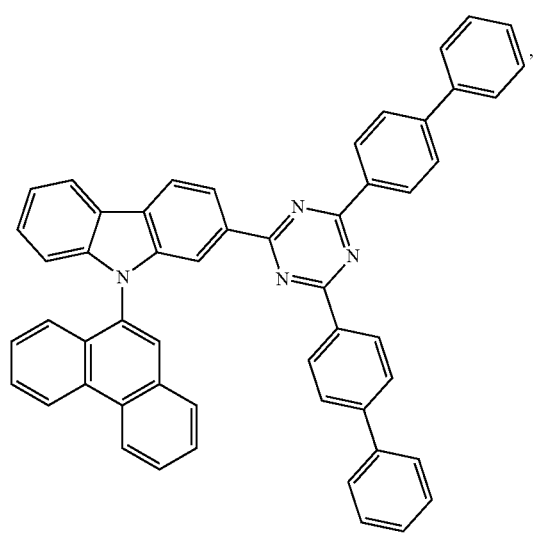
Compound 86
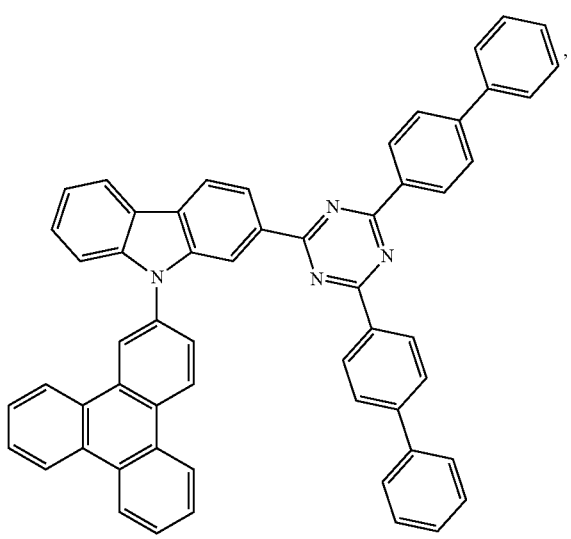
Compound 87
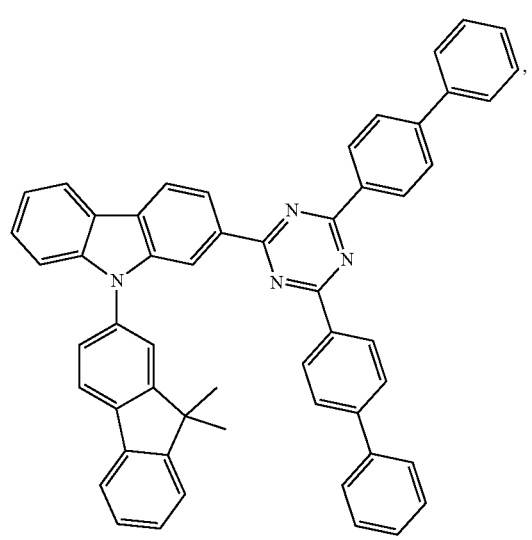
Compound 88
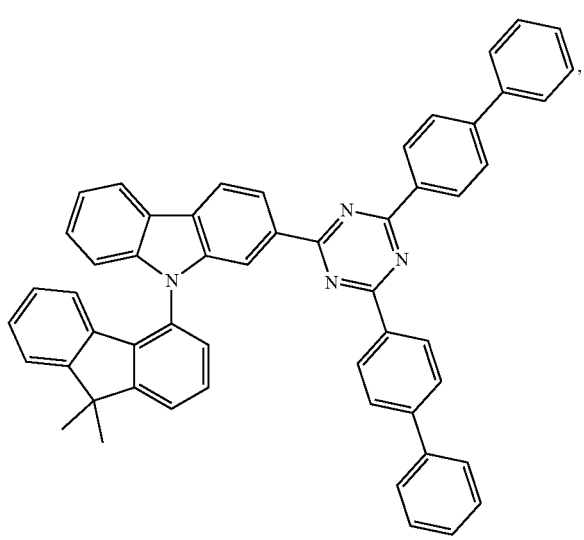

Compound 89
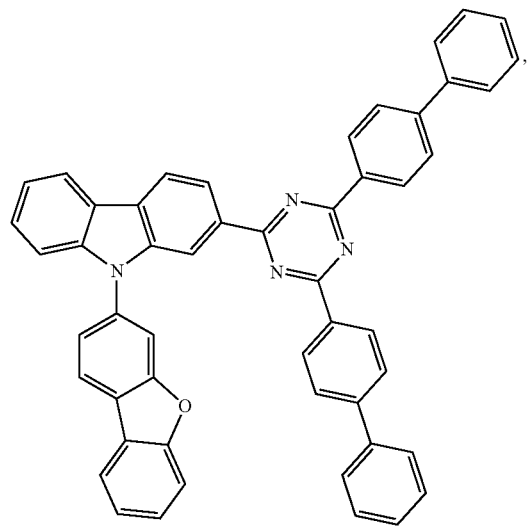
Compound 90
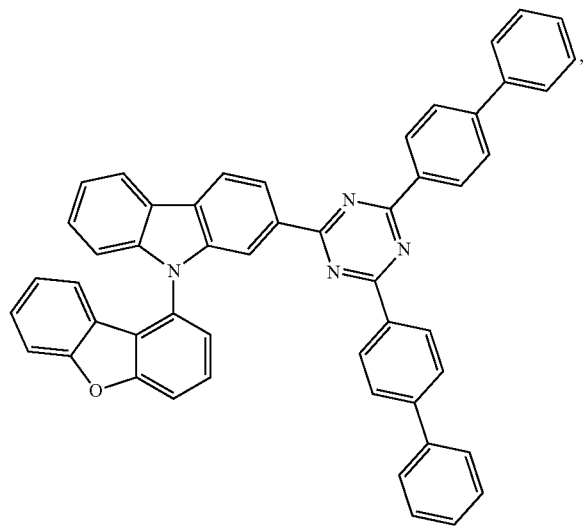
Compound 91
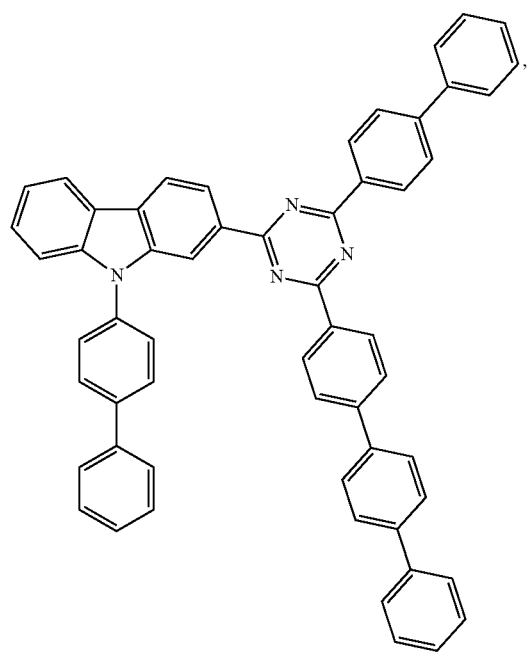
Compound 92
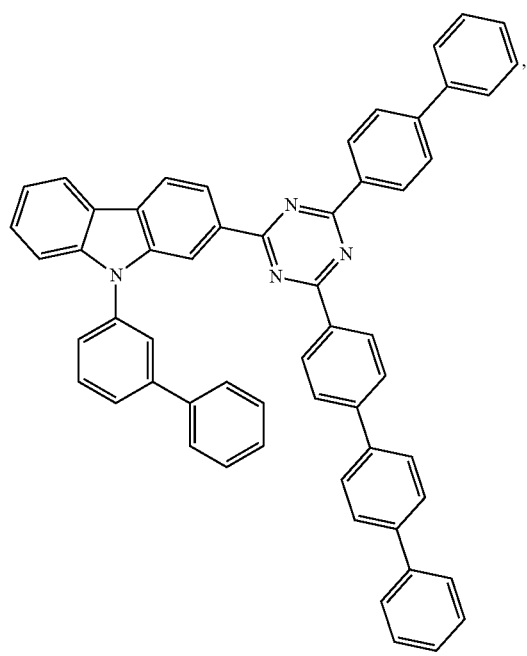

Compound 93
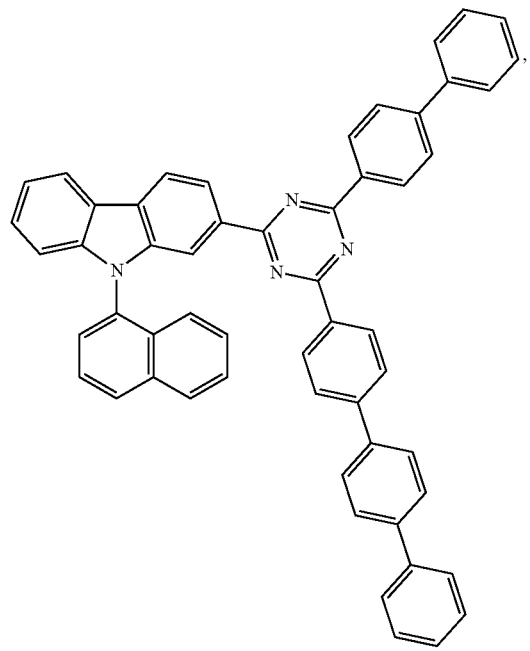
Compound 94
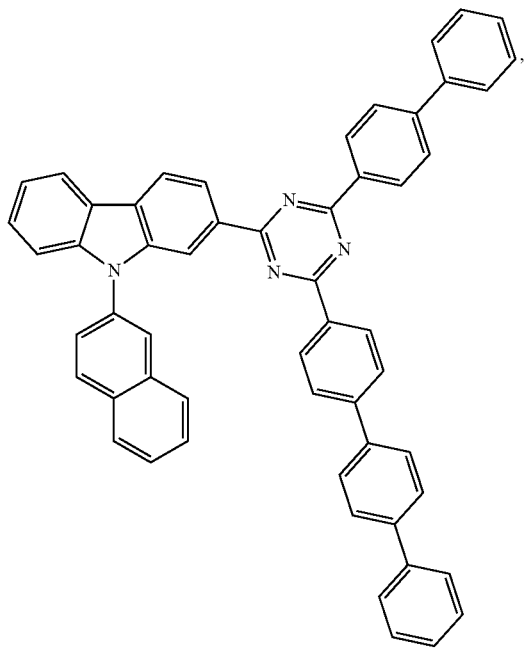
Compound 95
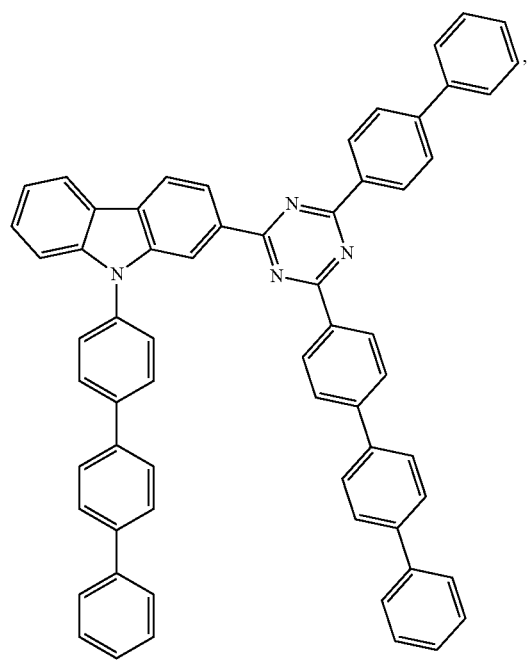
Compound 96
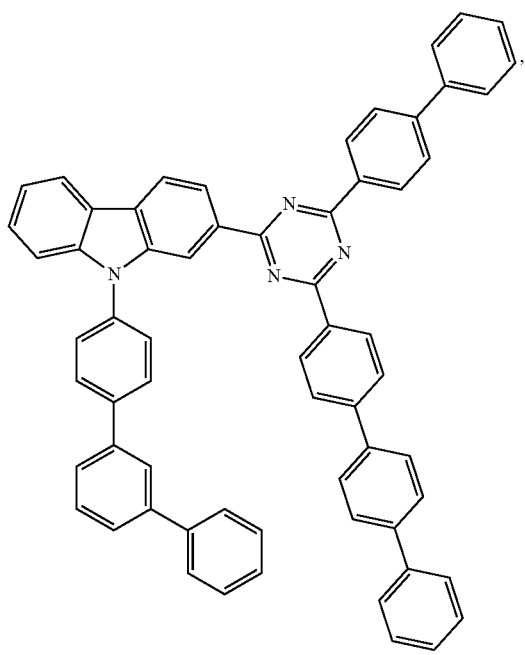

Compound 97
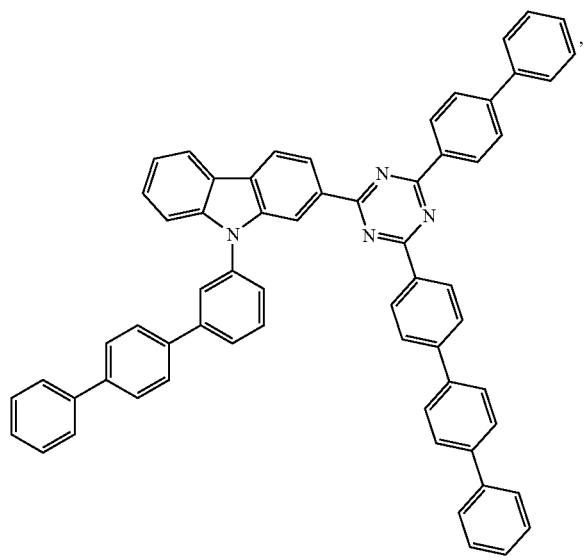
Compound 98
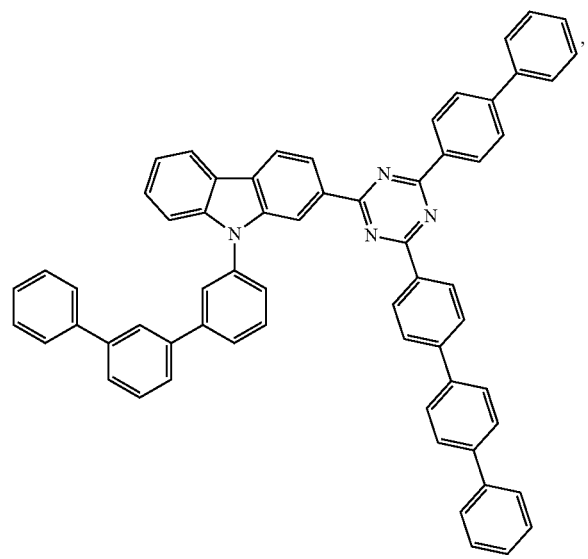
Compound 99
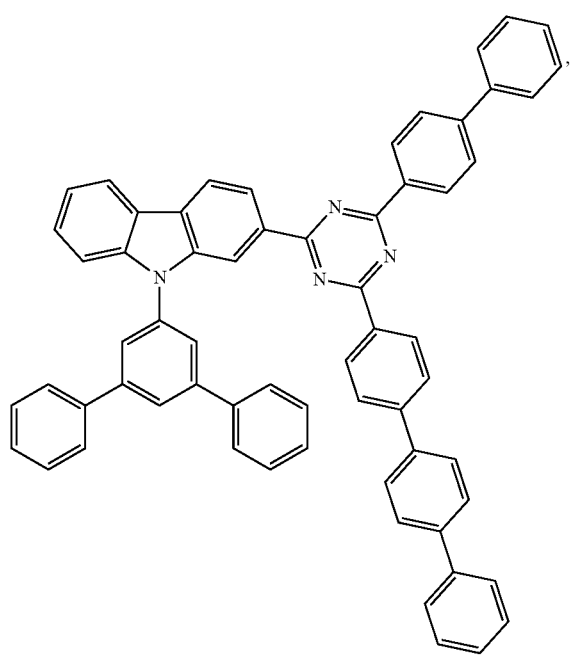
Compound 100
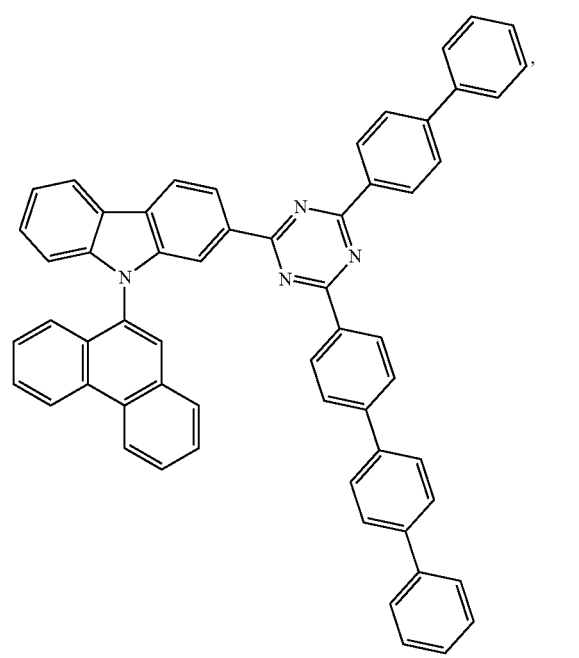

Compound 101
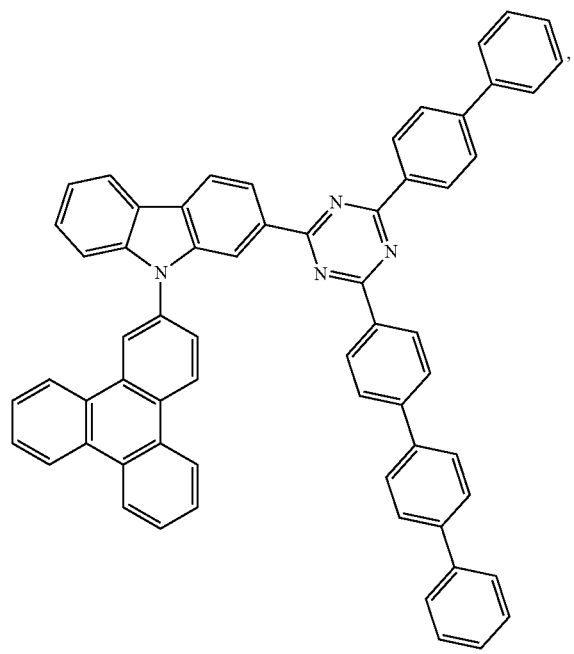
Compound 102
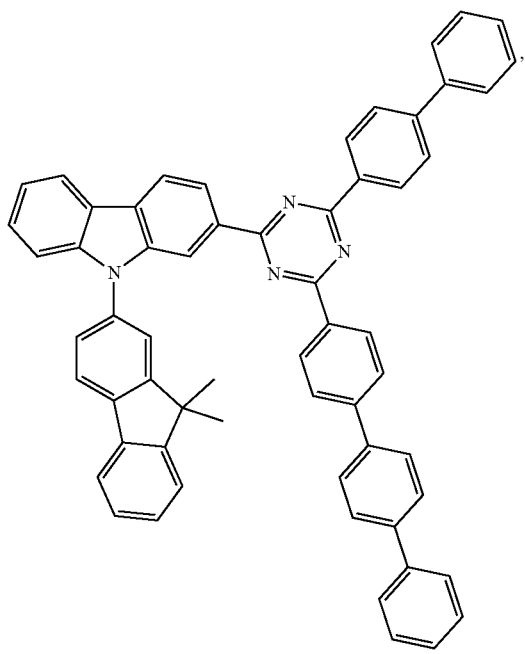
Compound 103
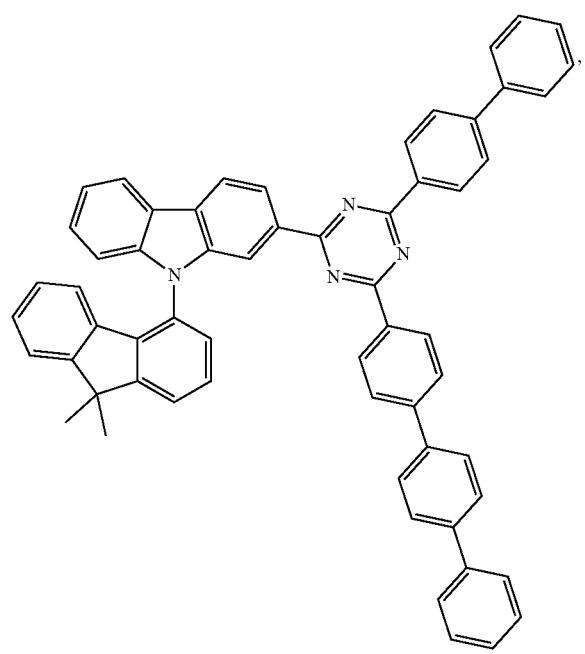
Compound 104
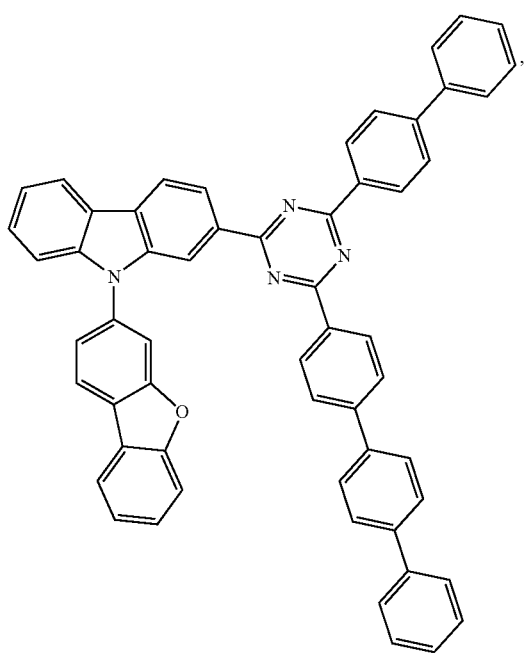

Compound 105
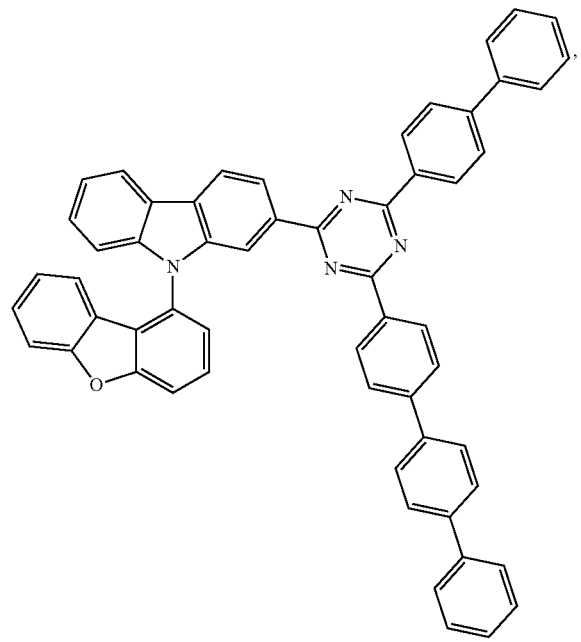
Compound 106
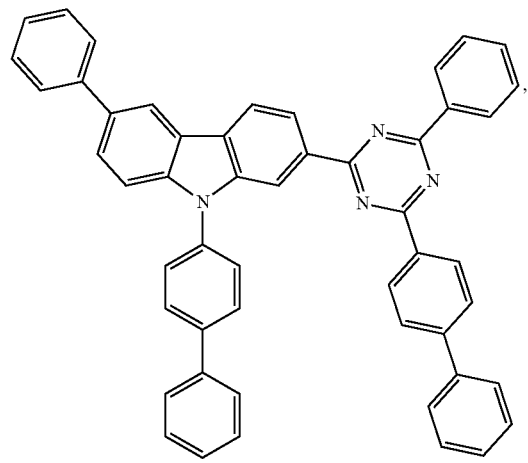
Compound 107
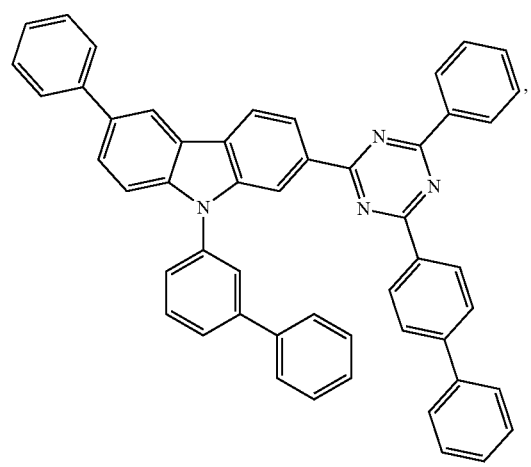
Compound 108
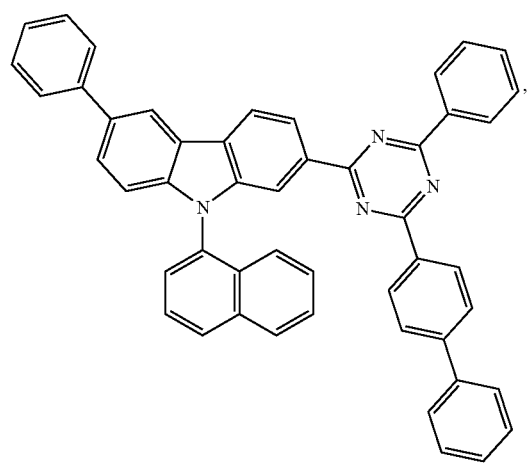

-continued
Compound 109
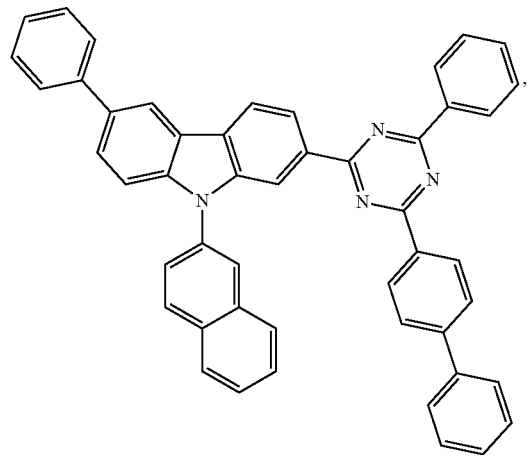
Compound 110
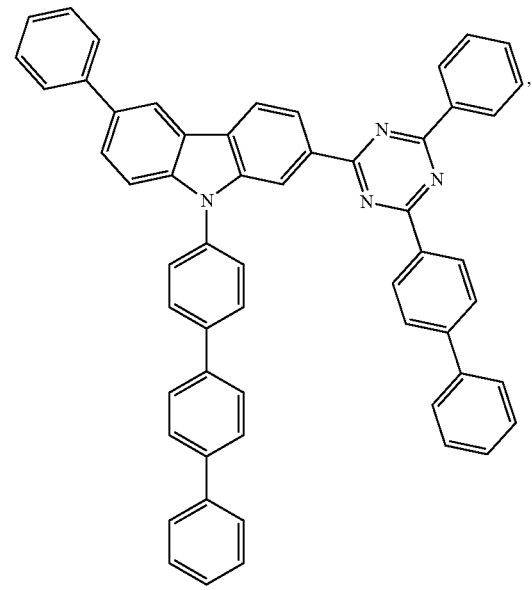
Compound 111
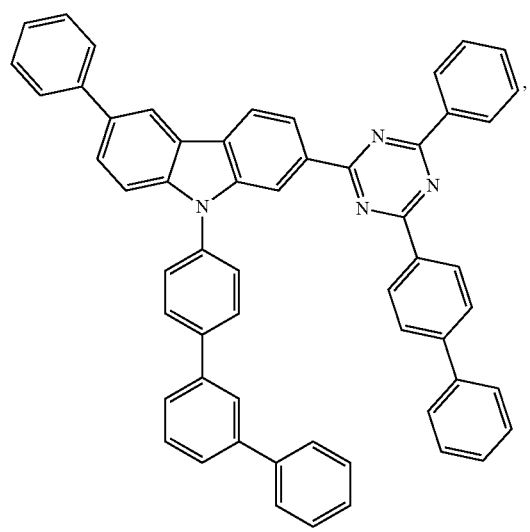
Compound 112
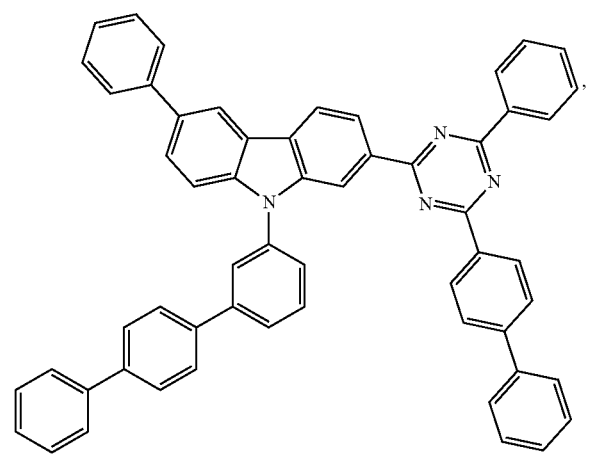
Compound 113
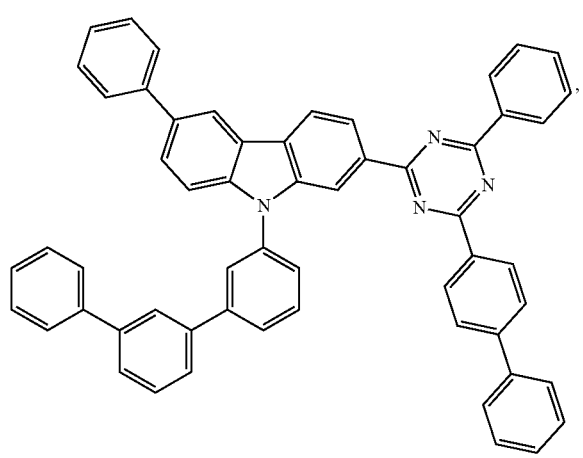
Compound 114
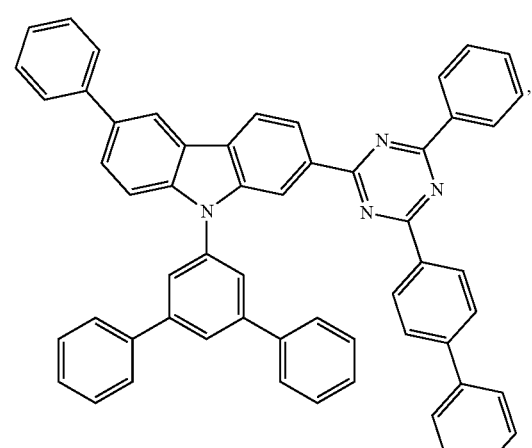

-continued
Compound 115
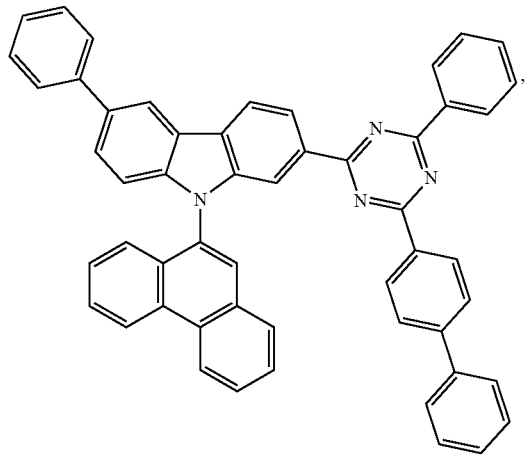
Compound 116
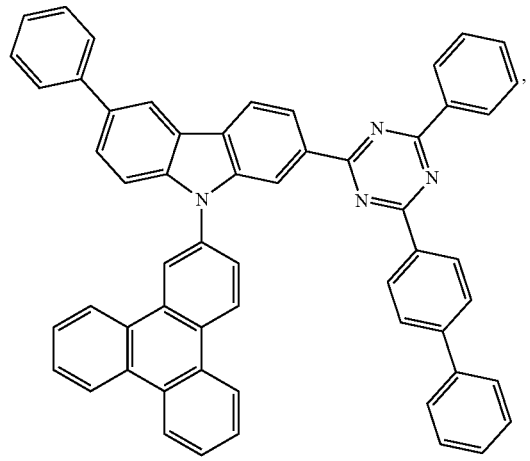
Compound 117
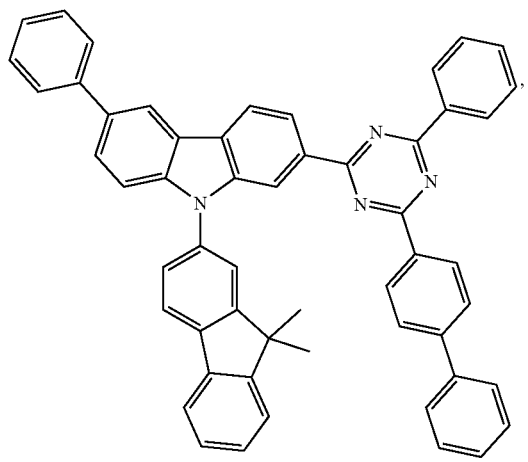
Compound 118
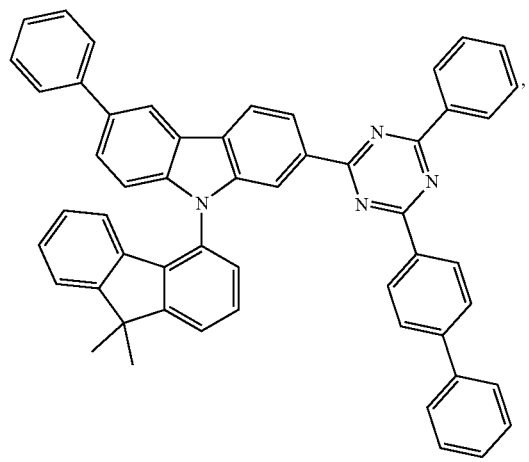
Compound 119
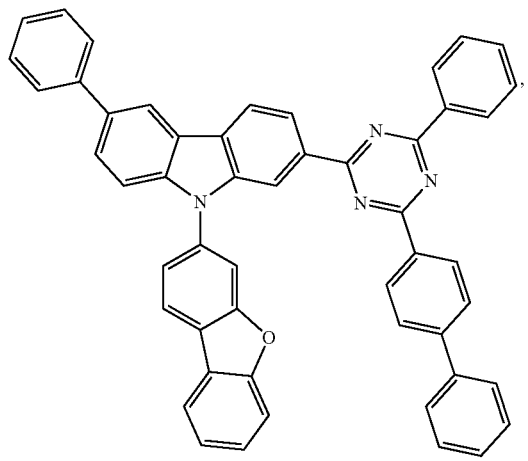
Compound 120
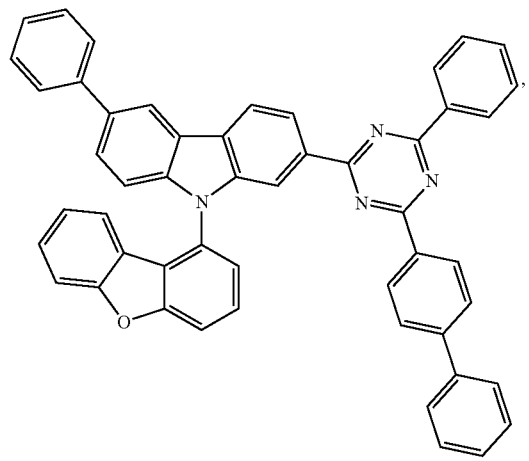

-continued
Compound 121
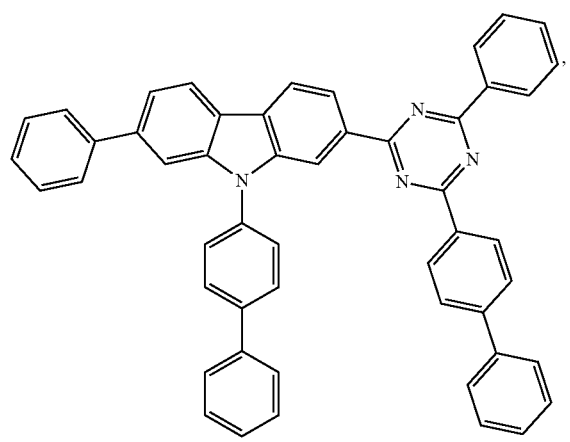
Compound 122
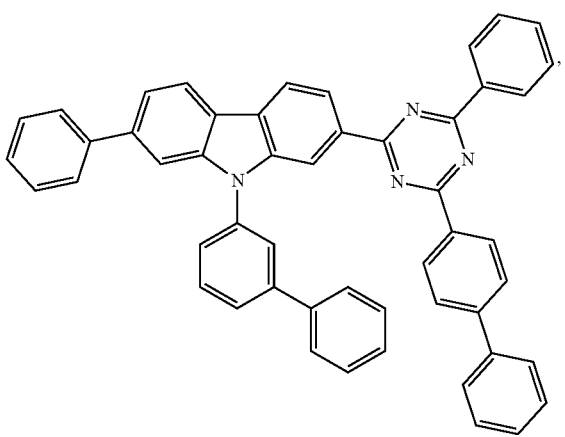
Compound 123
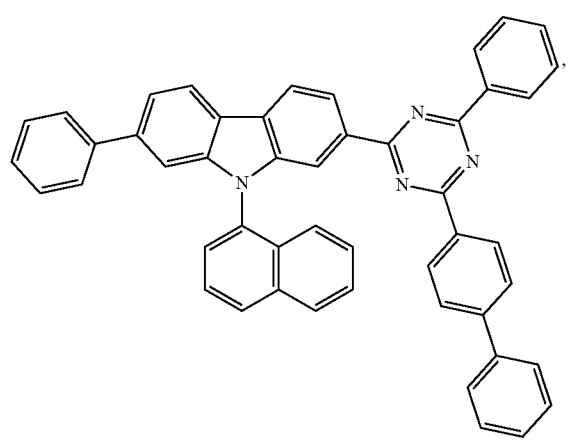
Compound 124
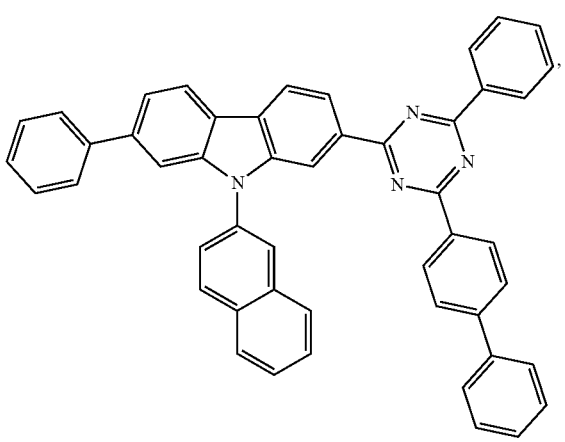
Compound 125
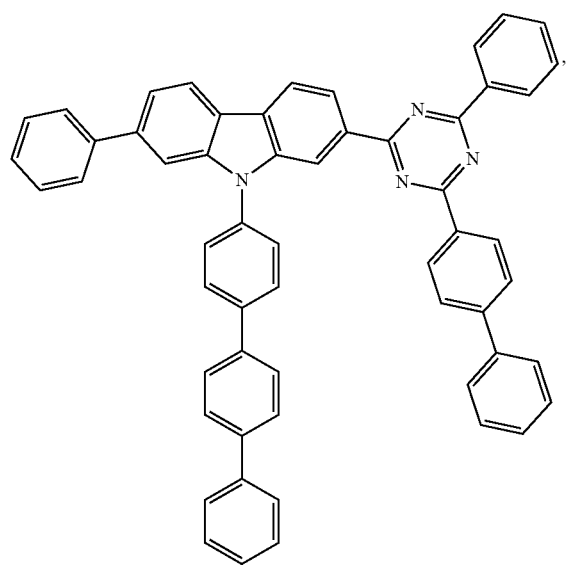
Compound 126
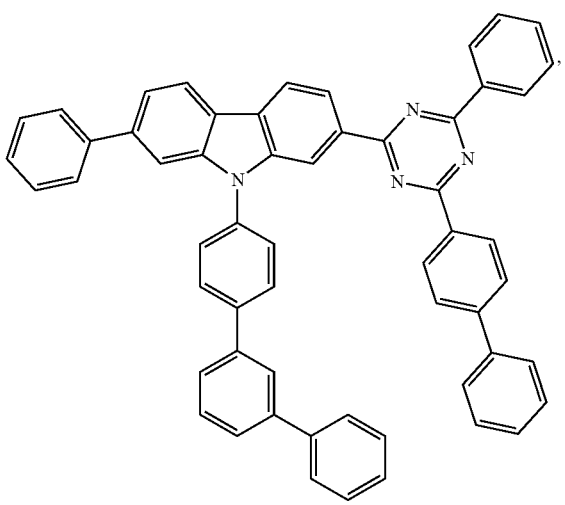

-continued
Compound 127
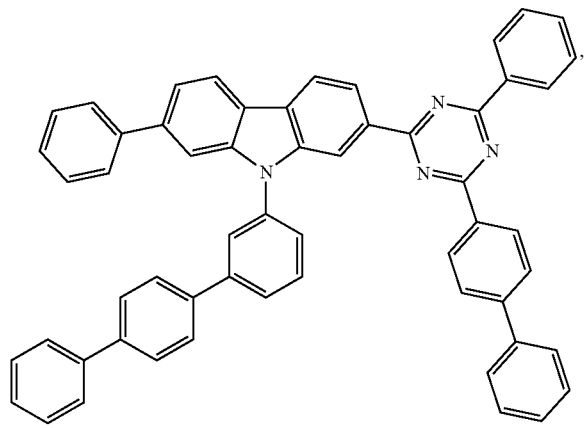
Compound 128
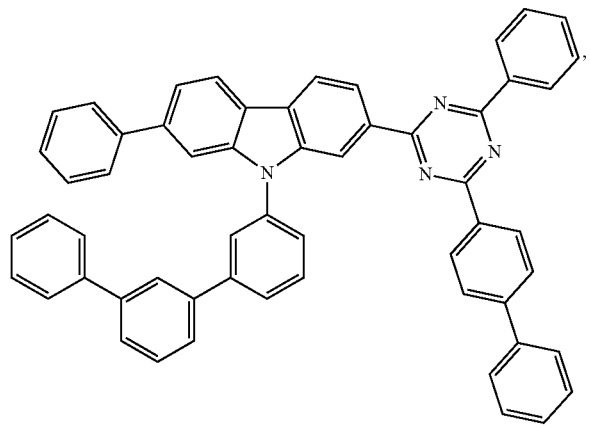
Compound 129
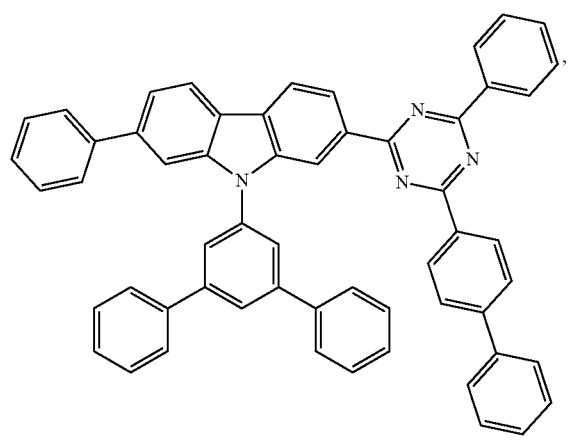
Compound 130
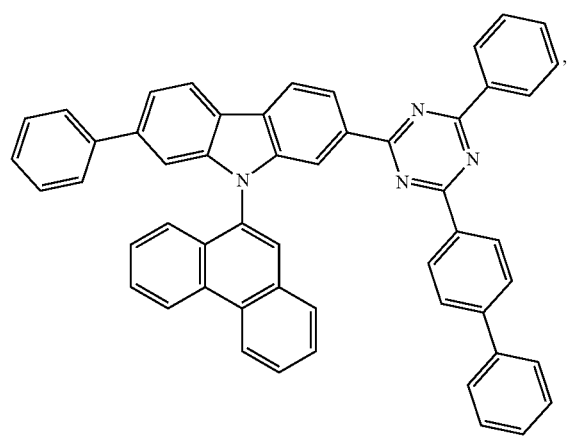
Compound 131
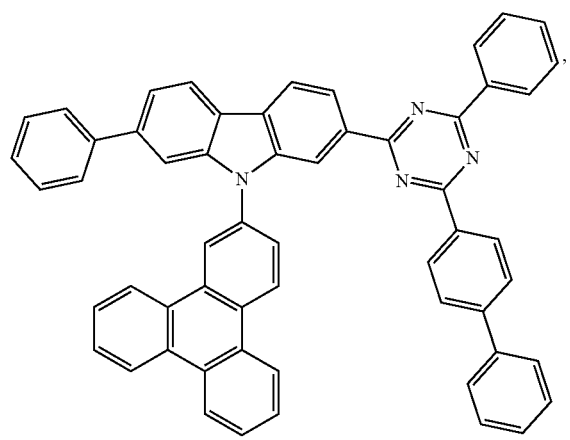
Compound 132
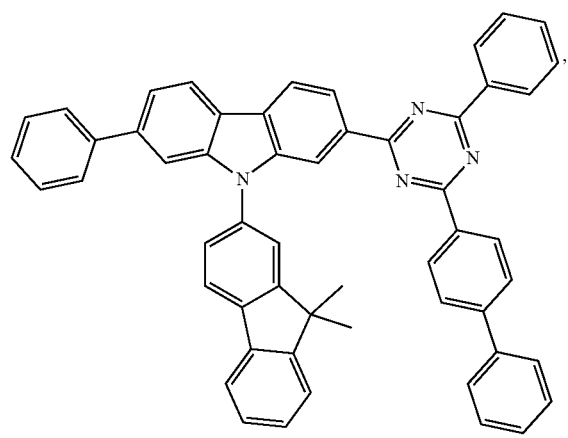

-continued
Compound 133
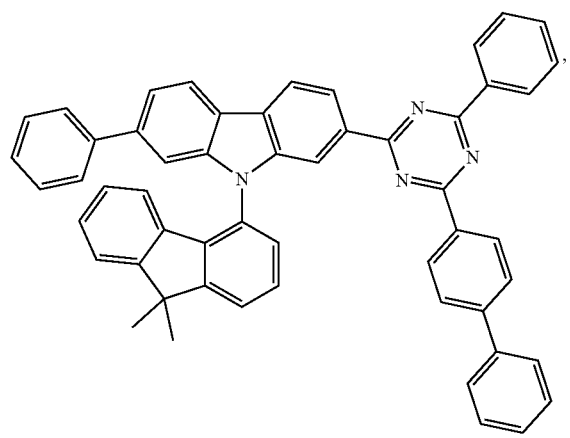
Compound 134
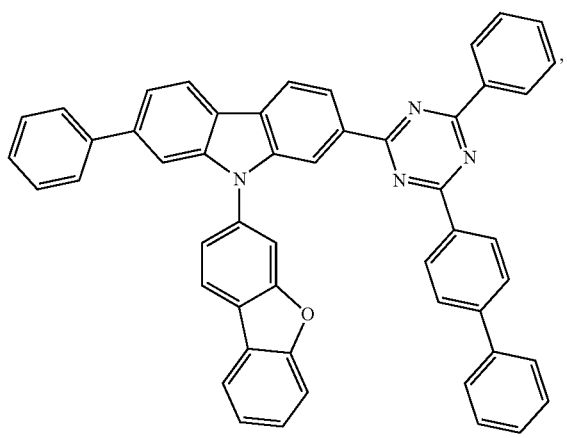
Compound 135
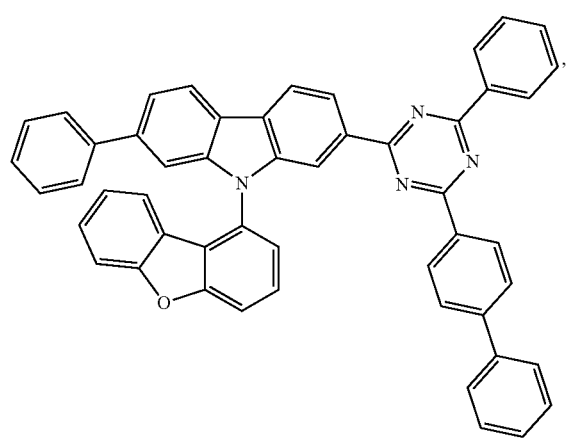
Compound 136
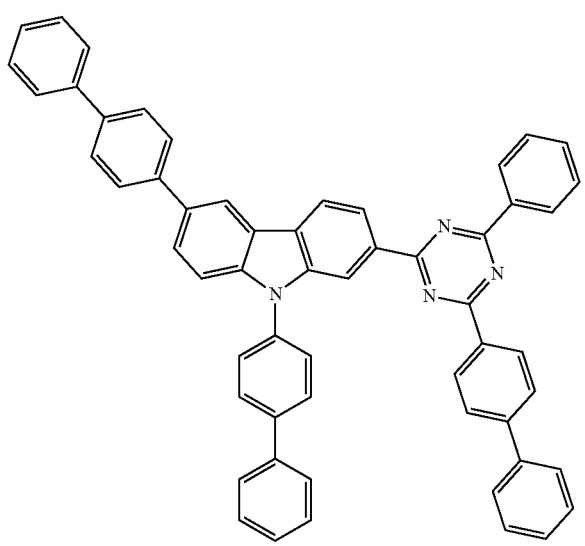
Compound 137
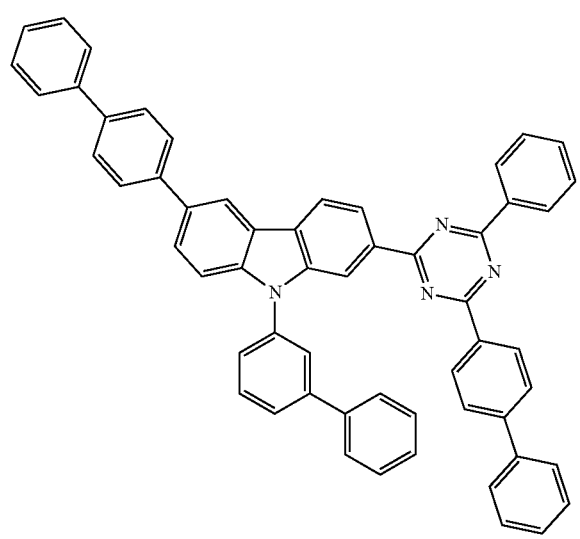
Compound 138
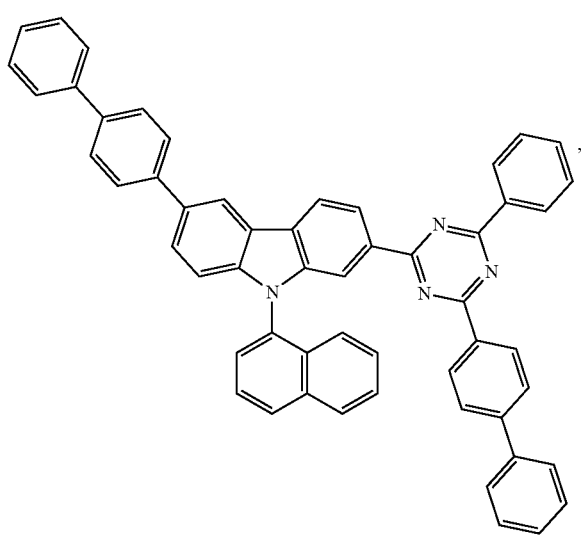

-continued
Compound 139
Compound 140
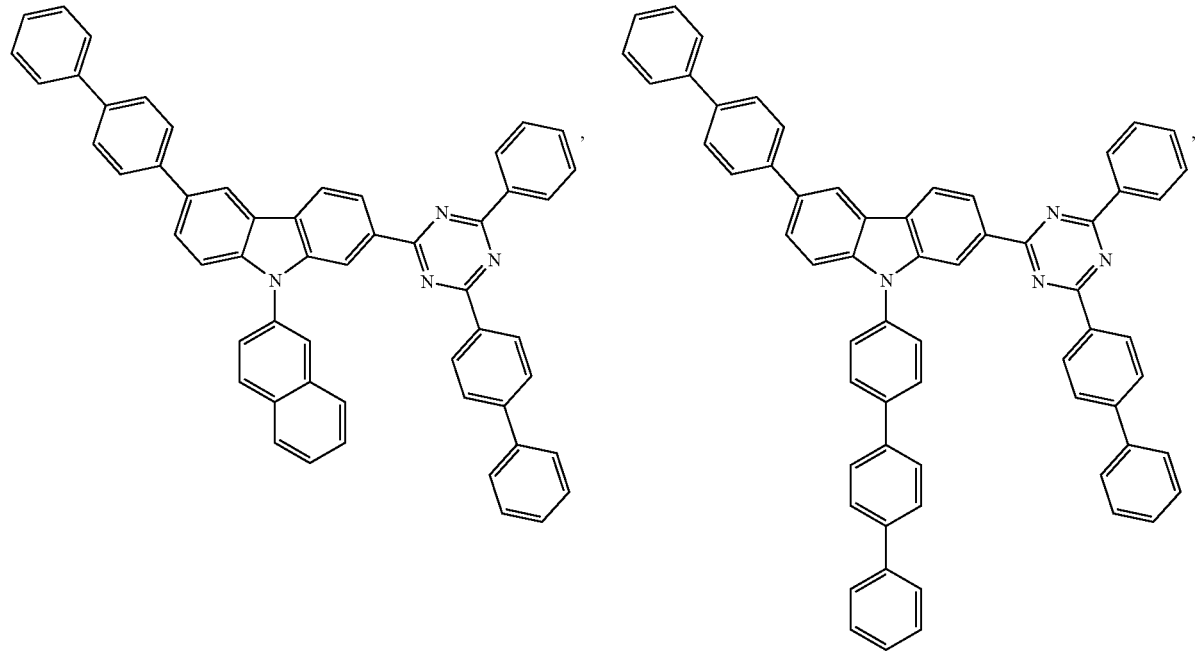
Compound 141
Compound 142
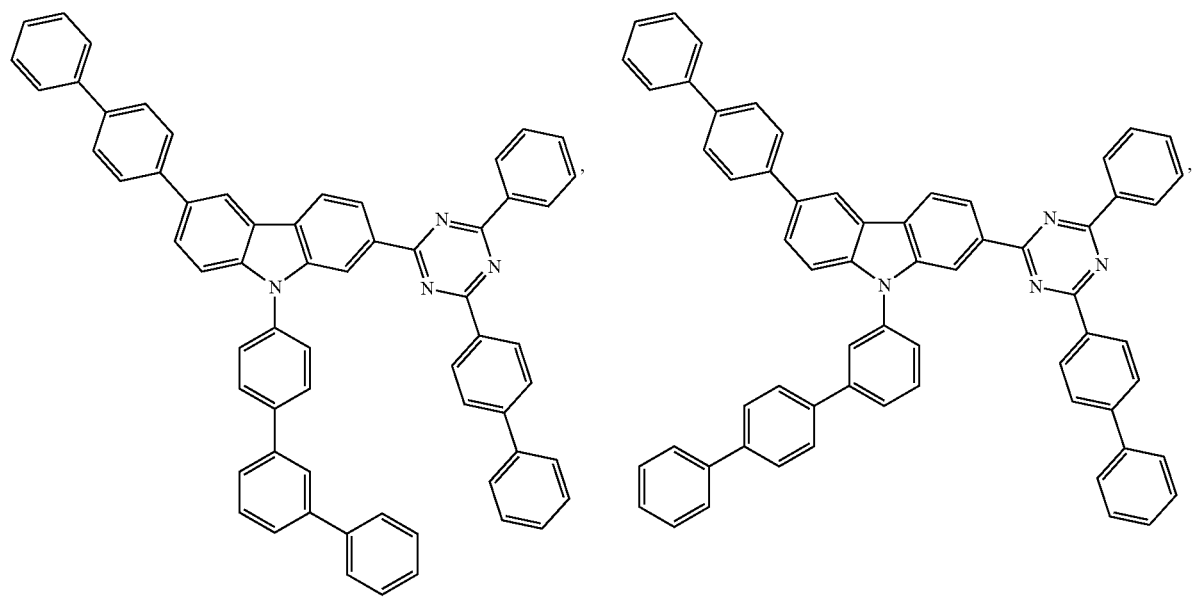

-continued
Compound 143
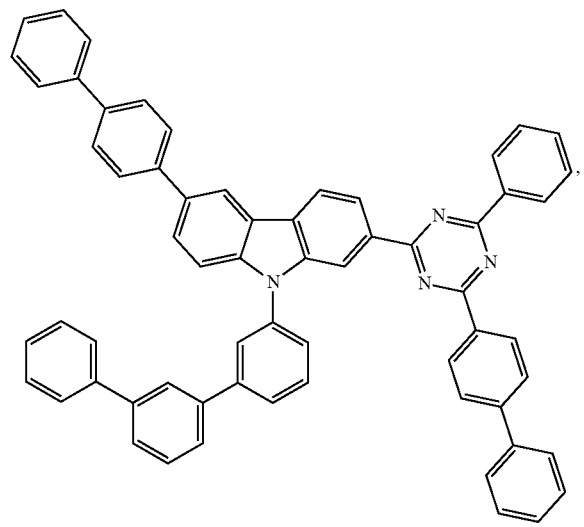
Compound 144
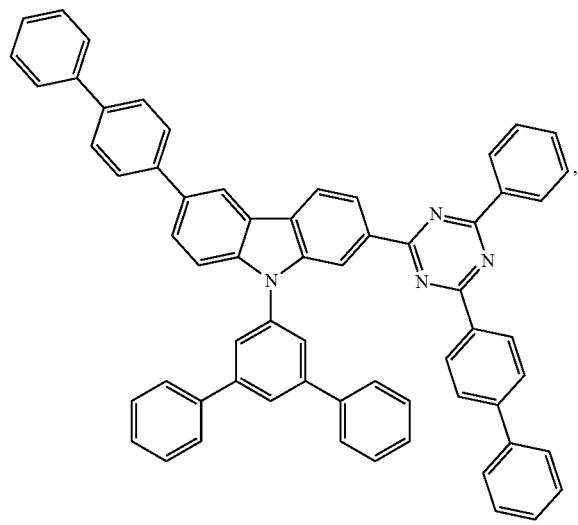
Compound 145
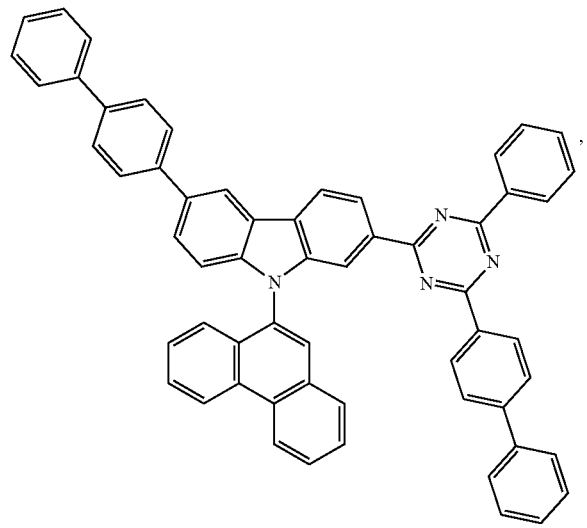
compound 146
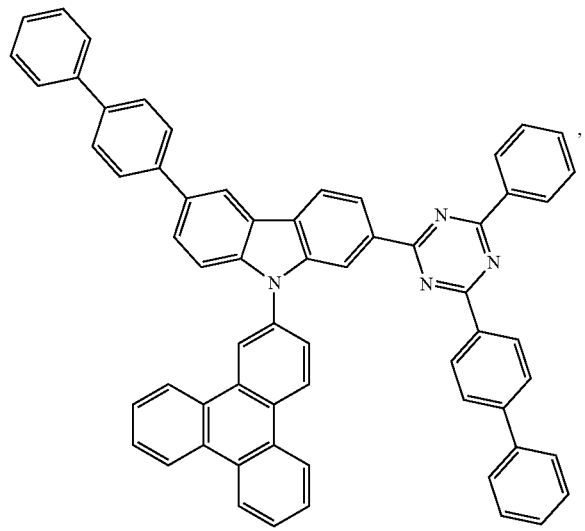
Compound 147
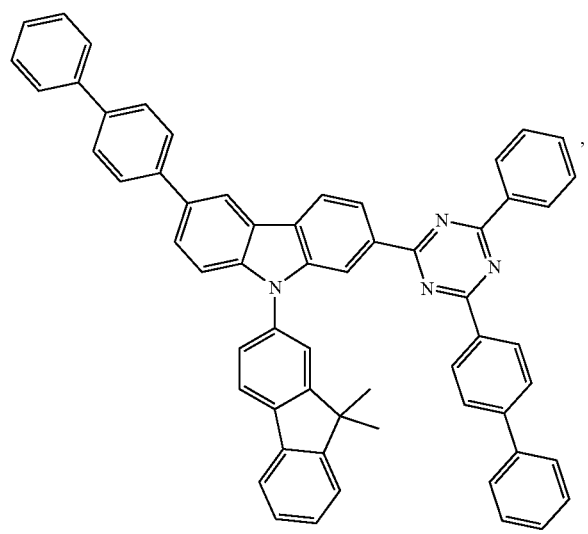
Compound 148
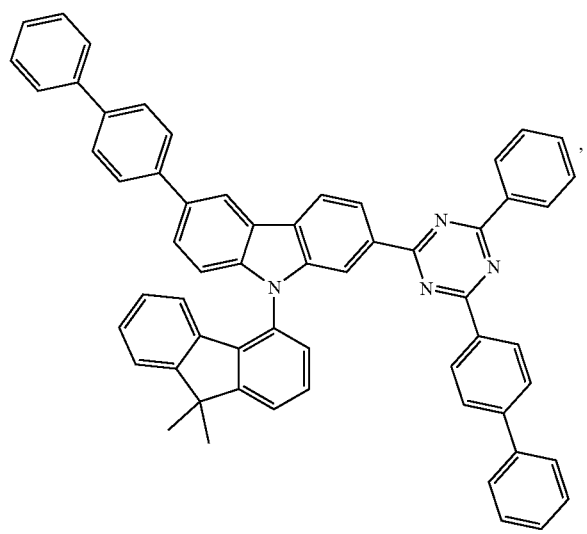

-continued
Compound 149
Compound 150
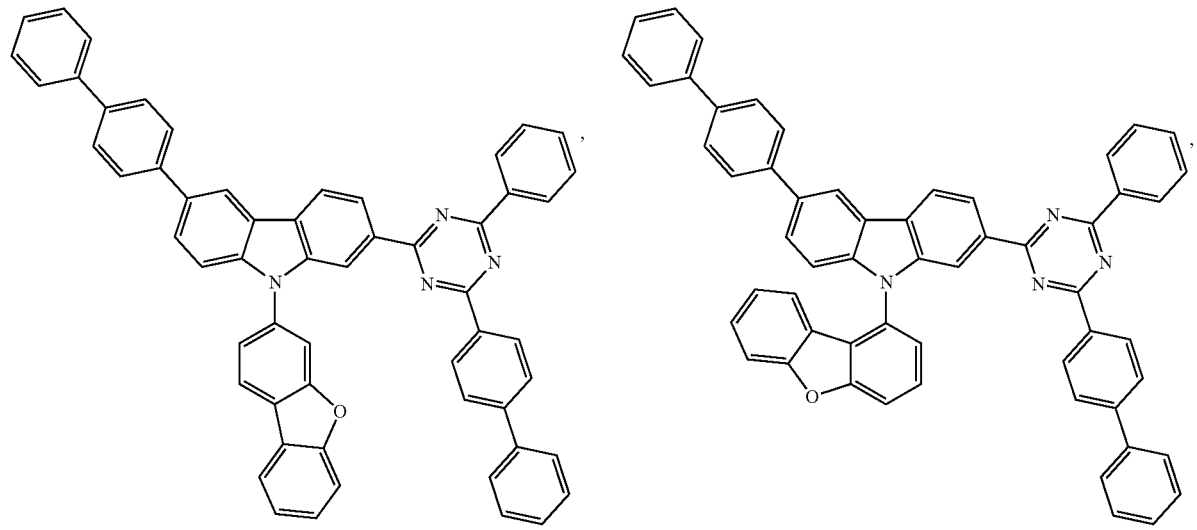
Compound 151
Compound 152
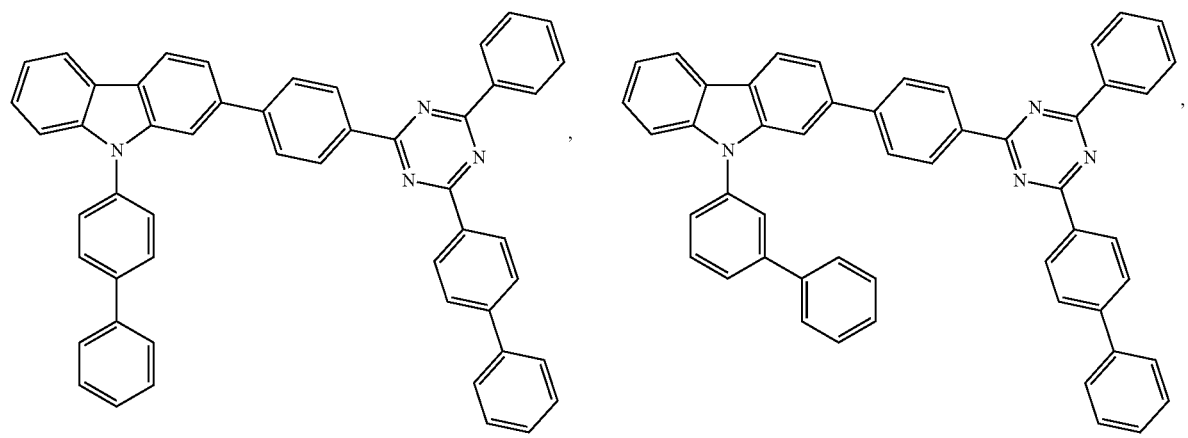
Compound 153
Compound 154
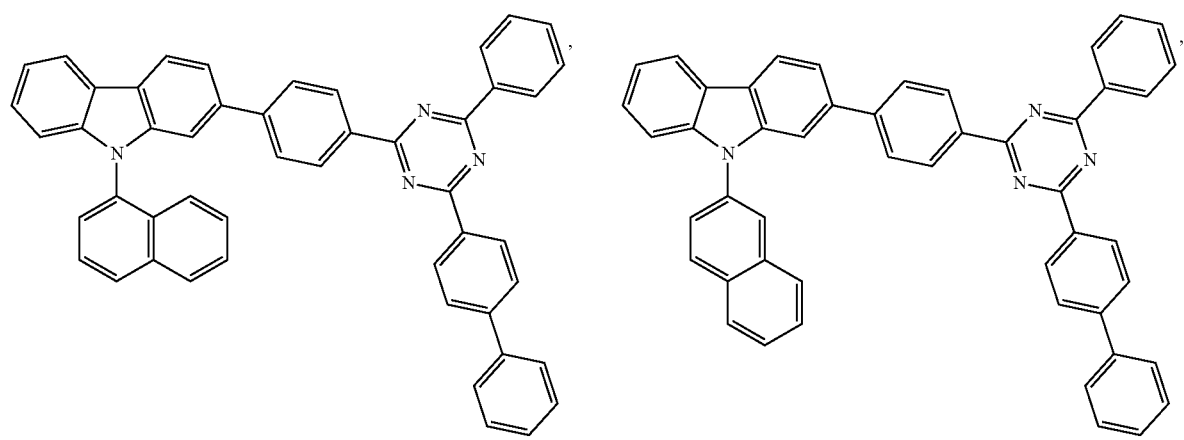

Compound 155
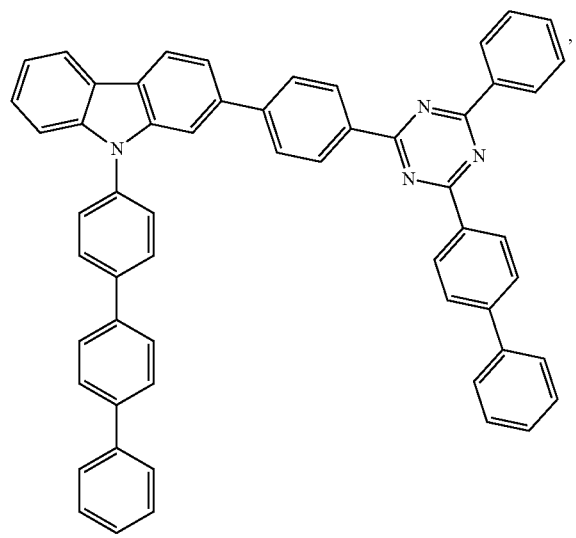
Compound 156
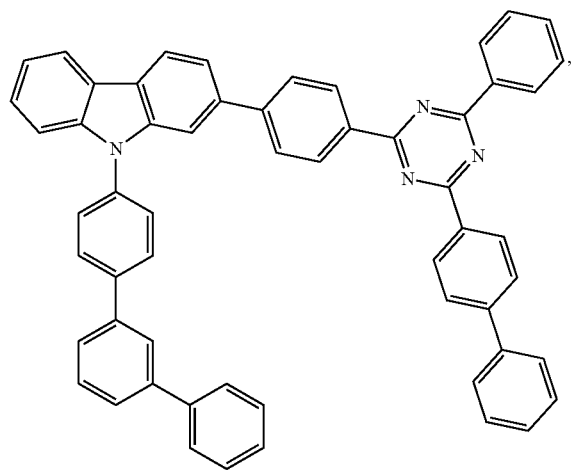
Compound 157
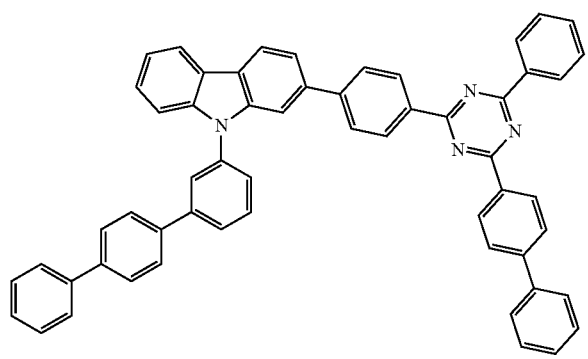
Compound 158
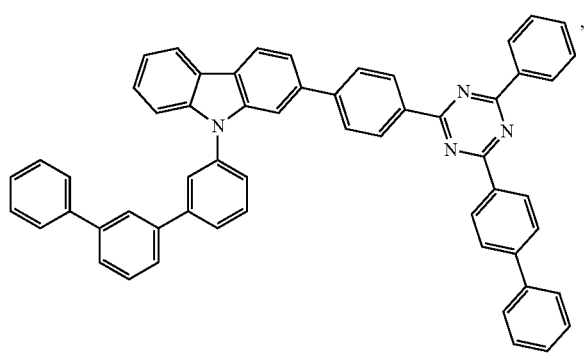
Compound 159
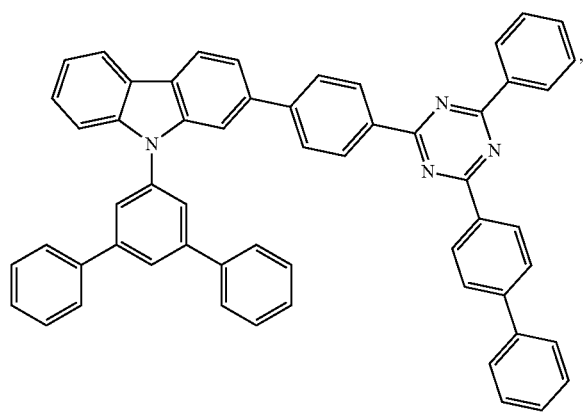
Compound 160
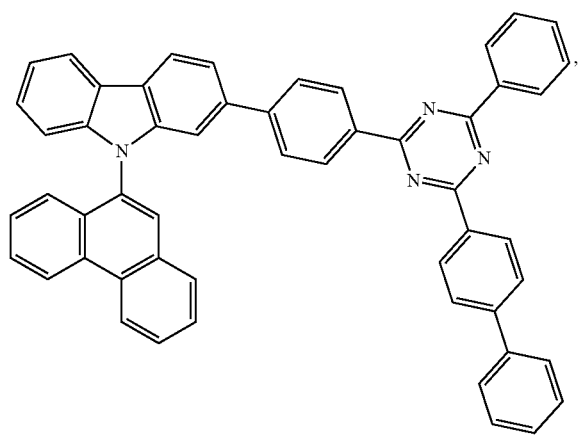

-continued
Compound 161
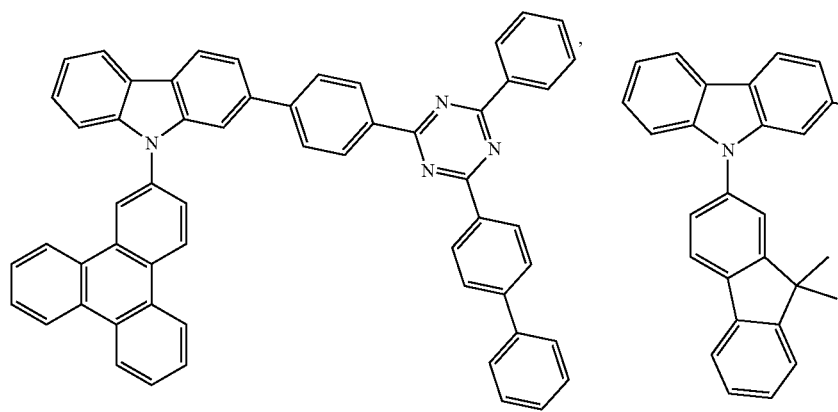
Compound 162
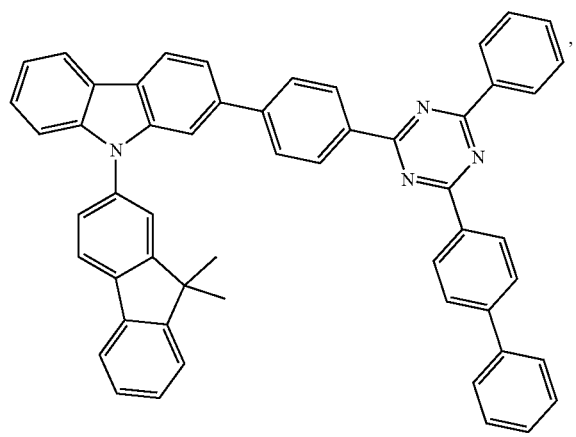
Compound 163
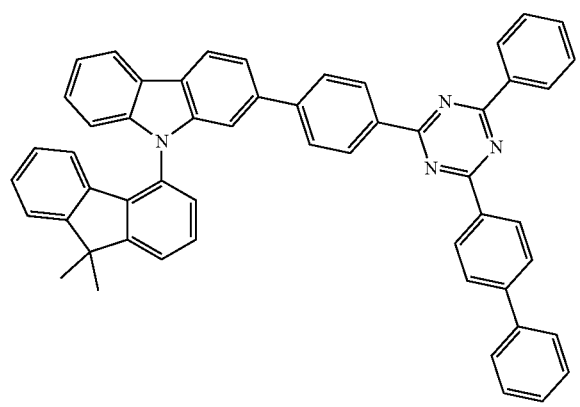
Compound 164
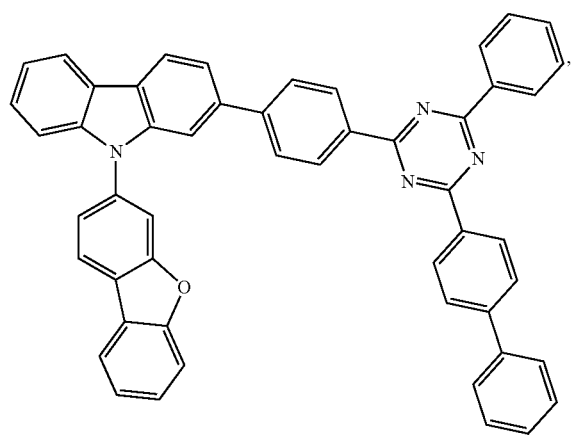
Compound 165
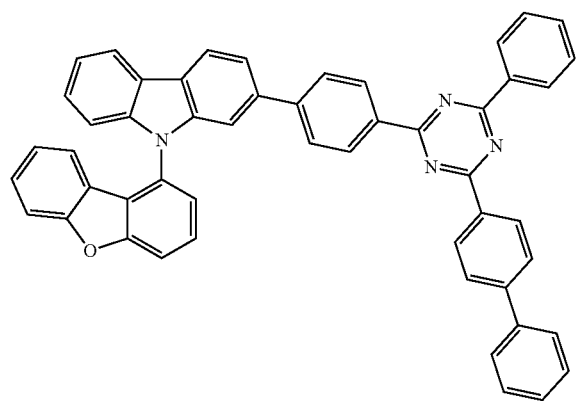
Compound 166
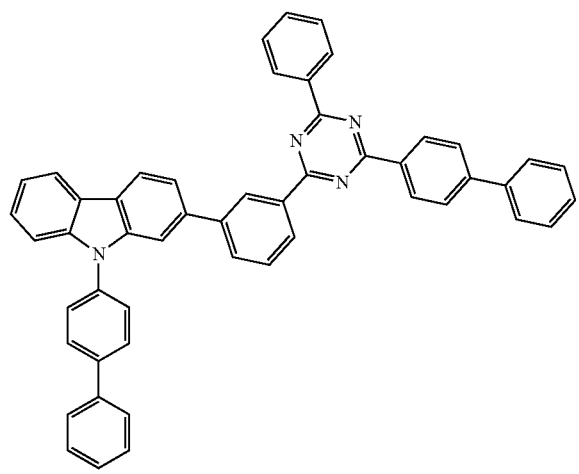

Compound 167
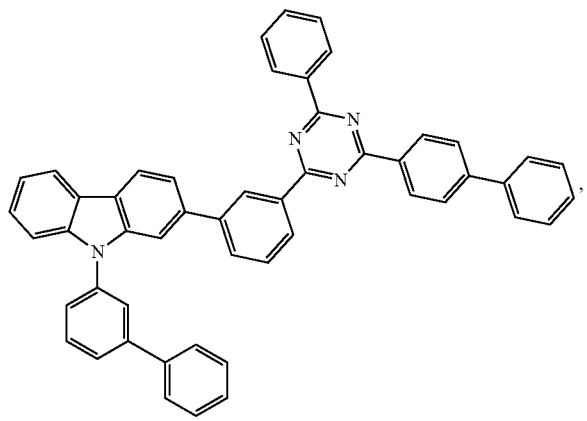
Compound 168
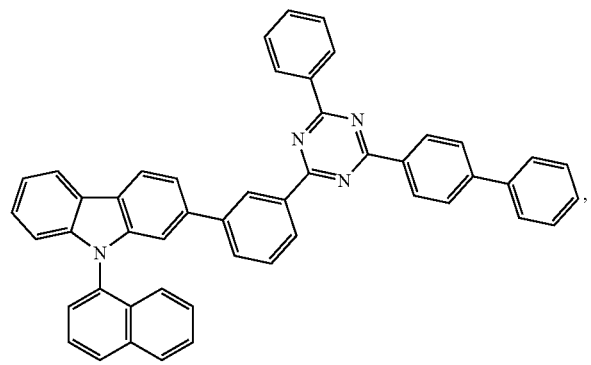
Compound 169
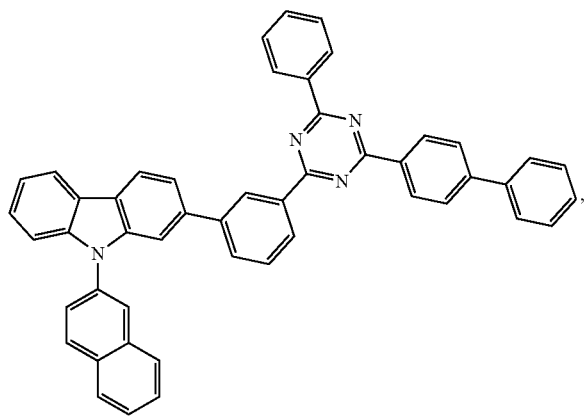
Compound 170
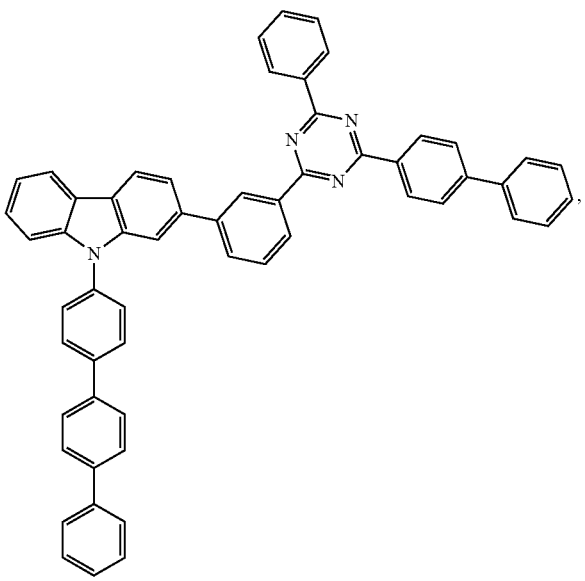
Compound 171
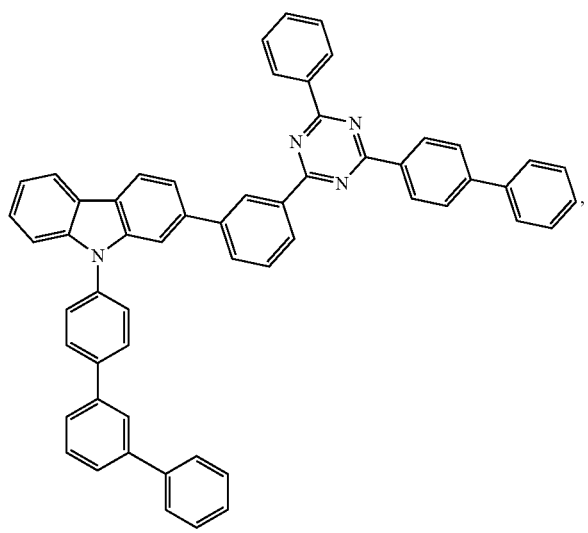

Compound 172
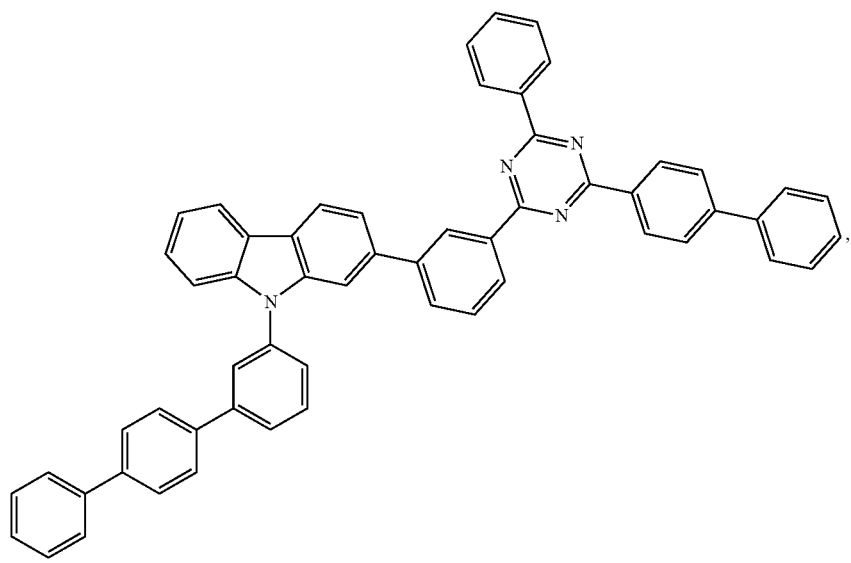
Compound 173
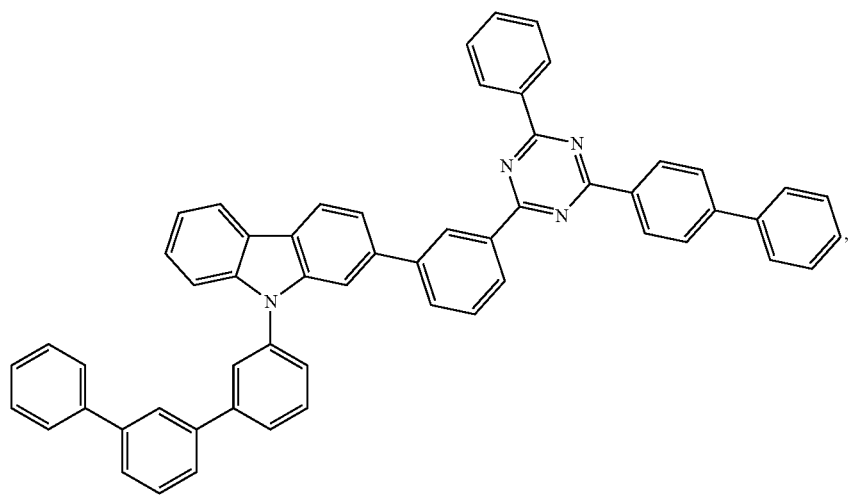
Compound 174
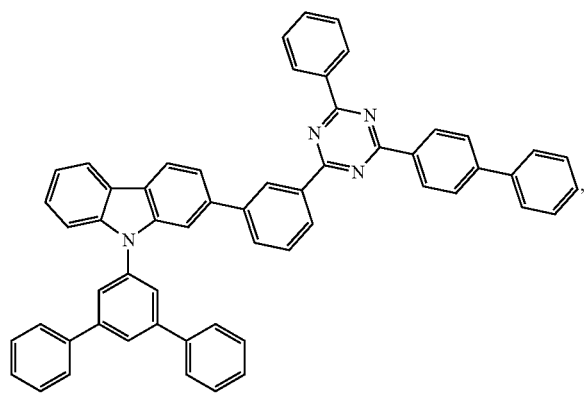
Compound 175
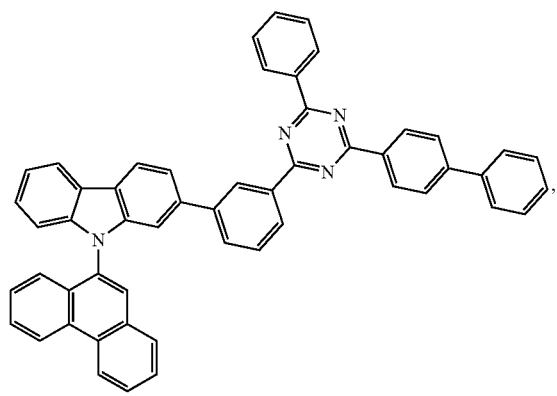

Compound 176
Compound 177
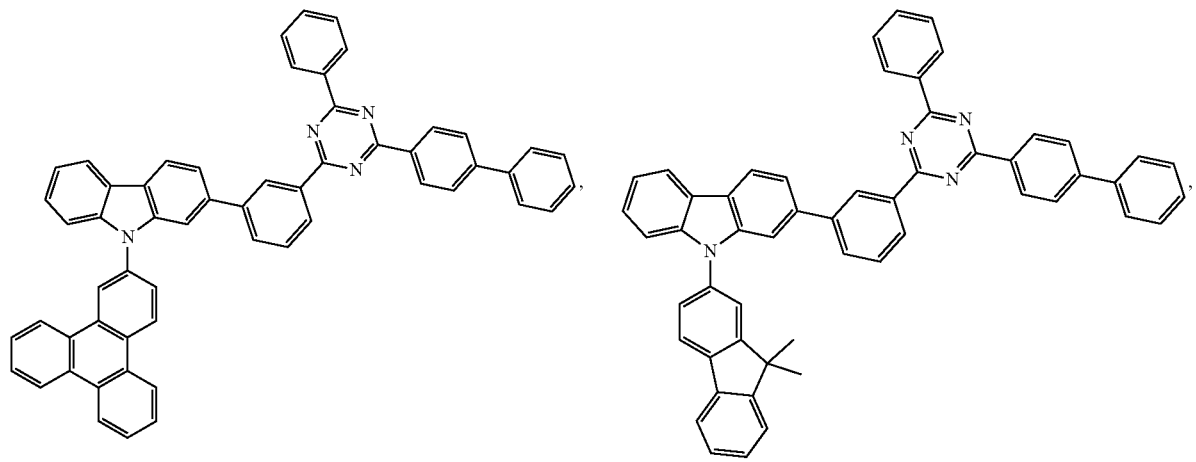
Compound 178
Compound 179
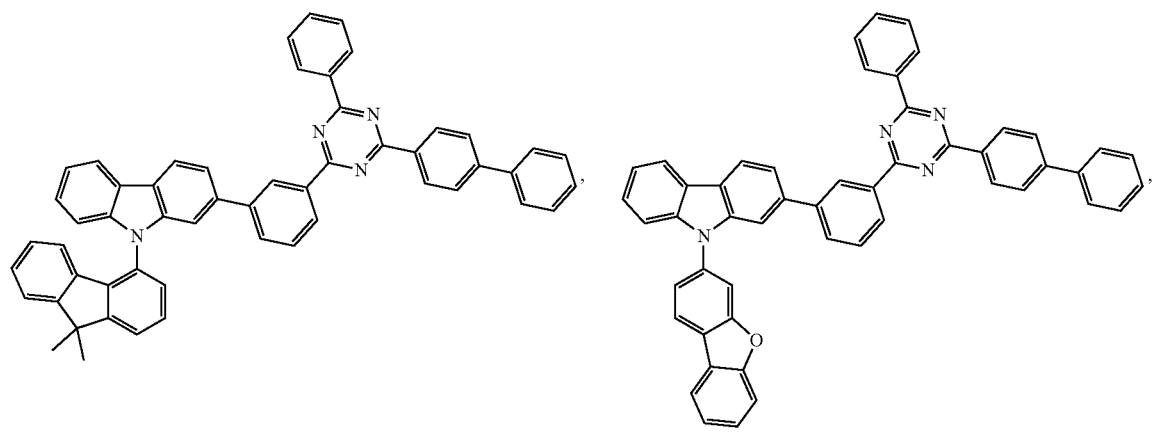
Compound 180
Compound 181
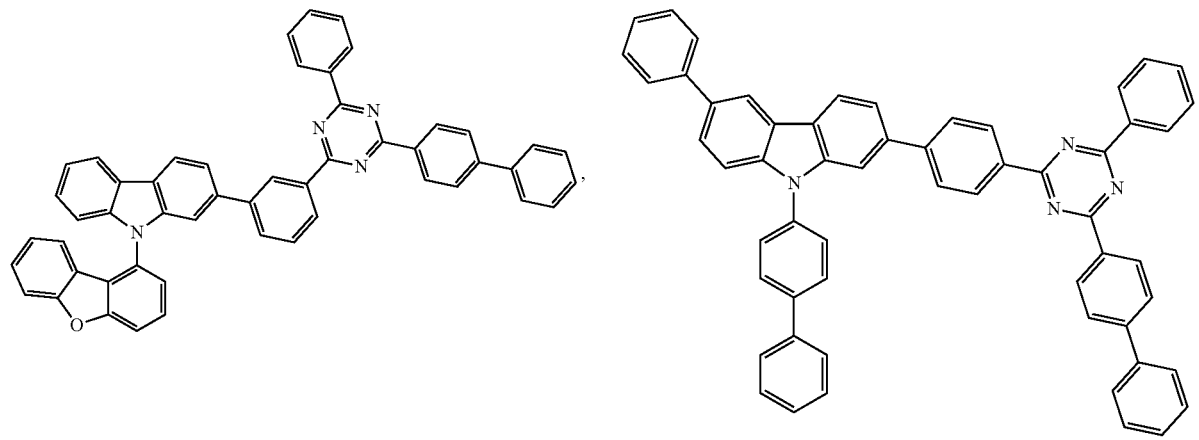

-continued
Compound 182
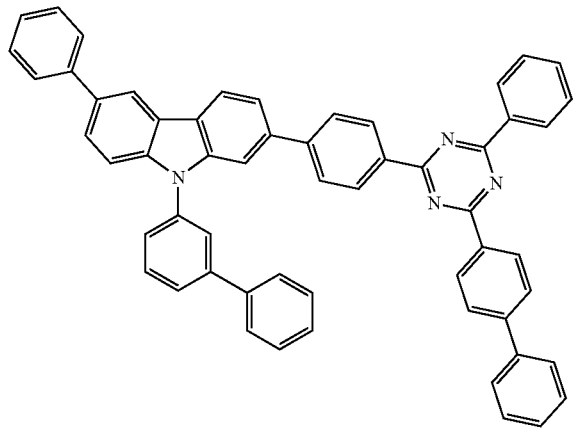
Compound 183
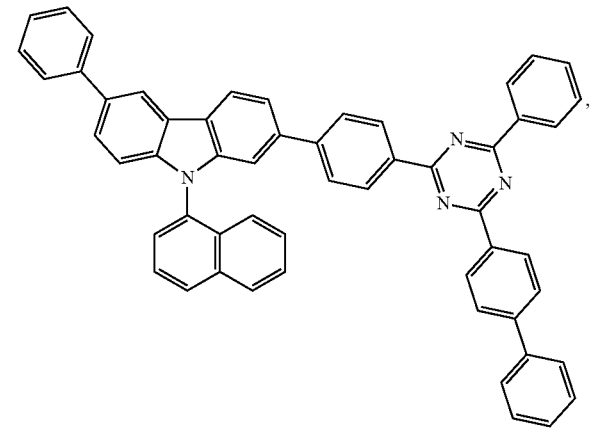
Compound 184
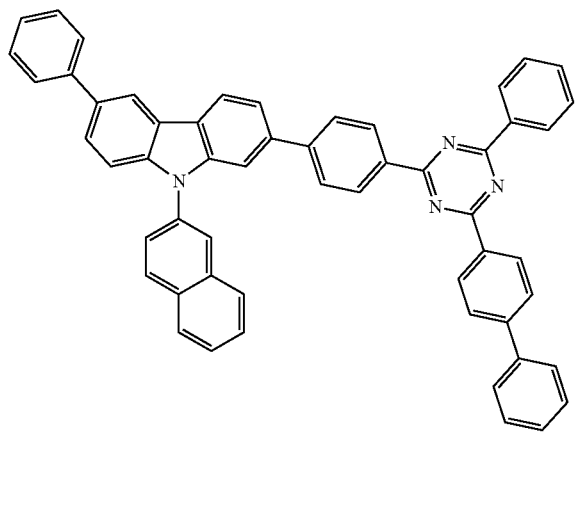
Compound 185
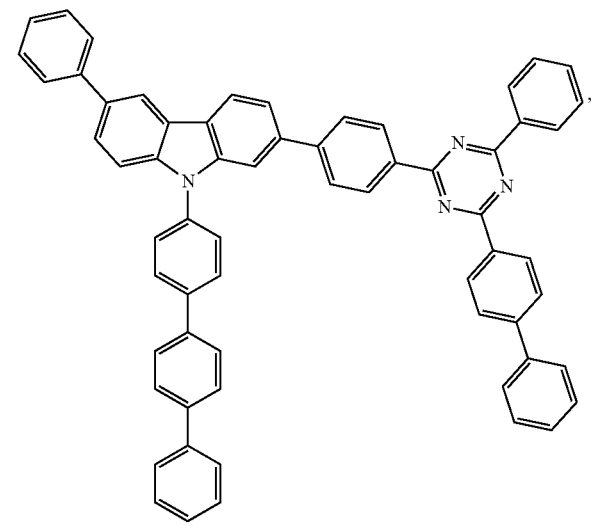
Compound 186
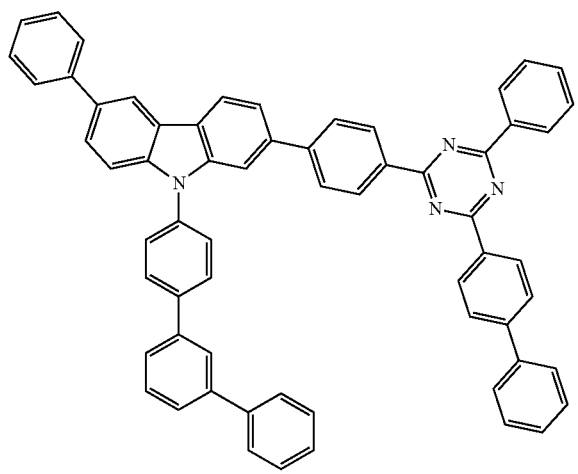
Compound 187
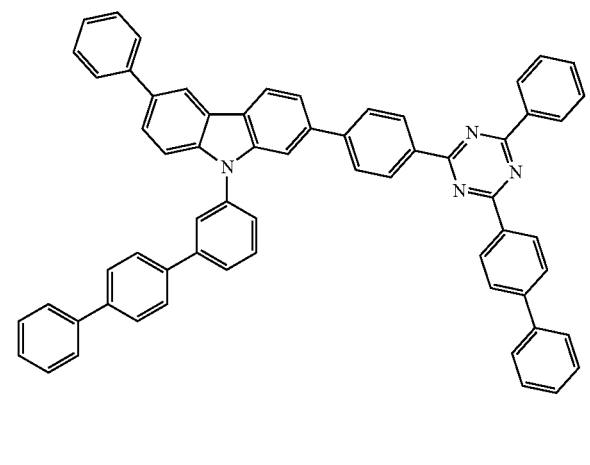

-continued
Compound 188
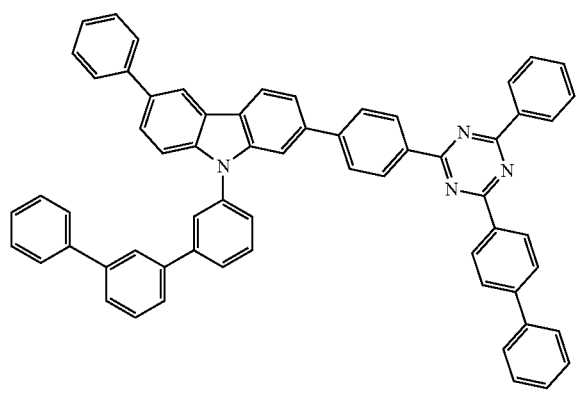
Compound 189
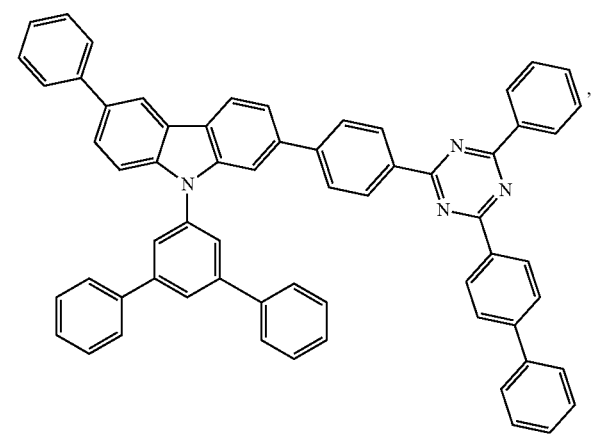
Compound 190
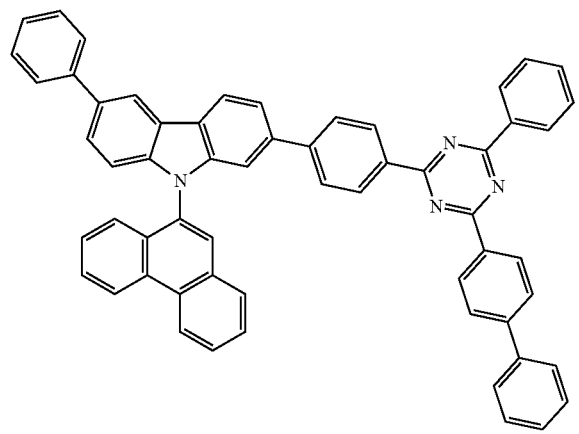
Compound 191
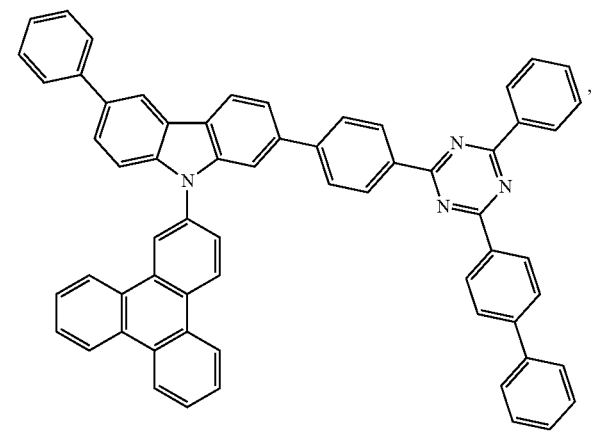
Compound 192
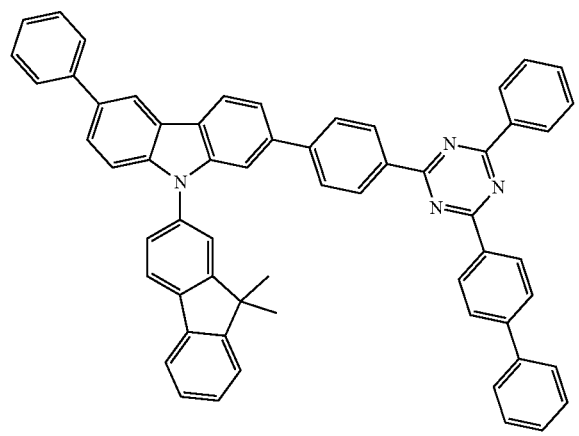
Compound 193
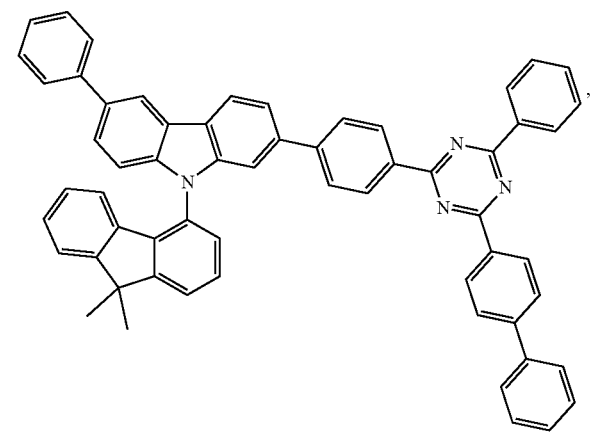

Compound 194
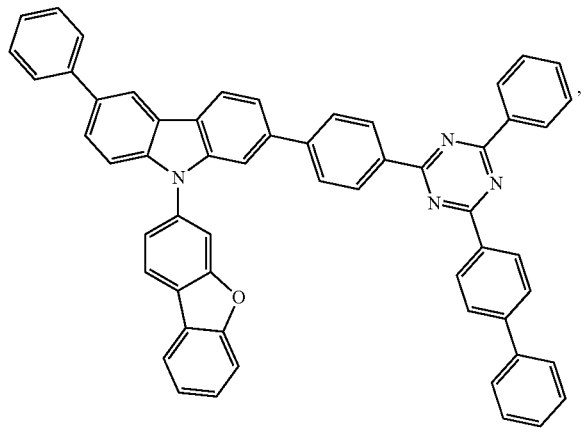
Compound 195
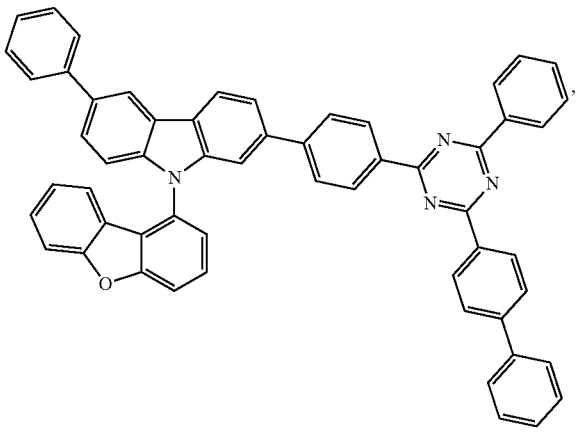
Compound 196
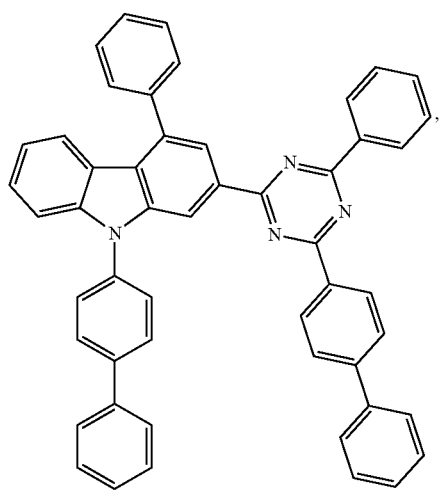
Compound 197
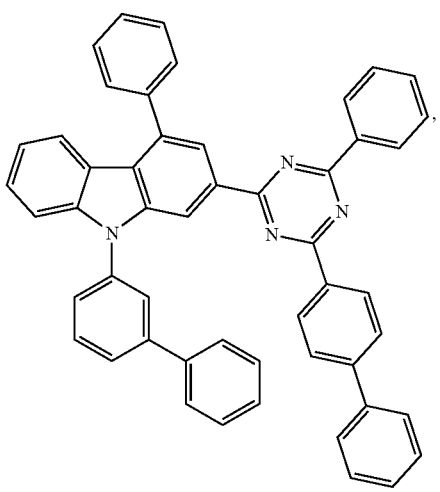
Compound 198
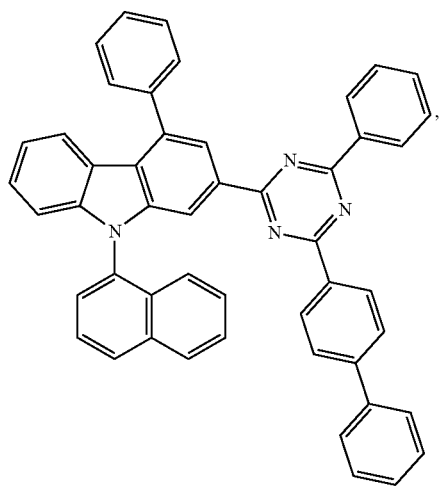
Compound 199
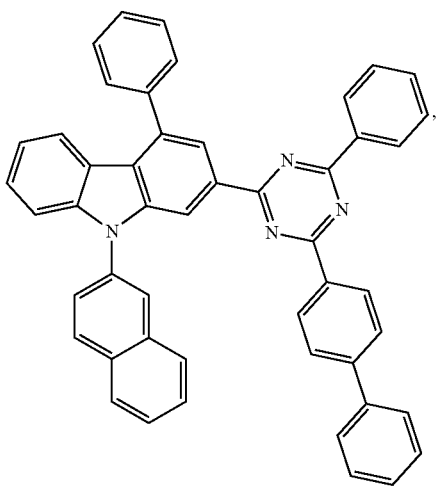

Compound 200
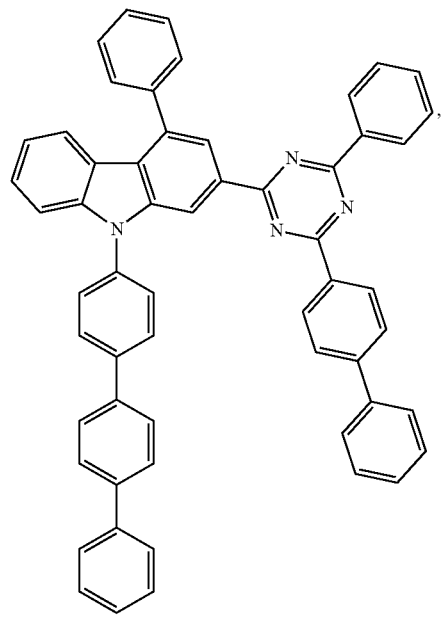
Compound 201
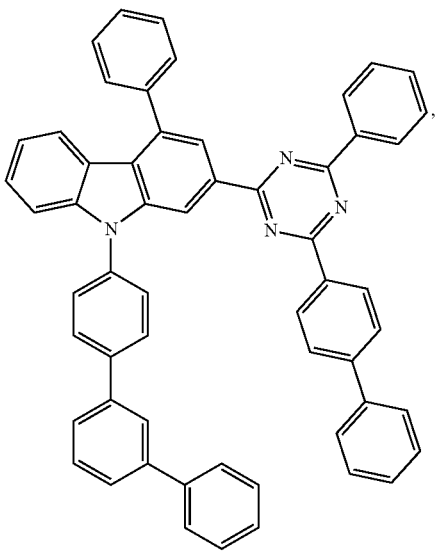
Compound 202
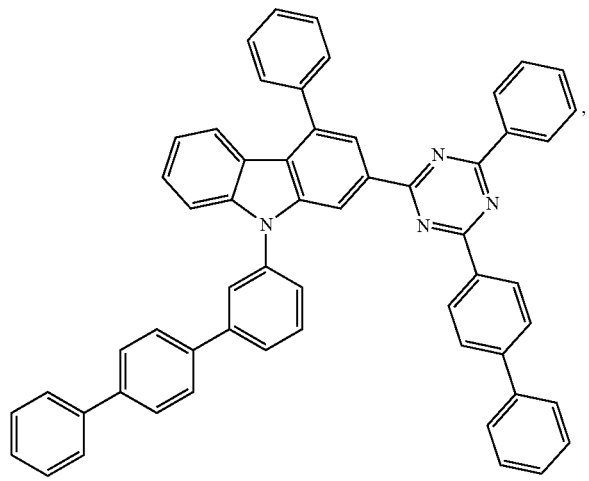
Compound 203
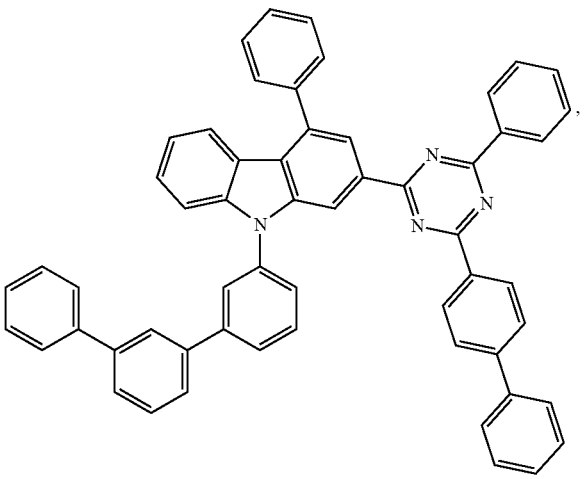
Compound 204
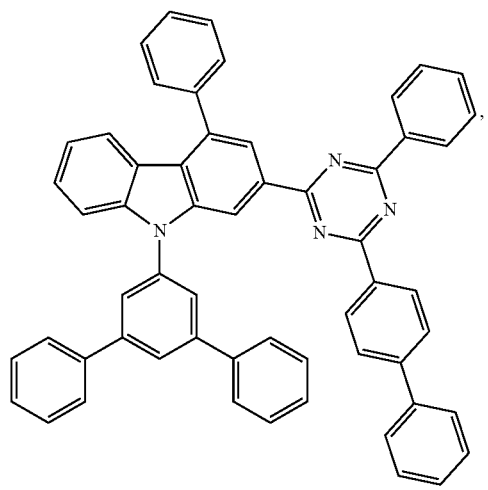
Compound 205
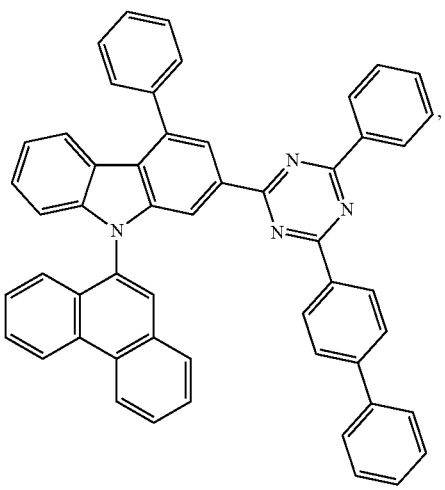

-continued
Compound 206
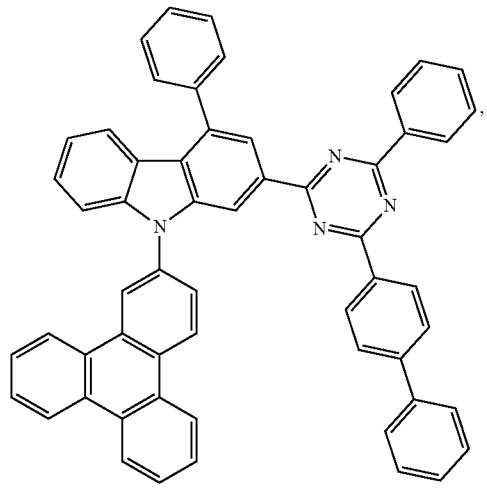
Compound 207
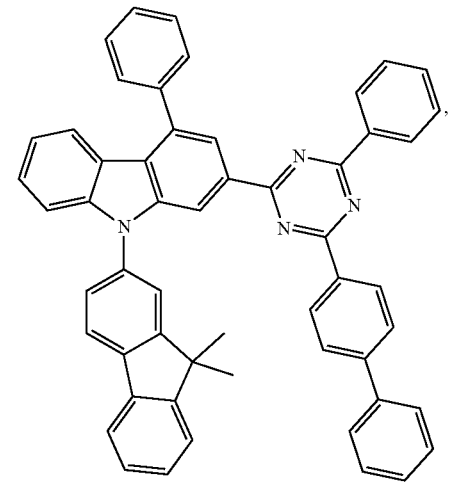
Compound 208
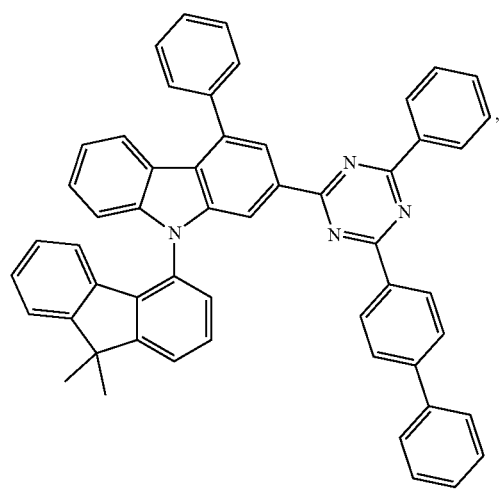
Compound 209
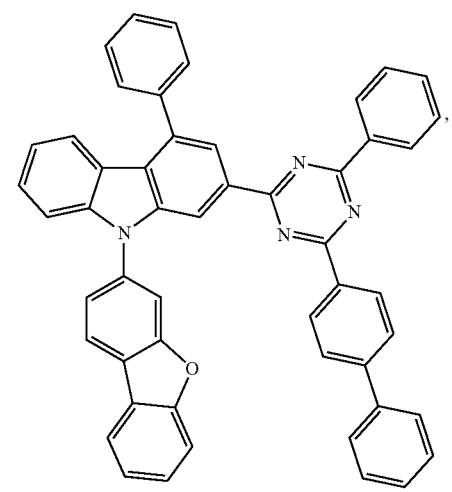
Compound 210
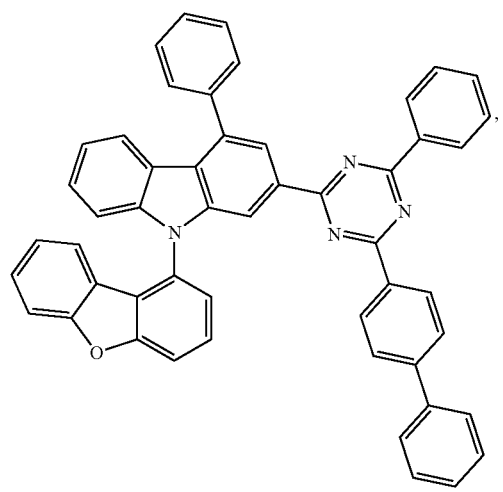
Compound 211
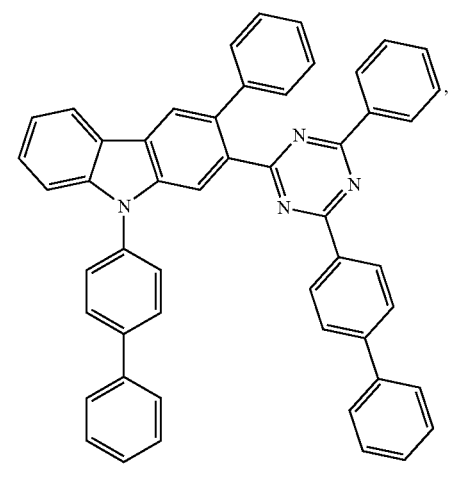

-continued
Compound 212
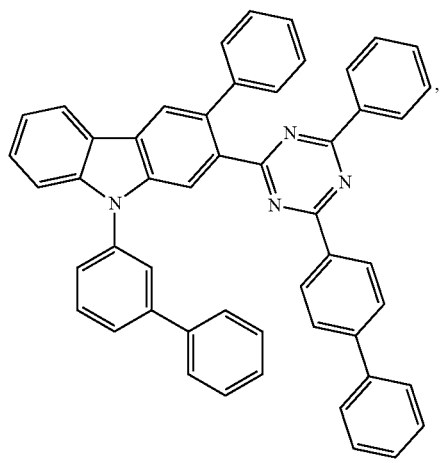
Compound 213
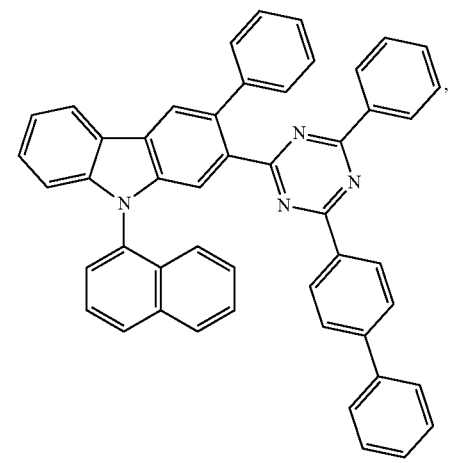
Compound 214
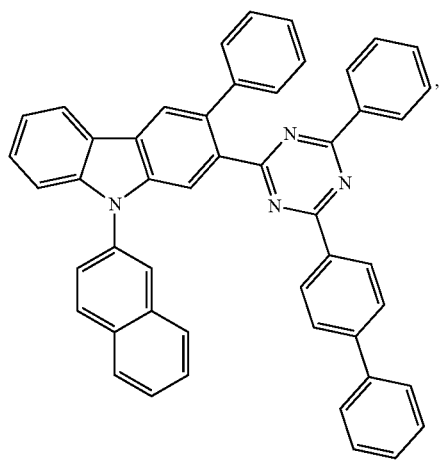
Comound 215
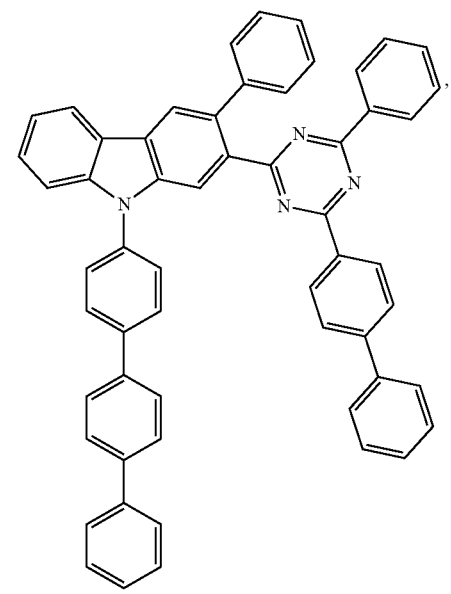
Compound 216
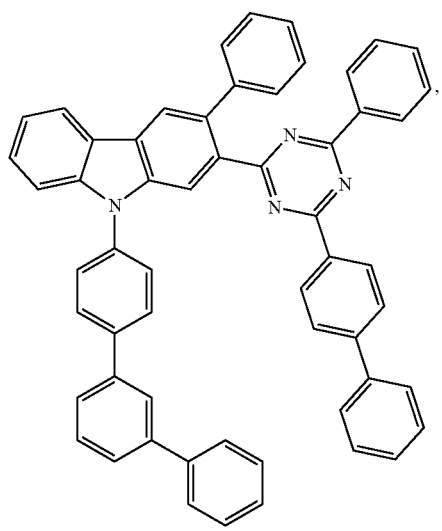
Compound 217
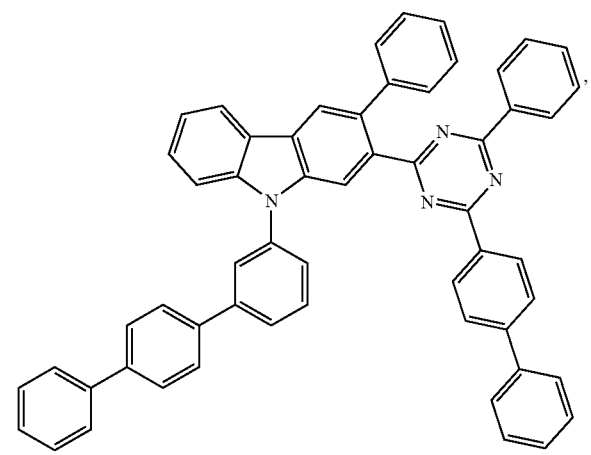

-continued
Compound 218, Compound 219
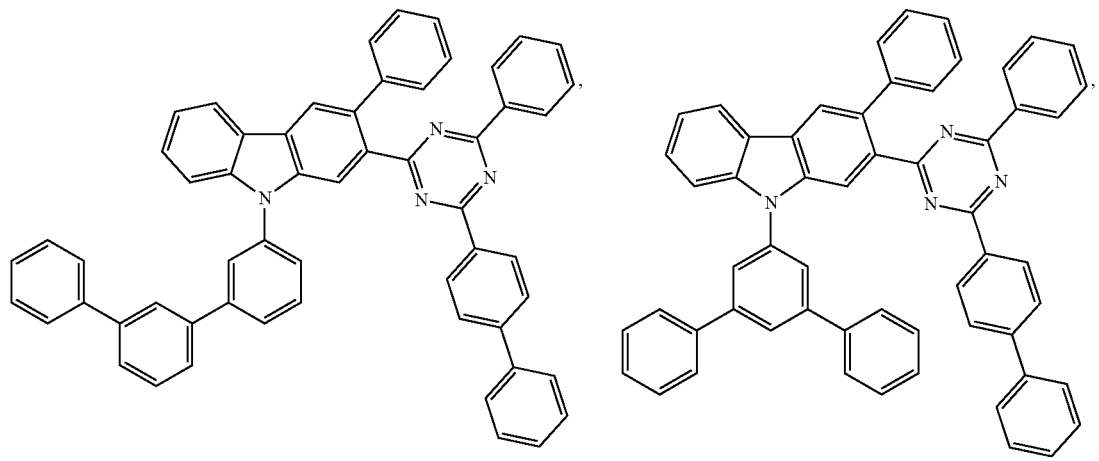
Compound 220, Compound 221
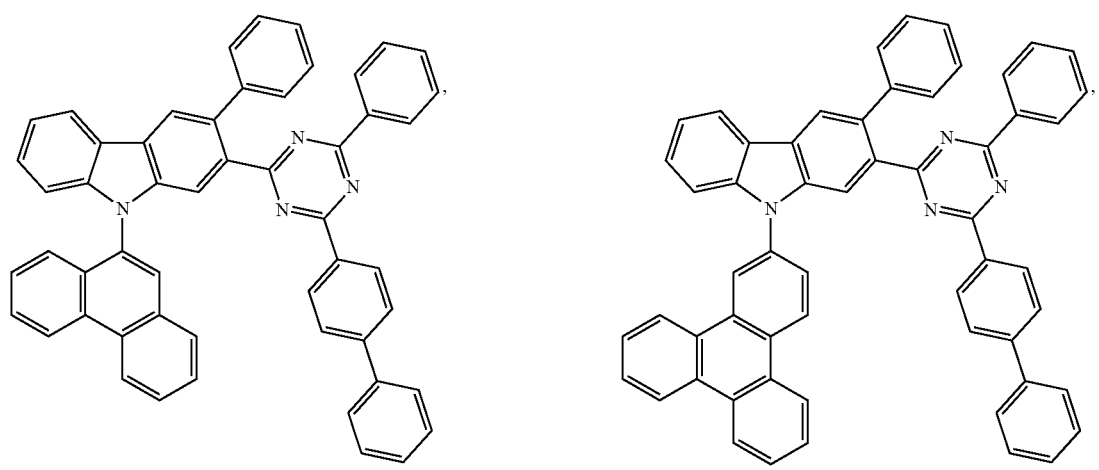
Compound 222, Compound 223
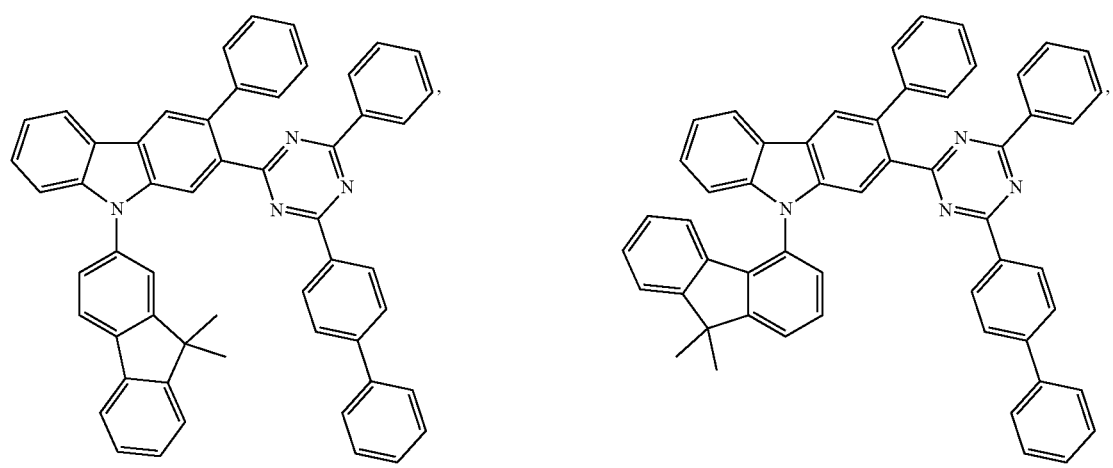

Compound 224
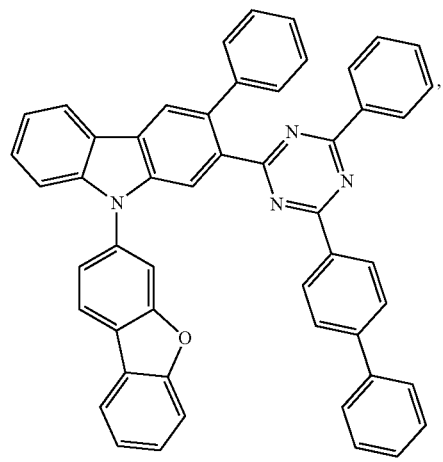
Compound 225
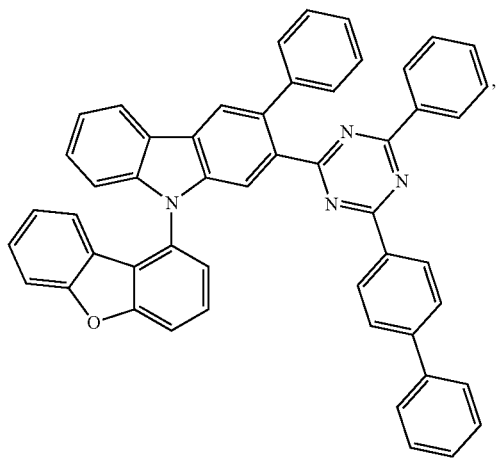
Compound 226
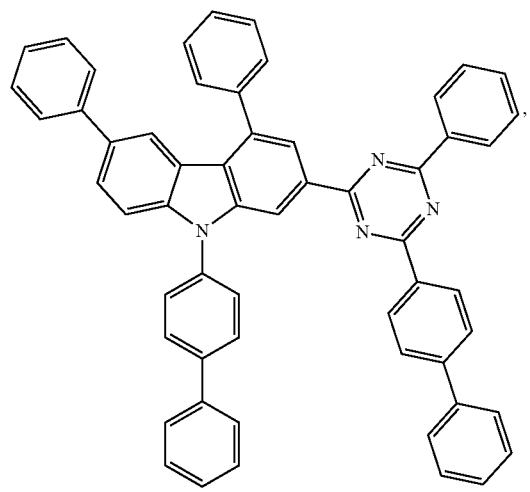
Compound 227
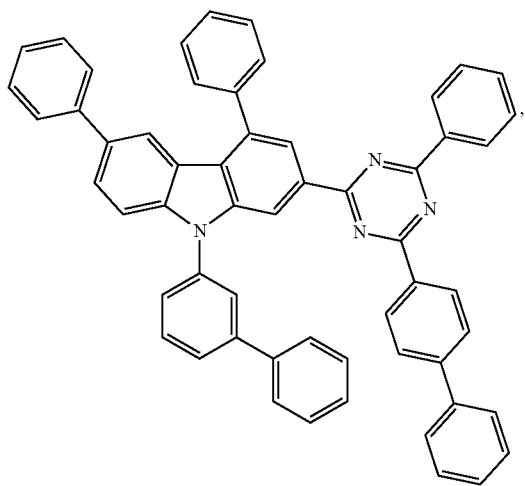
Compound 228
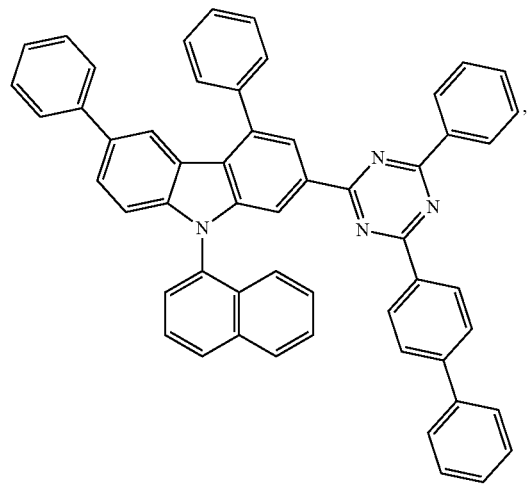
Compound 229
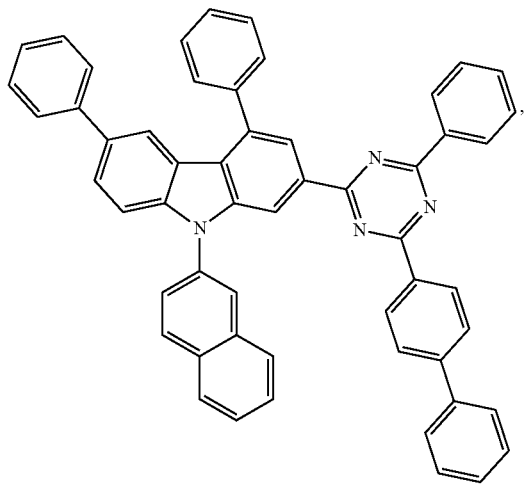

-continued
Compound 230
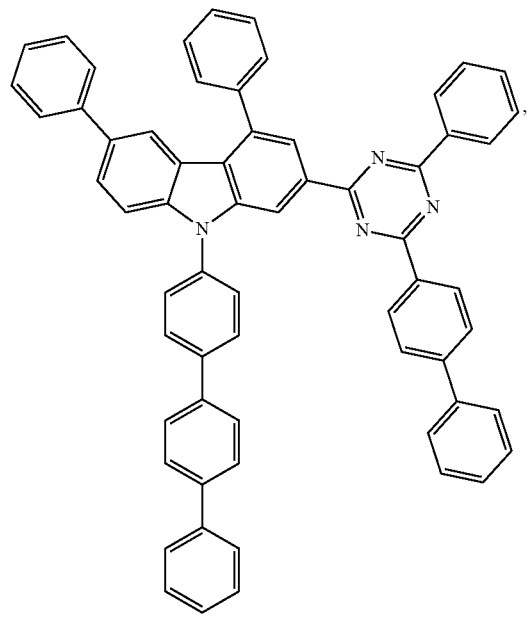
Compound 231
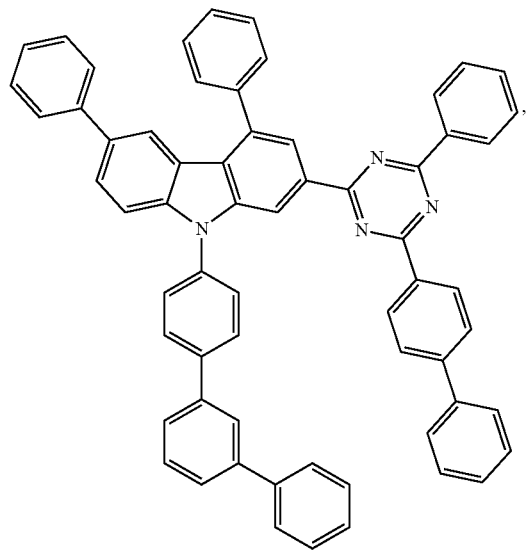
Compound 232
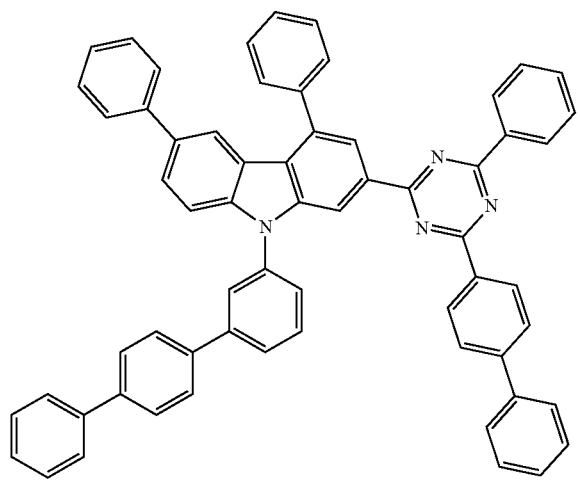
Compound 233
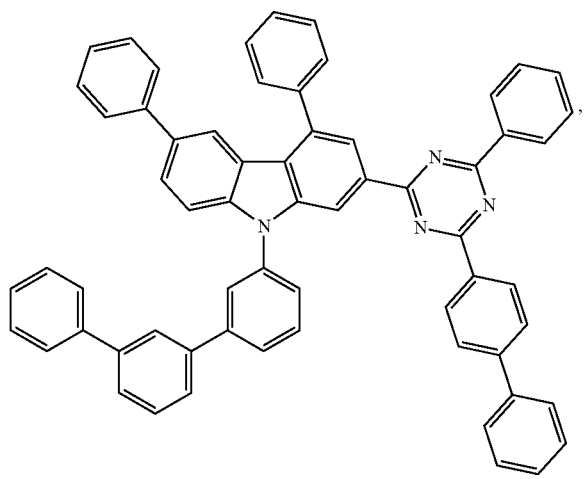
Compound 234
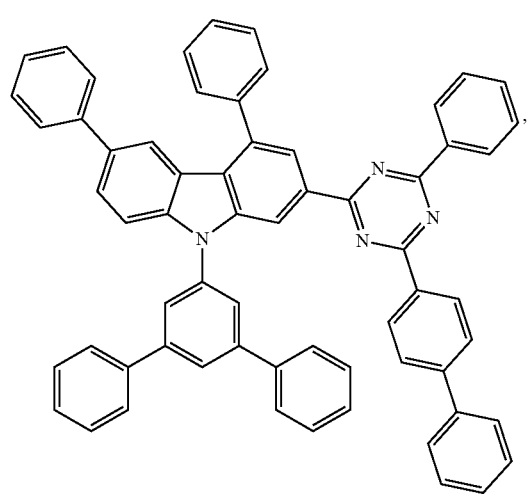
Compound 235
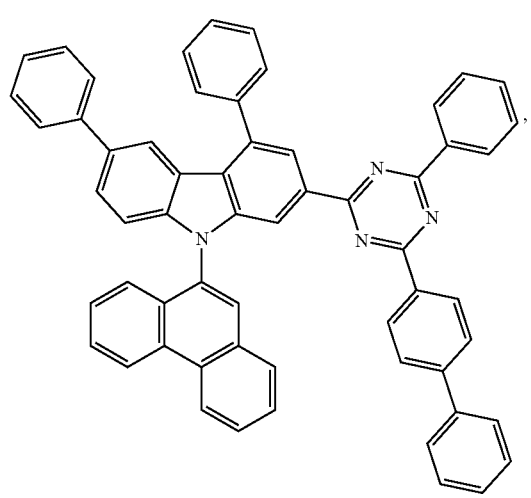

Compound 236
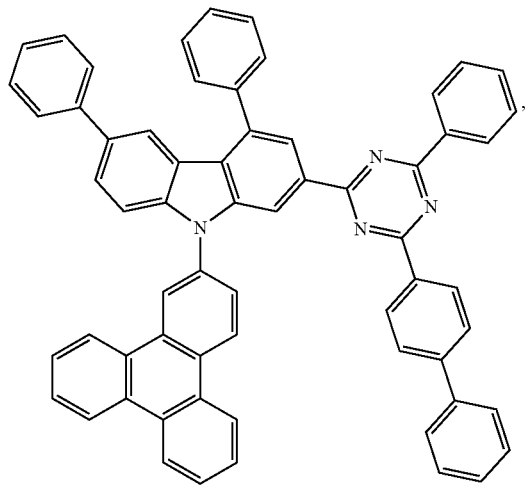
Compound 237
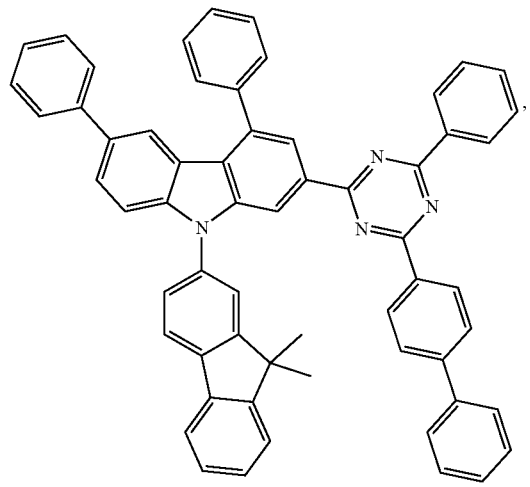
Compound 238
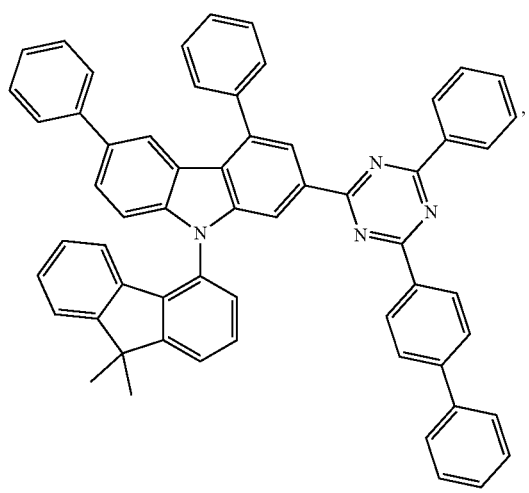
Compound 239
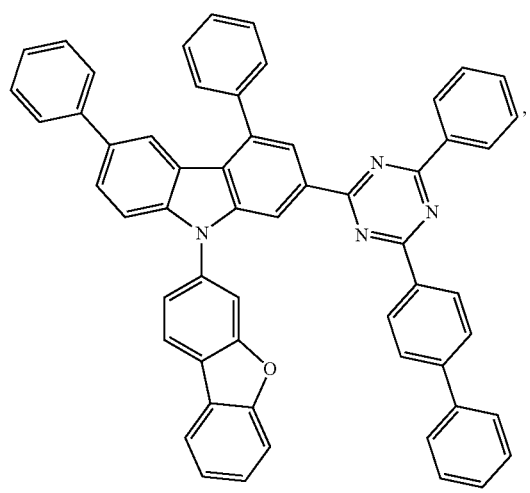
Compound 240
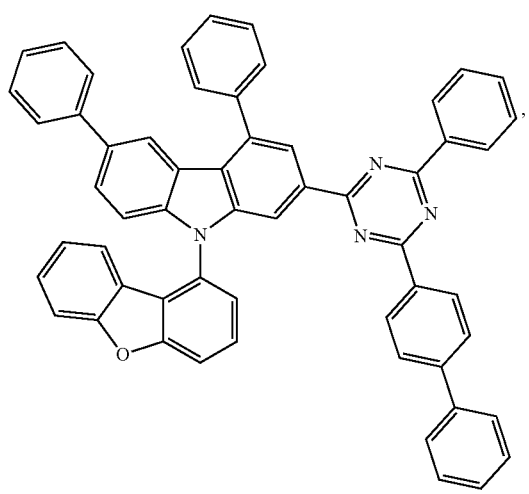
Compound 241
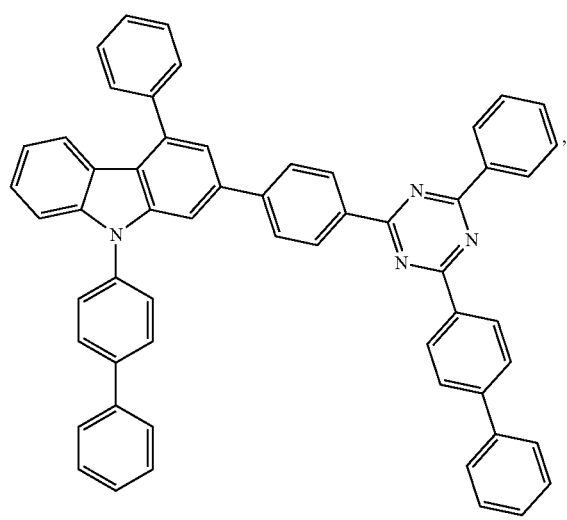

-continued
Compound 242
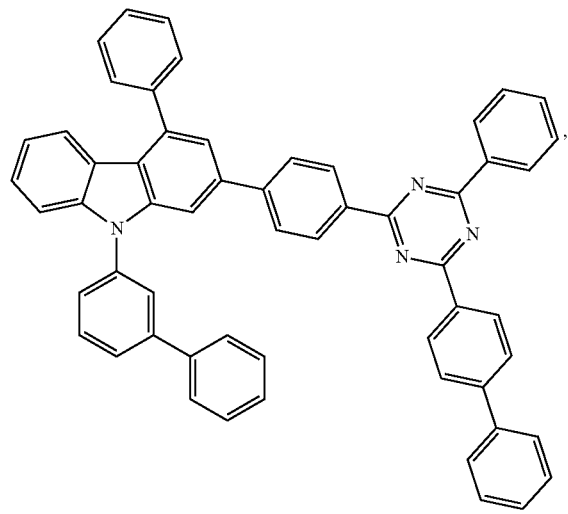
Compound 243
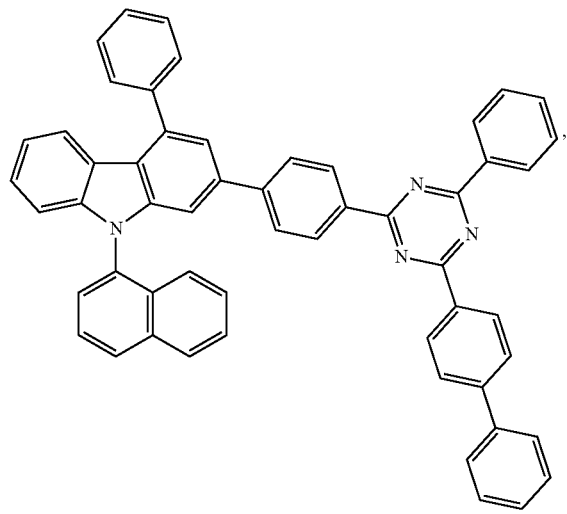
Compound 244
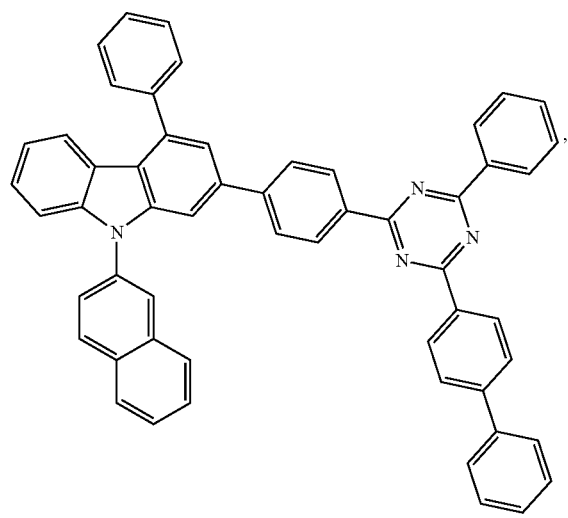
Compound 245
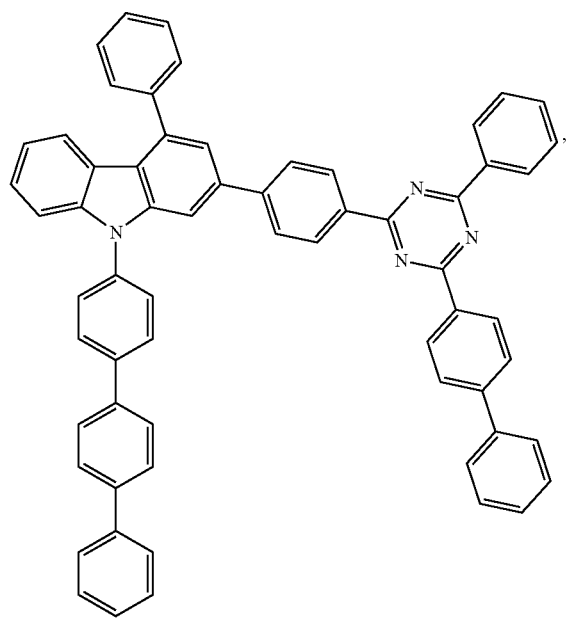

-continued
Compound 246
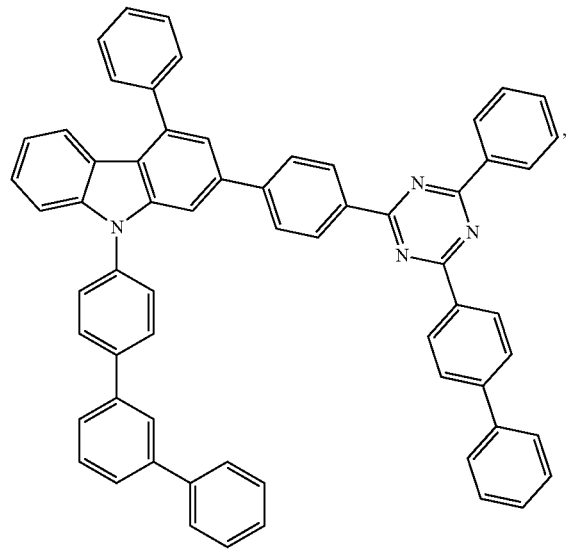
Compound 247
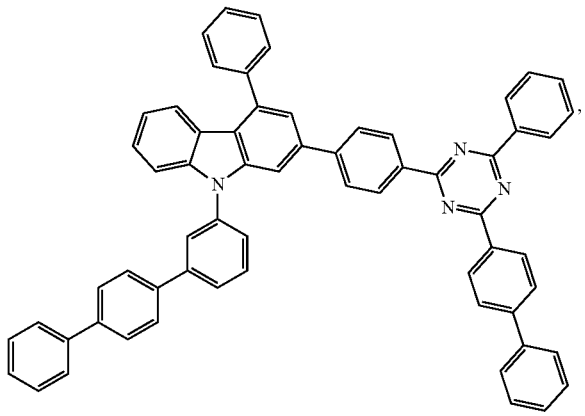
Compound 248
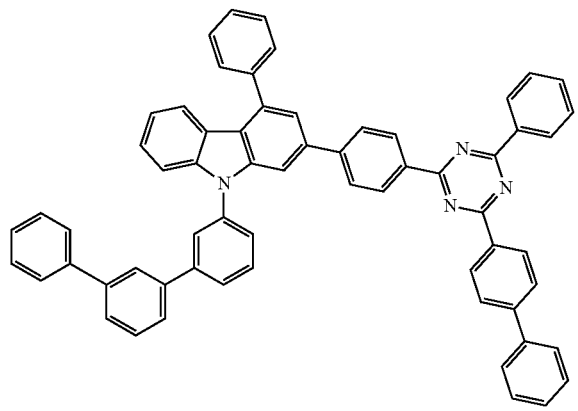
Compound 249
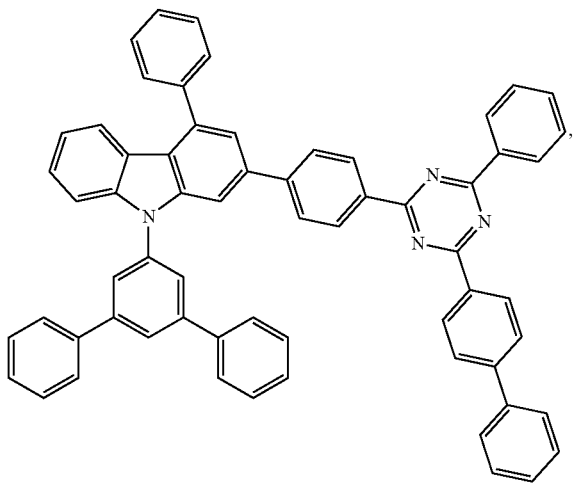
Compound 250
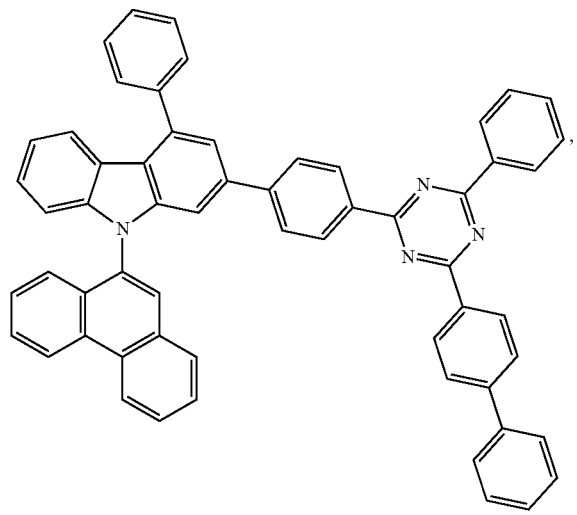
Compound 251
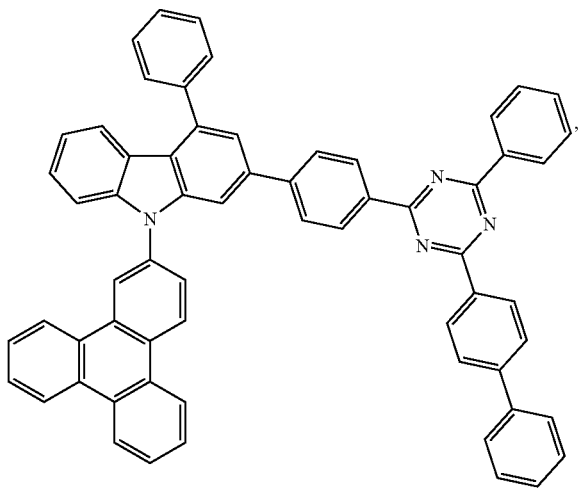

-continued
Compound 252
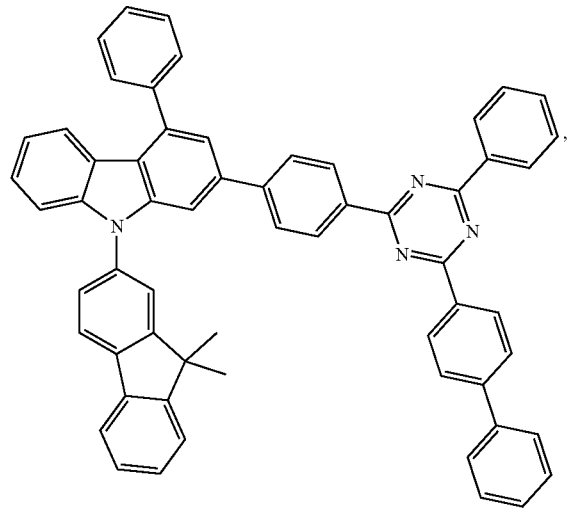
Comppound 253
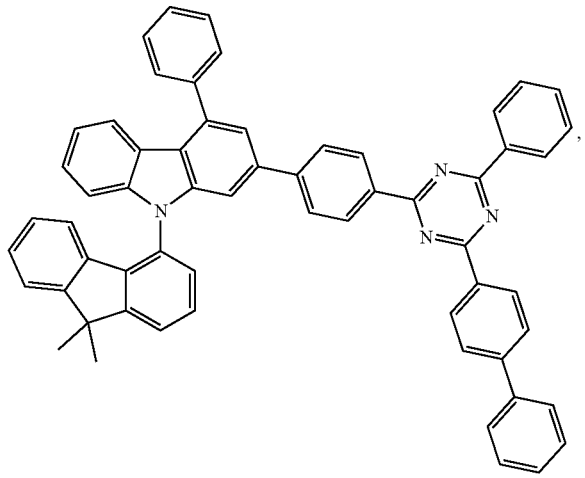
Compound 254
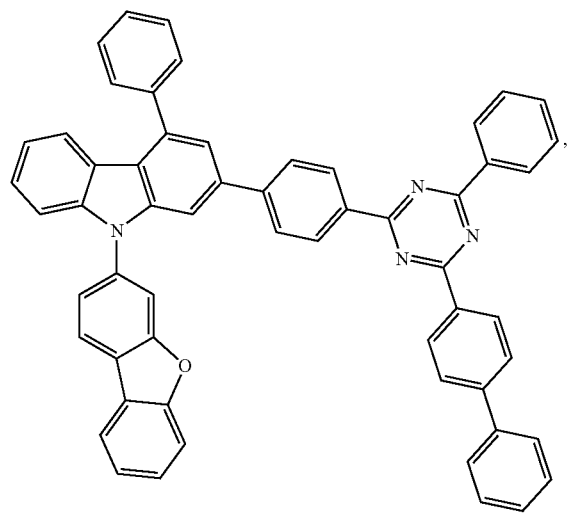
Compound 255
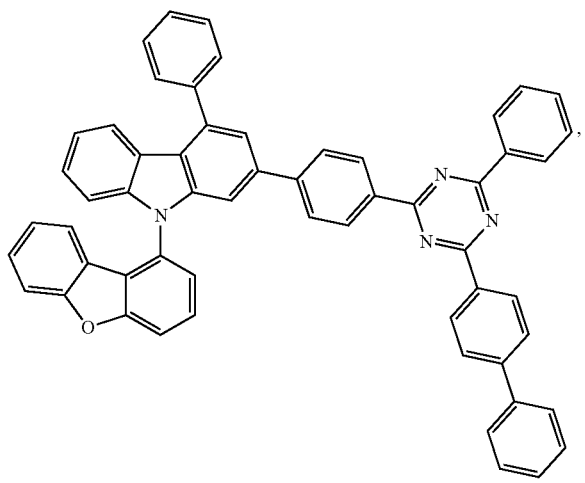
Compound 256
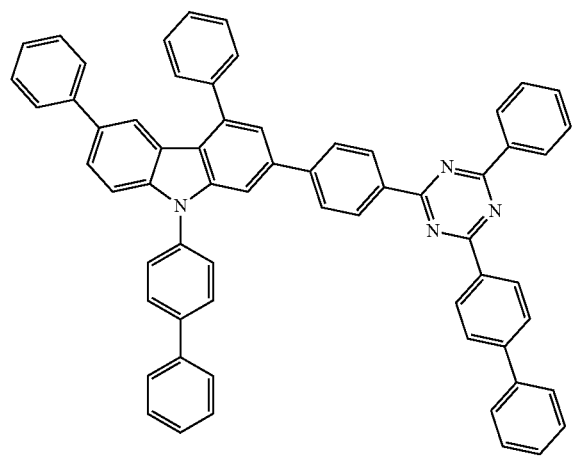
Compound 257
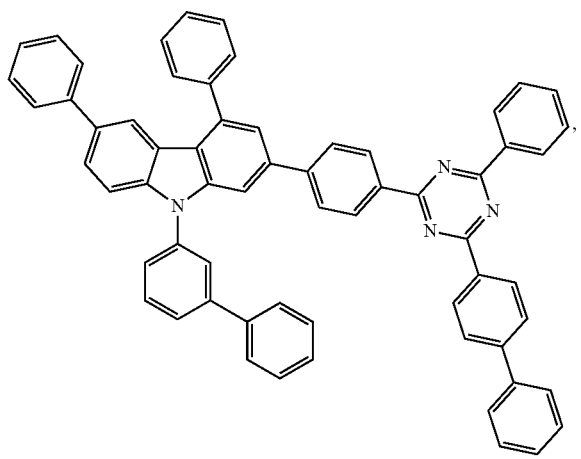

-continued
Compound 258
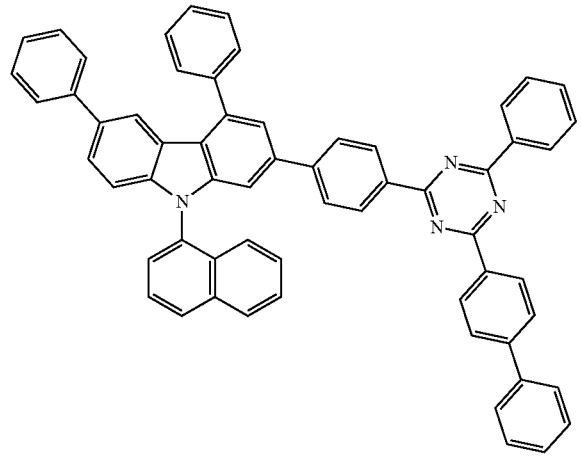
Compound 259
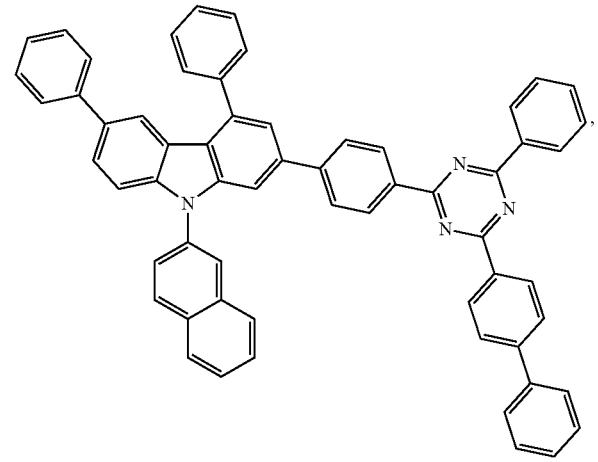
Compound 260
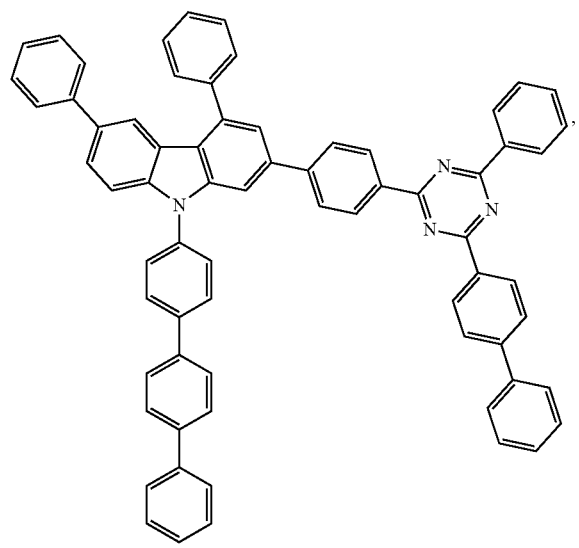
Compound 261
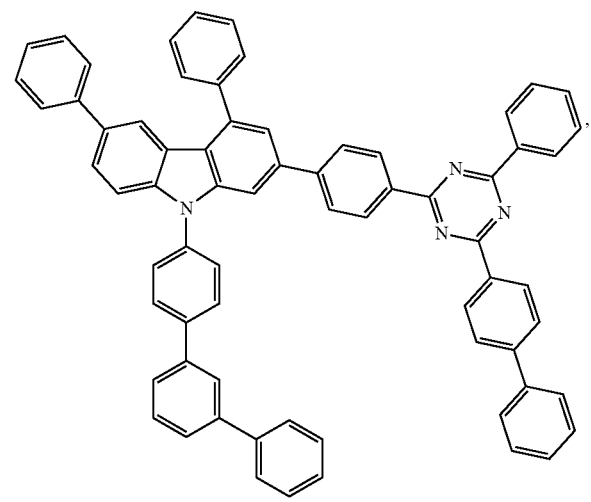
Compound 262
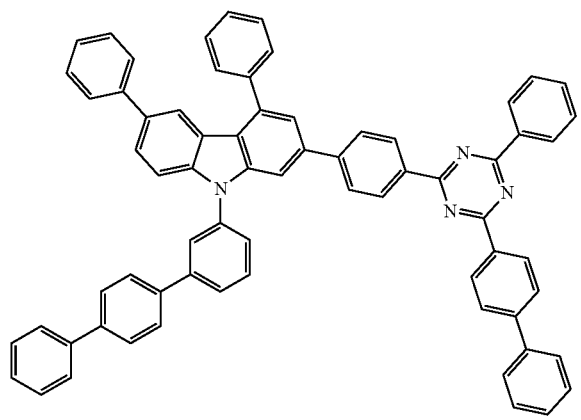
Compound 263
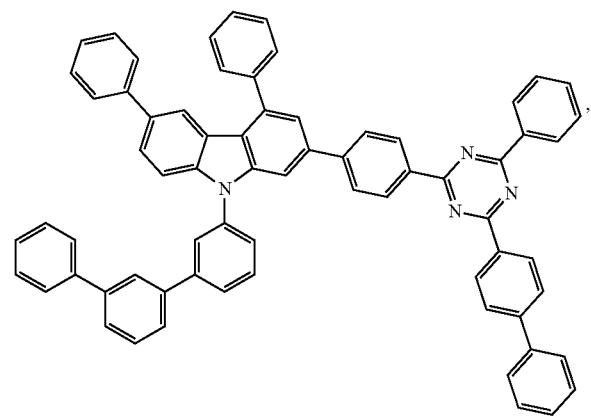

-continued
Compound 264
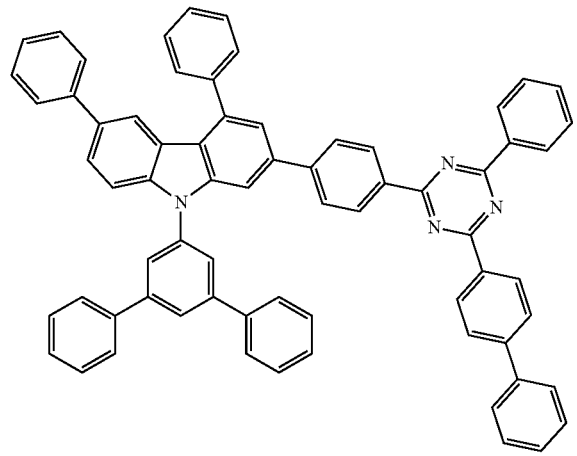
Compound 265
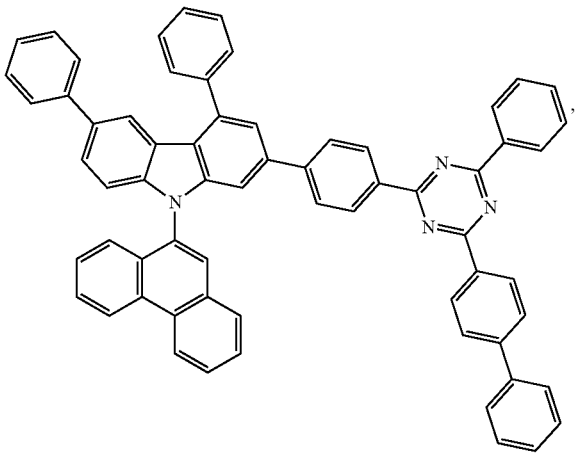
Compound 266
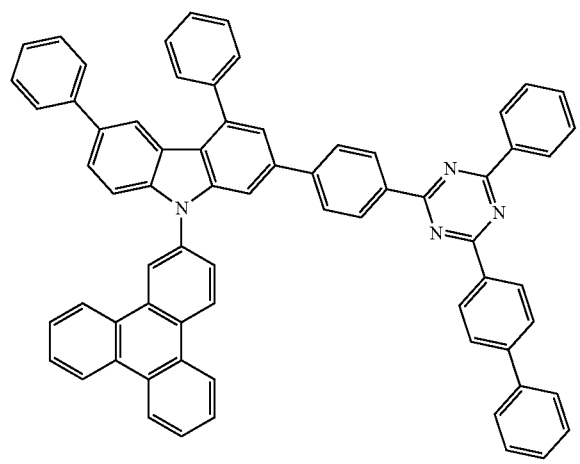
Compound 267
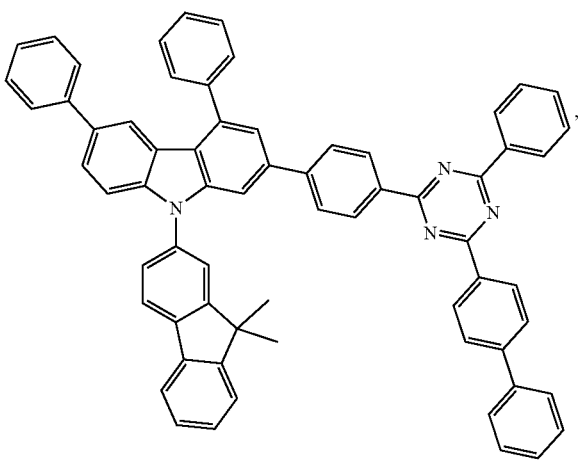
Compound 268
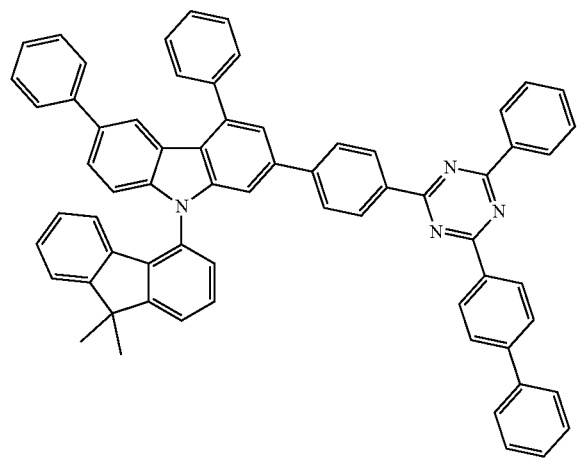
Compound 269
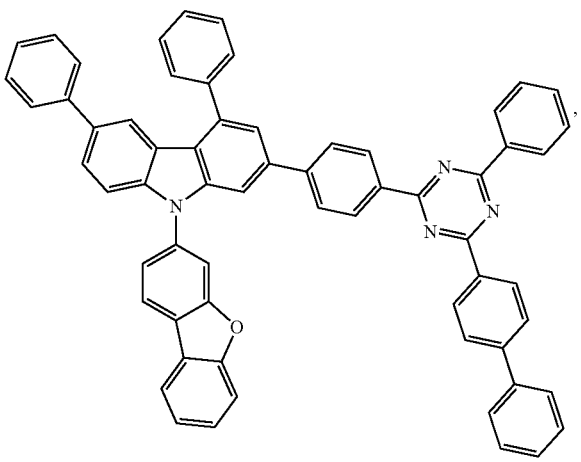

-continued

Compound 270

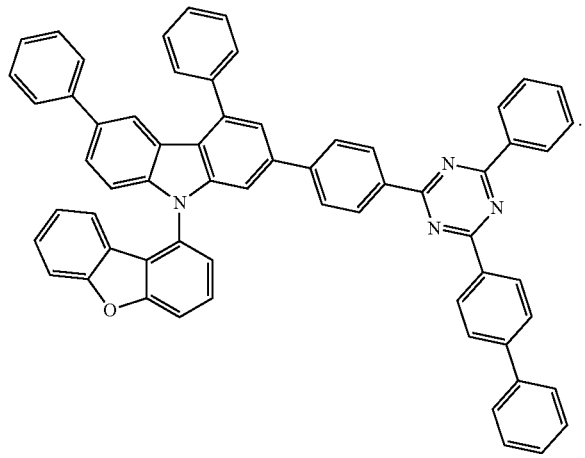

According to an embodiment of the present disclosure, wherein the hydrogen in the above-mentioned Compound 1 to Compound 270 can be partially or completely replaced by deuterium.

According to an embodiment of the present disclosure, an electroluminescent device is also disclosed, which comprises:
an anode,
a cathode,
and an organic layer disposed between the anode and the cathode, wherein the organic layer comprising the compound having the structure of Formula 1:

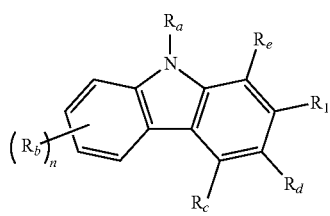

Formula 1 wherein $R_a$ is selected from biphenyl, terphenyl, naphthyl, phenanthryl, triphenylene, fluorenyl, dibenzofuranyl;

n is the number of $R_b$, n is selected from 1, 2, 3 or 4; when n≥2, the $R_b$ is selected from the same or different structures; each of $R_b$ is independently selected from the group consisting of: hydrogen, deuterium, phenyl, biphenyl and terphenyl;

$R_c$, $R_d$ and $R_e$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

and $R_1$ has the structure of Formula 2:

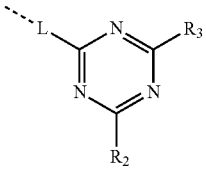

Formula 2

L is selected from a single bond, or a substituted or unsubstituted arylene having 6 to 60 carbon atoms;

$R_2$ and $R_3$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted aryl group having 6 to 30 carbon atoms, a substituted or unsubstituted alkylsilyl group having 3 to 20 carbon atoms, a substituted or unsubstituted arylsilyl group having 6 to 20 carbon atoms, and combinations thereof;

when $R_2$ and $R_3$ are selected from a substituted group in the group, the substitution in the substituted group is selected from deuterium, halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted arylalkyl group having 7 to 30 carbon atoms, an unsubstituted alkoxy group having 1 to 20 carbon atoms, an unsubstituted aryl group having 6 to 30 carbon atoms, and combinations thereof.

According to an embodiment of the present disclosure, wherein in the device, the organic layer is a light emitting layer, and the compound is a host material.

According to an embodiment of the present disclosure, wherein the organic layer is a hole blocking layer, and the compound is a hole blocking material.

According to an embodiment of the present disclosure, wherein in the device, the light emitting layer further comprises at least one host material different from the compound having Formula 1.

According to an embodiment of the present disclosure, wherein in the device, the light emitting layer further comprises phosphorescent material.

According to an embodiment of the present disclosure, wherein the phosphorescent material is a metal complex, the metal complex comprises at least one ligand, and the ligand comprises any one of the following structures:

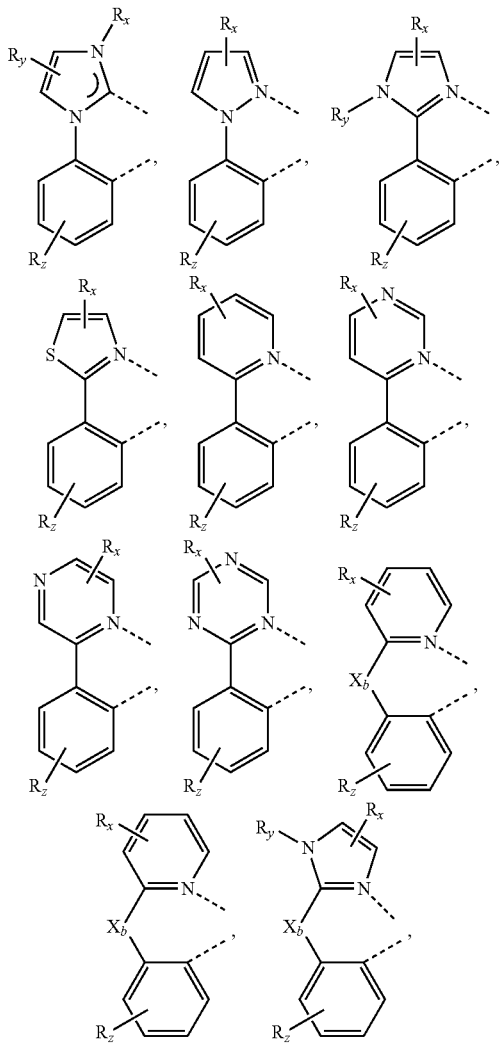

wherein $R_x$, $R_y$, and $R_z$ can represent mono substitution, multiple substitutions or no substitution;

$R_x$, $R_y$, and $R_z$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof;

$X_b$ is selected from the group consisting of O, S, Se, $NR_{N1}$, $CR_{C1}R_{C2}$;

$R_{N1}$, $R_{C1}$ and $R_{C2}$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a thioalkyl group, a sulfinyl group, a sulfonyl group, a phosphino group, and combinations thereof.

According to another embodiment of the present disclosure, a compound formulation comprising the compound represented by Formula 1 is further disclosed, the specific structure of the compound is described in any one of the embodiments aforementioned.

Combination with Other Materials

The materials described in the present disclosure for a particular layer in an organic light emitting device may be used in combination with various other materials present in the device. The combinations of these materials are described in more detail in U.S. Pat. App. No. 20160359122A1 at paragraphs 0132-0161, which is incorporated by reference herein in its entirety. The materials described or referred to the disclosure are non-limiting examples of materials that may be useful in combination with the materials disclosed herein, and one of skill in the art may readily consult the literature to identify other materials that may be useful in combination.

The materials described herein as useful for a particular layer in an organic light emitting device may be used in combination with a variety of other materials present in the device. For example, the compounds disclosed herein may be used in combination with a wide variety of emitting dopants, hosts, transporting layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the materials disclosed herein, and one of skill in the art may readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatography-mass spectrometer produced by SHIMADZU, gas chromatography-mass spectrometer produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this disclosure.

Synthesis Examples

The method for preparing the compound of the present invention is not limited. The following compounds are exemplified as a typical but non-limiting example, and the synthesis route and preparation method are as follows:

Synthesis Example 1: Synthesis of Compound 16

Step 1: Synthesis of Intermediate B

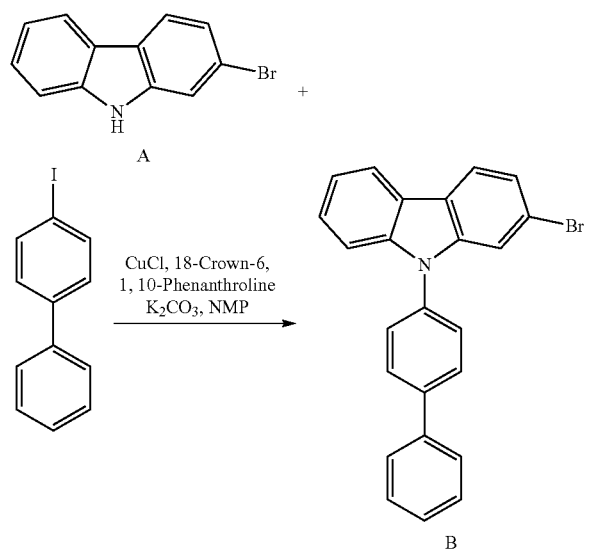

2-Bromo-carbazole (9.0 g, 36.57 mmol), 4-iodo-biphenyl (13.3 g, 47.54 mmol), CuCl (0.36 g, 3.66 mmol), 18-crown-6 (0.96 g, 3.66 mmol), 1,10-o-phenanthroline (0.66 g, 3.66 mmol), K₂CO₃ (12.63 g, 91.43 mmol) were added to N-methyl pyrrolidone (200 mL) in a three-necked round-bottomed flask, protected by nitrogen, and heated to 180° C., reacted overnight. The reaction solution was filtrated through celite, the filtrate was poured into a large amount of water, and extracted with DCM several times, dried over anhydrous Na₂SO₄, filtered, and rotary evaporated to dryness. Purified via silica gel column chromatography (PE/DCM=40:1) to give intermediate B (9.7 g, 24.36 mmol) as a white solid with a yield of 66.6%.

Step 2: Synthesis of Intermediate C

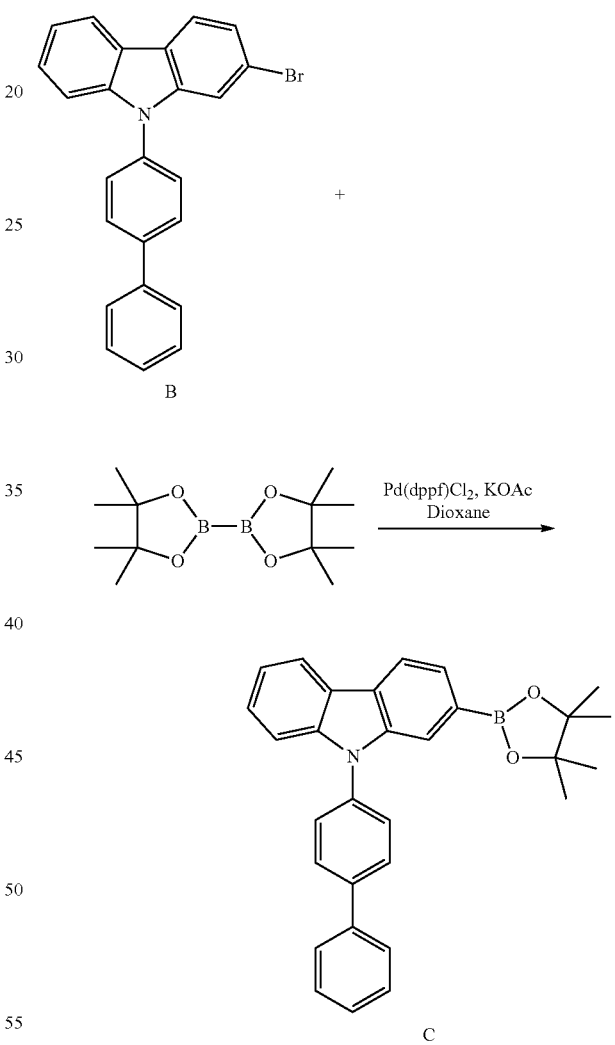

Intermediate B (9.7 g, 24.36 mmol), bis(pinacolato)diboron (12.37 g, 48.72 mmol), Pd(dppf)Cl₂ (0.53 g, 0.73 mmol), KOAc (4.68 g, 48.72 mmol) were added to 1,4-dioxane (120 mL) in a three-necked round bottom flask, protected by nitrogen, and heated to reflux overnight. Heating was stopped, the reaction was cooled to room temperature, filtered through celite, and the filtrate was rotary evaporated to dryness. The residue was purified via silica gel column chromatography (PE/DCM=2:1) to obtain a white solid intermediate C (6.1 g, 13.70 mmol) with a yield of 56.2%.

Step 3: Synthesis of Compound 16

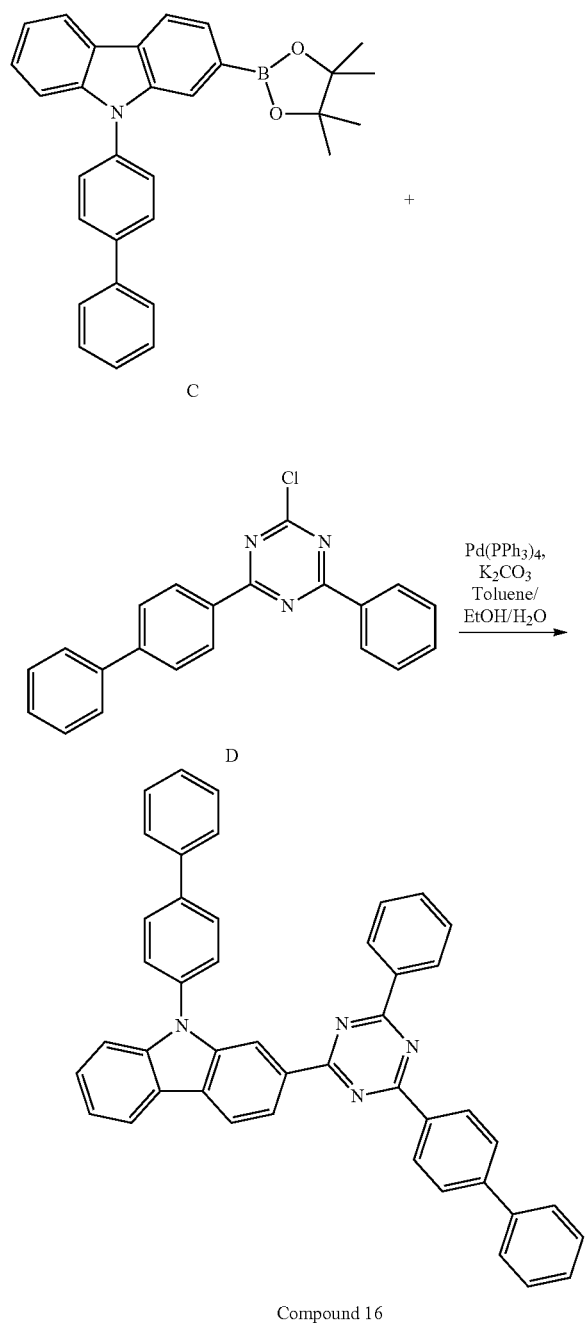

Compound 16

Intermediate C (4.6 g, 10.33 mmol), intermediate D (3.91 g, 11.36 mmol), Pd(PPh$_3$)$_4$ (0.60 g, 0.52 mmol), K$_2$CO$_3$ (2.86 g, 20.66 mmol) were added to toluene (48 mL), EtOH (12 mL), H$_2$O (12 mL) in a three-necked round bottom flask, protected by nitrogen, and heated to reflux overnight. Heating was stopped and the reaction was cooled to room temperature. The reaction was suctioned under reduced pressure, and the solid was sequentially washed with water and methanol several times. The solid was recrystallized from toluene to obtain Compound 16 (5.5 g, 8.78 mmol) as a white solid in a yield of 84.9%. The product was identified as the target product with a molecular weight of 627.

Synthesis Example 2: Synthesis of Compound 19

Step 1: Synthesis of Intermediate F

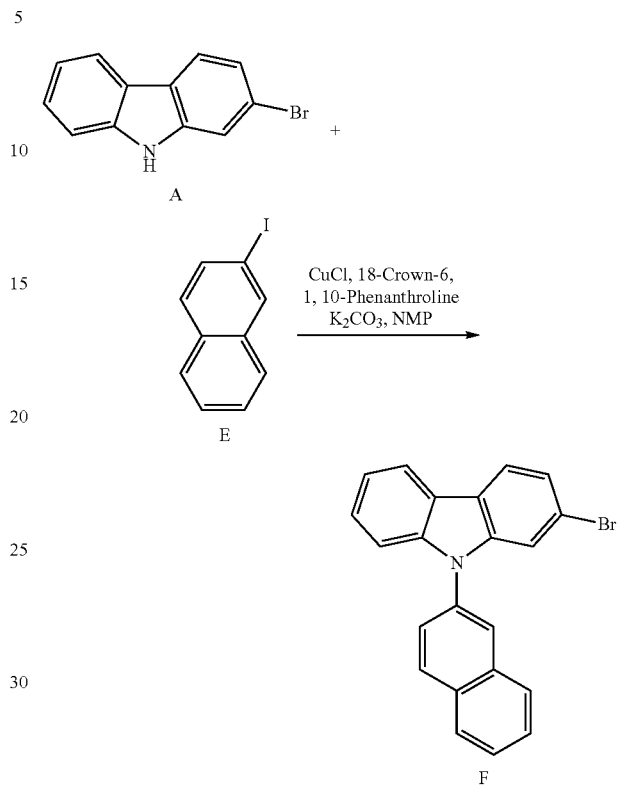

2-Bromo-carbazole (8.24 g, 33.46 mmol), 2-iodo-naphthalene (11.05 g, 43.5 mmol), CuCl (0.33 g, 3.35 mmol), 18-crown-6 (0.88 g, 3.35 mmol), 1,10-o-phenanthroline (0.60 g, 3.35 mmol), K$_2$CO$_3$ (11.56 g, 83.65 mmol) were added to N-methyl pyrrolidone (190 mL) in a three-neck round bottom flask, protected by nitrogen, heated to 180° C., and reacted overnight. Heating was stopped and the reaction was cooled to room temperature. The reaction solution was filtered through celite. The filtrate was poured into a large amount of water, extracted with DCM several times, dried over anhydrous Na$_2$SO$_4$, filtered and rotary evaporated to dryness. Purified via silica gel column chromatography (PE/DCM=50:1) to give intermediate F (11.0 g, 29.55 mmol) as a white solid with a yield of 88.3%.

Step 2: Synthesis of Intermediate G

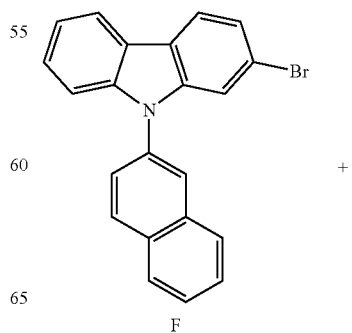

F

-continued

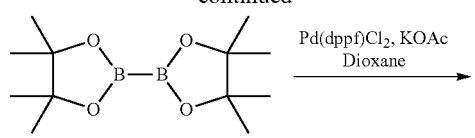

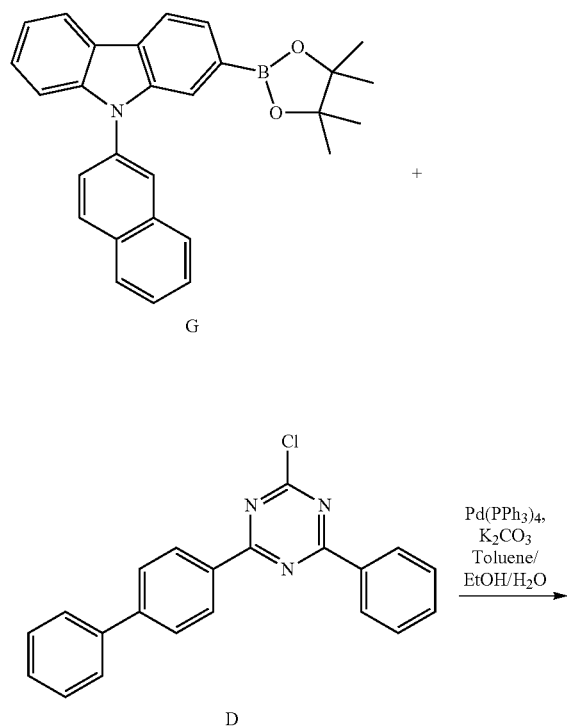

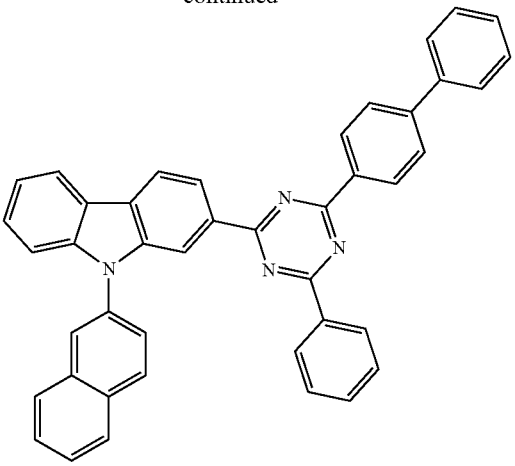

Compound 19

Intermediate F (11.0 g, 29.54 mmol), bis(pinacolato) diboron (11.25 g, 44.31 mmol), Pd(dppf)Cl₂ (0.65 g, 0.89 mmol), KOAc (5.8 g, 59.08 mmol) were added to 1,4-dioxane (130 mL) in a three-neck round bottom flask, protected by nitrogen, and heated to reflux overnight. Heating was stopped, and the reaction was cooled to room temperature, filtered through celite, and the filtrate was rotary evaporated to dryness. The residue was purified via silica gel column chromatography (PE/DCM=2:1) to obtain white solid intermediate G (8.7 g, 20.75 mmol) with a yield of 70.2%.

Step 3: Synthesis of Compound 19

Intermediate G (5.87 g, 14.0 mmol), intermediate D (5.29 g, 15.4 mmol), Pd(PPh₃)₄ (0.65 g, 0.56 mmol), K₂CO₃ (3.87 g, 28.0 mmol) were added to toluene (60 mL), EtOH (15 mL), H₂O (15 mL) in a three-necked round bottom flask, protected by nitrogen, and heated to reflux overnight. Heating was stopped and the reaction was cooled to room temperature. The reaction was suctioned under reduced pressure, and the solid was sequentially washed with water and methanol several times. The solid was recrystallized from toluene to obtain Compound 19 (6.7 g, 11.15 mmol) as a white solid in a yield of 79.7%. The product was identified as the target product with a molecular weight of 601.

The persons skilled in the art should know that the above preparation method is only an illustrative example, and the persons skilled in the art can obtain the structure of other compounds of the present invention by modifying the above preparation method.

Device Example 1

A glass substrate with an 80 nm thick of indium tin oxide (ITO) electrode was cleaned and subjected to UV ozone and oxygen plasma treatment. After the treatments, the substrate was dried in a glovebox to remove moisture, the substrate was then mounted on a substrate holder and loaded into a vacuum chamber. The organic layers specified below were deposited in sequence by thermal vacuum deposition on the ITO anode at a rate of 0.2-2 Å/s under a vacuum degree of around $10^{-8}$ torr. Compound HI was used as the hole injection layer (HIL). Compound HT was used as the hole transporting layer (HTL). Compound H1 was used as the electron blocking layer (EBL). Then the Compound GD was then doped in Compound H1 and Compound H2 be co-deposited as the emitting layer (EML). Compound 16 of the present disclosure was used as the hole blocking layer (HBL). On HBL, Compound ET and 8-hydroxyquinolino-lato-lithium (Liq) were co-deposition as an electron transporting layer (ETL). Finally, 1 nm-thick 8-hydroxyquino-linolato-lithium (Liq) was deposited as the electron injection layer (EIL) and 120 nm of Al was deposited as the cathode. Then, the device was transferred back to the glovebox and encapsulated with a glass lid and a moisture getter to complete the device.

Device Example 2

Device Example 2 was fabricated in the same manner as in Device Example 1, except that using Compound 19 of the present disclosure instead of Compound 16 of the present disclosure as the hole blocking layer (HBL).

Comparative Example 1

Comparative Example 1 was fabricated in the same manner as in Device Example 1, except that using Compound H2 instead of Compound 16 of the present disclosure as the hole blocking layer (HBL).

Comparative Example 2

Comparative Example 2 was fabricated in the same manner as in Device Example 1, except that using Compound H3 instead of Compound 16 of the present disclosure as the hole blocking layer (HBL).

Comparative Example 3

Comparative Example 3 was fabricated in the same manner as in Device Example 1, except that using compound H4 instead of Compound 16 of the present disclosure as the hole blocking layer (HBL).

Device Example 3

Device Example 3 was fabricated in the same manner as in Comparative Example 1, except that using Compound 16 instead of Compound H2 in the emitting layer (EML).

Comparative Example 4

Comparative Example 4 was fabricated in the same manner as in Comparative Example 1, except that using the Compound H3 instead of Compound H2 in the emitting layer (EML).

Comparative Example 5

Comparative Example 5 was fabricated in the same manner as in Comparative Example 1, except that using the Compound H4 instead of Compound H2 in the emitting layer (EML).

The detailed partial structures of devices and thicknesses are shown in the following table. In the layers in which more than one material were used, they were obtained by doping different compounds in the weight ratios described therein.

TABLE 1

Device Structure

| Device ID | HIL | HTL | EBL | EML | HBL | ETL |
|---|---|---|---|---|---|---|
| Device Example 1 | Compound HI (100 Å) | Compound HT (350 Å) | Compound H1 (50 Å) | Compound H1:Compound H2:Compound GD (45:45:10) (400 Å) | Compound 16 (100 Å) | Compound ET:Liq (40:60) (350 Å) |
| Device Example 2 | Compound HI (100 Å) | Compound HT (350 Å) | Compound H1 (50 Å) | Compound H1:Compound H2:Compound GD (45:45:10) (400 Å) | Compound 19 (100 Å) | Compound ET:Liq (40:60) (350 Å) |
| Comparative Example 1 | Compound HI (100 Å) | Compound HT (350 Å) | Compound H1 (50 Å) | Compound H1:Compound H2:Compound GD (45:45:10) (400 Å) | Compound H2 (100 Å) | Compound ET:Liq (40:60) (350 Å) |
| Comparative Example 2 | Compound HI (100 Å) | Compound HT (350 Å) | Compound H1 (50 Å) | Compound H1:Compound H2:Compound GD (45:45:10) (400 Å) | Compound H3 (100 Å) | Compound ET:Liq (40:60) (350 Å) |
| Comparative Example 3 | Compound HI (100 Å) | Compound HT (350 Å) | Compound H1 (50 Å) | Compound H1:Compound H2:Compound GD (45:45:10) (400 Å) | Compound H4 (100 Å) | Compound ET:Liq (40:60) (350 Å) |
| Device Example 3 | Compound HI (100 Å) | Compound HT (350 Å) | Compound H1 (50 Å) | Compound H1:Compound 16:Compound GD (45:45:10) (400 Å) | Compound H2 (100 Å) | Compound ET:Liq (40:60) (350 Å) |
| Comparative Example 4 | Compound HI (100 Å) | Compound HT (350 Å) | Compound H1 (50 Å) | Compound H1:Compound H3:Compound GD (45:45:10) (400 Å) | Compound H2 (100 Å) | Compound ET:Liq (40:60) (350 Å) |
| Comparative Example 5 | Compound HI (100 Å) | Compound HT (350 Å) | Compound H1 (50 Å) | Compound H1:Compound H4:Compound GD (45:45:10) (400 Å) | Compound H2 (100 Å) | Compound ET: Liq (40:60) (350 Å) |

Structure of the materials used in the devices are shown as below:
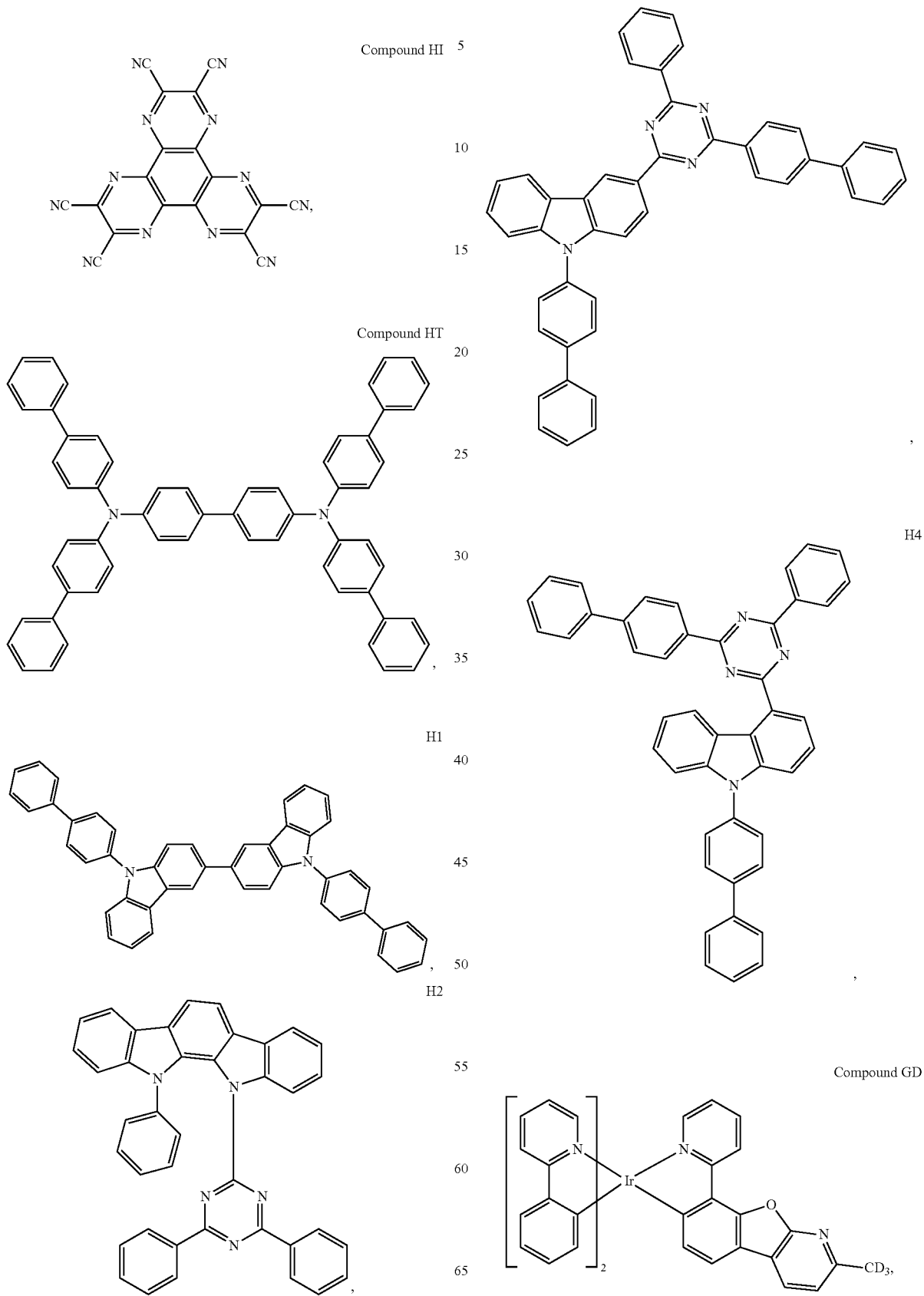

-continued

Compound ET

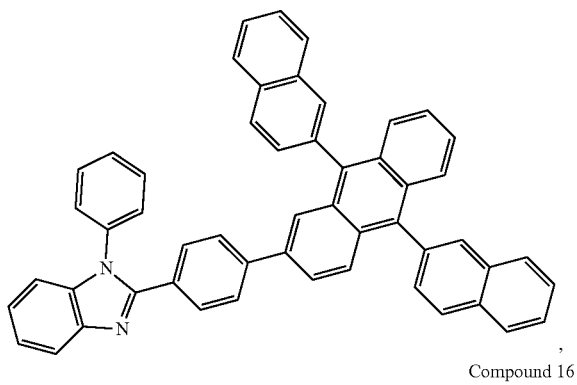

Compound 16

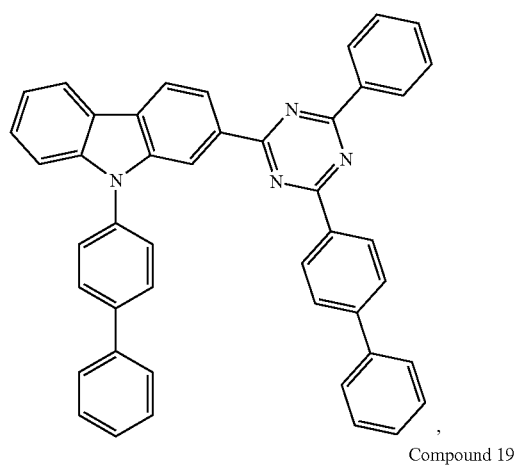

Compound 19

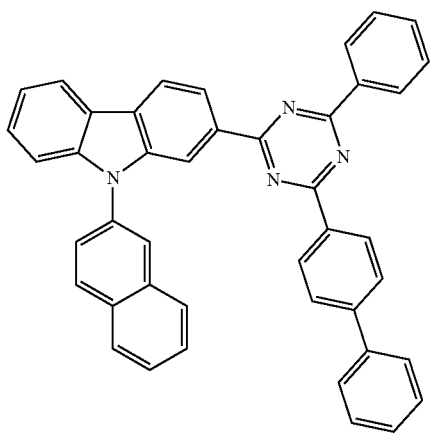

Device Examples 1-2 show the use of the material of the present disclosure in the hole blocking layer. At 1000 nits, the driving voltage of Device Example 1 was 2.78 V, the power efficiency was 103 lm/W, the maximum wavelength was 528 nm, and the CIE was 0.345, 0.627. The driving voltage of Example 2 was 2.81 V, the power efficiency was 103 lm/W, the maximum wavelength was 528 nm, and the CIE was 0.344, 0.628. The driving voltage of Comparative Example 1 was 2.94 V, the power efficiency was 95 lm/W, the maximum wavelength was 527 nm, and the CIE was 0.332 and 0.637. The driving voltage of Comparative Example 2 was 2.97 V, the power efficiency was 99 lm/W, the maximum wavelength was 528 nm, and the CIE was 0.344, 0.628. The driving voltage of Comparative Example 3 was 2.96 V, the power efficiency was 98 lm/W, the maximum wavelength was 528 nm, and the CIE was 0.342, 0.629. The above data shows that the emitting light of Device Examples 1-2 and Comparative Examples 1-3 are very close, but the power efficiency of Device Examples 1-2 are higher than that of Comparative Examples 1-3, and the driving voltage of Device Examples 1-2 are all lower than Examples 1-3. Especially in Device Example 1, the driving voltage is 2.78 V, which is very low.

Device Example 3 shows the use of the material of the present invention as a host material in the light emitting layer. The test was performed at a constant current of 15 mA/cm$^2$. The efficiency and driving voltage of Device Example 3 and Comparative Example 1 and Comparative Examples 4-5 were basically equivalent, but the lifetime of LT97 were respectively 335 h, 310 h, 222.6 h, and 254.5 h.

The above data proves the structural characteristics of the compound of the present invention. The compound can be used as the hole blocking layer or a host material in the light-emitting layer by connecting a specific structure such as Formula 2 at a specific position of the carbazole ring in Formula 1, with specific selected substituents, which can improve the lifetime and efficiency of the device, reduce the driving voltage, and have important help to the industry.

It is understood that the various embodiments described herein are by way of example only, and are not intended to limit the scope of the disclosure. The present disclosure as claimed may therefore include variations from the particular examples and preferred embodiments described herein, as will be apparent to one of skill in the art. Many of the materials and structures described herein may be substituted with other materials and structures without deviating from the spirit of the present disclosure. It is understood that various theories as to why the disclosure works are not intended to be limiting.

What is claimed is:

1. A compound having the structure of Formula 1:

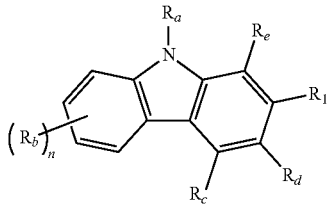

Formula 1 wherein $R_a$ is selected from biphenyl, terphenyl, naphthyl, phenanthryl, triphenylene, or fluorenyl;

n is the number of $R_b$, n is selected from 1, 2, 3 or 4; when n≥2, the structures of the $R_b$ may be the same or different; each of $R_b$ is independently selected from the group consisting of hydrogen, deuterium, phenyl, biphenyl and terphenyl;

$R_c$, $R_d$ and $R_e$ are each independently selected from the group consisting of hydrogen, deuterium, halogen, a substituted or unsubstituted aryl group having 6 to 30 carbon atoms, a substituted or unsubstituted heteroaryl group having 3 to 30 carbon atoms, and combinations thereof;

and, wherein $R_1$ has the structure of Formula 2:

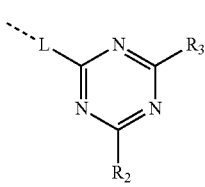

Formula 2 wherein L is selected from a single bond, or a substituted or unsubstituted arylene having 6 to 12 carbon atoms;
wherein $R_2$ and $R_3$ are each independently selected from a substituted or unsubstituted aryl group having 6 to 30 carbon atoms;
when $R_2$ and $R_3$ are selected from the substituted group in the group, the substitution in the substituted group is selected from deuterium, halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted arylalkyl group having 7 to 30 carbon atoms, an unsubstituted alkoxy group having 1 to 20 carbon atoms, an unsubstituted aryl group having 6 to 30 carbon atoms, and combinations thereof;
wherein at least one of $R_2$ and $R_3$ is biphenyl or terphenyl.

2. The compound of claim 1, wherein at least one of $R_2$ and $R_3$ is biphenyl or terphenyl, and the other one is phenyl, biphenyl or terphenyl.

3. The compound of claim 1, wherein L is a single bond.

4. The compound of claim 2, wherein L is a single bond.

5. The compound of claim 1, wherein $R_b$ is hydrogen.

6. The compound of claim 1, wherein $R_c$, $R_d$ and $R_e$ are hydrogen.

7. The compound of claim 1, wherein the compound is selected from the group consisting of:

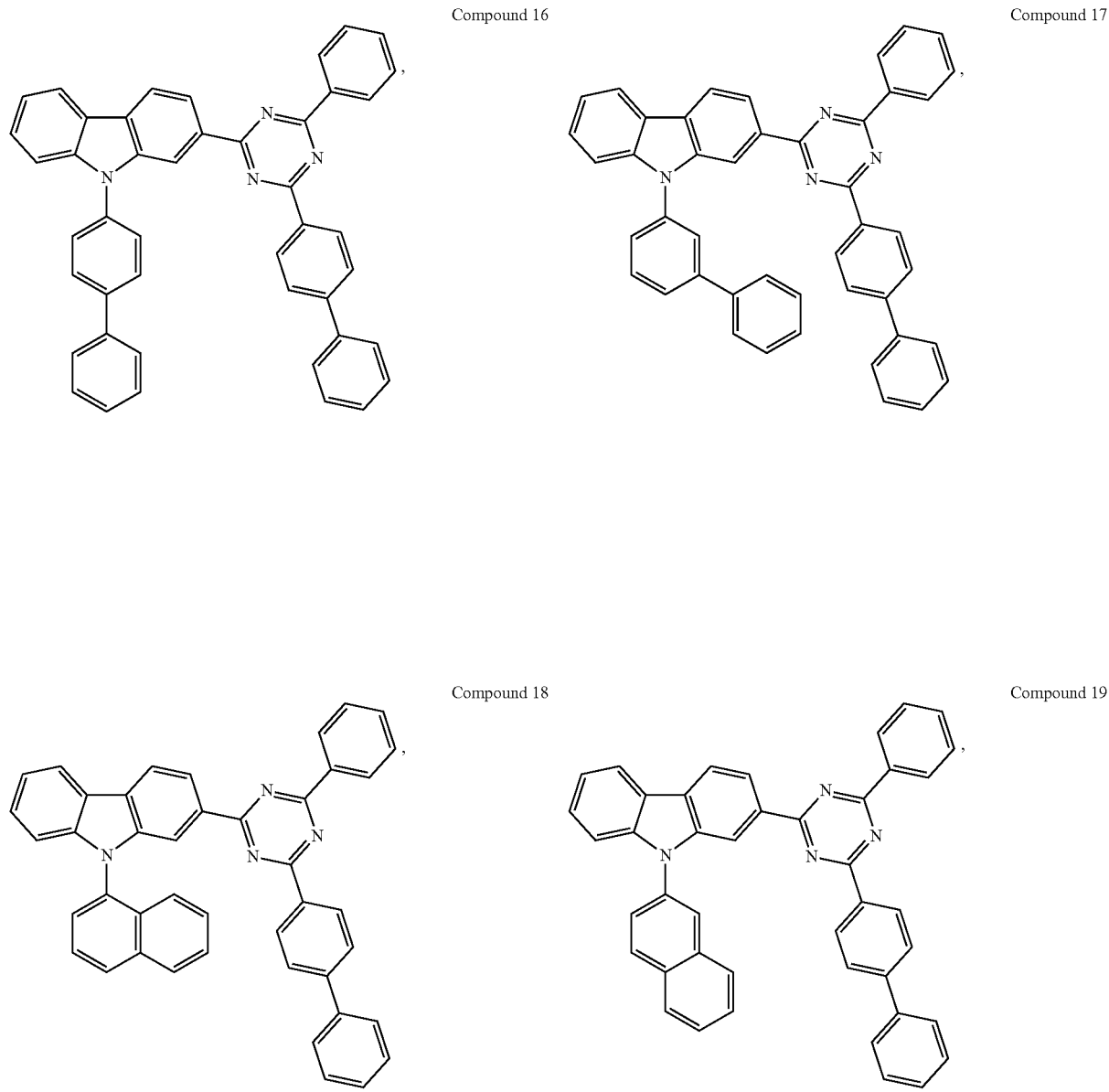

-continued
Compound 20
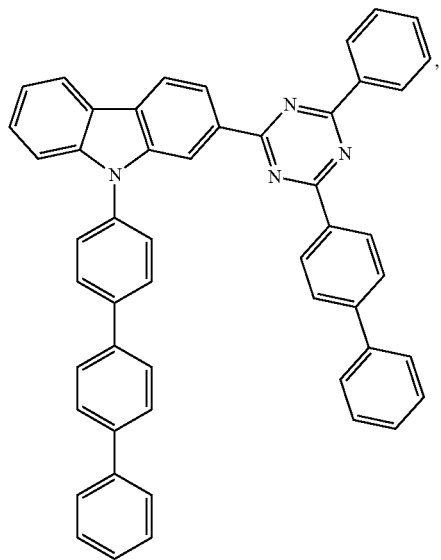
Compound 21
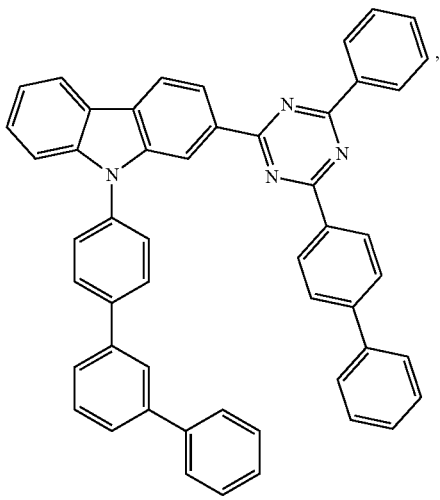
Compound 22
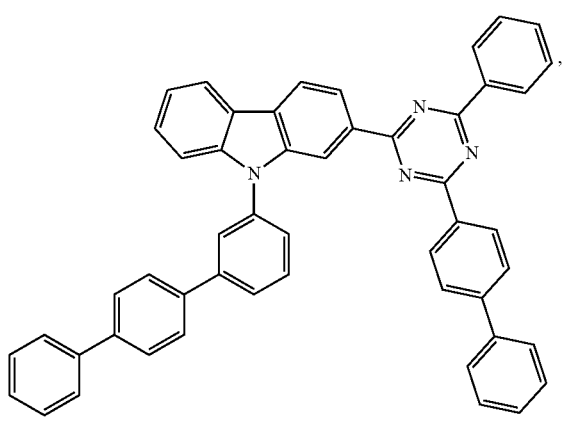
Compound 23
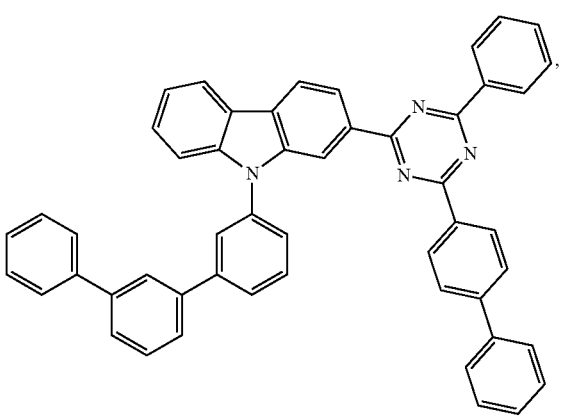
Compound 24
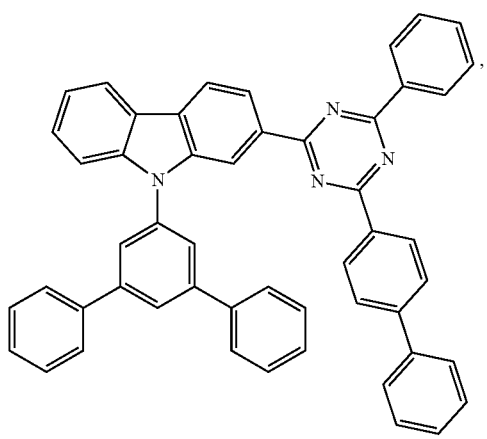
Compound 25
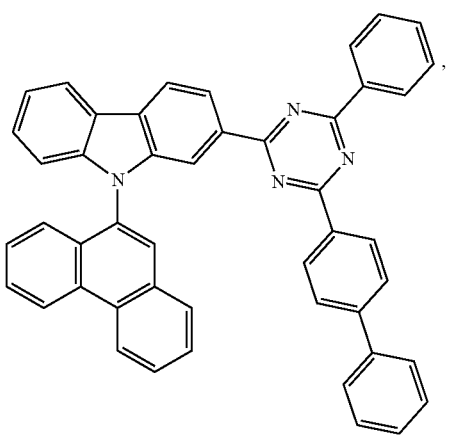

-continued
Compound 26
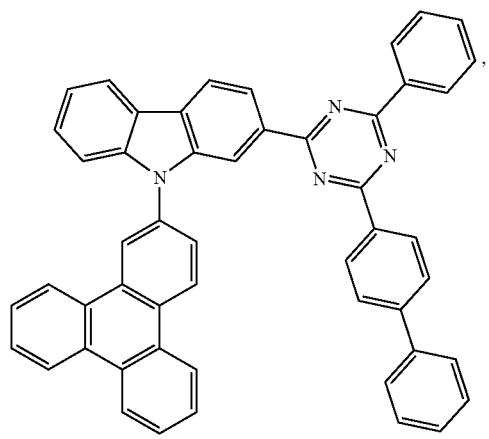
Compound 27
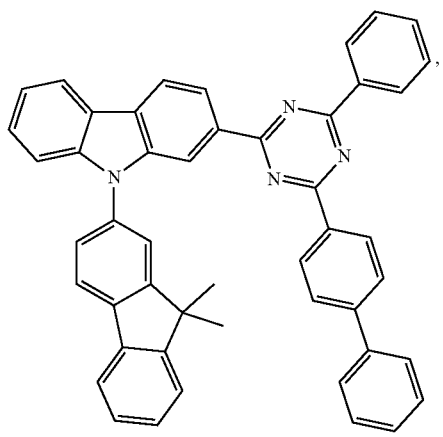
Compound 28
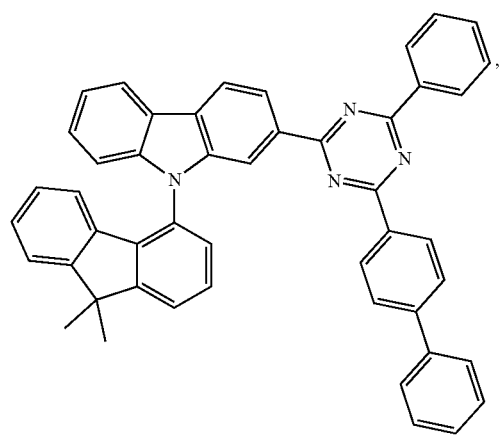
Compound 31
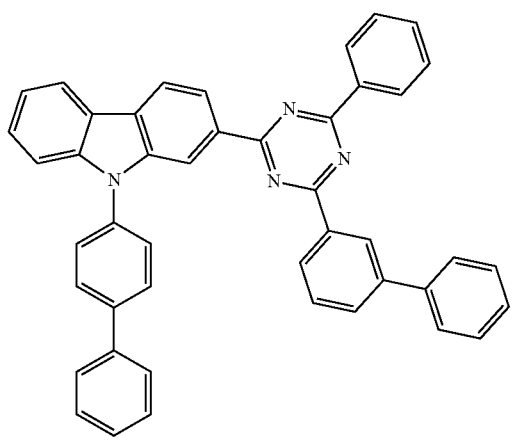
Compound 32
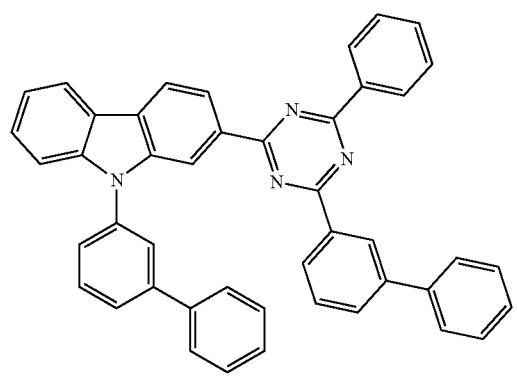
Compound 33
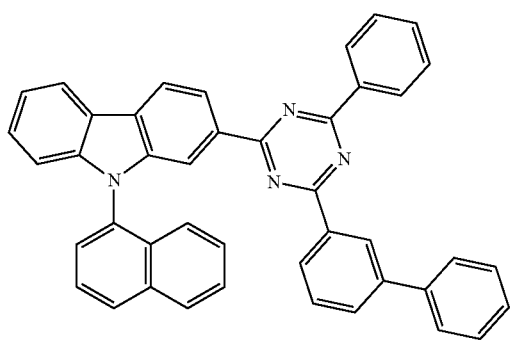

-continued
Compound 34
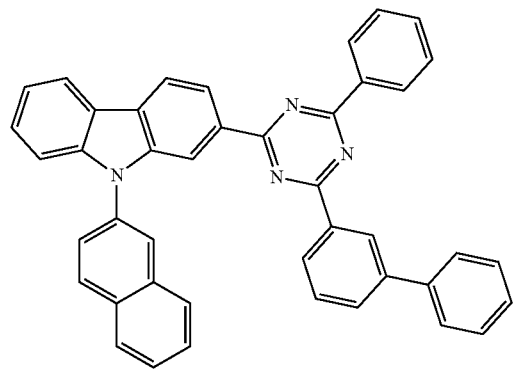
Compound 35
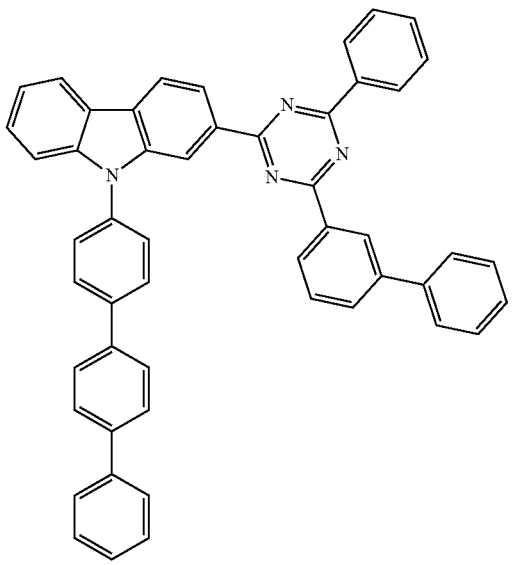
Compound 36
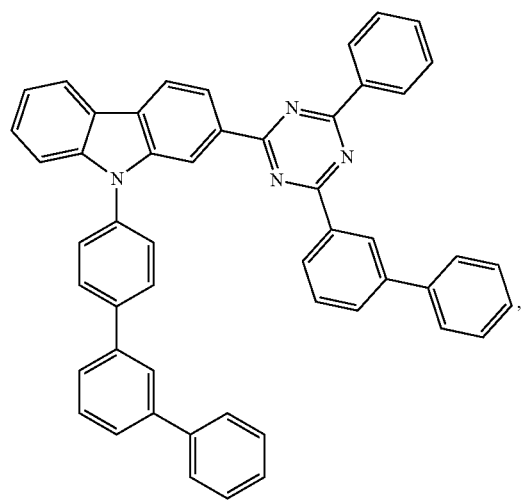
Compound 37
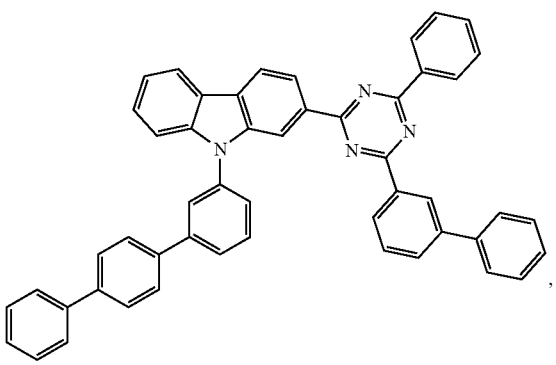
Compound 38
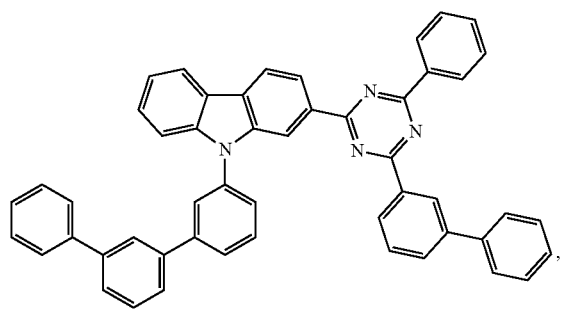
Compound 39
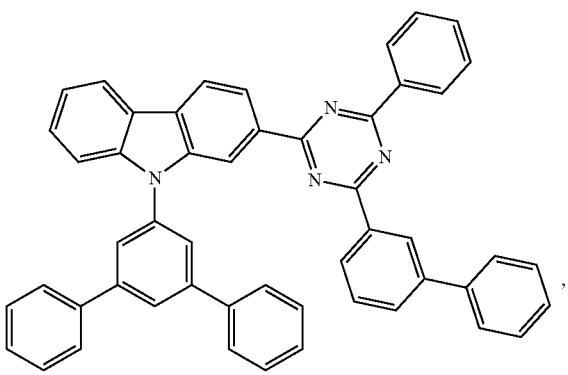

-continued
Compound 40
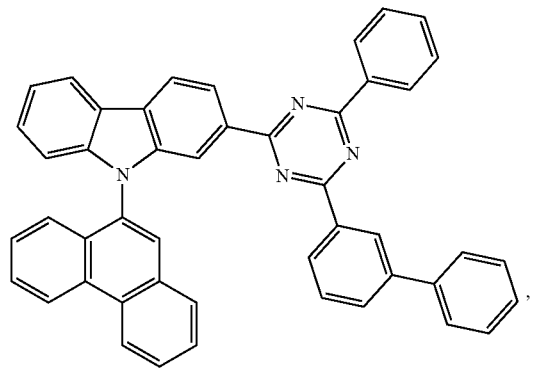
Compound 41
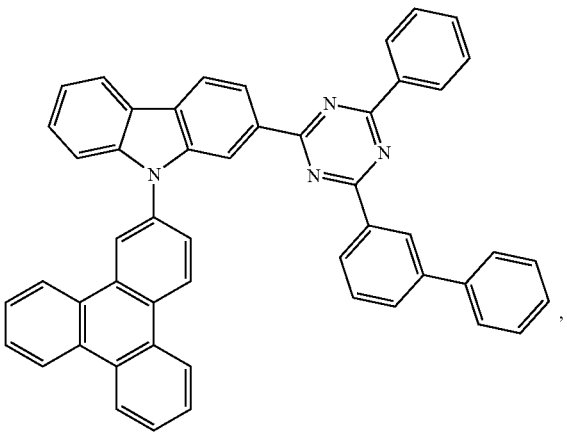
Compound 42
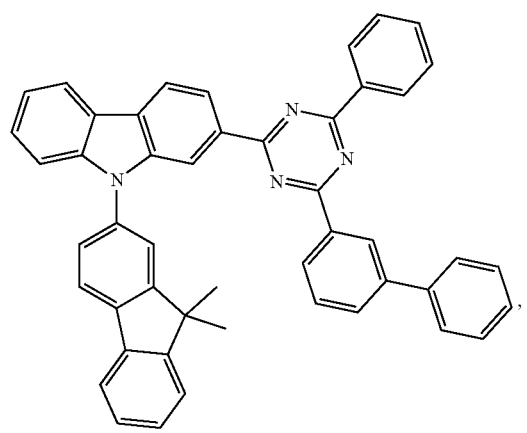
Compound 43
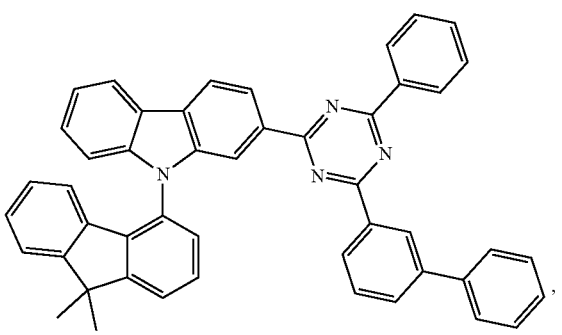
Compound 46
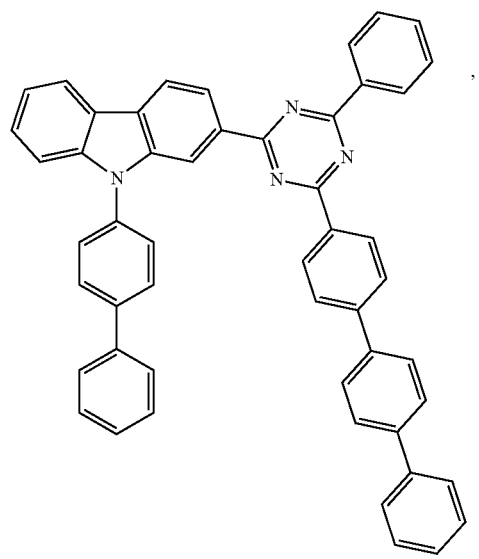
Compound 47
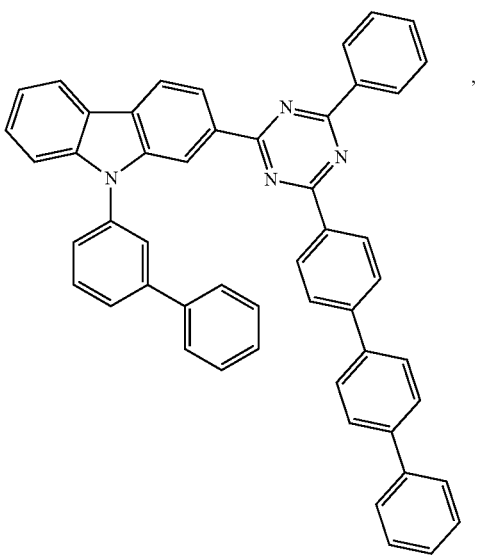

Compound 48
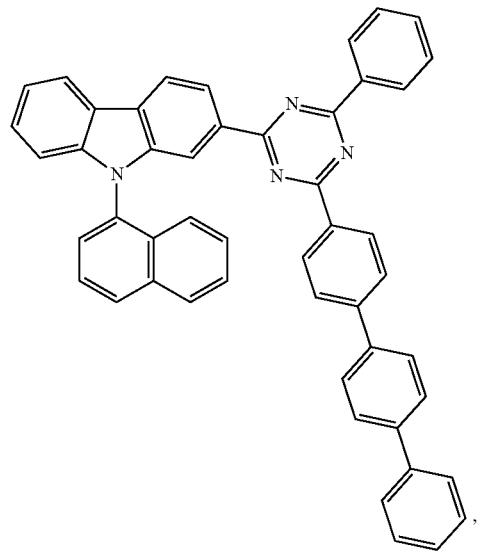
Compound 49
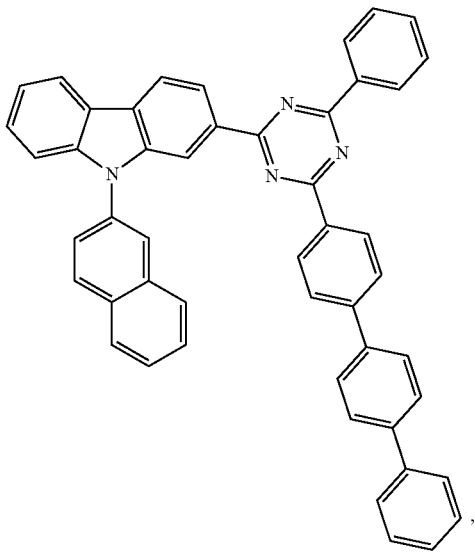
Compound 50
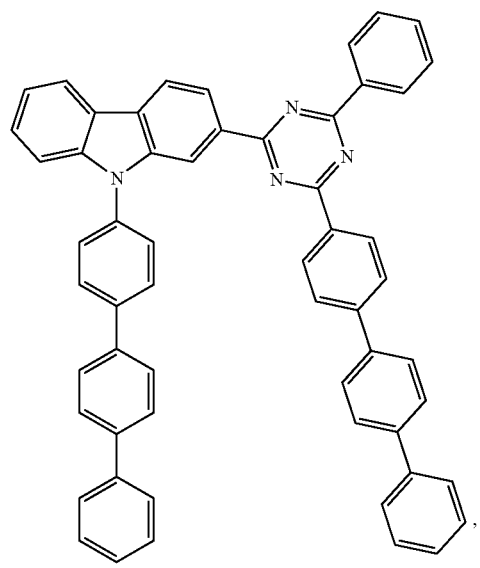
Compound 51
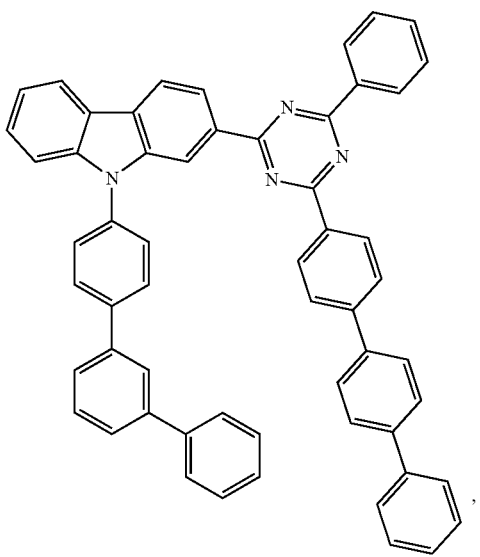
Compound 52
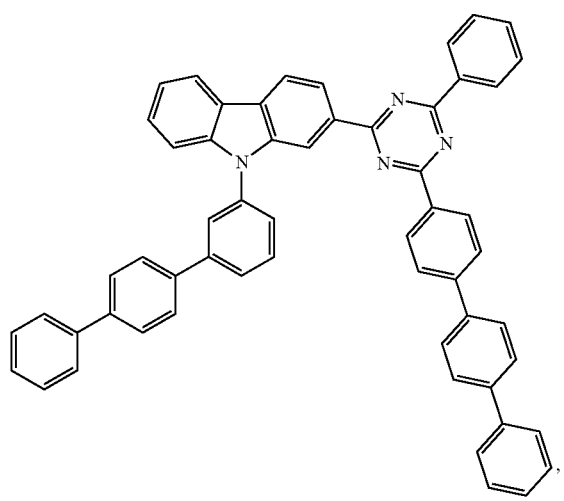
Compound 53
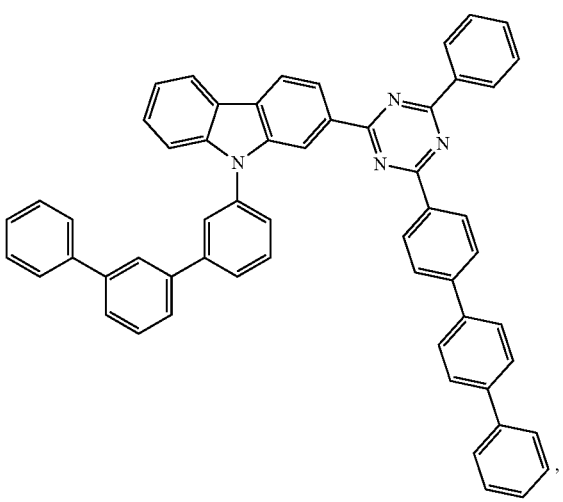

Compound 54
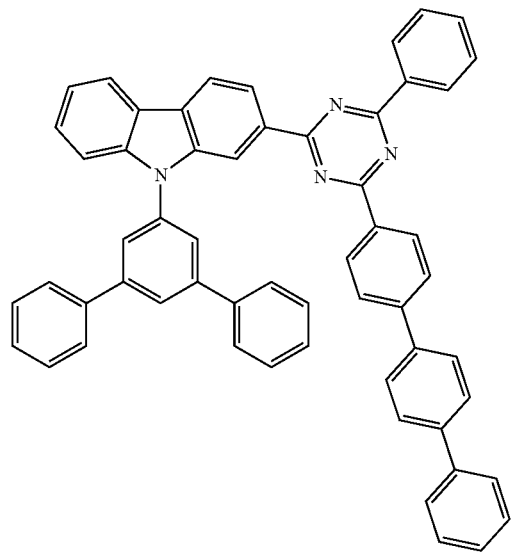
Compound 55
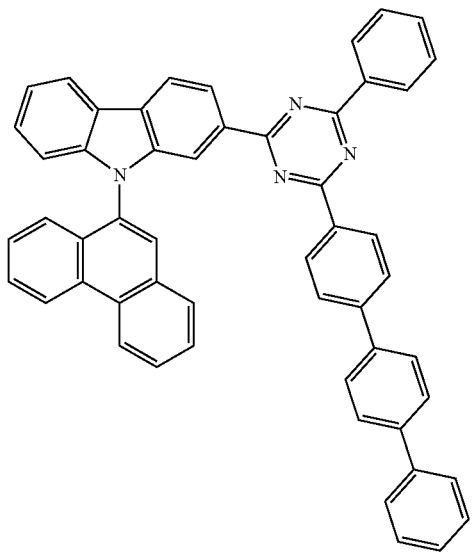
Compound 56
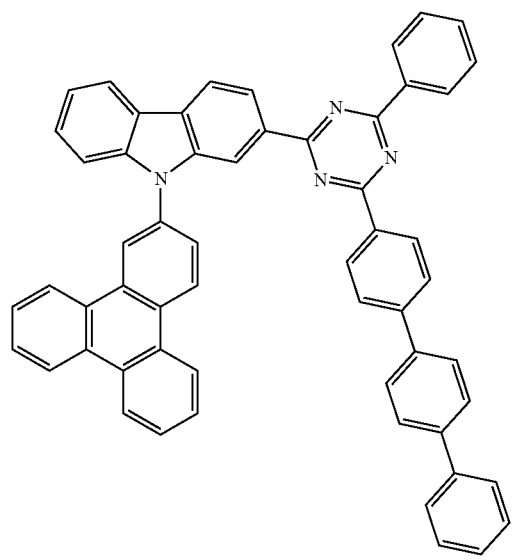
Compound 57
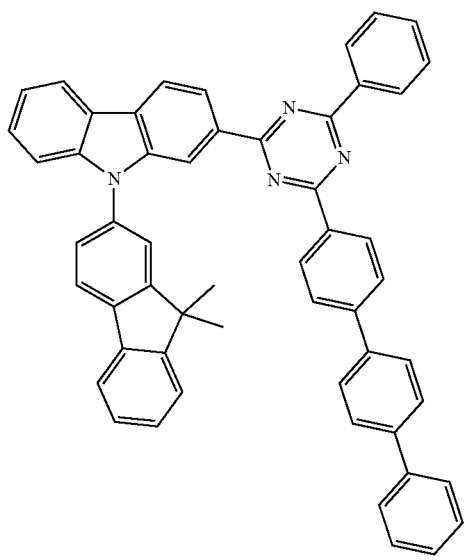

-continued
Compound 58
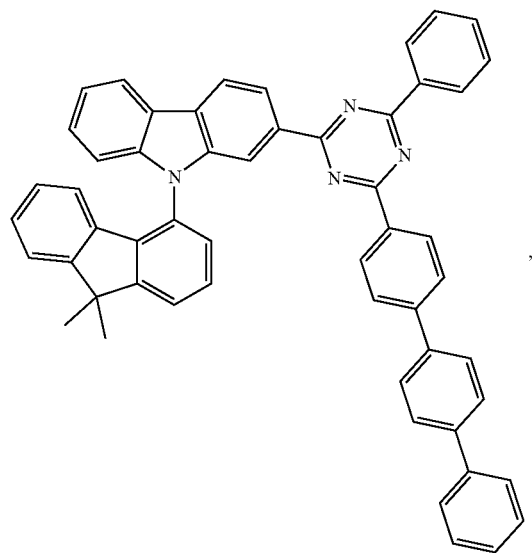
Compound 61
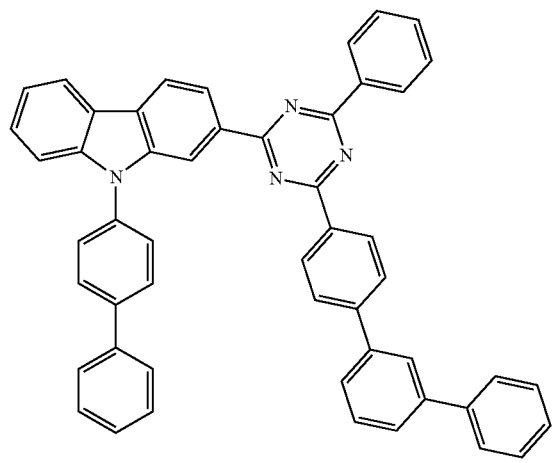
Compound 62
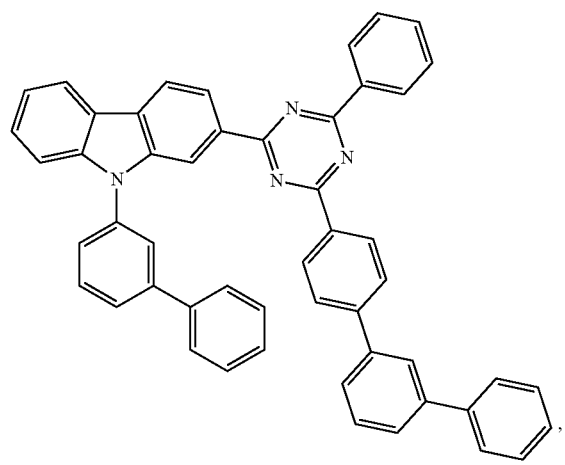
Compound 63
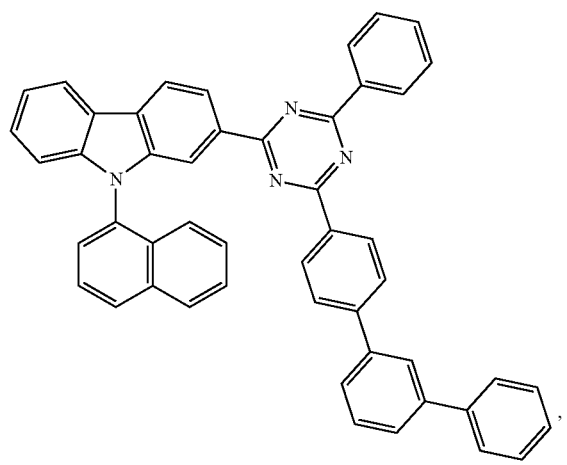
Compound 64
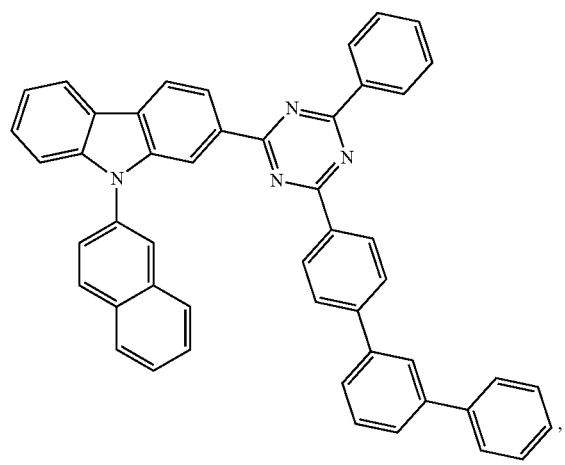
Compound 65
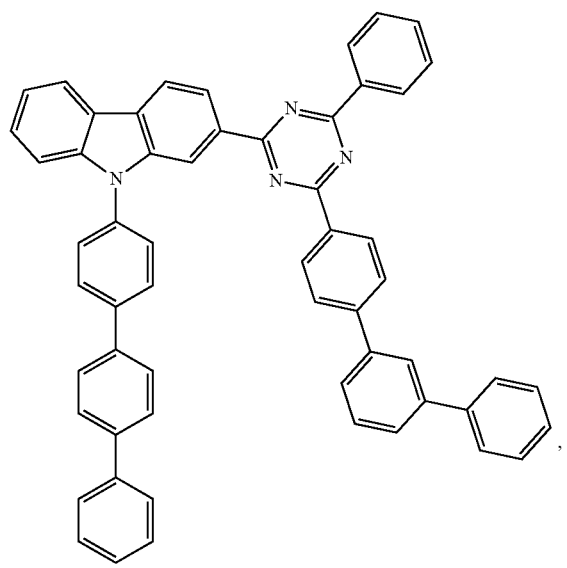

-continued
Compound 66
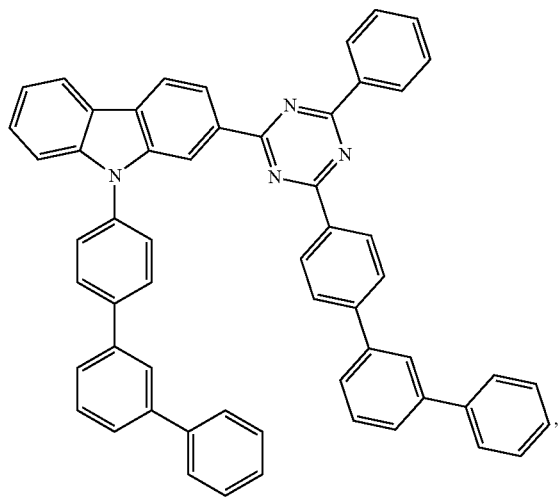
Compound 67
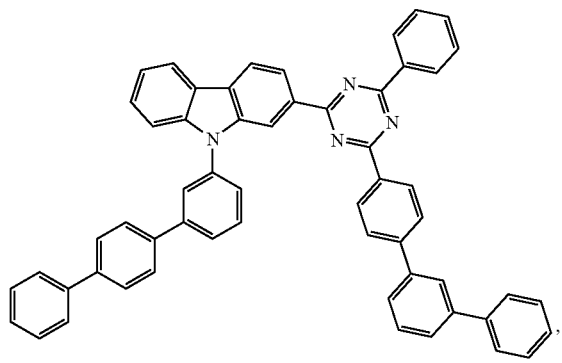
Compound 68
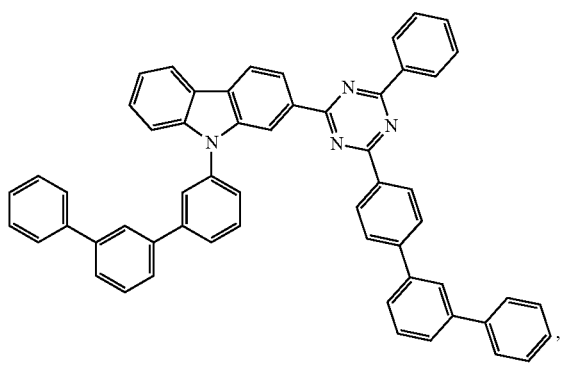
Compound 69
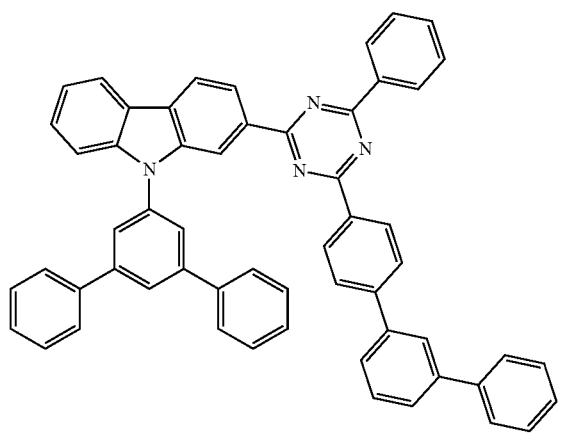
Compound 70
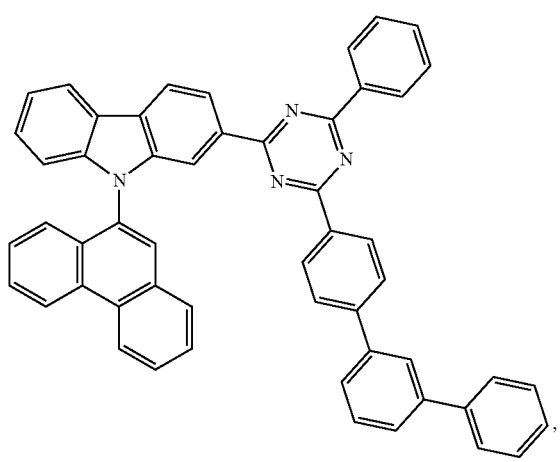
Compound 71
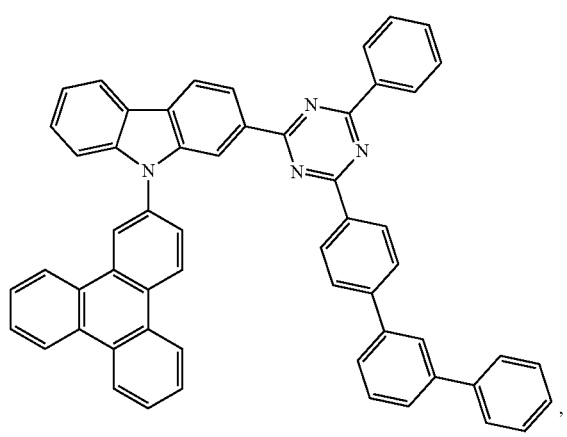

-continued
Compound 72
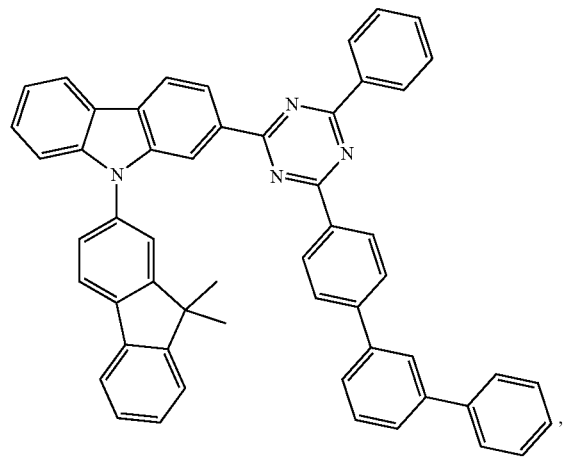
Compound 73
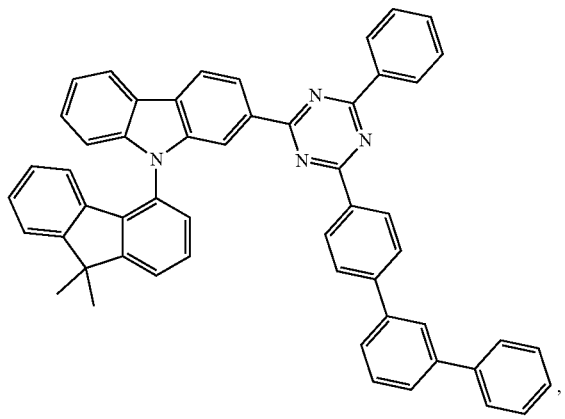
Compound 76
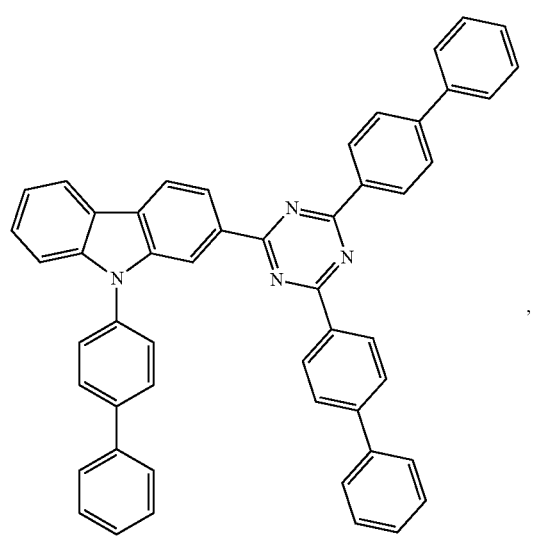
Compound 77
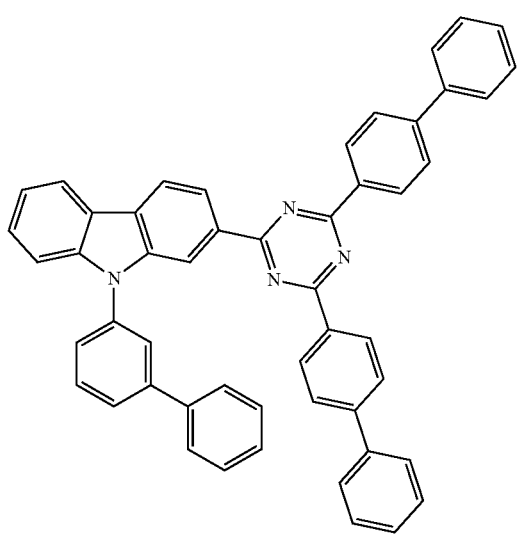
Compound 78
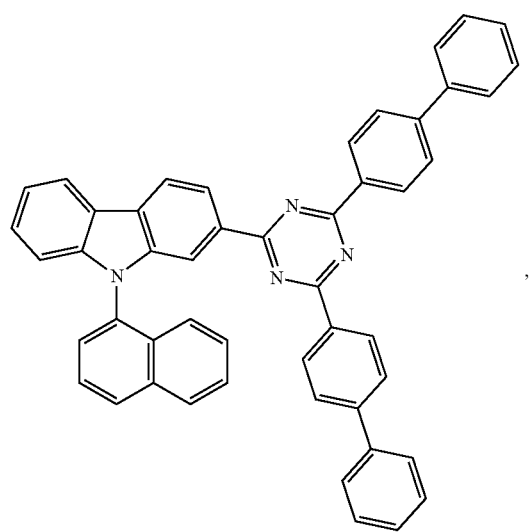
Compound 79
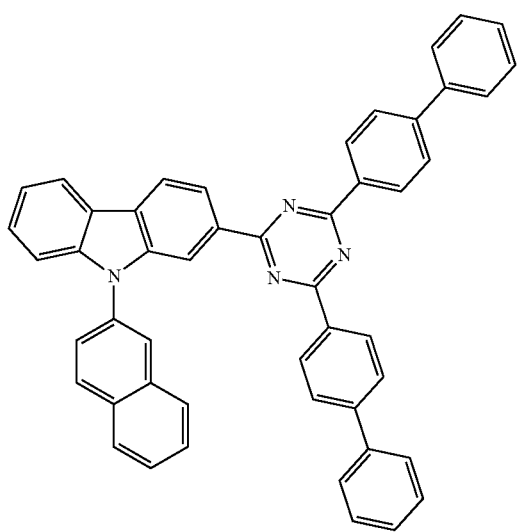

Compound 80
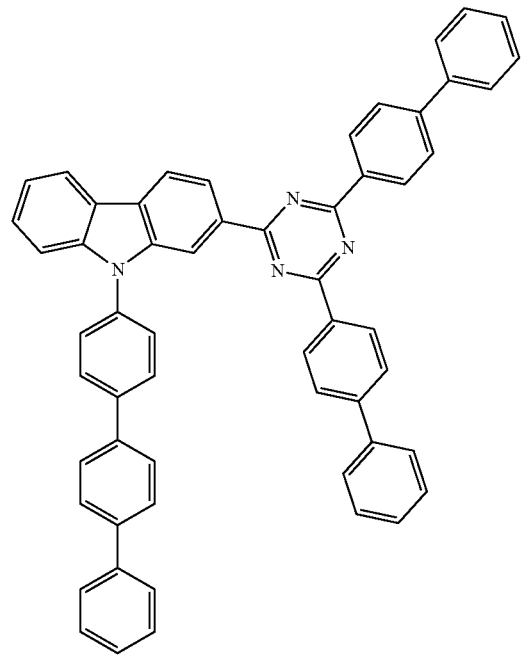
Compound 81
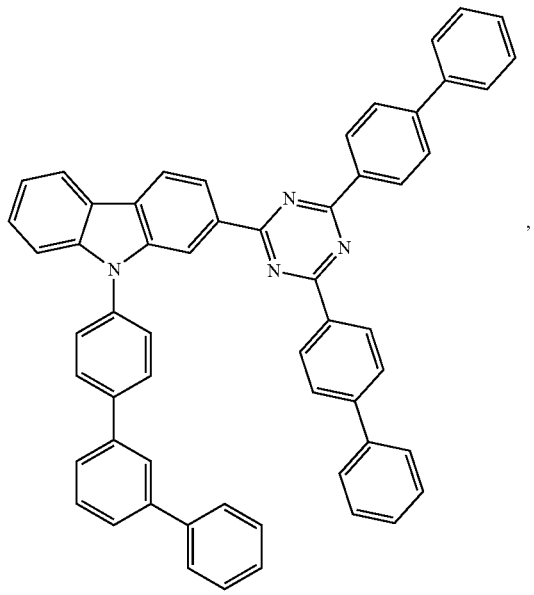
Compound 82
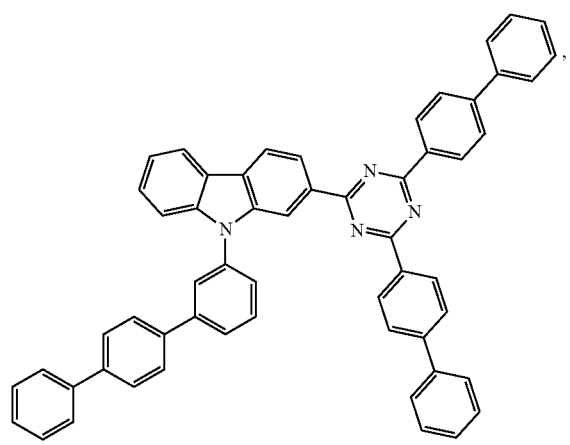
Compound 83
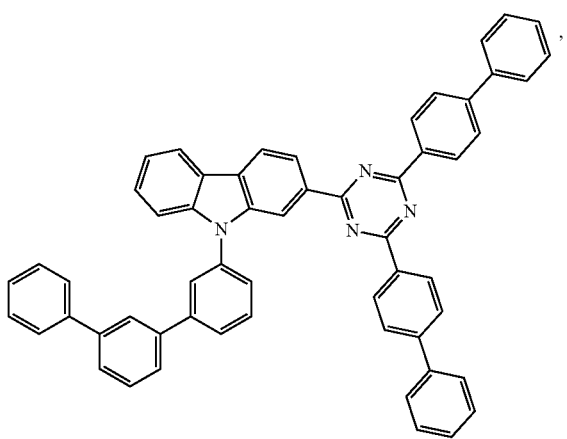

Compound 84
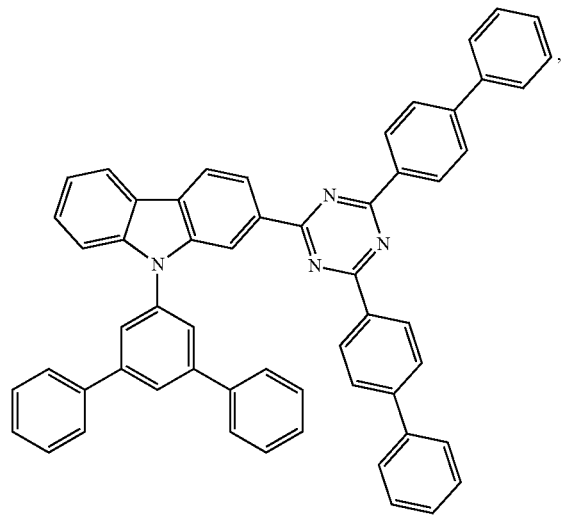
Compound 85
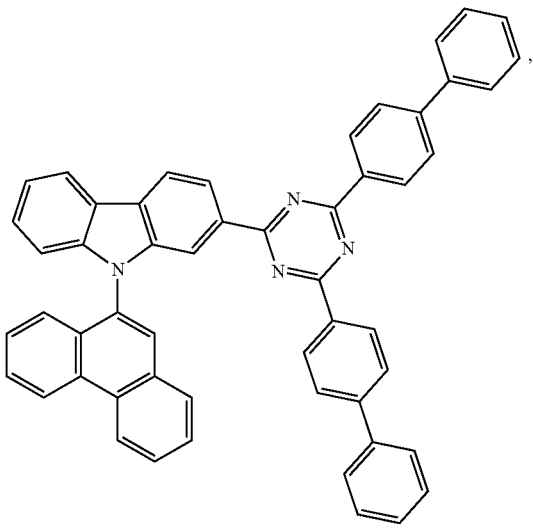
Compound 86
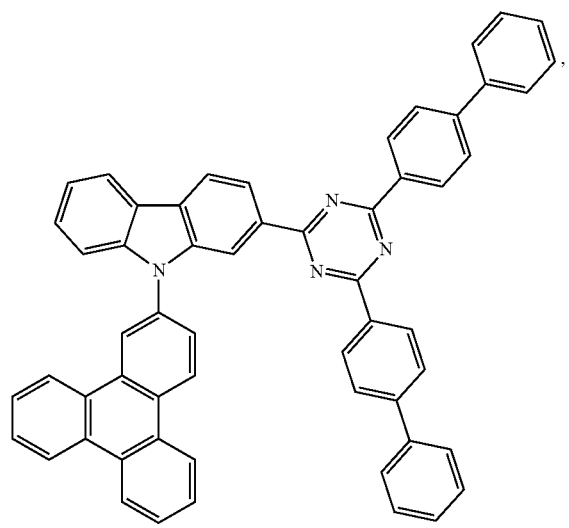
Compound 87
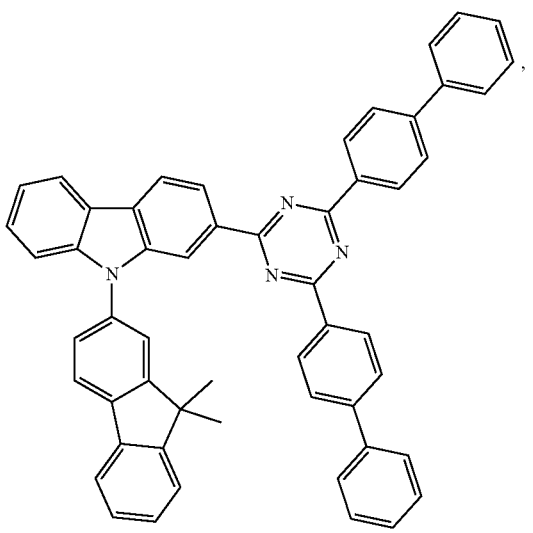

Compound 88
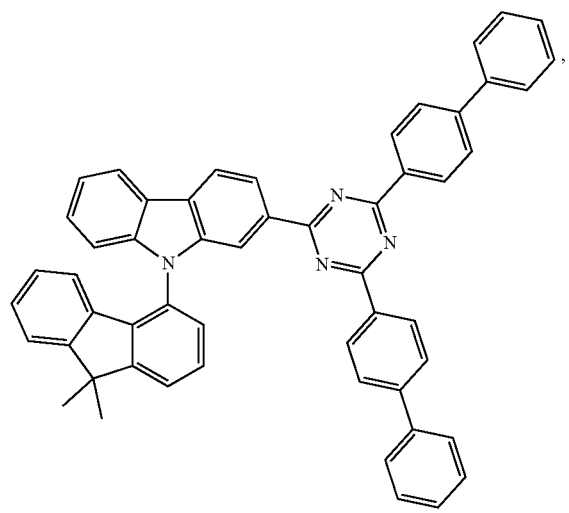
Compound 91
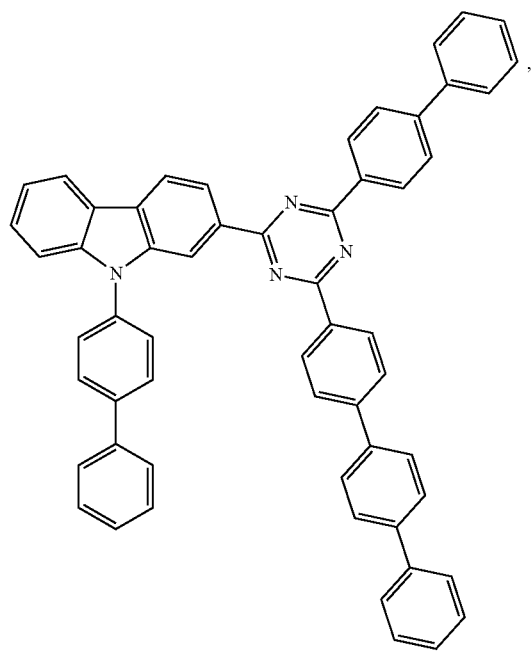
Compound 92
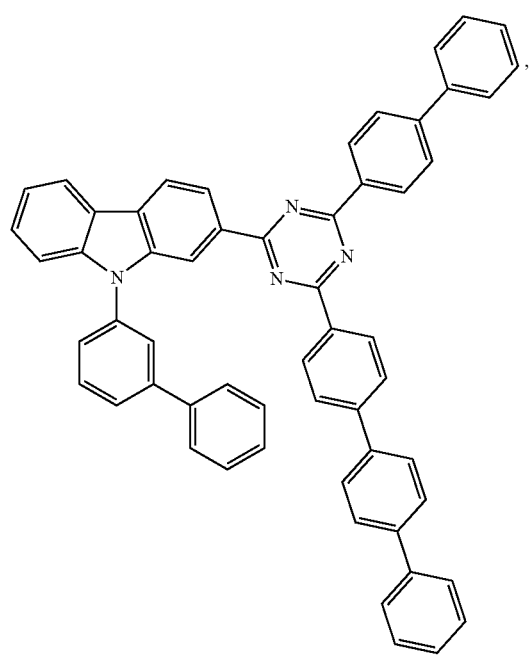
Compound 93
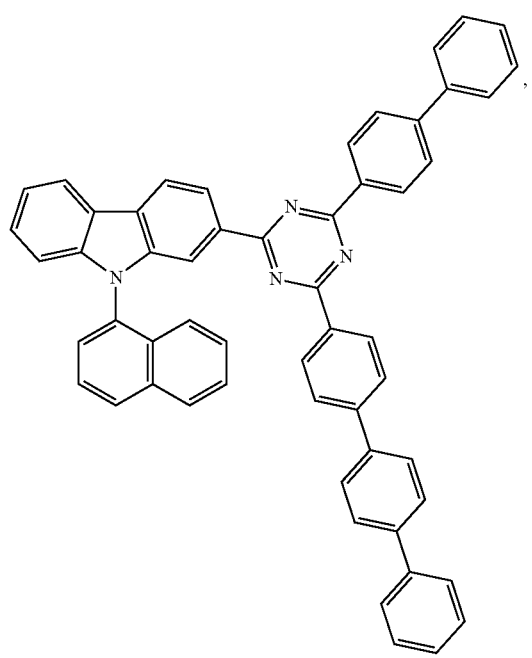

Compound 94
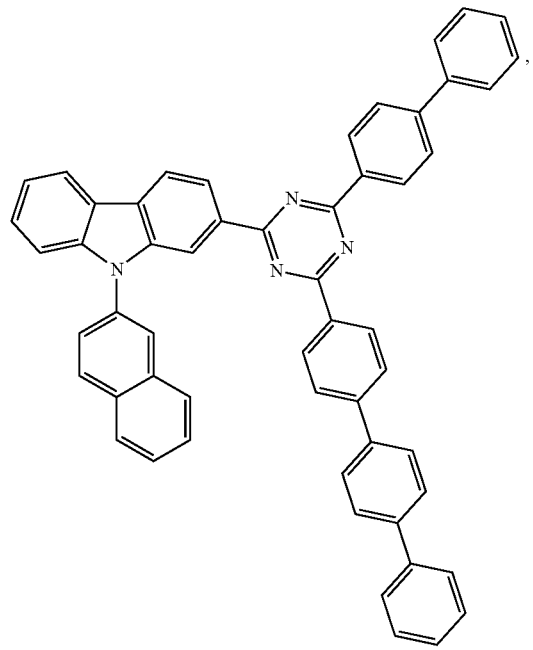
Compound 95
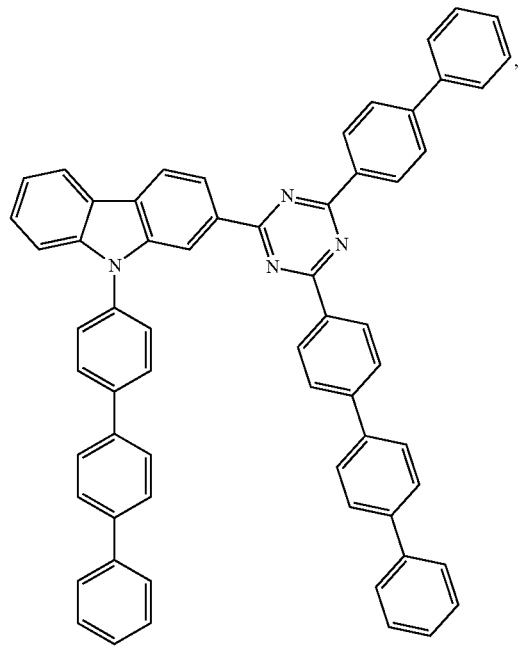
Compound 96
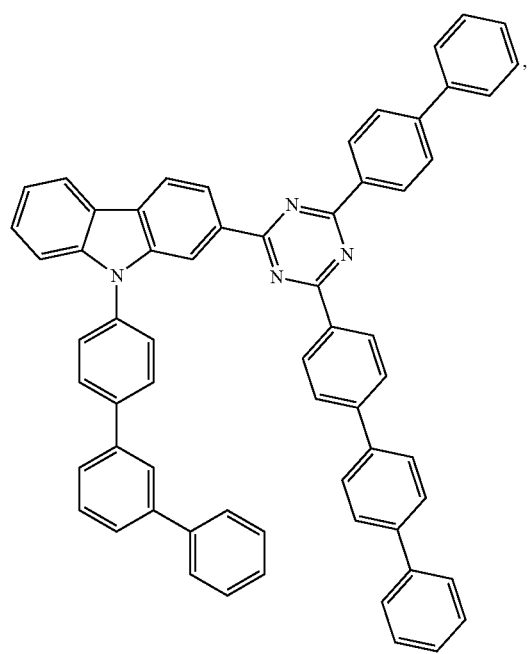
Compound 97
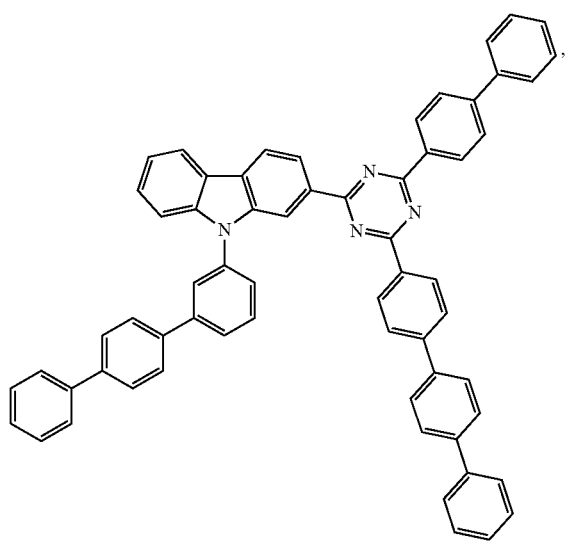

-continued
Compound 98
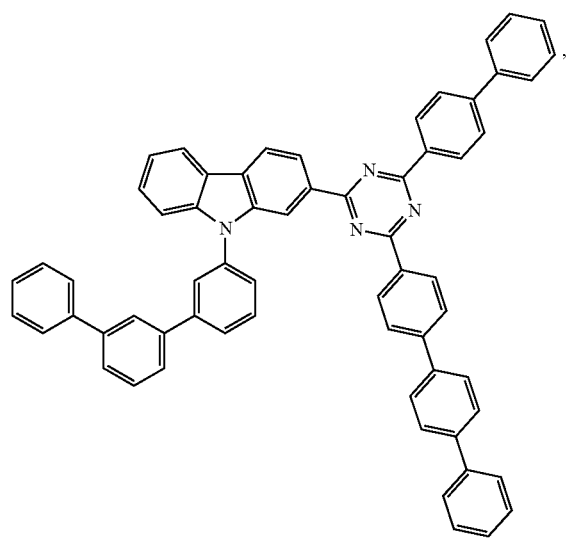
Compound 99
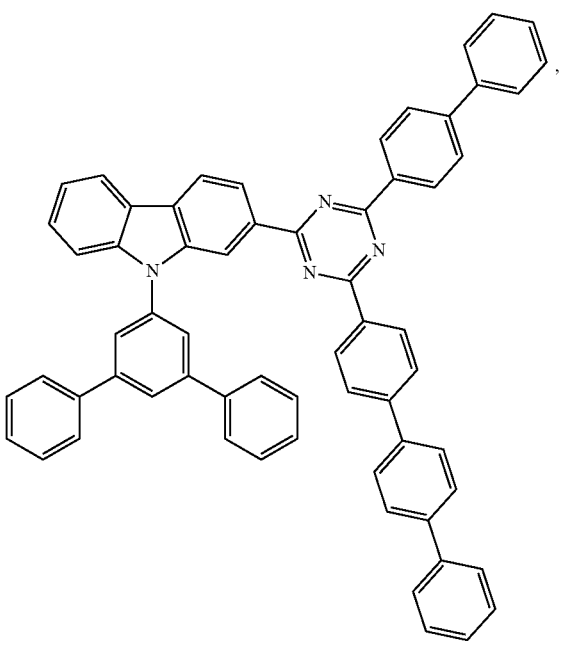
Compound 100
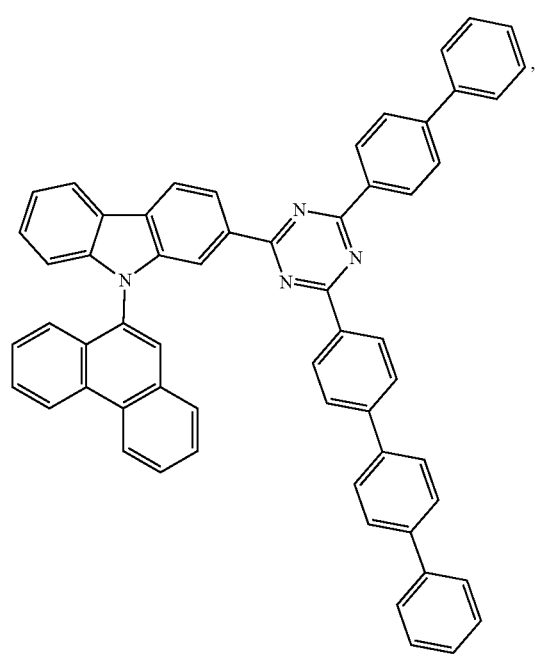
Compound 101

-continued
Compound 102
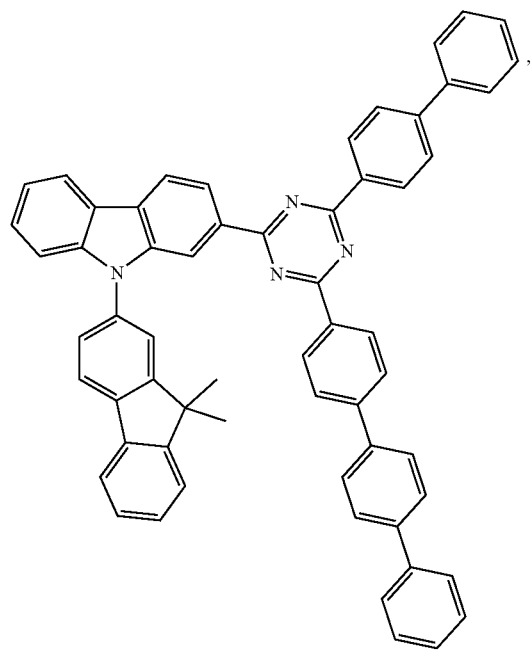
Compound 103
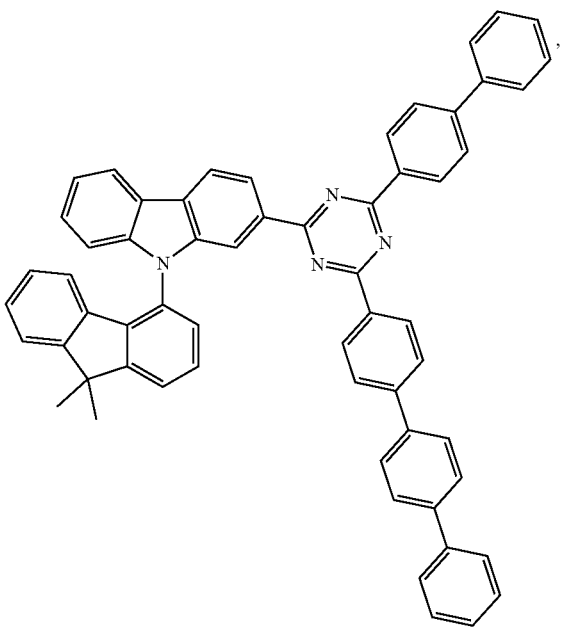
Compound 106
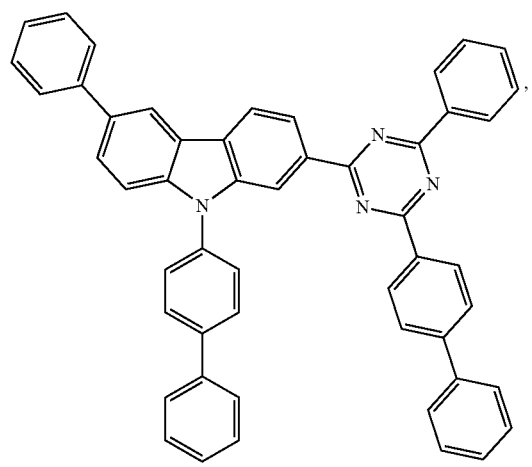
Compound 107
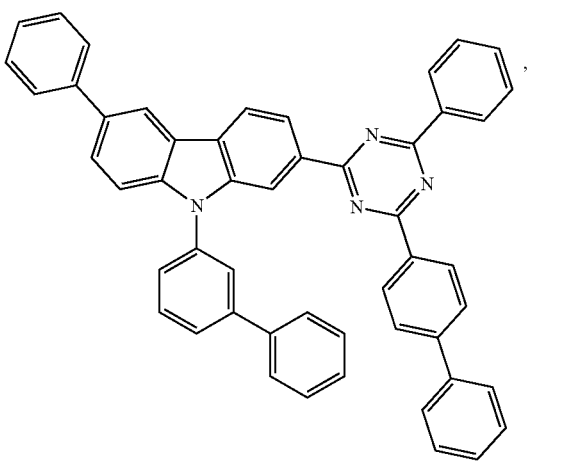
Compound 108
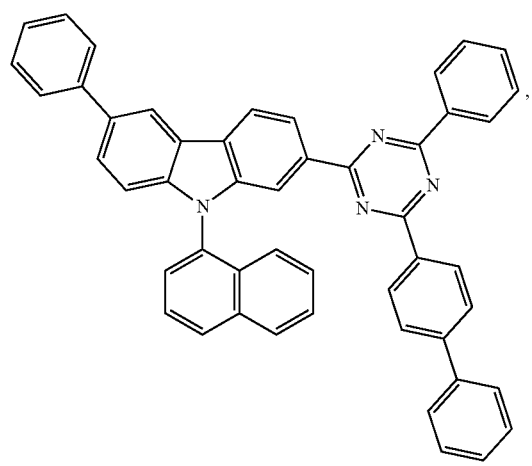
Compound 109
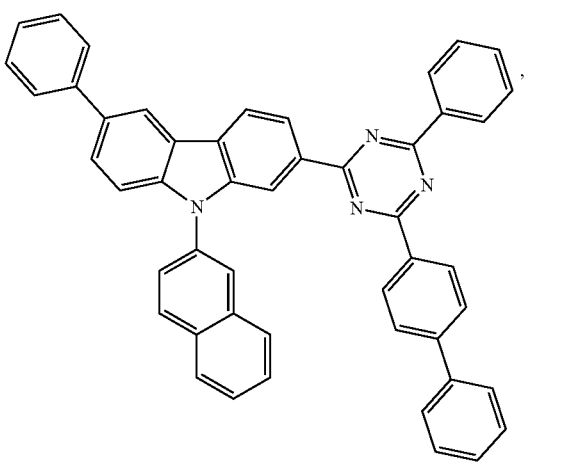

-continued
Compound 110
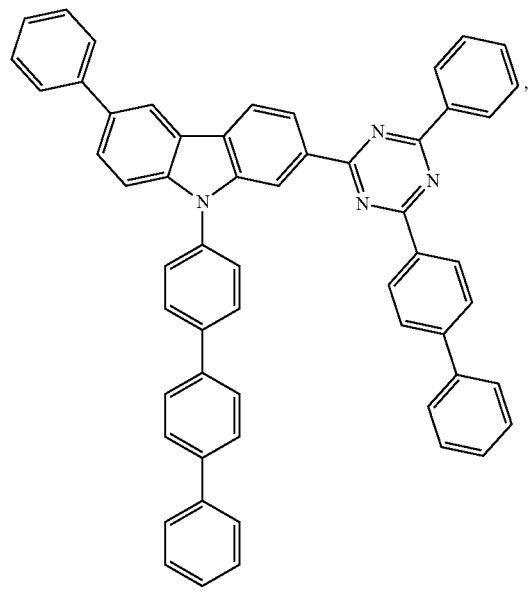
Compound 111
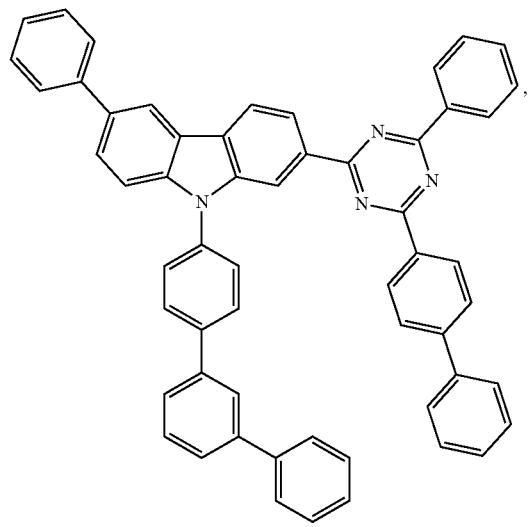
Compound 112
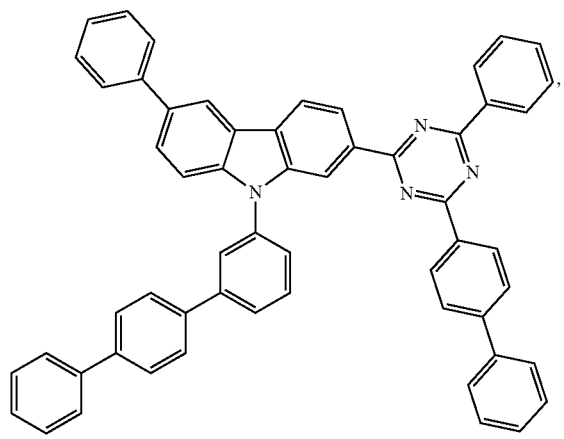
Compound 113
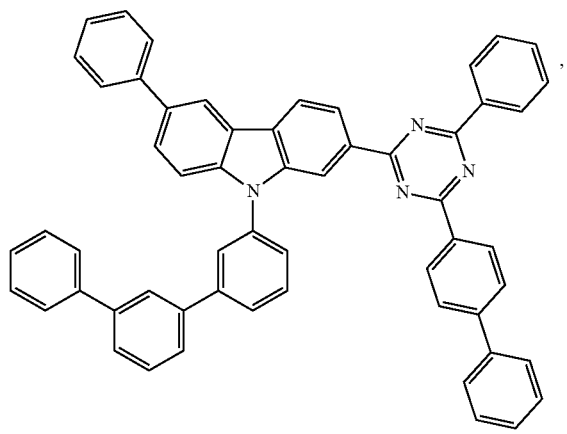
Compound 114
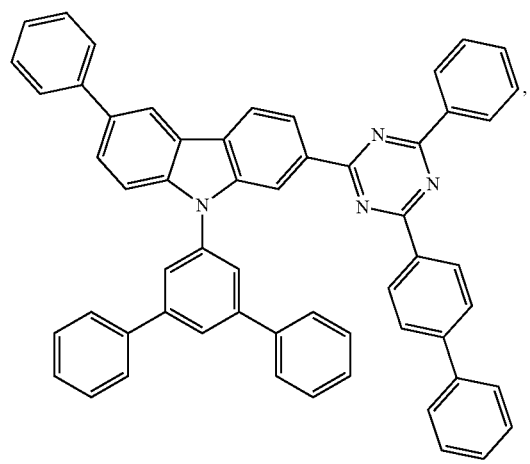
Compound 115
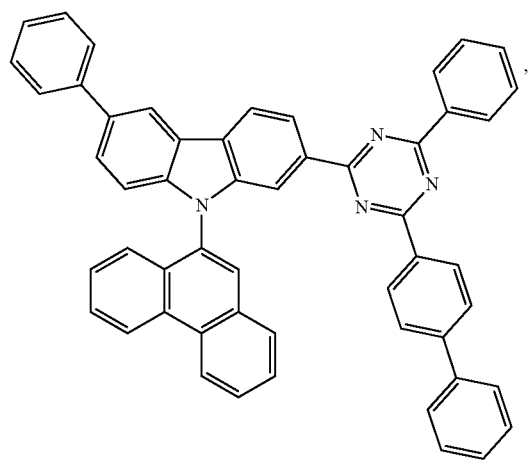

-continued
Compound 116
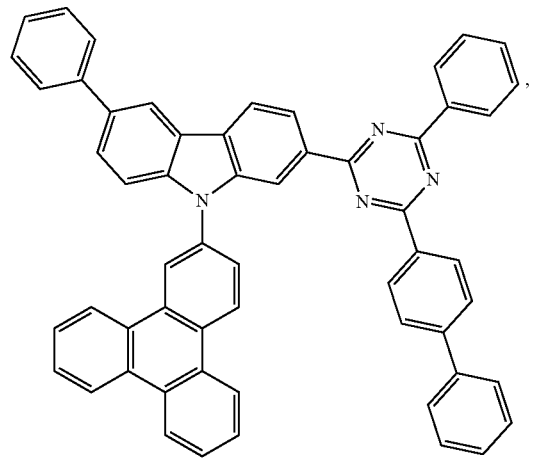
Compound 117
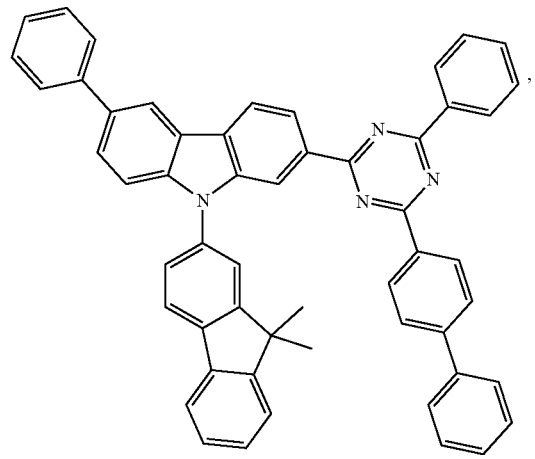
Compound 118
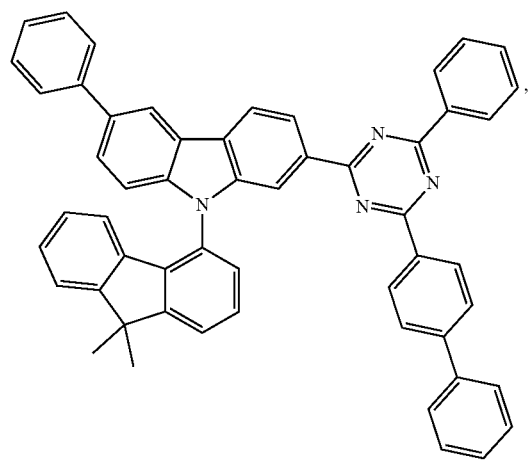
Compound 121
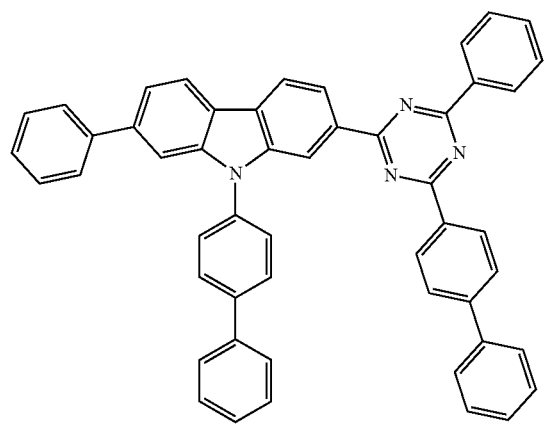
Compound 122
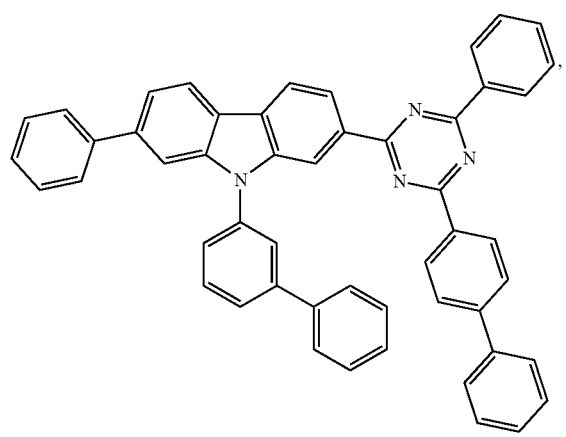
Compound 123
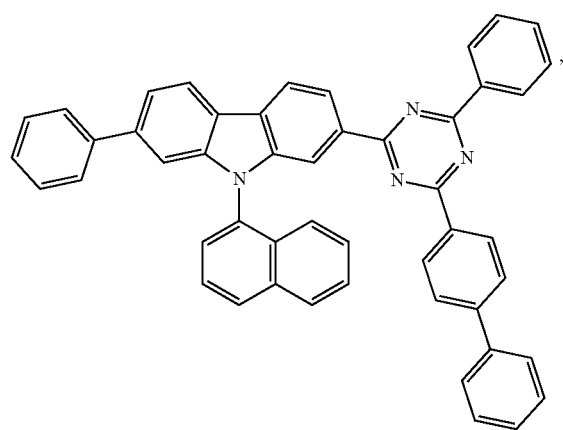

-continued
Compound 124
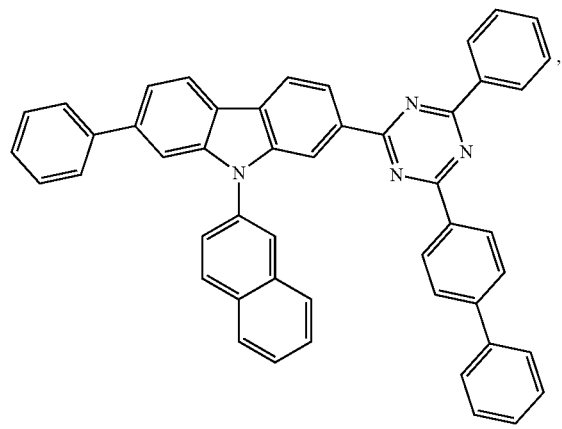
Compound 125
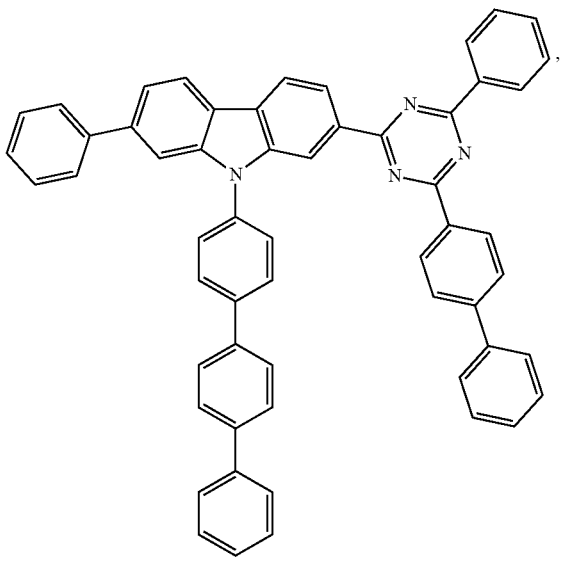
Compound 126
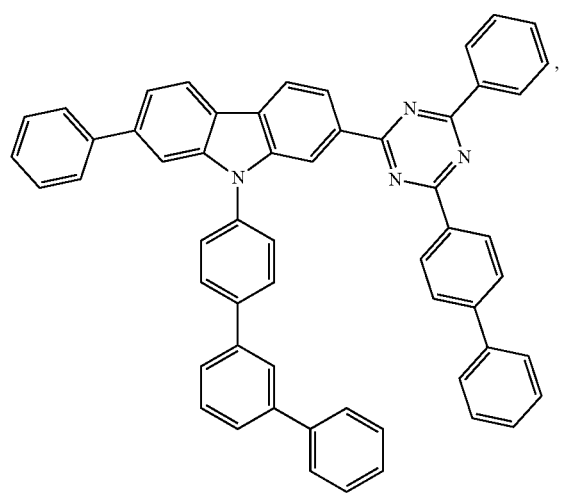
Compound 127
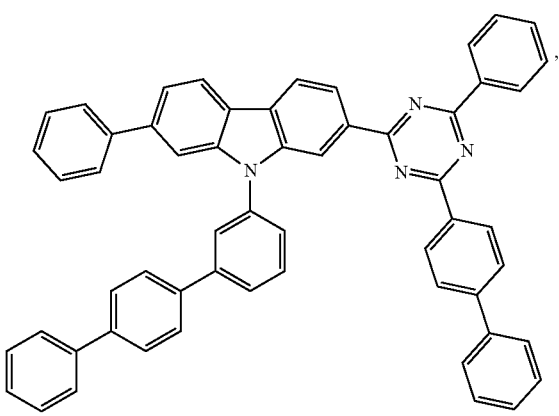
Compound 128
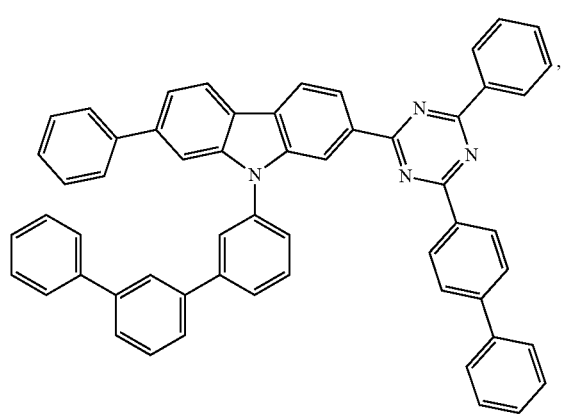
Compound 129
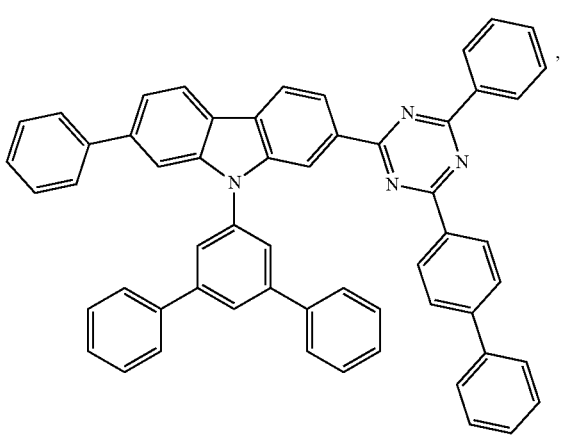

-continued
Compound 130
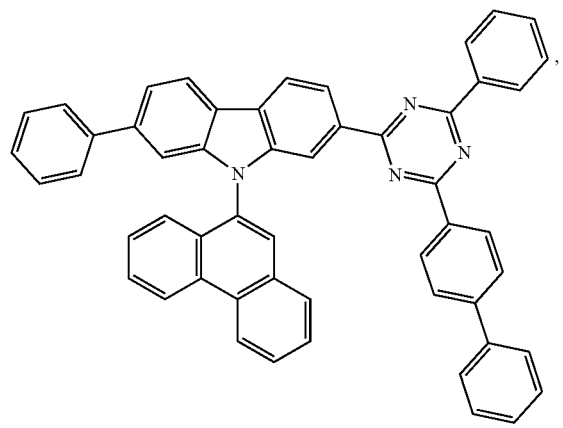
Compound 131
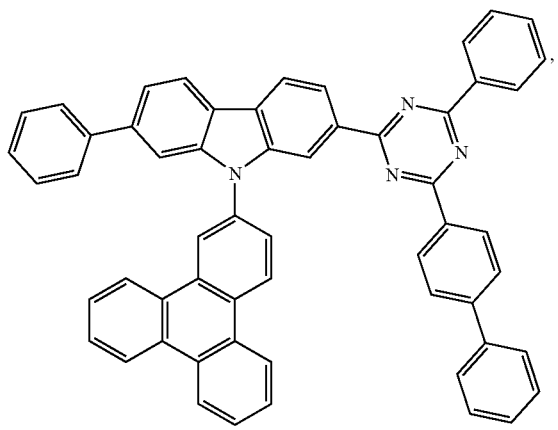
Compound 132
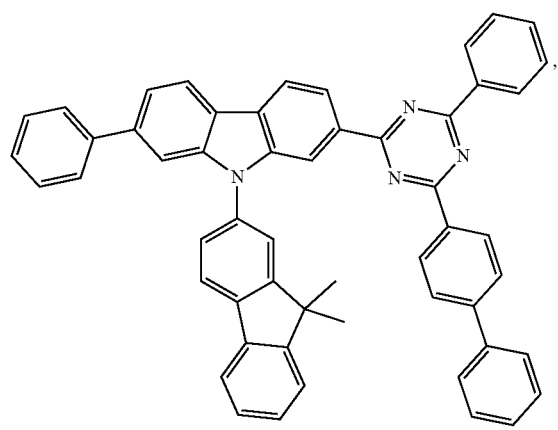
Compound 133
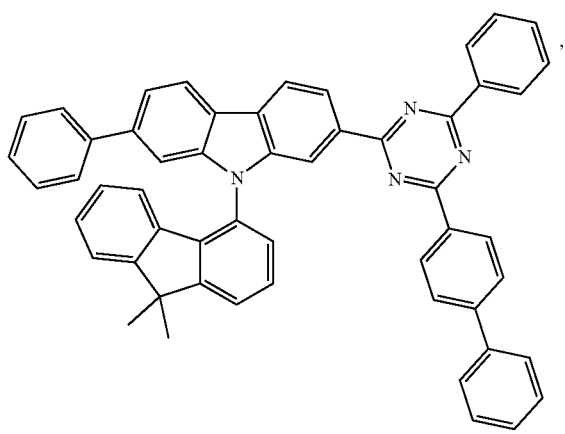
Compound 136
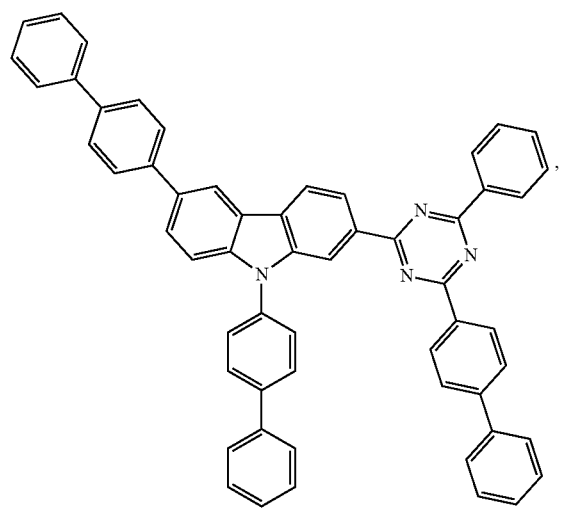
Compound 137
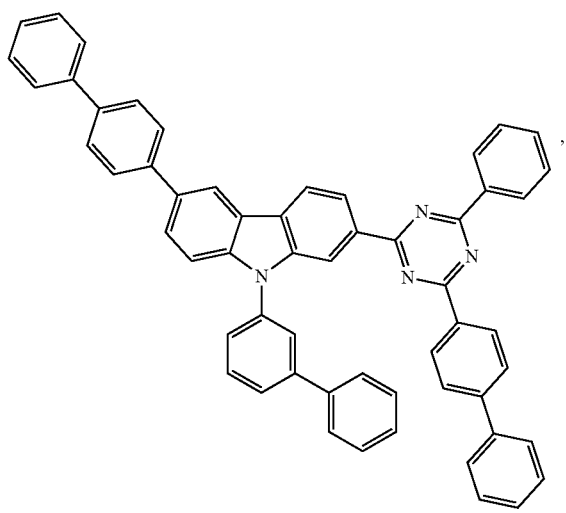

Compound 138
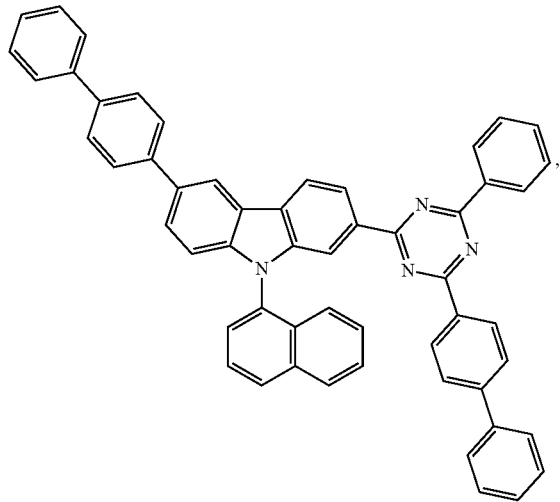
Compound 139
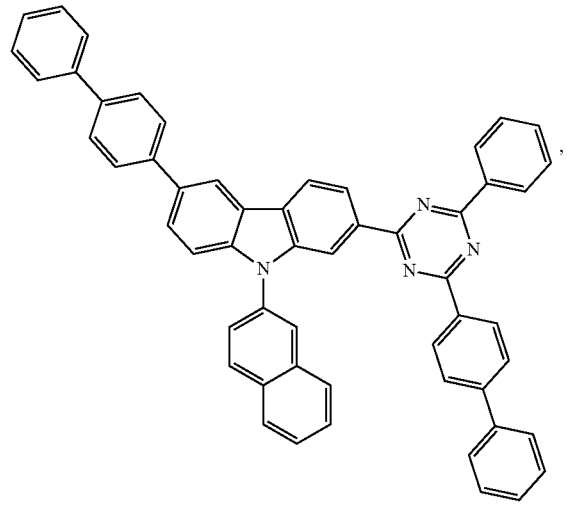
Compound 140
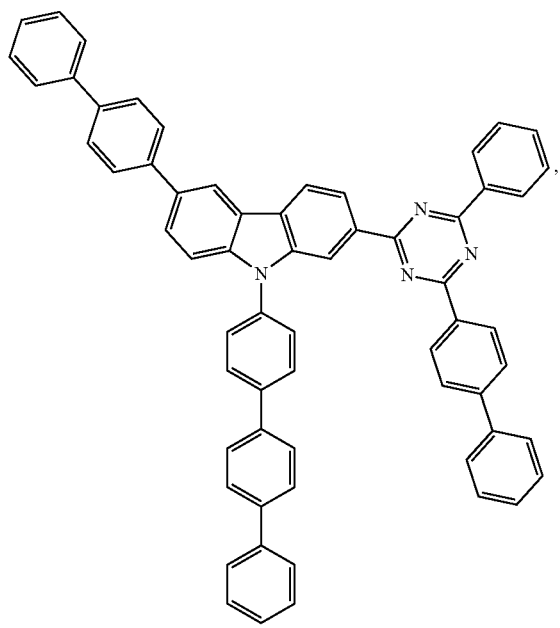
Compound 141
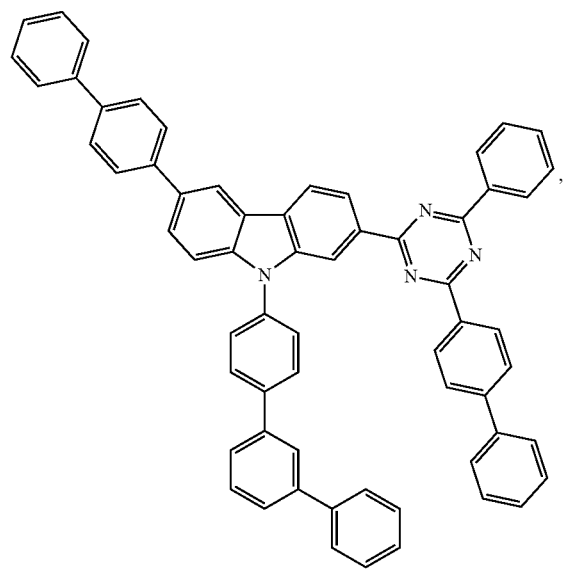

-continued
Compound 142
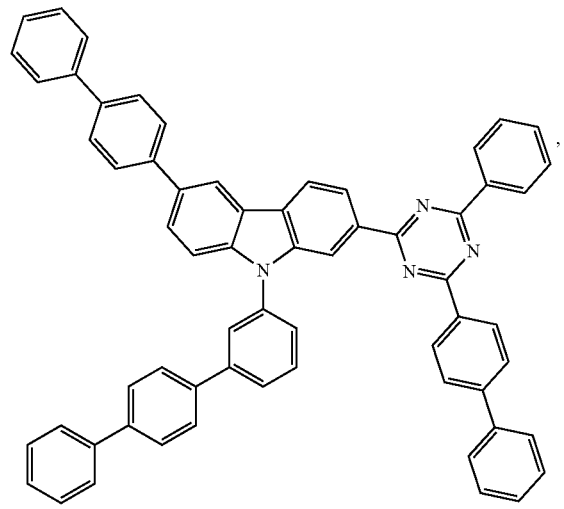
Compound 143
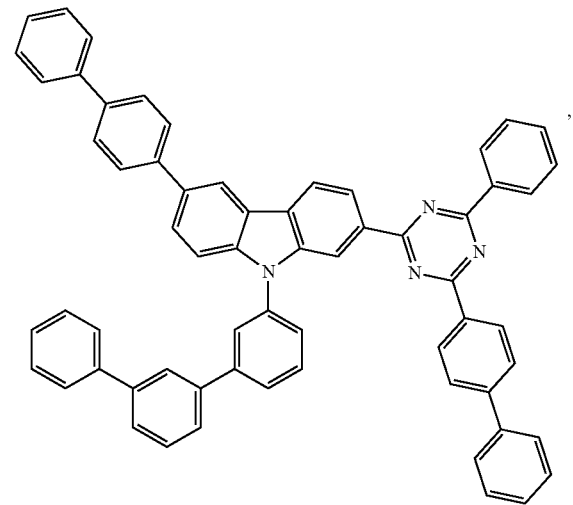
Compound 144
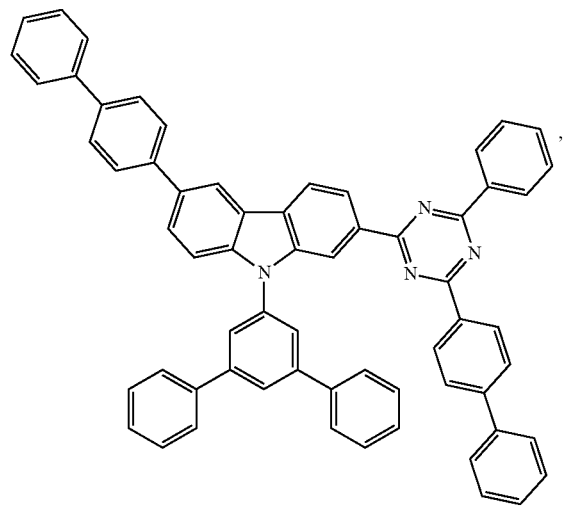
Compound 145
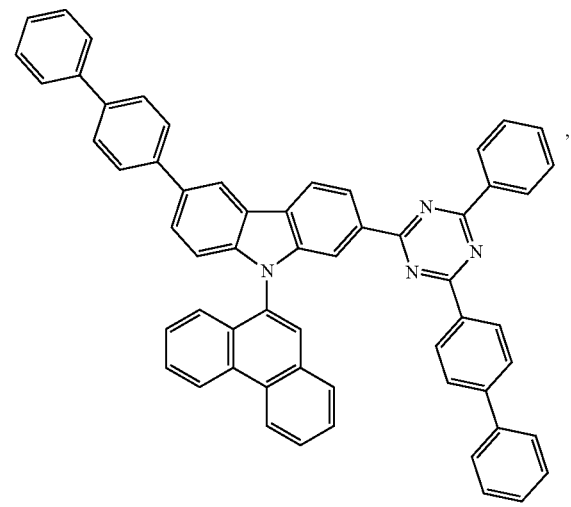
Compound 146
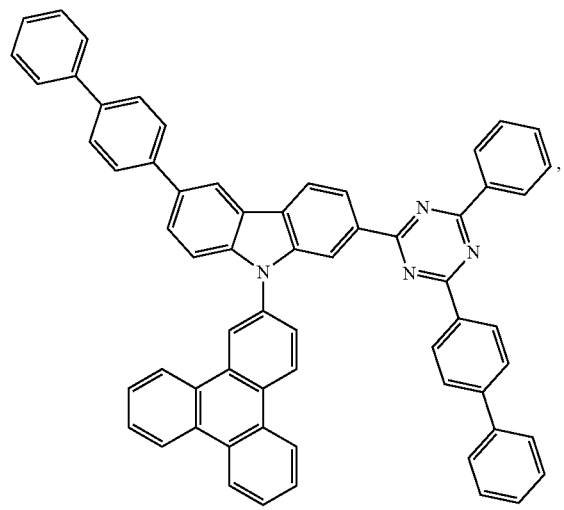
Compound 147
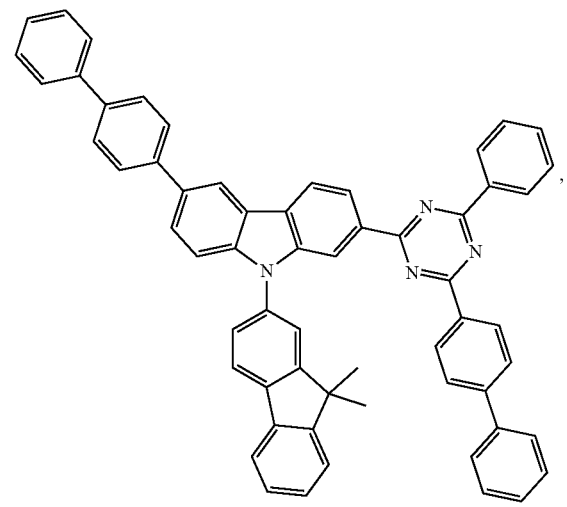

-continued
Compound 148
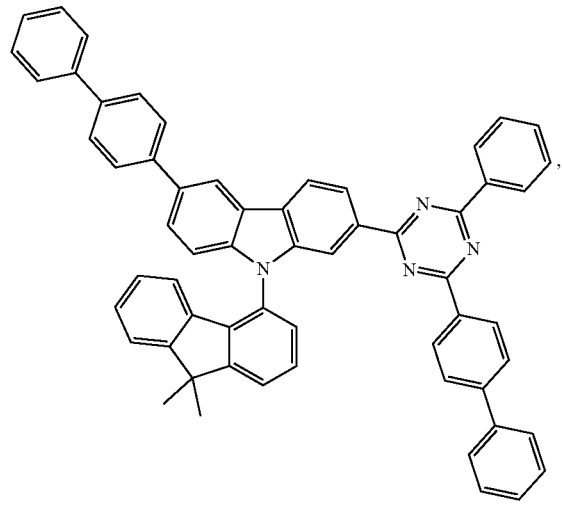
Compound 151
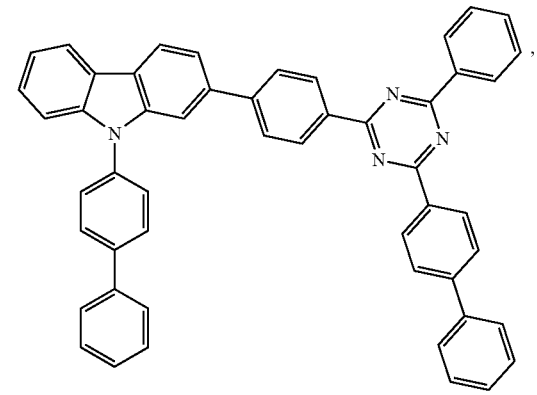
Compound 152
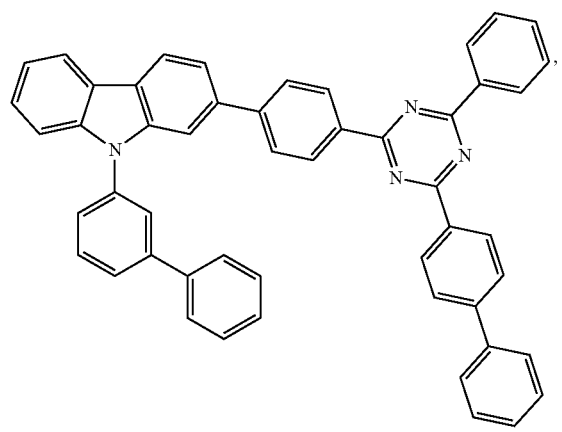
Compound 153
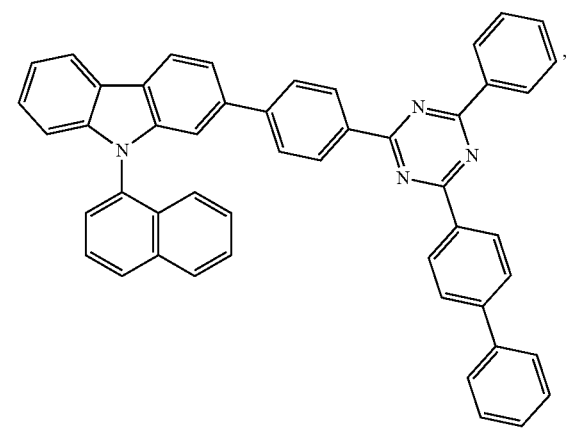
Compound 154
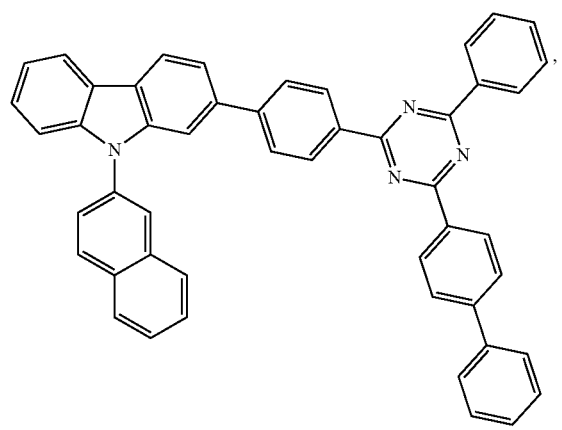
Compound 155
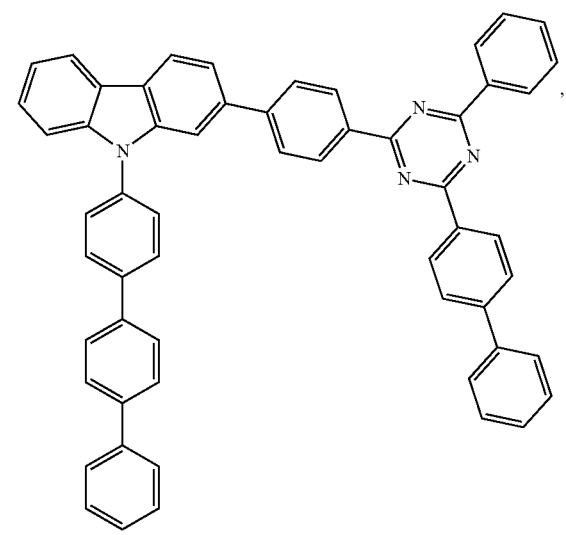

Compound 156
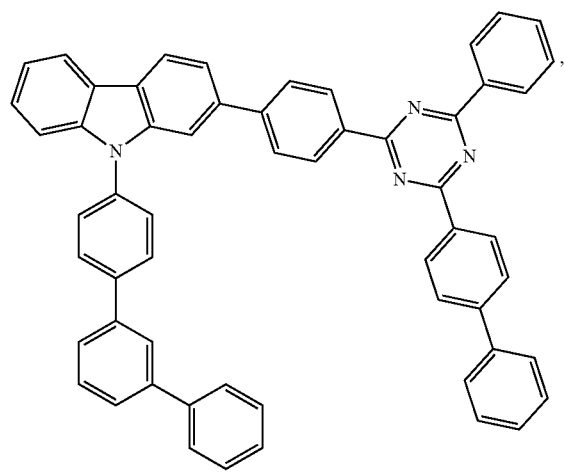
Compound 157
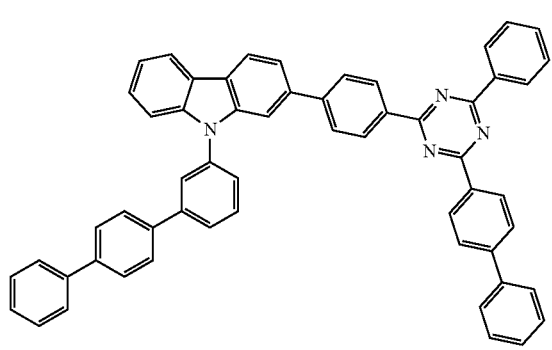
Compound 158
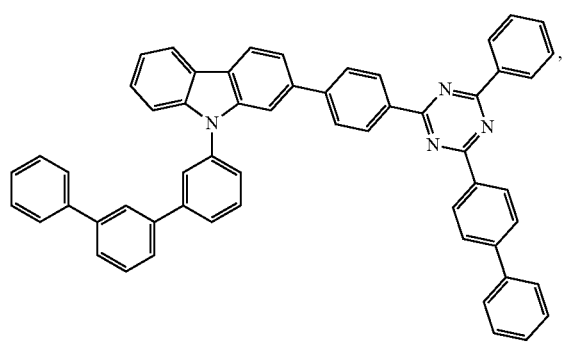
Compound 159
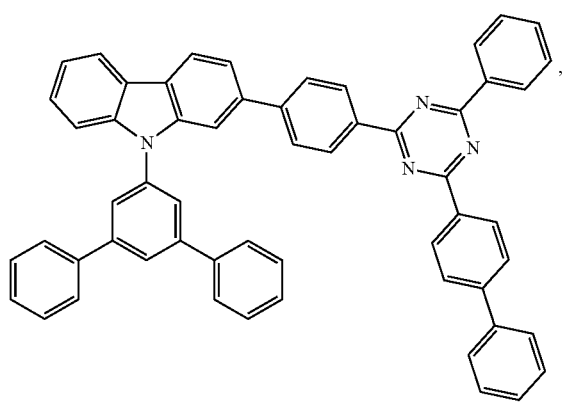
Compound 160
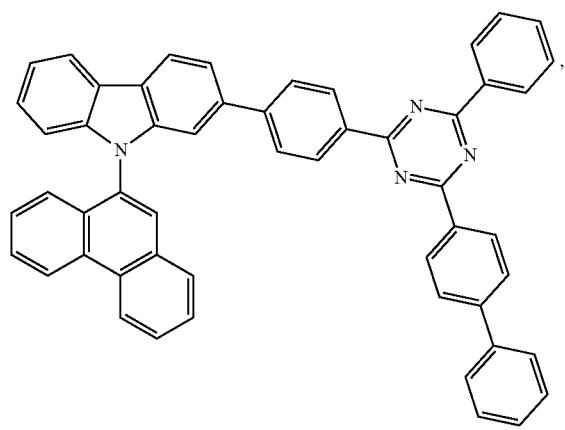
Compound 161
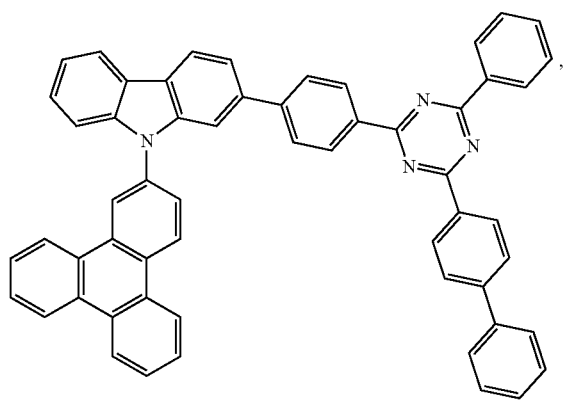

-continued
Compound 162
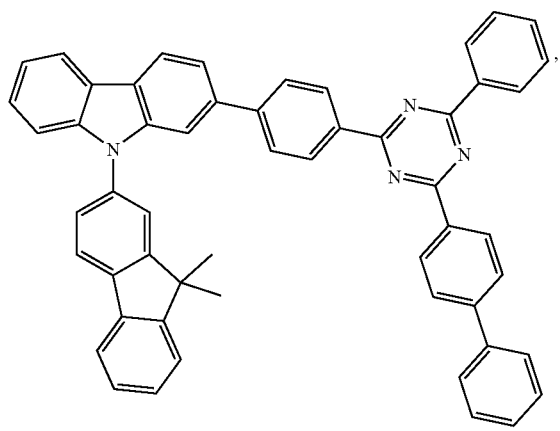
Compound 163
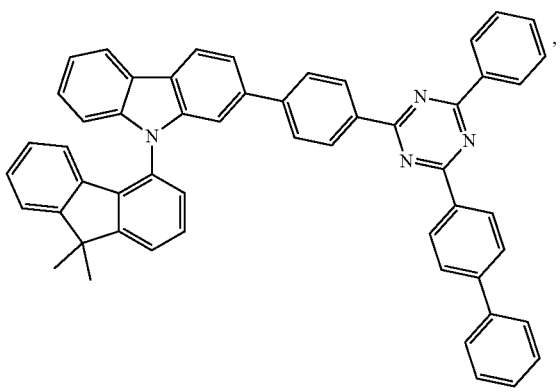
Compound 166
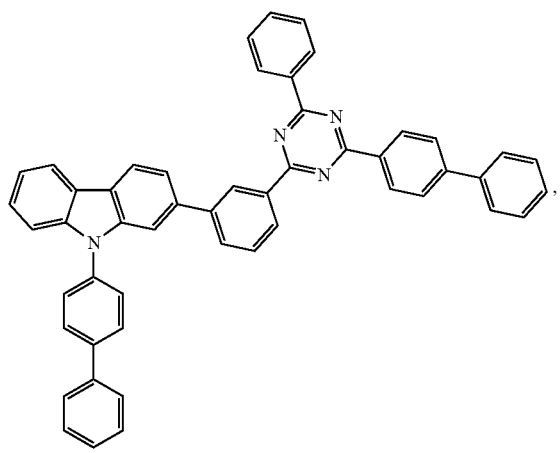
Compound 167
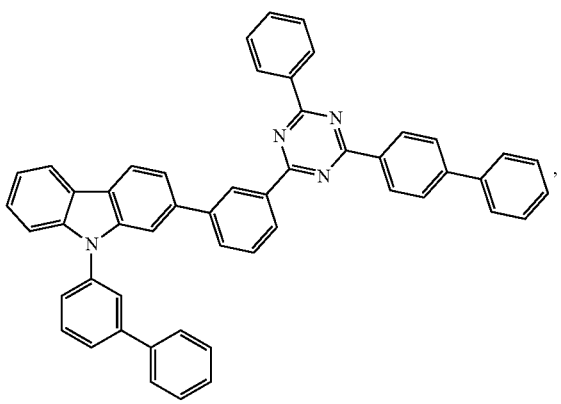
Compound 168
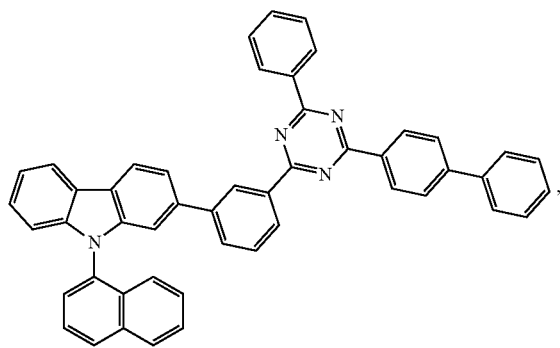
Compound 169
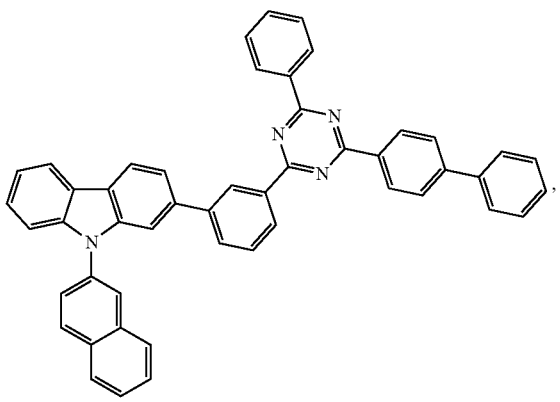

-continued
Compound 170
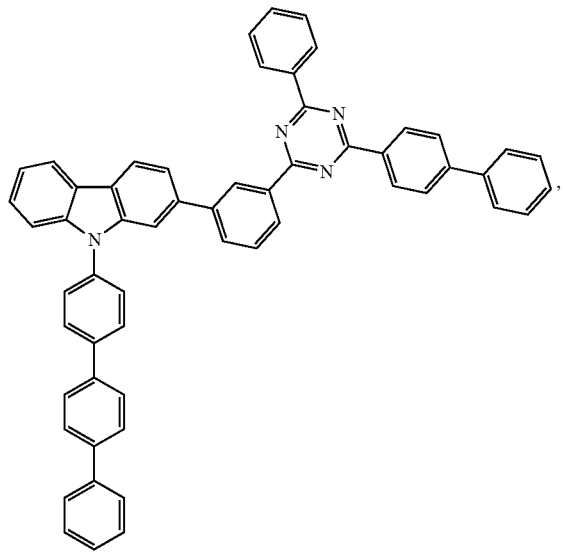
Compound 171
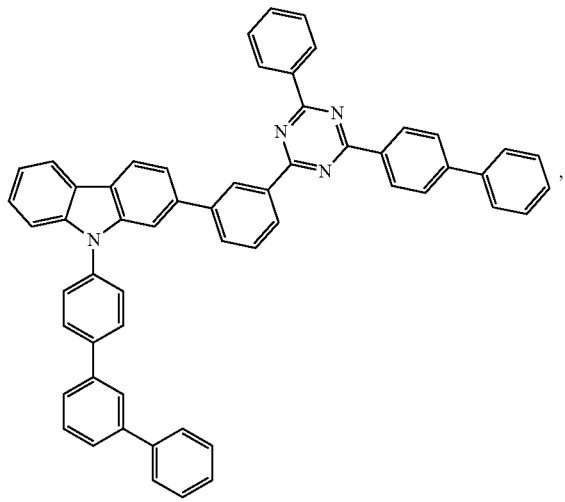
Compound 172
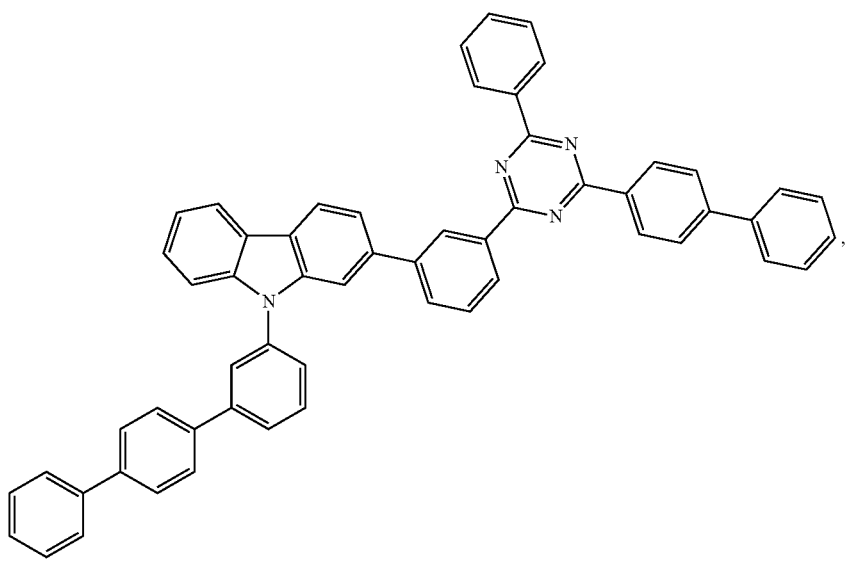
Compound 173
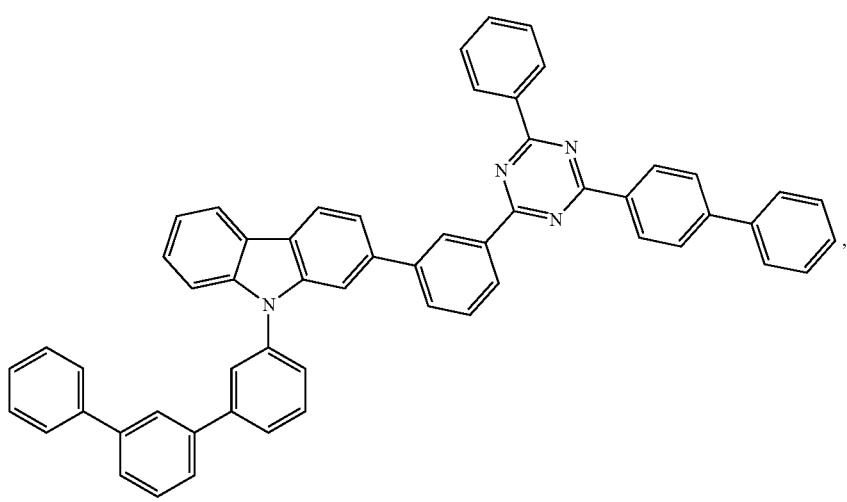

-continued
Compound 174
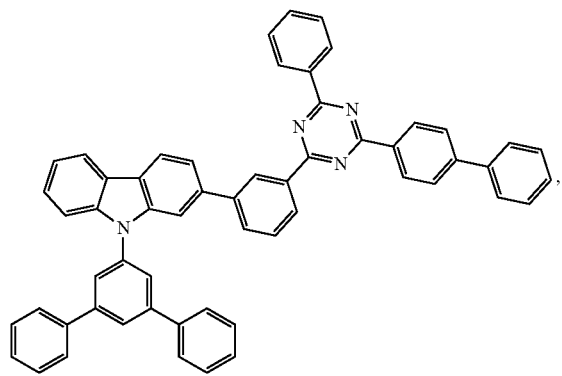
Compound 175
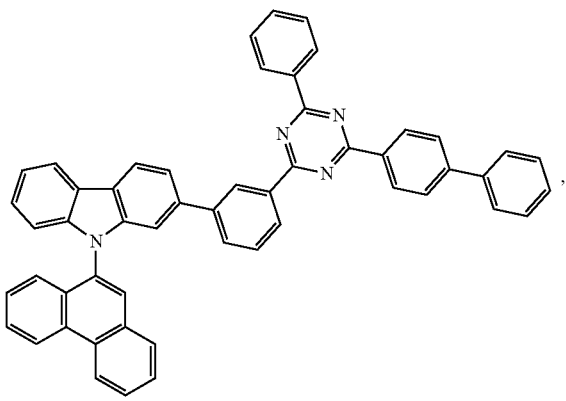
Compound 176
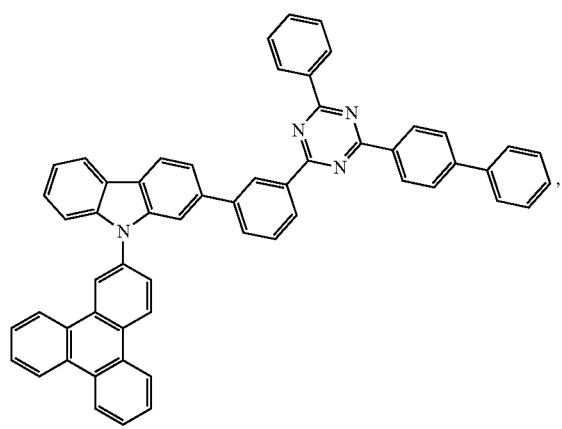
Compound 177
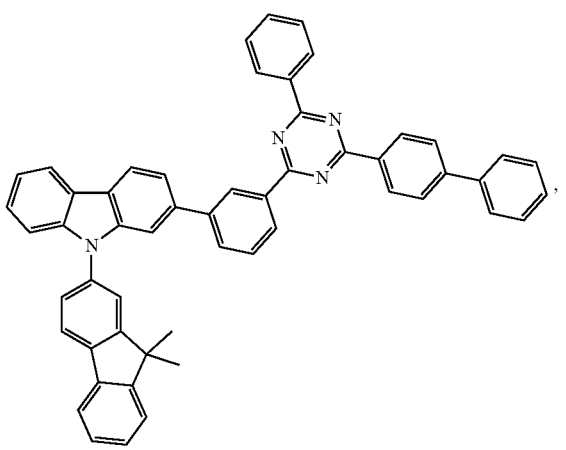
Compound 178
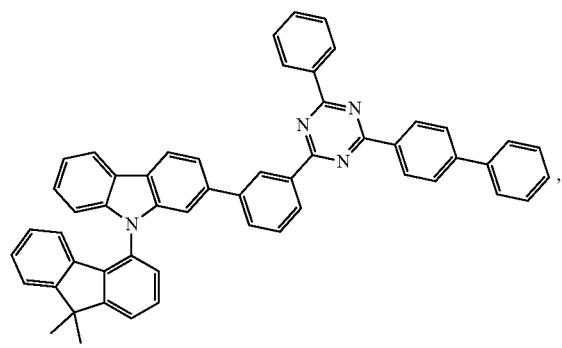
Compound 181
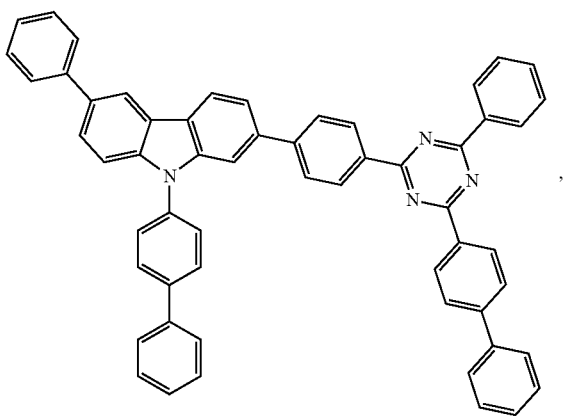

-continued
Compound 182
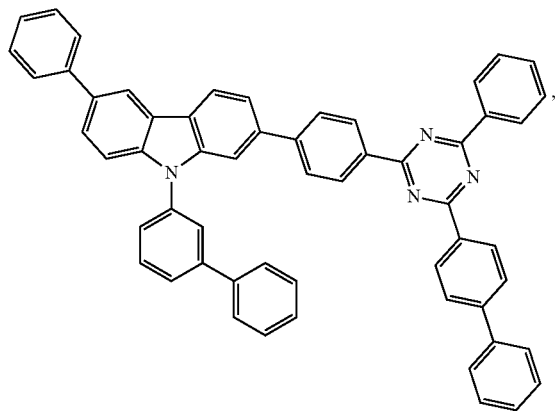
Compound 183
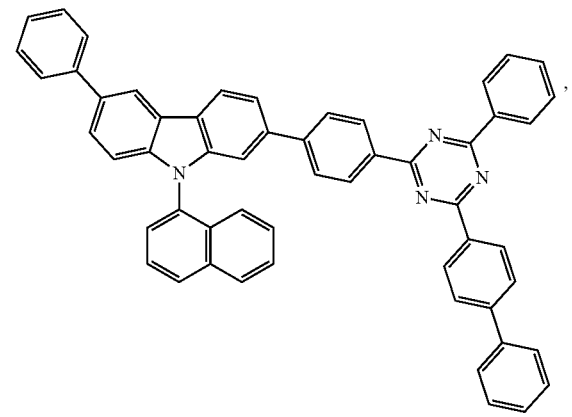
Compound 184
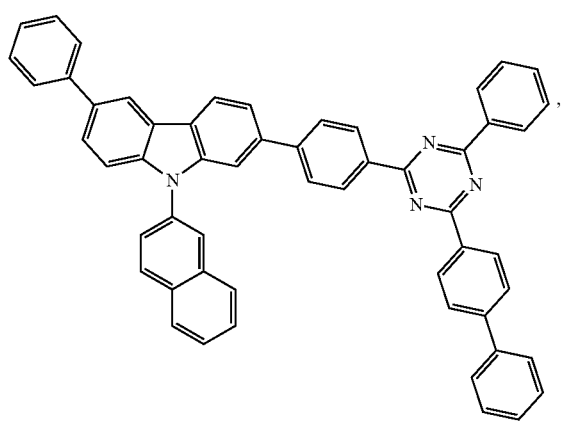
Compound 185
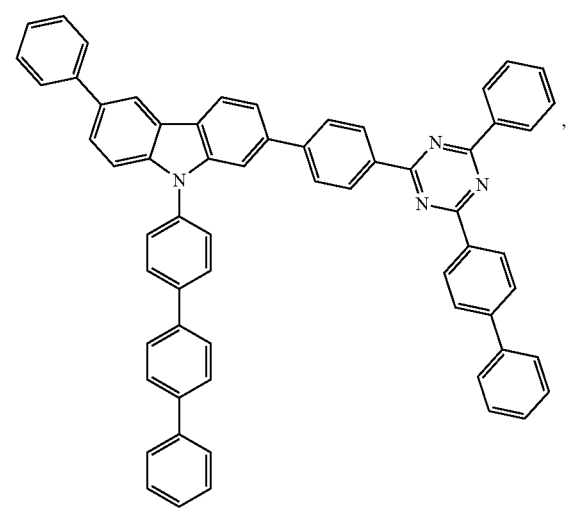
Compound 186
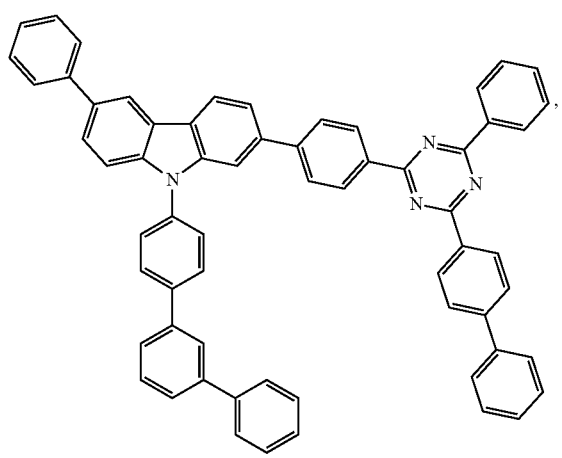
Compound 187
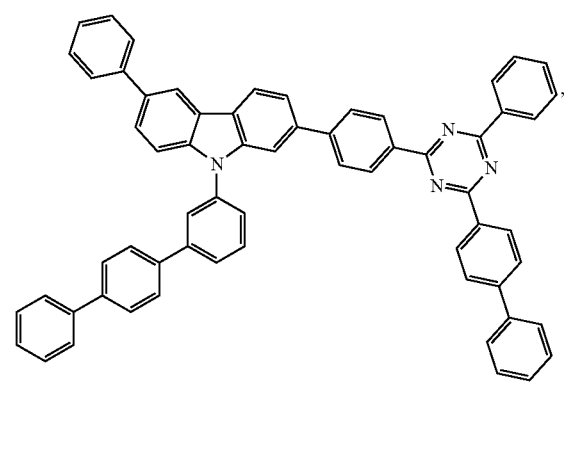

-continued
Compound 188
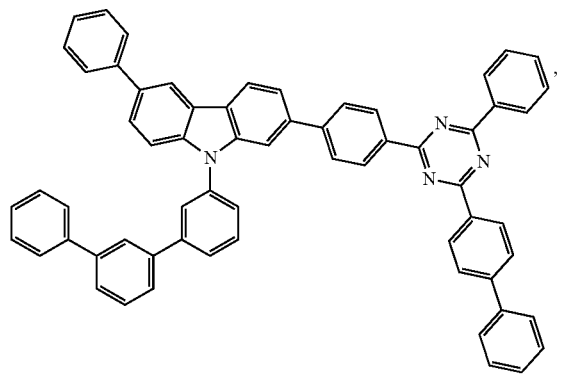
Compound 189
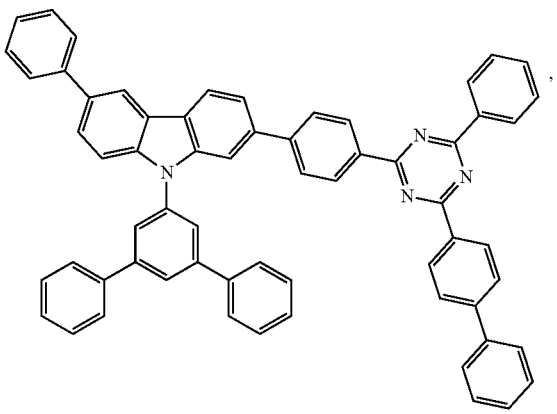
Compound 190
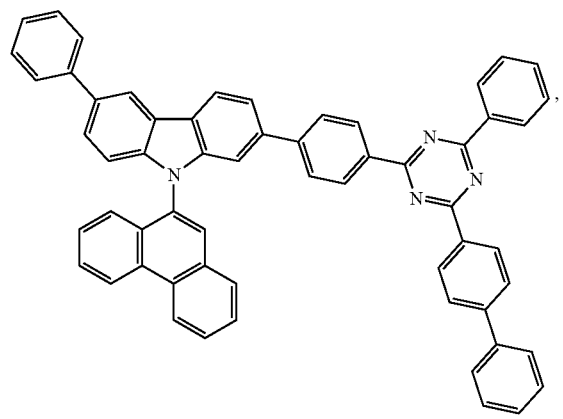
Compound 191
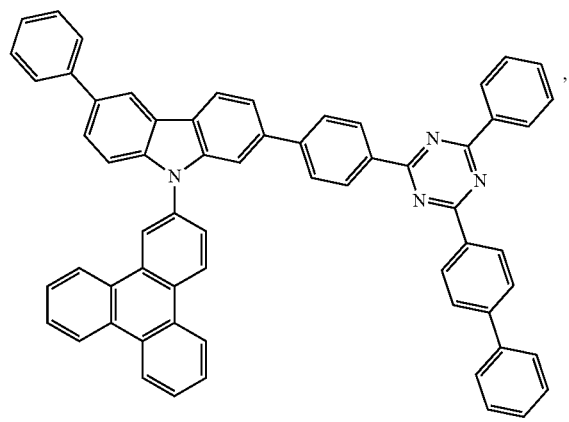
Compound 192
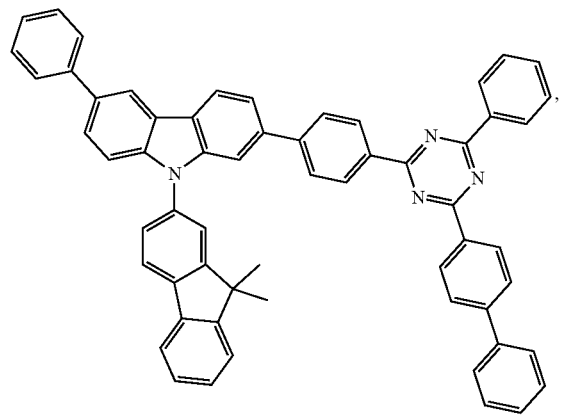
Compound 193
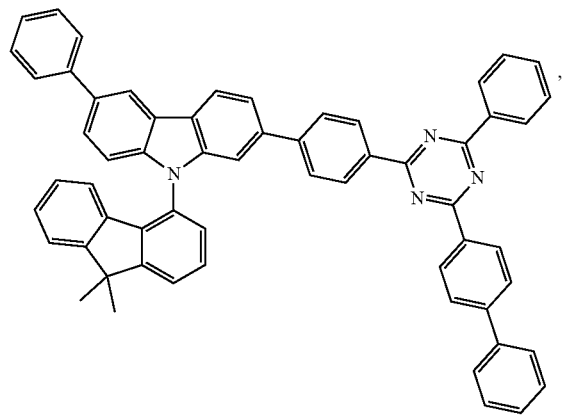

-continued
Compound 196
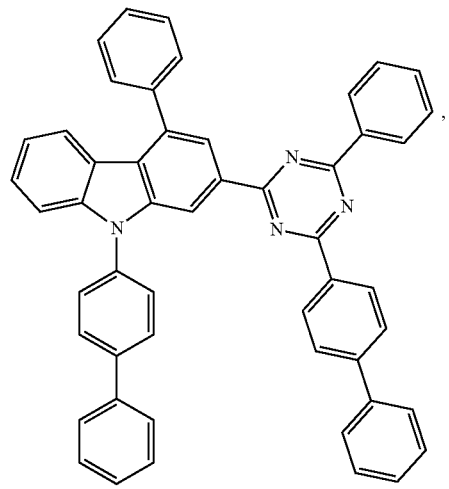
Compound 197
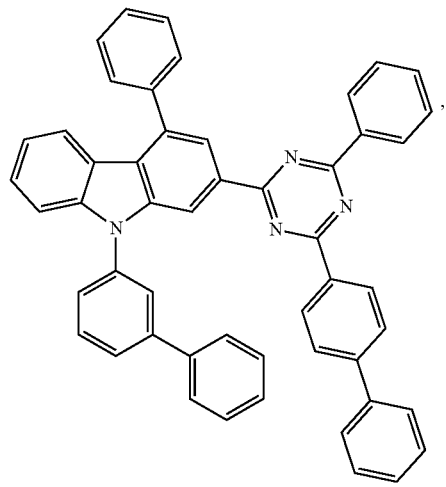
Compound 198
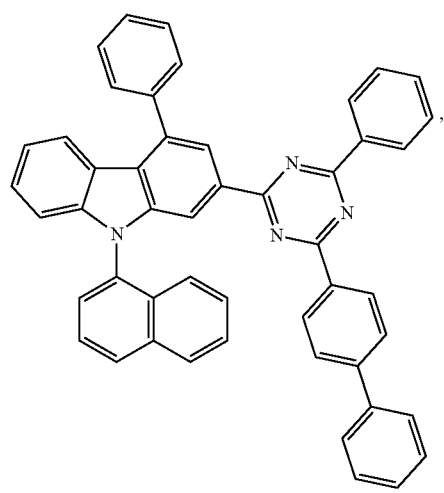
Compound 199
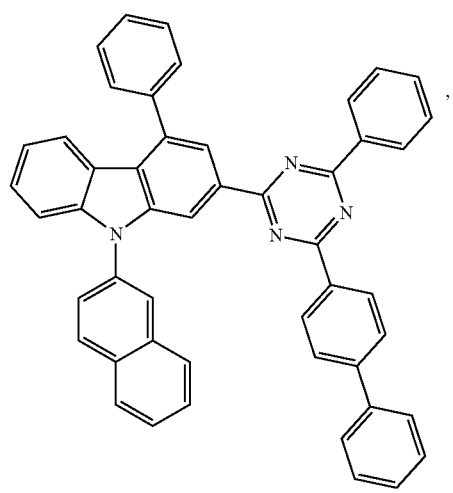
Compound 200
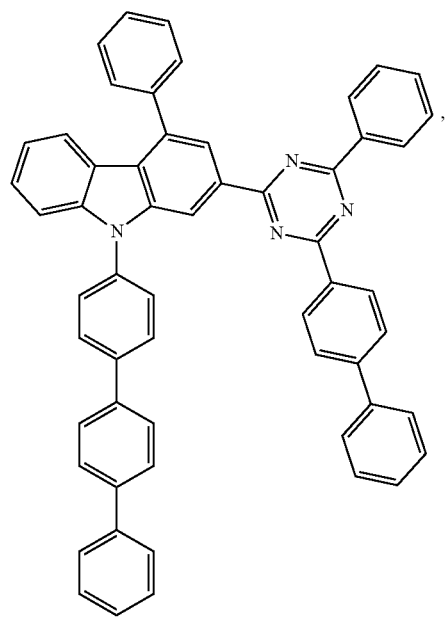
Compound 201
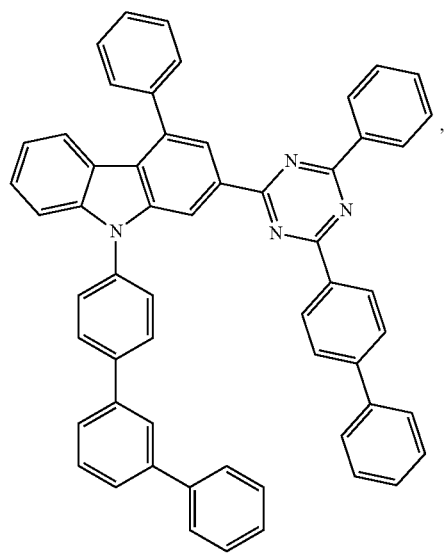

-continued
Compound 202
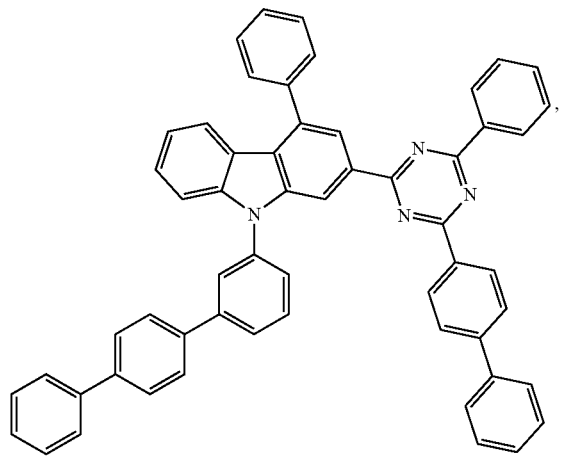
Compound 203
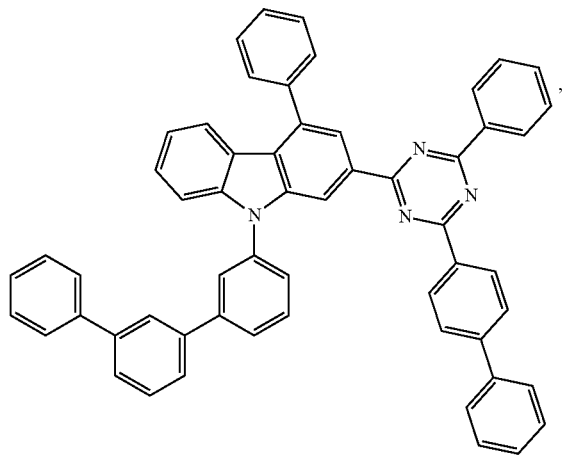
Compound 204
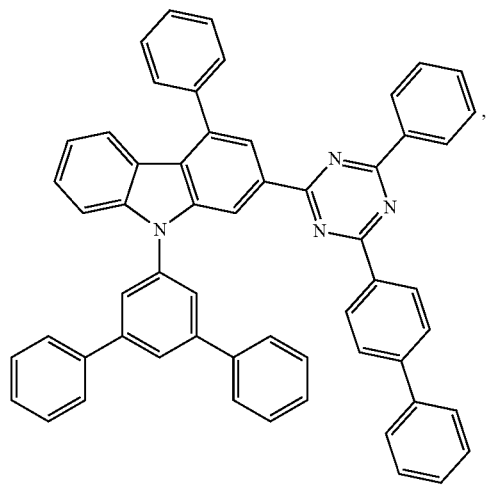
Compound 205
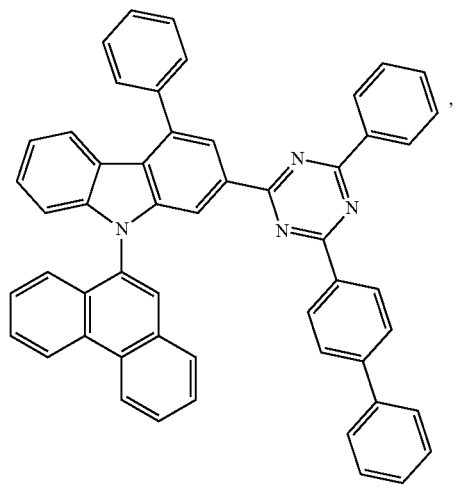
Compound 206
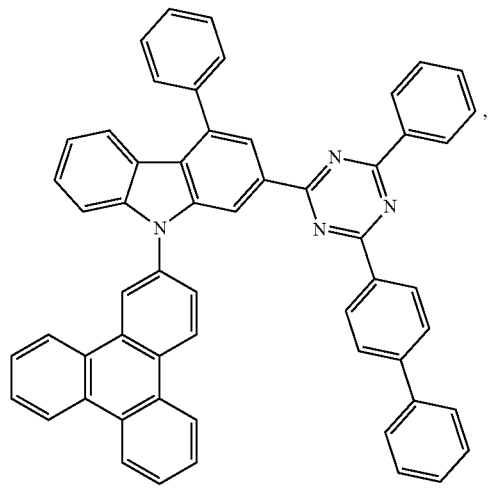
Compound 207
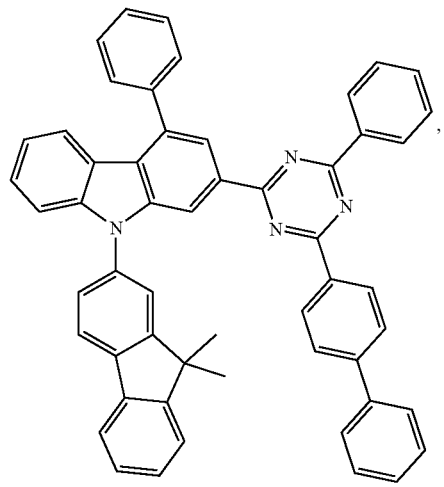

-continued
Compound 208
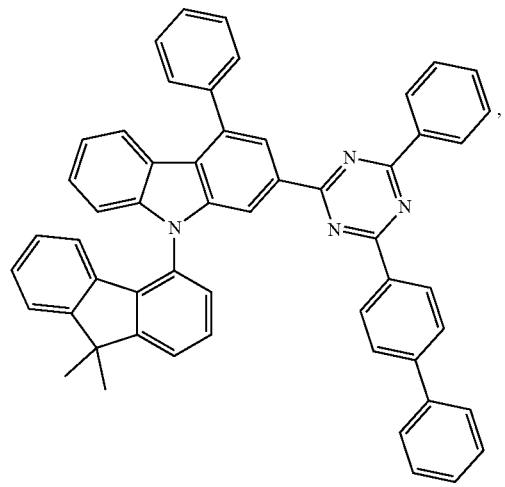
Compound 211
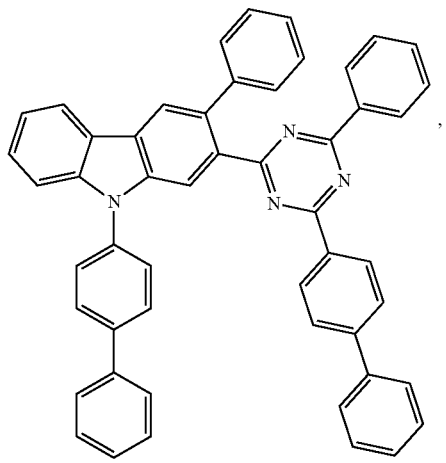
Compound 212
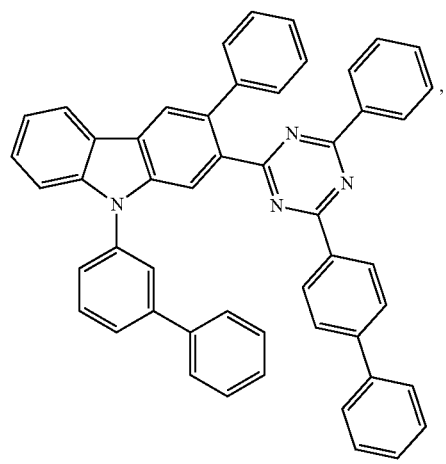
Compound 213
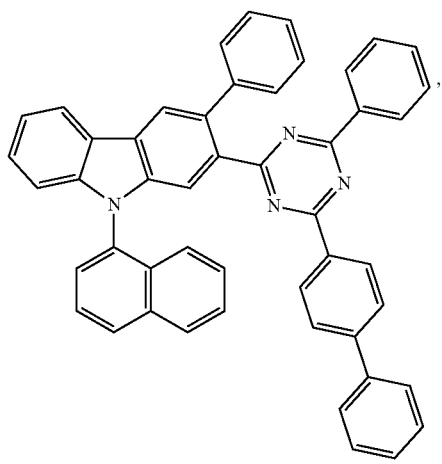
Compound 214
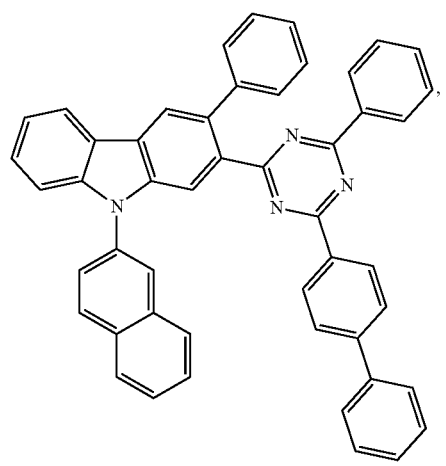
Compound 215
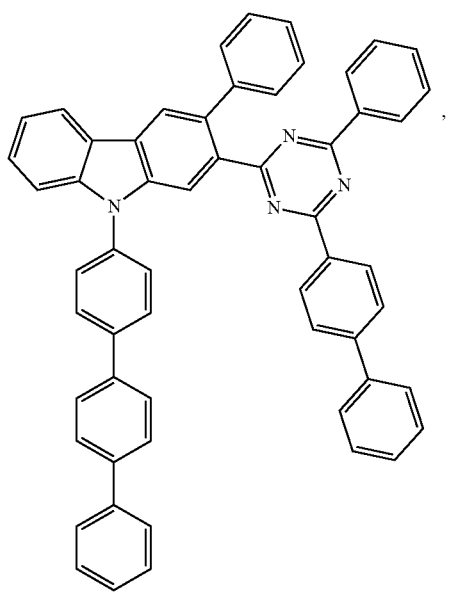

-continued
Compound 216
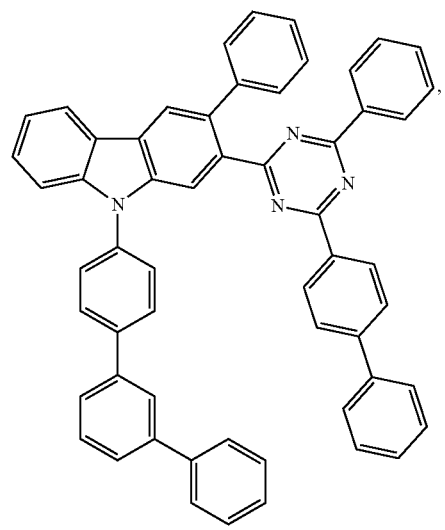
Compound 217
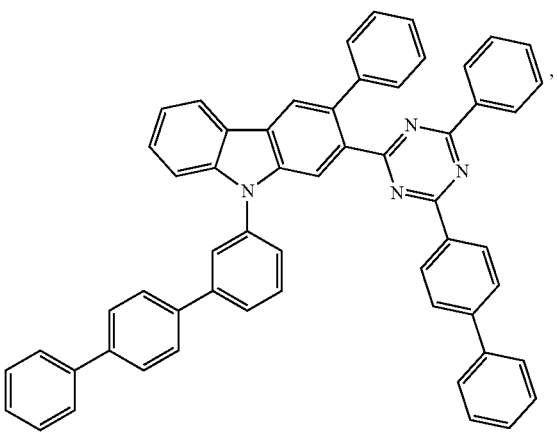
Compound 218
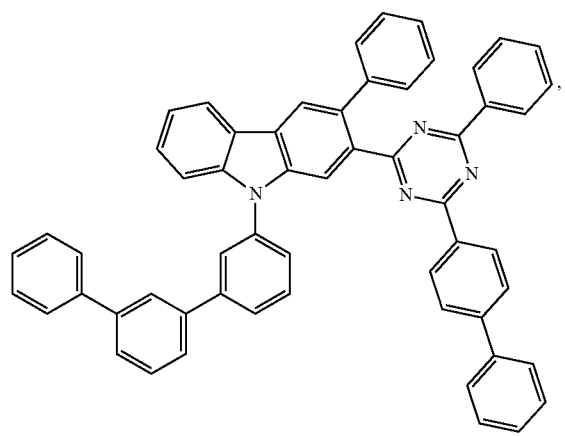
Compound 219
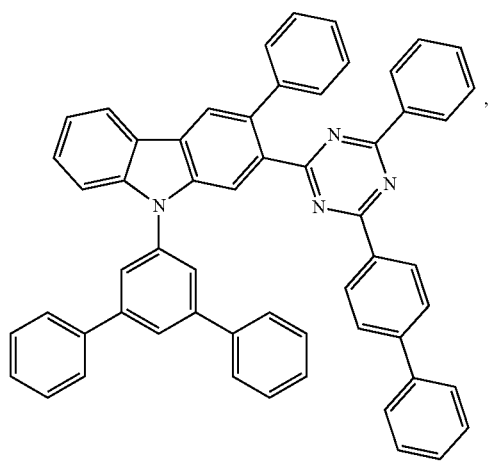
Compound 220
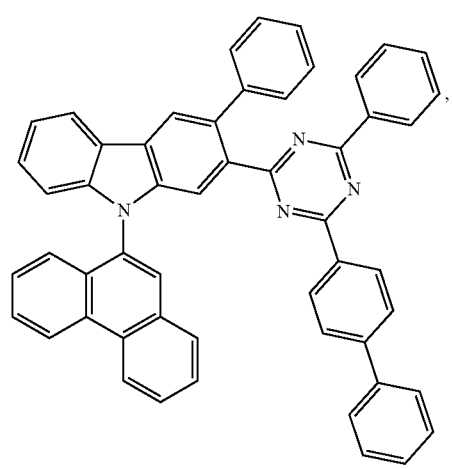
Compound 221
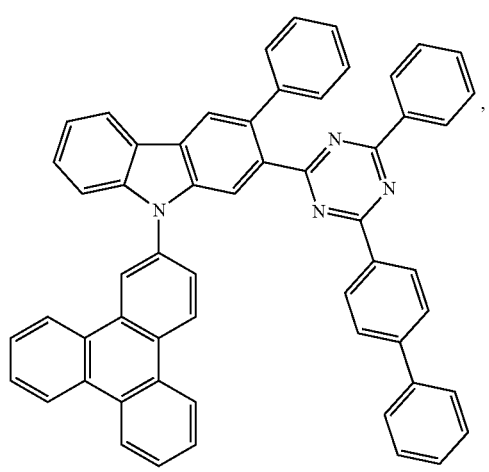

-continued
Compound 222
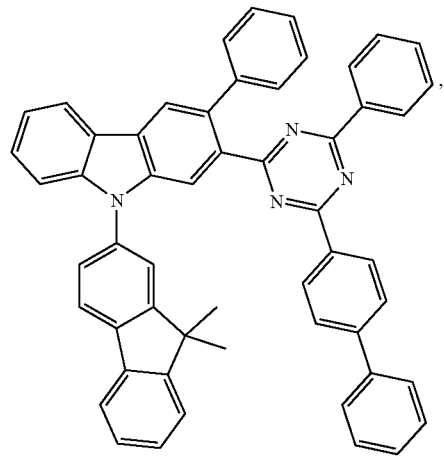
Compound 223
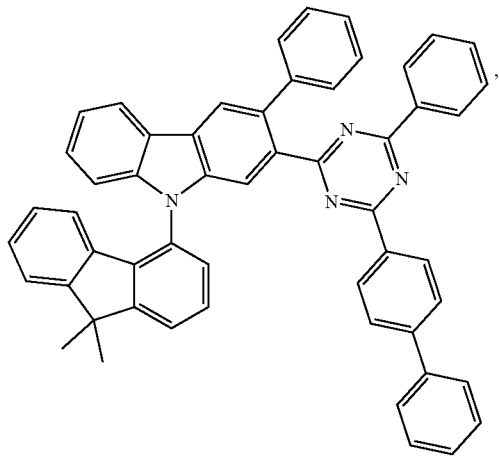
Compound 226
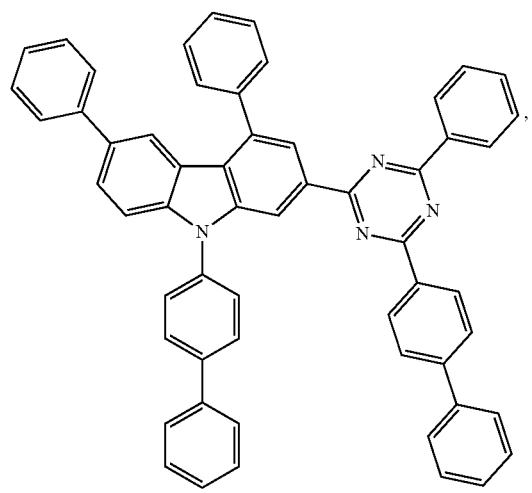
Compound 227
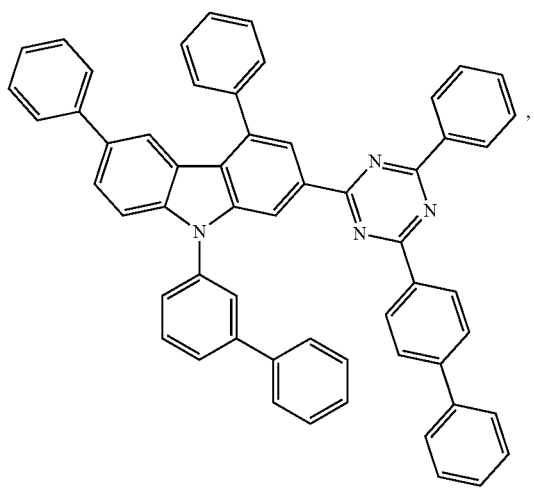
Compound 228
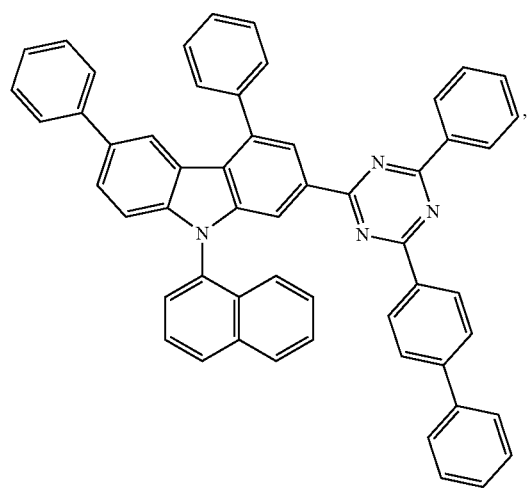
Compound 229
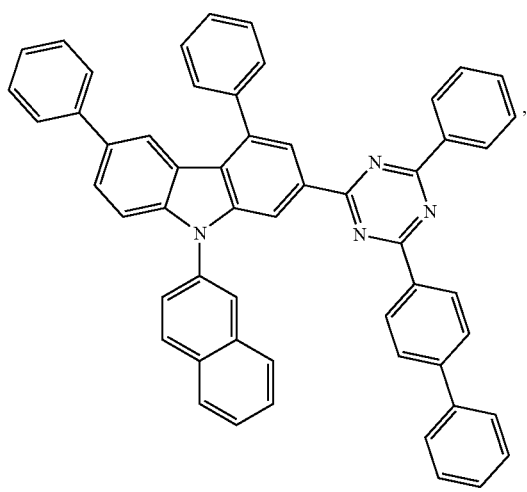

-continued
Compound 230
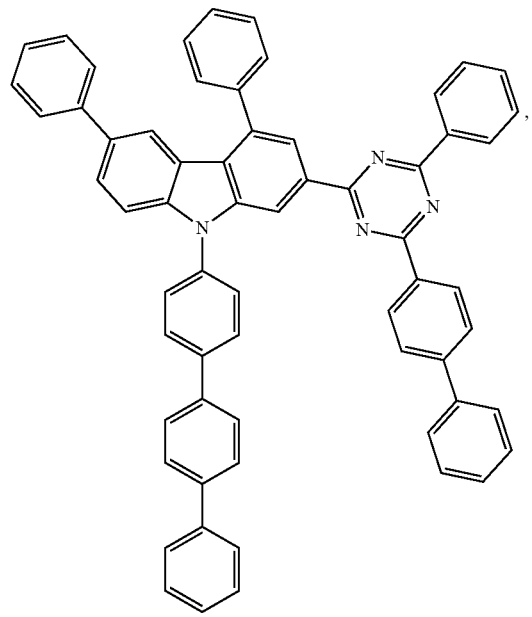
Compound 231
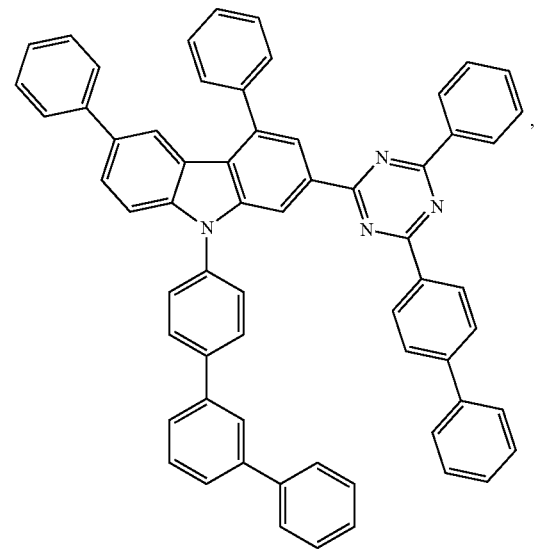
Compound 232
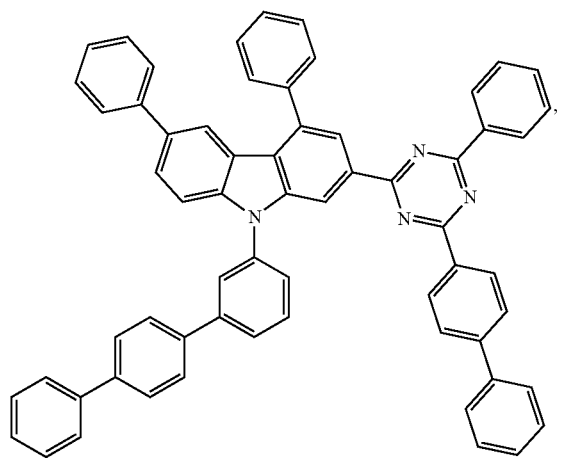
Compound 233
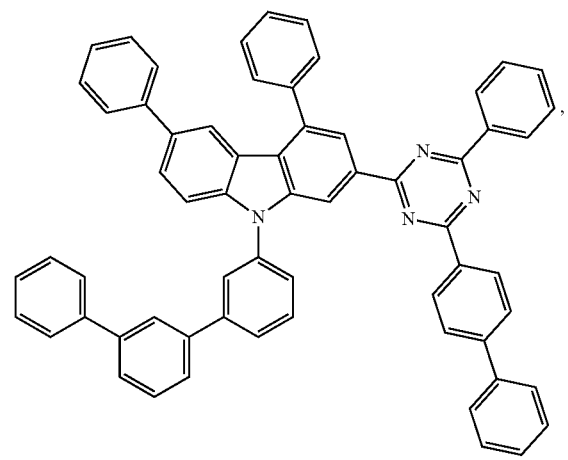
Compound 234
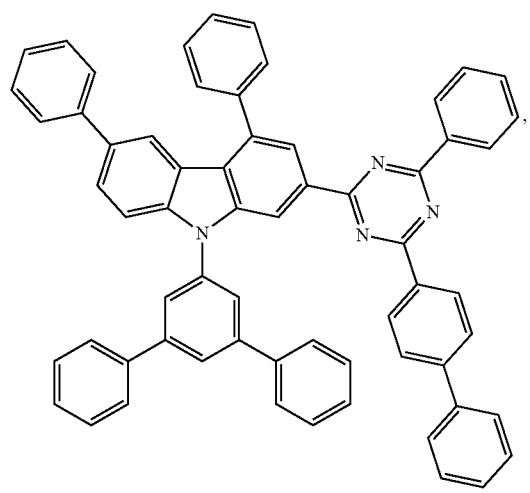
Compound 235
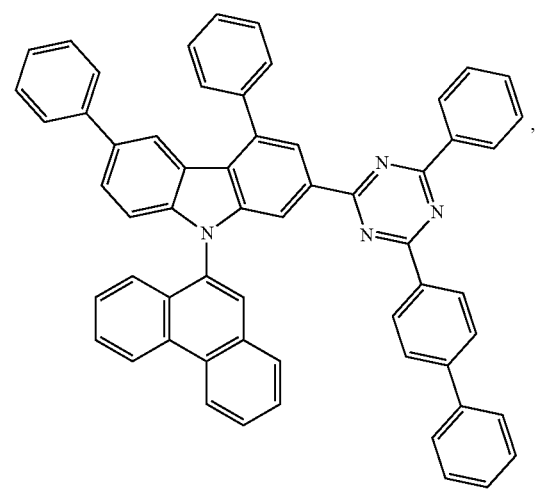

Compound 236
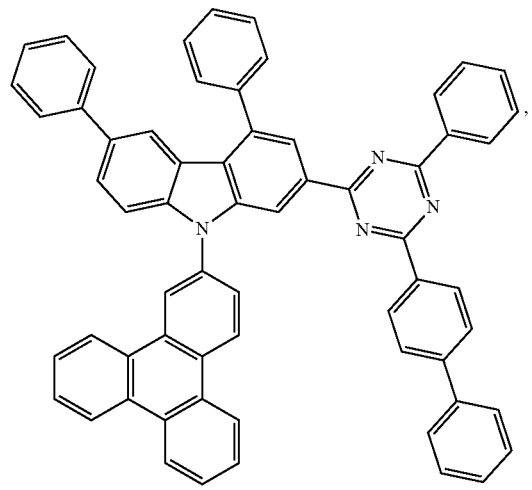
Compound 237
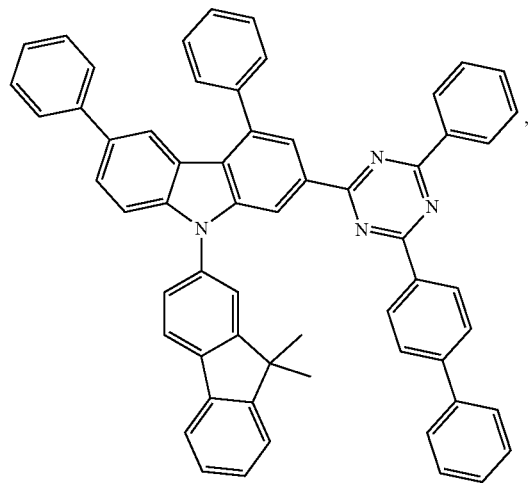
Compound 238
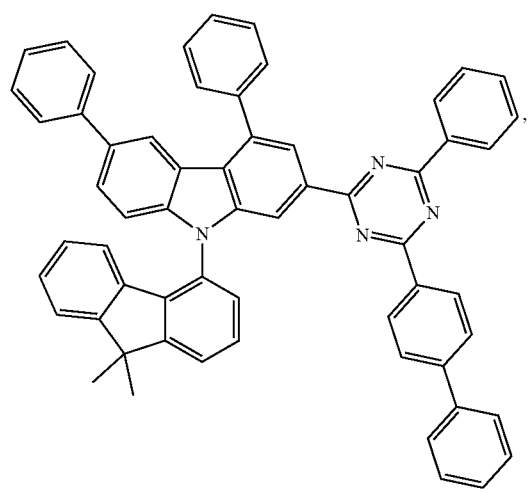
Compound 241
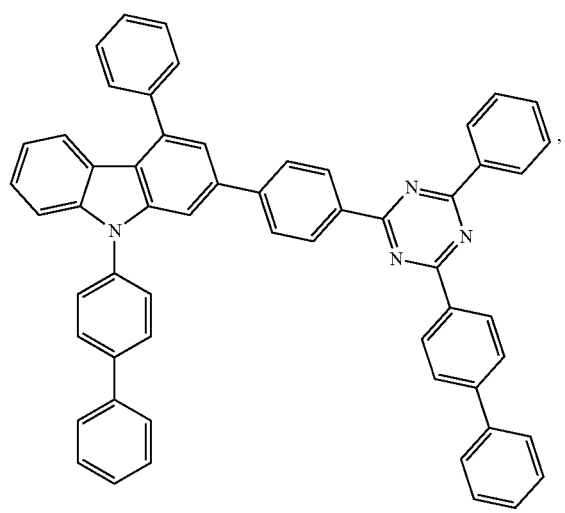
Compound 242
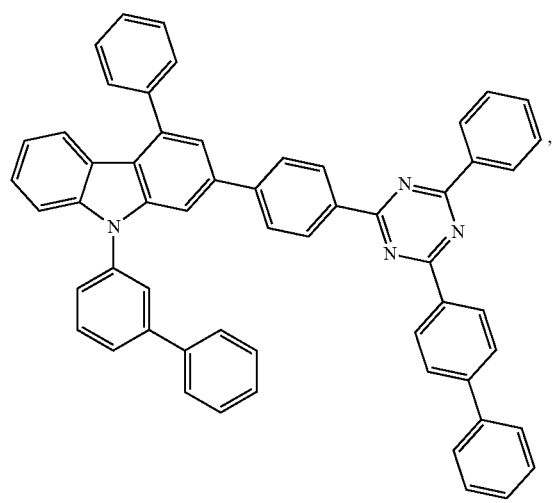
Compound 243
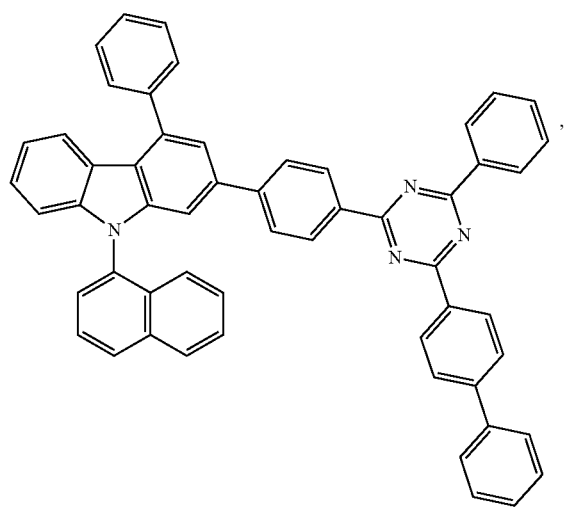

Compound 244
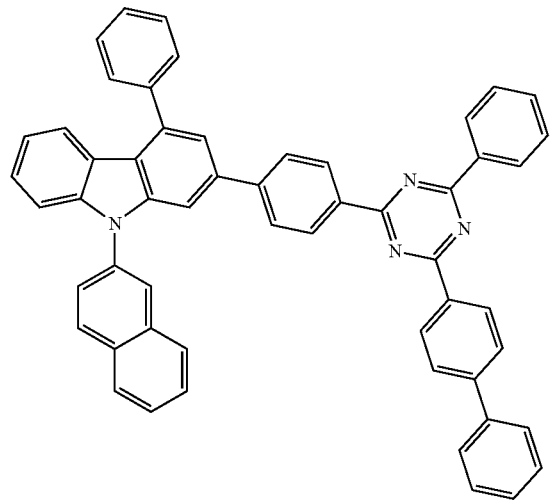
Compound 245
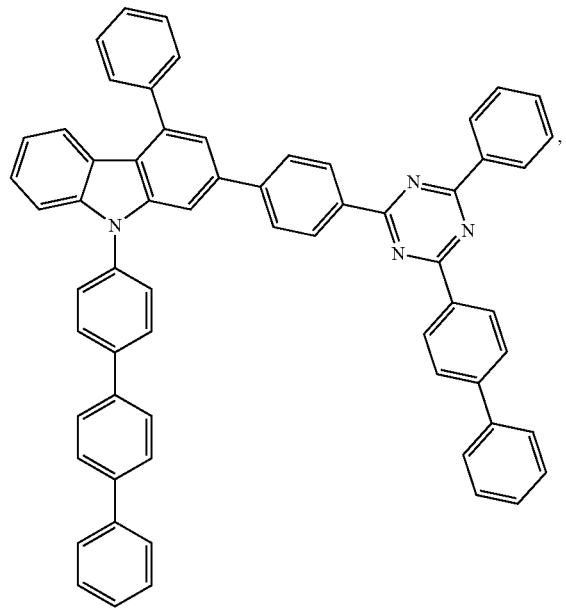
Compound 246
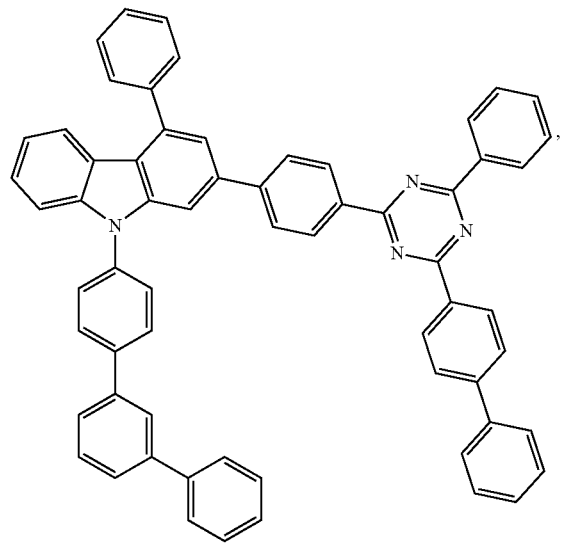
Compound 247
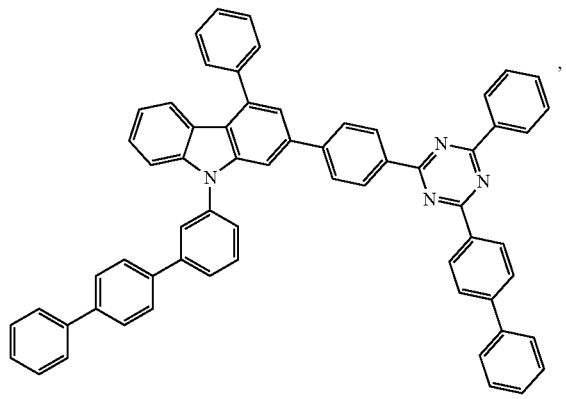

-continued
Compound 248
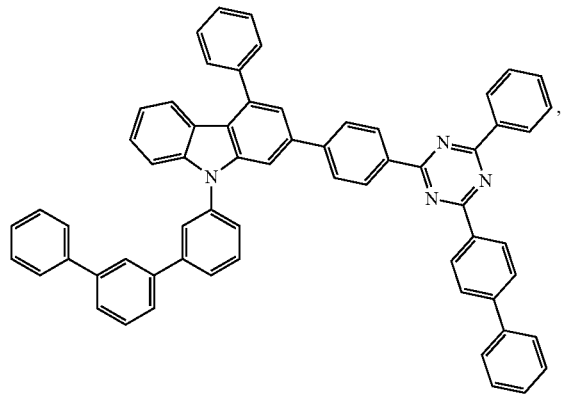
Compound 249
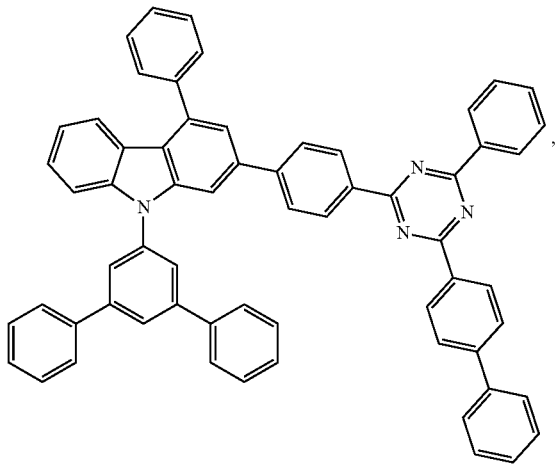
Compound 250
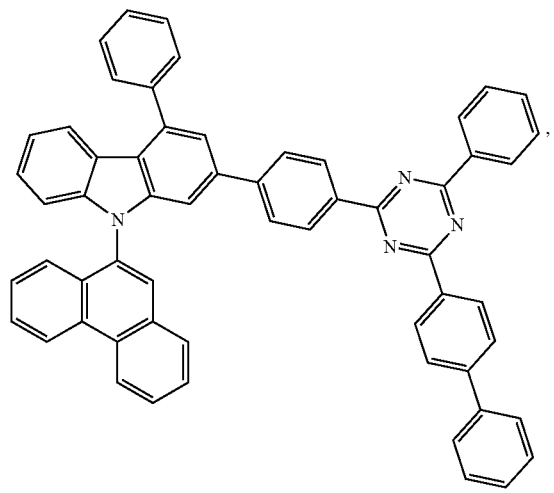
Compound 251
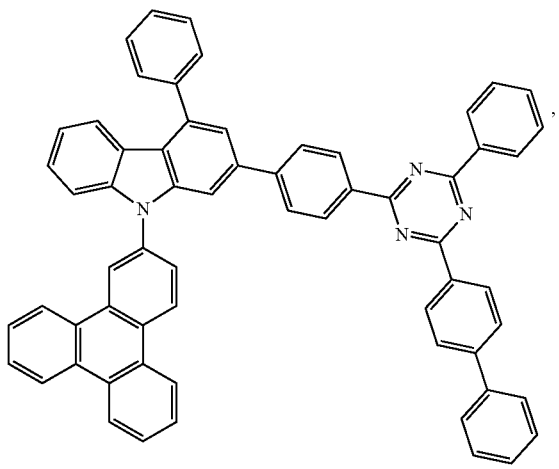
Compound 252
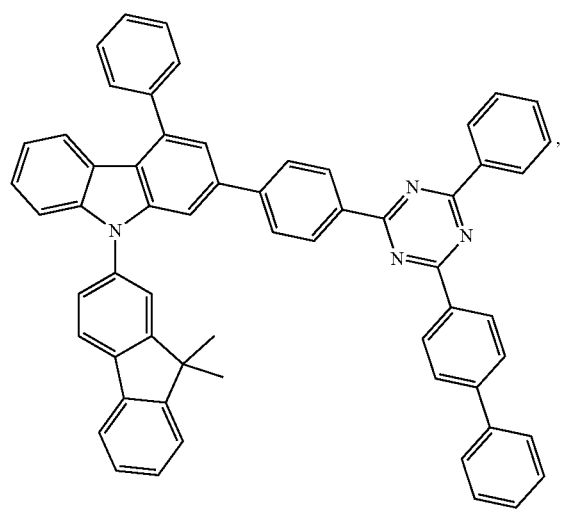
Compound 253
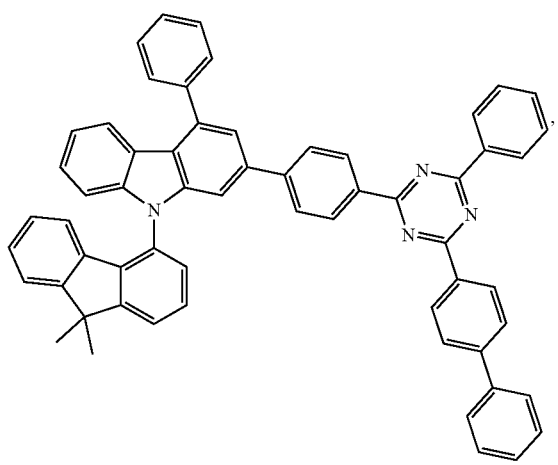

-continued
Compound 256
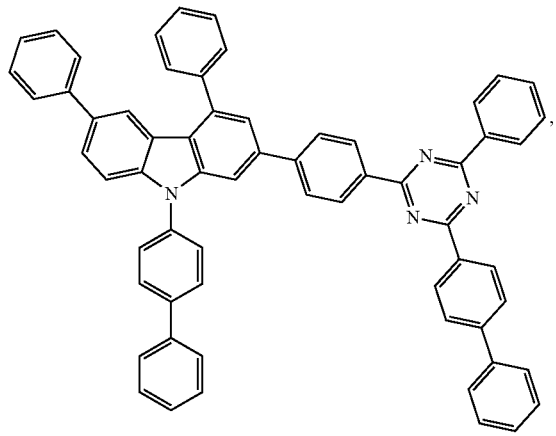
Compound 257
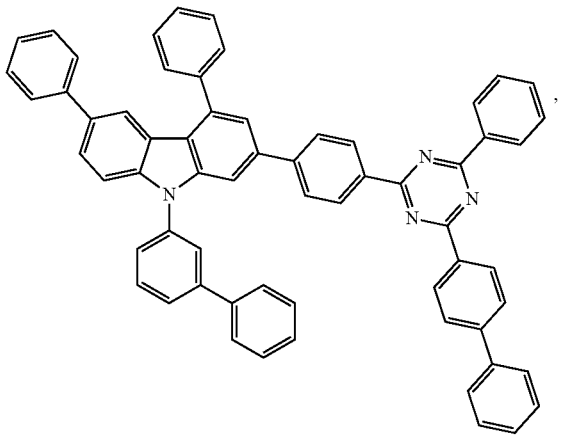
Compound 258
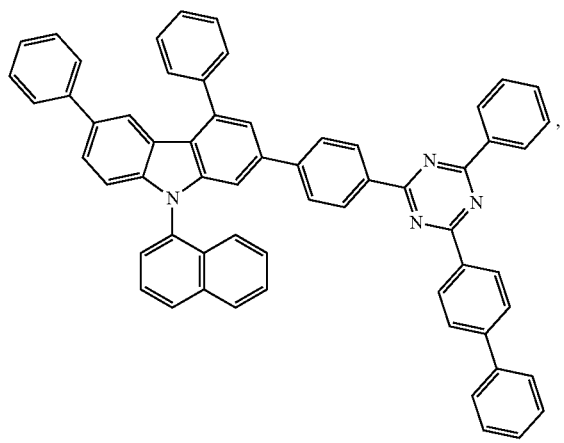
Compound 259
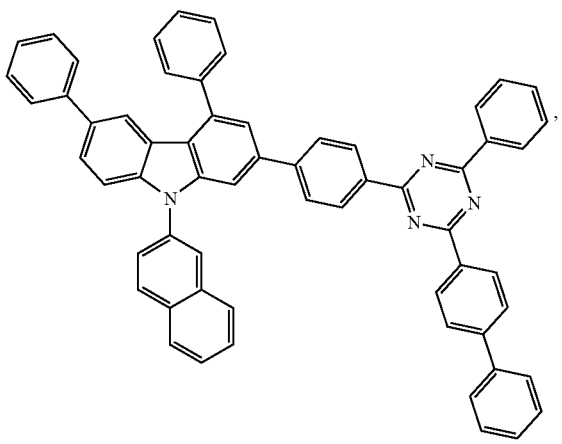
Compound 260
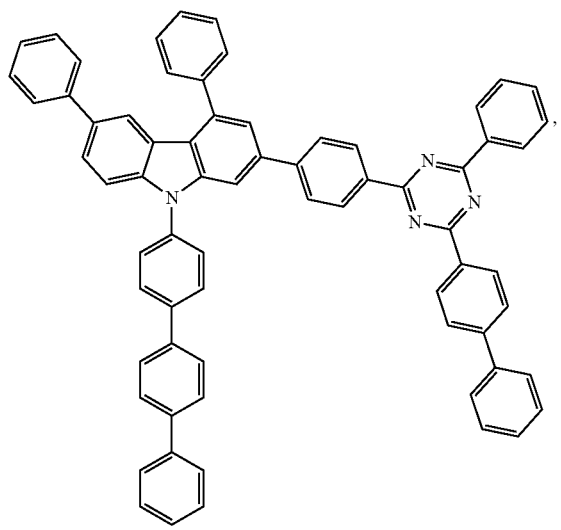
Compound 261
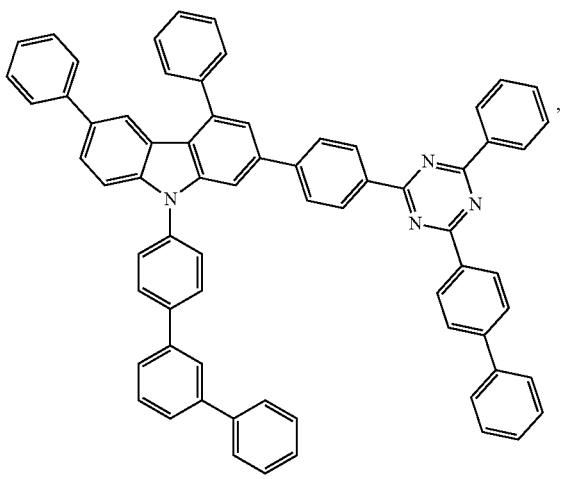

-continued
Compound 262
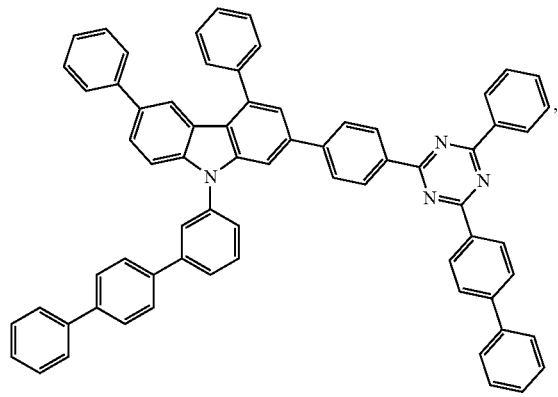
Compound 263
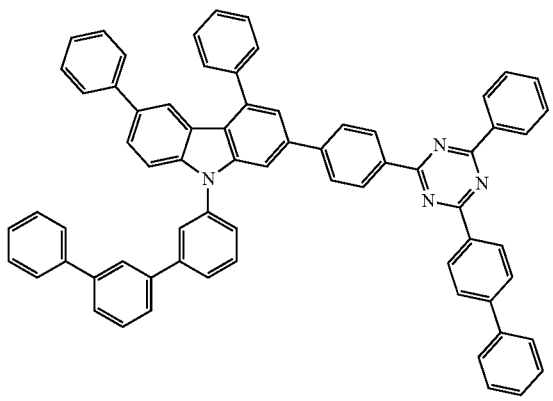
Compound 264
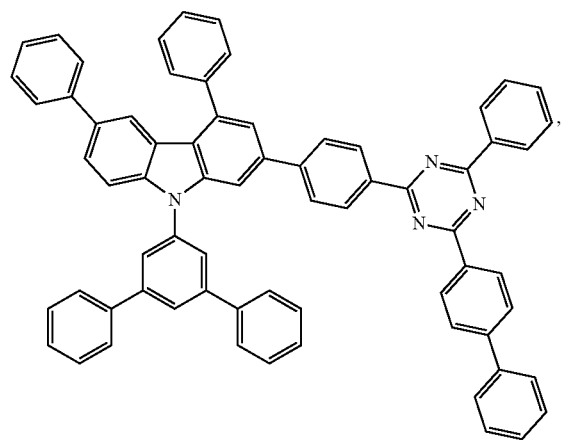
Compound 265
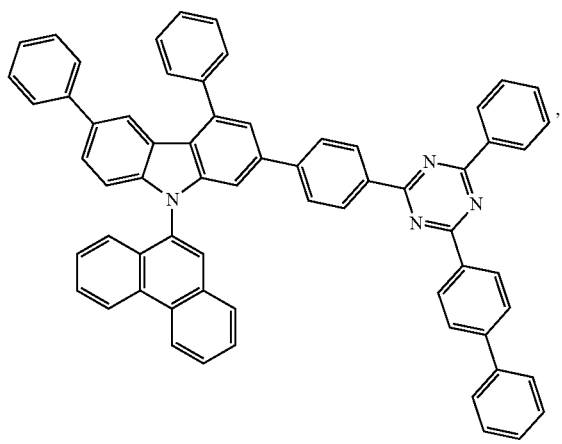
Compound 266
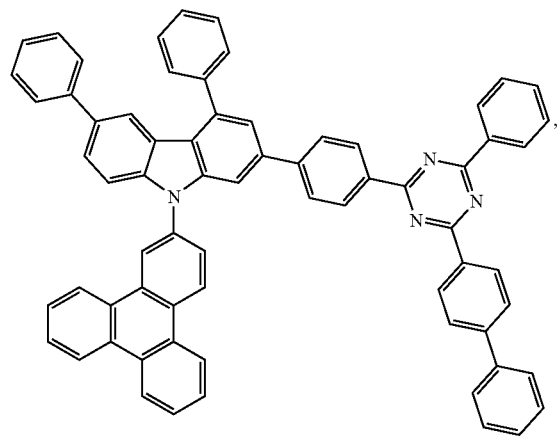
Compound 267
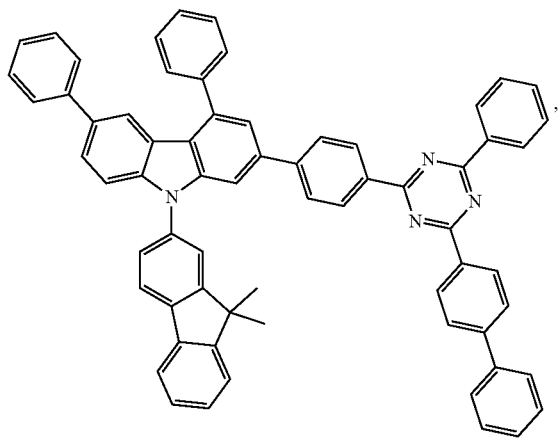

-continued

Compound 268

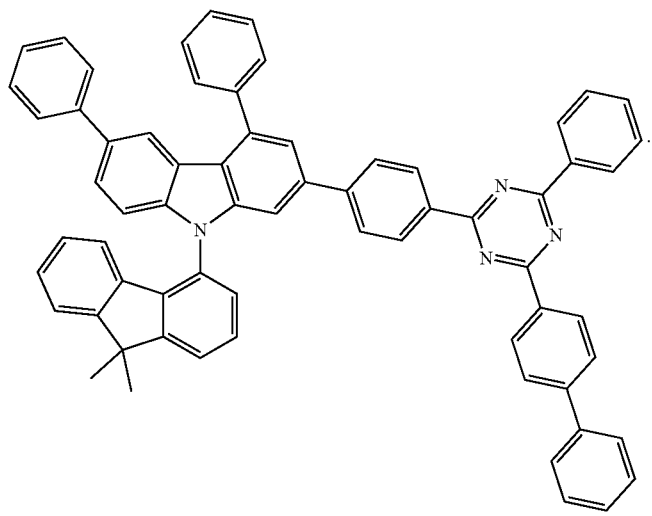

8. An electroluminescent device, which comprises
an anode,
a cathode,
and an organic layer disposed between the anode and the cathode, wherein the organic layer comprising the compound of claim 1.

9. The device of claim 8, wherein the organic layer is a hole blocking layer, and the compound is a hole blocking material.

10. The device of claim 8, wherein the organic layer is a light emitting layer and the compound is a host material.

11. The device of claim 10, wherein the organic layer further comprises phosphorescent material.

12. The device of claim 11, wherein the phosphorescent material is a metal complex, wherein the metal complex comprises at least one ligand, and the ligand comprises any one of the following structures:

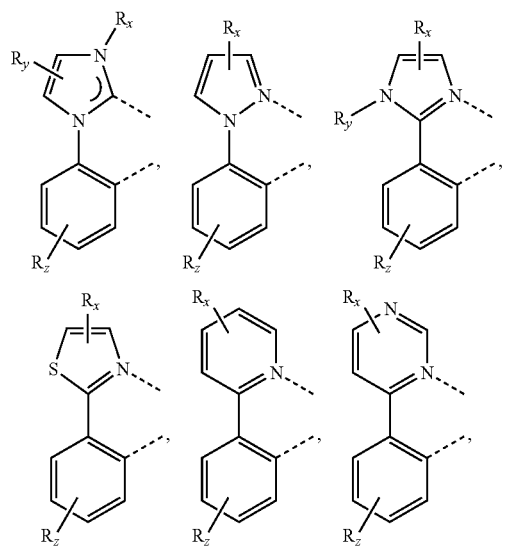

-continued

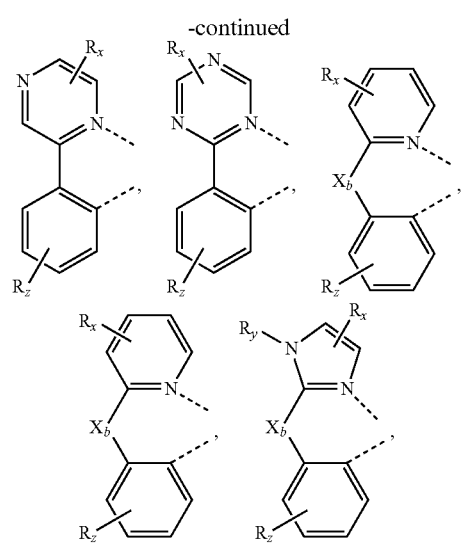

wherein $R_x$, $R_y$, and $R_z$, may represent mono substitution, multiple substitutions or no substitution;

$R_x$, $R_y$, and $R_z$, are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof;

$X_b$ is selected from the group consisting of O, S, Se, $NR_{N1}$, and $CR_{C1}R_{C2}$;

$R_{N1}$, $R_{C1}$ and $R_{C2}$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a thioalkyl group, a sulfinyl group, a sulfonyl group, a phosphino group, and combinations thereof.

13. The device of claim 10, wherein the organic layer further comprises at least one host material different from the compound having Formula 1.

14. A compound formulation comprising the compound of claim 1.

* * * * *